US010724013B2

(12) United States Patent
Natunen et al.

(10) Patent No.: US 10,724,013 B2
(45) Date of Patent: Jul. 28, 2020

(54) O-MANNOSYLTRANSFERASE DEFICIENT FILAMENTOUS FUNGAL CELLS AND METHODS OF USE THEREOF

(71) Applicant: Glykos Finland OY, Helsinki (FI)

(72) Inventors: Jari Natunen, Vantaa (FI); Jukka Hiltunen, Helsinki (FI); Anne Huuskonen, Helsinki (FI); Markku Saloheimo, Helsinki (FI); Christian Ostermeier, Basel (CH); Benjamin Patrick Sommer, Basel (CH); Ramon Wahl, Basel (CH)

(73) Assignee: GLYKOS FINLAND OY, Helsinki (FI)

( * ) Notice: Subject to any disclaimer, the term of this patent is extended or adjusted under 35 U.S.C. 154(b) by 0 days.

(21) Appl. No.: 16/124,679

(22) Filed: Sep. 7, 2018

(65) Prior Publication Data

US 2020/0040314 A1 Feb. 6, 2020

Related U.S. Application Data

(63) Continuation of application No. 14/902,492, filed as application No. PCT/EP2014/064248 on Jul. 3, 2014, now abandoned.

(30) Foreign Application Priority Data

Jul. 4, 2013 (EP) .................................. 13175141

(51) Int. Cl.
*C12N 9/10* (2006.01)
*C07K 16/00* (2006.01)
(Continued)

(52) U.S. Cl.
CPC ............ *C12N 9/1051* (2013.01); *C07K 14/37* (2013.01); *C07K 16/00* (2013.01); *C07K 16/18* (2013.01);
(Continued)

(58) Field of Classification Search
CPC ..... C07K 16/00; C07K 2317/41; C07K 16/18; C07K 14/37; C12N 9/1051; C12Y 204/01109
(Continued)

(56) References Cited

U.S. PATENT DOCUMENTS 5,714,377 A 2/1998 Tanner et al.
5,958,727 A 9/1999 Brody et al.
(Continued)

FOREIGN PATENT DOCUMENTS

WO 2006/036817 A2 4/2006
WO 2007061631 A2 5/2007
(Continued)

OTHER PUBLICATIONS

Gorka-Niec et al., (Acta Biochimicha Polonica. vol. 55 No. 2/2008, 251-259) (Year: 2008).*
(Continued)

*Primary Examiner* — Jana A Hines
(74) *Attorney, Agent, or Firm* — Patrick J. Halloran

(57) ABSTRACT

The present disclosure relates to compositions and methods useful for the production of heterologous proteins with reduced O-mannosylation in filamentous fungal cells, such as *Trichoderma* cells. More specifically, the invention provides a PMT-deficient filamentous fungal cell comprising a) at least a first mutation that reduces an endogenous protease activity compared to a parental filamentous fungal cell which does not have said first mutation, and, b) at least a second mutation in a PMT gene that reduces endogenous O-mannosyltransferase activity compared to a parental filamentous fungal cell which does not have said second mutation, wherein said filamentous fungal cell is selected
(Continued)

from the group consisting of *Trichoderma*, *Neurospora*, *Myceliophthora* or *Chrysosporium* cell.

6 Claims, 6 Drawing Sheets

Specification includes a Sequence Listing.

(51) Int. Cl.
*C07K 16/18* (2006.01)
*C07K 14/37* (2006.01)

(52) U.S. Cl.
CPC .. *C12Y 204/01109* (2013.01); *C07K 2317/41* (2013.01)

(58) Field of Classification Search
USPC ...................................................... 530/387.3
See application file for complete search history.

(56) References Cited

U.S. PATENT DOCUMENTS

| | | | |
|---|---|---|---|
| 7,105,554 | B2 | 9/2006 | Orchard et al. |
| 7,993,877 | B2 | 8/2011 | Van Urk et al. |
| 8,680,252 | B2 | 3/2014 | Emalfarb et al. |
| 2002/0068325 | A1 | 6/2002 | Ng et al. |
| 2006/0014254 | A1 | 1/2006 | Haseltine et al. |
| 2007/0048282 | A1 | 3/2007 | Rosen et al. |
| 2007/0155956 | A1 | 7/2007 | Chapman et al. |
| 2008/0292581 | A1 | 11/2008 | Kroz et al. |
| 2009/0170159 | A1 | 7/2009 | Bobrowicz et al. |
| 2009/0171070 | A1 | 7/2009 | Van Urk et al. |
| 2009/0191587 | A1 | 7/2009 | Chiba et al. |
| 2010/0222267 | A1 | 9/2010 | Finnis et al. |
| 2010/0311122 | A1 | 12/2010 | Choi et al. |
| 2011/0021378 | A1 | 1/2011 | Callewaert et al. |
| 2011/0076721 | A1 | 3/2011 | Desai et al. |
| 2011/0124576 | A1 | 5/2011 | Sleep et al. |
| 2011/0143396 | A1 | 6/2011 | Choi |
| 2011/0312032 | A1* | 12/2011 | Choi ............... C07K 14/4725 435/69.4 |
| 2011/0313133 | A1 | 12/2011 | Finnis et al. |
| 2012/0059155 | A1 | 3/2012 | Evans et al. |
| 2012/0135461 | A1 | 5/2012 | Cook et al. |
| 2012/0149873 | A1 | 6/2012 | Blackwell et al. |
| 2012/0232007 | A1 | 9/2012 | Bobrowicz et al. |
| 2012/0309935 | A1 | 12/2012 | Govindappa et al. |
| 2012/0328626 | A1 | 12/2012 | Sethuraman et al. |
| 2013/0071390 | A1 | 3/2013 | Stadheim et al. |
| 2013/0171692 | A1 | 7/2013 | Abe et al. |
| 2013/0295608 | A1 | 11/2013 | Bobrowicz et al. |
| 2014/0086916 | A1 | 3/2014 | Zha |
| 2014/0235537 | A1 | 8/2014 | Meehl et al. |
| 2014/0286946 | A1 | 9/2014 | Stadheim et al. |
| 2014/0302028 | A1 | 10/2014 | Zha |
| 2014/0302556 | A1 | 10/2014 | Jiang et al. |
| 2015/0176044 | A1 | 6/2015 | Natunen et al. |
| 2015/0275222 | A1 | 10/2015 | Jiang et al. |
| 2015/0337274 | A1 | 11/2015 | Chen et al. |
| 2015/0376249 | A1 | 12/2015 | Choi |
| 2016/0017343 | A1 | 1/2016 | Jin et al. |
| 2016/0115216 | A1 | 4/2016 | Hubalek et al. |

FOREIGN PATENT DOCUMENTS

| | | |
|---|---|---|
| WO | 2008073914 A2 | 6/2008 |
| WO | 2009105357 A1 | 8/2009 |
| WO | 2010019487 A1 | 2/2010 |
| WO | 2010/034708 A1 | 4/2010 |
| WO | 2011075677 A2 | 6/2011 |
| WO | 2013/066765 A1 | 5/2013 |
| WO | WO-2013174927 A1 * | 11/2013 ........... C07K 14/435 |
| WO | 2014/182684 A2 | 11/2014 |
| WO | 2015/013116 A1 | 1/2015 |
| WO | 2015/054039 A1 | 4/2015 |
| WO | 2015/073307 A2 | 5/2015 |

OTHER PUBLICATIONS

Berka, et al. Comparative Genomic Analysis of the thermophilic biomass-degrading fungi *Myceliophthora thermophilia* and *Thielavia terrestris*. Nal Biotech. 29: 922-927 (2011).

Agaphonov et al., "Mutation of the protein-O-mannosyltransferase enhances secretion of the human urokinase-type plasminogen activator in Hansenula polymorpha", Yeast, vol. 22, No. 13, Oct. 2005, pp. 1037-1047.

Baldwin et al., "Develop Systems for Manufacturing 100,000,000 Doses of an Emergency Pharmaceutical (e.g. Vaccine or Monoclonal Antibody) Within 2 Months of Product Identification", Genencor International, Jun. 2006, 21 pages.

Bourdineaud et al., "Pmt1 mannosyl transferase is involved in cell wall incorporation of several proteins in *Saccharomyces cerevisiae*", Molecular Microbiology, vol. 27, No. 1, 1998, pp. 85-98.

Cantero and Ernst, "Damage to the glycoshield activates PMT-directed O-mannosylation via the Msb2-Cek1 pathway in Candida albicans", Molecular Microbiology, vol. 80, No. 3, May 2011, pp. 715-725. doi: 10.1111/.1365-2958.2011.07604.x.

Ecker et al., "O-mannosylation precedes and potentially controls the N-glycosylation of a yeast cell wall glycoprotein", EMBO Reports, vol. 4, No. 6, Jul. 2003, pp. 628-632.

Gentzsch et al., "The PMT gene family: protein O-glycosylation in *Saccharomyces cerevisiae* is vital", The EMBO Journal, vol. 15, No. 21, Nov. 1, 1996, pp. 5752-5759.

Gentzsch et al., "Protein-O-glycosylation in yeast: protein-specific mannosyltransferases", Glycobiology, vol. 7, No. 4, 1997, pp. 481-486.

Górka-Niec et al., "Protein glycosylation in pmt mutants of *Saccharomyces cerevisiae*. Influence of heterologously expressed cellobiohydrolase II of Trichoderma reesei and elevated levels of GDP-mannose and cis-prenyltransferase activity", Biochim Biophys Acta, vol. 1770, No. 5, 2007, pp. 774-780.

Górka-Niec et al., "Disruption of Trichoderma reesei gene encoding protein O-mannosyltransferase I results in a decrease of the enzyme activity and alteration of cell wall composition", Acta Biochim, vol. 55, No. 2, 2008, pp. 251-259.

Górka-Niec et al., "Integration of additional copies of Trichoderma reesei gene encoding protein O-mannosyltransferase I results in a decrease of the enzyme activity and alteration of cell wall composition", Fungal Biol, vol. 115, 2011, pp. 124-132. doi: 10.1016/j.funbio.2010.11.001.

Goto et al., "Functional analysis of O-linked oligosaccharides in threonine/serine-rich region of Aspergillus glucoamylase by expression in mannosyltransferase-disruptants of yeast", Eur J Biochem, vol. 260, No. 3, Mar. 1999, pp. 596-602.

Goto et al., "Protein O-glycosylation in fungi: diverse structures and multiple functions", Biosci Biotechnol Biochem, vol. 71, No. 6, 2007, pp. 1415-1427.

Goto et al., "Protein O-mannosyltransferases B and C support hyphal development and differentiation in Aspergillus nidulans", Eukaryot Cell., American Society for Microbiology,doi:10.1128/EC.00371-08, vol. 8, No. 10, Oct. 2009, pp. 1465-1474.

Hintz et al., "Improved gene expression in Aspergillus nidulans", Canadian Journal of Botanic, 1995, pp. 876-884.

Kriangkripipat, et al., "Aspergillus nidulans protein O-mannosyltransferases play roles in cell wall integrity and developmental patterning. Eukaryot Cell.", American Society for Microbiology, doi:10.1128/EC.00040-09, vol. 8, No. 10, Oct. 2009, pp. 1475-1485.

Kruszewska et al., "Alterations in protein secretion caused by metabolic engineering of glycosylation pathways in fungi", Acta Biochimica Polonica, vol. 55, No. 3, 2008, pp. 447-456.

Kuroda et al., "Efficient antibody production upon suppression of O mannosylation in the yeast *Ogataea minuta*", Applied and Environmental Microbiology, vol. 74, No. 2, Jan. 2008, pp. 446-453.

(56) References Cited

OTHER PUBLICATIONS

Lengeler et al., "Protein-O-mannosyltransferases in virulence and development", Cellular and Molecular Life Sciences, vol. 65, No. 4, Mar. 2008, pp. 528-544.
Lussier et al., "Protein O-glycosylation in yeast. The PMT2 gene specifies a second protein O-mannosyltransferase that functions in addition to the PMT1-encoded activity", The Journal of Biological Chemistry, vol. 270, No. 6, Feb. 10, 1995, pp. 2770-2775.
Mouyna et al., "Members of protein O-mannosyltransferase family in Aspergillus fumigatus differentially affect growth, morphogenesis and viability", Molecular Microbiol, doi: 10.1111/j.1365-2958. 2010.07164.x, vol. 76, No. 5,Jun. 2010, pp. 1205-1221.
Nett et al., "Characterization of the Pichia pastoris protein-O-mannosyltransferase gene family", PLoS One, doi:10.1371/journal. pone.006832, vol. 8 , No. 7, pp. e68325, Jul. 1, 2013.
Oka et al., "Molecular characterization of protein O-mannosyltransferase and its involvement in cell-wall synthesis in Aspergillus nidulans", Microbiology, vol. 150, No. 6, 2004, pp. 1973-1982.
Oka et al., "Protein O-mannosyltransferase A of Aspergillus awamori is involved in O-mannosylation of glucoamylase I", Microbiology, vol. 151, No. 11, 2005, pp. 3657-3667.
Prill et al., "PMT family of Candida albicans: five protein mannosyltransferase isoforms affect growth, morphogenesis and antifungal resistance", Molecular Microbiology, vol. 55, No. 2, Jan. 2005, pp. 546-560.
Rouabiaia et al., "Virulence of the fungal pathogen Candida albicans requires the five isoforms of protein mannosyltransferases", Infection and Immunity, vol. 73, No. 8, Aug. 2005, pp. 4571-4580.
Strahl-Bolsinger et al., "PMT1, the gene for a key enzyme of protein O-glycosylation in *Saccharomyces cerevisiae*", Proceedings of the National Academy of Sciences USA, vol. 90, No. 17, Sep. 1, 1993, pp. 8164-8168.
Timpel et al., "Multiple functions of Pmt1p-mediated protein O-mannosylation in the fungal pathogen Candida albicans", Journal of Biological Chemistry, vol. 273, No. 33, Aug. 14, 1998, pp. 20837-20846.
Weber et al., "Pmt-mediated O mannosylation stabilizes an essential component of the secretory apparatus, Sec20p, in Candida albicans" , Eukaryotic Cell, vol. 3, No. 5, Oct. 2004, pp. 1164-1168.
Willger et al., "Characterization of the PMT gene family in Cryptococcus neoformans", PLoS One, doi:10.1371/journal.pone.0006321 vol. 4, No. 7, Jul. 27, 2009, pp. - e6321.
Zakrzewska et al., "cDNA encoding protein O-mannosyltransferase from the filamentous fungus *Trichoderma reesei*; functional equivalence to *Saccharomyces cerevisiae* PMT2", Current Genetics, vol. 43, May 2003, pp. 11-16.
Berka, et al. Comparative genomic analysis of the thermophilic biomass-degrading fungi *Myceliophthora thermophila* and *Thielavia terrestris*. Nature Biotech. 29(10: 922-929 (2011).
International Preliminary Report on Patentability for PCT/EP2014/064248 (dated Jan. 5, 2016).
Agaphonov et al., "Mutation of the protein-O-mannosyltransferase enhances secretion of the human urokinase-type blasminogen activator in Hansenula polymorpha", Yeast, vol. 22, No. 13, Oct. 2005, pp. 1037-1047.
Baldwin et al., "Develop Systems far Manufacturing 100,000,000 Doses of an Emergency Pharmaceutical (e.g. Vaccine or Monoclonal Antibody) Within 2 Months of Product Identification", Genencor International, Jun. 2006, 21 pages.
Górka-Niec et al., "Protein glycosylation in pmt mutants of *Saccharomyces cerevisiae*. Influence of heterologously expressed cellobiohydrolase II of Trichoderma reesei and elevated levels of GDP-mannose and cis-prenyltransferase activity", Biochim Biophys Ada, vol. 1770, No. 5, 2007, pp. 774-780.
Górka-Niec et al., "Disruption of Trichoderma reesei gene encoding protein O-mannosyltransferase I results in a decrease of the enzyme activity and alteration of cell wall composition", Ada Biochim, vol. 55, No. 2, 2008, pp. 251-259.
Górka-Niec et al., "Integration of additional copies of Trichaderma reesei gene encoding protein mannosyttransferase I results in a decrease of the enzyme activity and alteration of cell wall composition", Fungal Biol, vol. 115, 2011, pp. 124-132. doi: 10.1016/j.funbio.2010.11.001.
Goto et al., "Protein O-mannosyltransferases B and C support hyphal development and differentiation in Aspergillus hidulans", Eukaryot Cell., American Society for Microbiology,doi:10.1128/Ec. 00371-08, vol. 8, No. 10, Oct. 2009, pp. 1465-1474.
Kruszewska el al., "Alterations in protein secretion caused by metabolic engineering of glycosylation pathways in fungi", Acta Biochimica Polonica, vol. 55, No. 3, 2008, pp. 447-456.
Mouyna et al., "Members of protein O-mannosyltransferase family in Aspergillus fumigatus differentially affect growth, morphogenesis and viability", Molecular Microbicl, doi: 10.1111/j.1365-2958. 2010.07164.x, vol. 76, No. 5,Jun. 2010, pp. 1205-1221.
Oka et al., "Protein O-mannosyltransferase A of Aspergillus awamori is involved in O-mannosylation of glucoamylaser", Microbiology, vol. 151, No. 11, 2005, pp. 3657-3667.
Ruabhia et al., "Virulence of the fungal pathogen *Candida albicans* requires the five isoforms of protein mannosyltransferases", Infection and Immunity, vol. 73, No. 8, Aug. 2005, pp. 4571-4580.
Weber et al., "PMT-mediated O mannosylation stabilizes an essential component of the secretory apparatus, Sec20p.n Candida albicans" , Eukaryotic Cell, vol. 3, No. 5, Oct. 2004, pp. 1164-1168.
Berka et al. (2011) Comparative genomic analysis of the thermophilic biomass-degrading fungi *Myceliophthora thermophila* and *Thielavia terrestris*. Nat Biotechnol. 29(10):922-7.
Heerikhuisen et al. Production of full length antibody chains in Chrysosporium. Poster, 9th European Conference on Fungal Genetics (Apr. 5-8, 2008) Edinburgh, UK.
Herpoël-Gimbert et al. (2008) Comparative secretome analyses of two Trichoderma reesei RUT-C30 and CL847 hypersecretory strains. Biotechnol Biofuels 1(18).
Martinez D et al. (2008) Nat. Biotechnol. 26:553-560.
Punt, P. Fungal Cell Factories. Slides for presentation held at the Fifth Annual World Congress on Industrial Biotechnology and Bioprocessing in Chicago, US, from Apr. 27-30, 2008 on Apr. 28, 2008.
Press release by Dyadic International dated Dec. 15, 2009, published at http://laboratorytalk.com/article/362097/scripps-to-reannotate-dyadic.
Verdoes JC and Burlinggame RP (2006) Maximizing Protein Expression in Filamentous Fungi. BioPharm International 19(5):40-47.
Visser H et al. (2011) Development of a mature fungal technology and production platform for industrial enzymes based on a Myceliophthora thermophila isolate, previously known as Chrysosporium lucknowense C1. Industrial Biotechnology 7(3):214-223.
Opposition document regarding European patent application EP 14734515.1 dated Feb. 20, 2020.

* cited by examiner

```
Aniger_gi145238926          IVTWDEAHFGKFGSHYLKREFYFDVHPPLGKMLVGLSGFLAGYNGSFEFK 132
Aoryzae_gi169764100         IVTWDEAHFGKFGSHYLKREFYFDVHPPLGKMLVGLSGYLAGYNGSFEFK 132
Anidulans_gi67537870        IVTWDEAHFGKFGSHYLKREFYFDVHPPLGKMLVGLSGLLAGYNGSFEFK 131
Pchrysogenum_gi255931607    IVTWDEAHFGKFGSHYLKREFYFDVHPPLGKMLVGLSGYLAGYNGSFEFK 133
Mthermophila_gi367035654    IVTWDEAHFGKFGSHYLKREFYFDVHPPAGKLLVGLSGYLAGYNGSFEFK 135
Ncrassa_gi164428088         IVTWDEAHFGKFGSHYLKREFYFDVHPPAGKLLVGLSGLLAGYNGSFEFK 140
Tvirens_gi358378327         IVTWDEAHFGKFGSYYIKHEYYFDVHPPLGKMLVGLSGVLAGYNGSFEFK 130
Tatroviride_gi358397085     IVTWDEAHFGKFGSYYIKHEYYFDVHPPLGKMLVGLSGVLAGYNGSFEFK 131
TreeseiPMT3                 IVTWDEAHFGKFGSYYIKHEYYFDVHPPLGKMLVGLSGVLAGYNGSFEFK 131
Foxysporum_gi342878828      IVTWDEAHFGKFGSYYIKHEYYFDVHPPLGKMLVGLSGVLAGYNGTFEFK 131
Gzeae_gi46109306            IVTWDEAHFGKFGSYYIKHEYYFDVHPPLGKMLVGLSGVLAGYNGTFEFK 132
Nrassa_gi85118928           SVVFDEVHFGGFASKYIKGKFFMDVHPPLAKLMITLFGWLAGFDGSFDFK 141
Mthermophila_gi367034055    SVVFDEVHFGGFATKYIKGKFFMDVHPPLAKLMITLFGWLAGFKGNFDFK 129
Tvirens_gi358385113         SVVFDEVHFGGFASKYIKGKFFMDVHPPLAKMLIALTGWLAGFDGNFDFK 127
Tatroviride_gi358393368     SVVFDEVHFGGFASKYIKGRFFMDVHPPLAKMLIALTGWLAGFDGDFDFK 131
TreeseiPMT2                 SVVFDEVHFGGFASKYIKGRFFMDVHPPLAKMLIALTGWLAGFDGNFDFK 132
Foxysporum_gi342886036      SVVFDEVHFGGFATKYIKGKFFMDVHPPLAKMLIALTGWLAGFDGSFDFK 145
Gzea_gi46130662             SVVFDEVHFGGFATKYIKGKFFMDVHPPLAKMLIALTGWLAGFDGSFDFK 142
Anidulans_gi67537182        SVVFDEVHFGGFATKYIKGRFFMDVHPPLAKLLITLAGWLAGFKGDFDFK 127
Aoryzae_gi317151146         SVVFDEVHFGGFASKYIKGRFFMDVHPPLAKLLITLAGWLAGFNGDFDFK 130
Aniger_gi145245359          SVVFDEVHFGGFATKYIKGRFFMDVHPPLAKLLITLAGWLAGFDGEFDFK 131
Pchrysogenum_gi255945045    SVVFDEVHFGGFASKYIKGKFFMDVHPPLAKLLLTLAGWLAGFDGNFDFK 129
TreeseiPMT1                 EVVFDEVHFGKFASYYLQRTYFFDVHPPFAKLLFAFVGWLVGYDGHFHFD 127
Tvirens_gi358379774         EVVFDEVHFGKFASYYLQRTYFFDVHPPFAKLLFAFVGWLVGYDGHFHFE 128
Tatroviride_gi358400594     EVVFDEVHFGKFASYYLQRTYFFDVHPPFAKLLFAFVGWLVGYDGHFHFE 127
Foxysporum_gi342879728      EVVFDEVHFGKFASYYLERTYFFDVHPPGKLLFAFVGWLVGYDGNFHFE 125
Gzeae_gi46107450            EVVFDEVHFGKFASYYLERTYFFDVHPPGKLLFAFVGWLVGYDGHFHFD 125
Mthermophila_gi367020262    EVVFDEVHFGKFASYYLERTYFFDVHPPLGKLLFAFMGWLVGYDGHFHFE 125
Ncrassa_gi164423013         EVVFDEVHFGKFASYYLERTYFFDVHPPFGKLLFAFMGWLVGYDGHFHFE 125
Anidulans_gi67522004        QVVFDEVHFGKFASYYLRRTYFFDVHPPFAKLLLAFTGWLVGYDGHFLFE 116
Aniger_gi317036343          EVVFDEVHFGKFASYYLQRTYFFDVHPPFGKLLFAFMGWLVGYDGHFLFD 115
Aoryzae_gi391865791         EVVFDEVHFGKFASYYLQRTYFFDVHPPFGKLLFAAVGWLIGYDGHFLFE 118
Pchrysogenum_gi255953619    EVVFDEVHFGKFASYYLQRTYFFDVHPPFGKLLFALMGWLVGFDGSFLFE 115
                             *.:**.***  *.:  *:.   :::******  .*::.    *  * *:.* * *.
```

Figure 6

US 10,724,013 B2

O-MANNOSYLTRANSFERASE DEFICIENT FILAMENTOUS FUNGAL CELLS AND METHODS OF USE THEREOF

RELATED APPLICATIONS

This application is a continuation of U.S. Ser. No. 14,902,492 filed on Dec. 31, 2015, which was filed under 35 U.S.C. § 371 and claims priority to International Application No. PCT/EP2014/064248 filed Jul. 3, 2014, and claims priority to EP 13175141.4 filed Jul. 4, 2013, which are hereby incorporated by reference into this disclosure in their entirety.

FIELD OF THE INVENTION

The present disclosure relates to compositions and methods useful for the production of heterologous proteins in filamentous fungal cells.

BACKGROUND

Posttranslational modification of eukaryotic proteins, particularly therapeutic proteins such as immunoglobulins, is often necessary for proper protein folding and function. Because standard prokaryotic expression systems lack the proper machinery necessary for such modifications, alternative expression systems have to be used in production of these therapeutic proteins. Even where eukaryotic proteins do not have posttranslational modifications, prokaryotic expression systems often lack necessary chaperone proteins required for proper folding. Yeast and fungi are attractive options for expressing proteins as they can be easily grown at a large scale in simple media, which allows low production costs, and yeast and fungi have posttranslational machinery and chaperones that perform similar functions as found in mammalian cells. Moreover, tools are available to manipulate the relatively simple genetic makeup of yeast and fungal cells as well as more complex eukaryotic cells such as mammalian or insect cells (De Pourcq et al., Appl Microbiol Biotechnol, 87(5):1617-31).

However, posttranslational modifications occurring in yeast and fungi may still be a concern for the production of recombinant therapeutic protein. In particular, O-mannosylation is one of the biggest hurdles to overcome in the production of biopharmaceuticals for human applications in fungi. More specifically, yeasts like *Pichia pastoris* and *Saccharomyces cerevisiae* tend to hyper-mannosylate heterologously expressed biopharmaceuticals, thereby triggering adverse effects when applied to humans.

O-mannosylation to Serine and Threonine residues includes in mammals GalNAc based oligosaccharides or GlcNAc/N-acetyllactosamine comprising O-linked mannose glycans. In fungi O-mannosylation occurs as hexose monomers or oligomers. In yeasts, there are typically several protein(/polypeptide) O-mannosyltransferases, which often function as complexes. Part of the knock-outs are harmfull, at least for cell structures and stability and not all yeast knock-outs or combinations are tolerated (for a review, see Goto 2007, *Biosci. Biotechnol. Biochem.* 71(6), 1415-1427).

There have been reports of knock-outs of yeast O-mannosyltransferase genes, aiming to reduce the O-mannosylation levels, and even multiple knock-out mutants involving two or three pmt genes in *S. cerevisiae* (WO/1994/004687). Pmt1 or pmt2 knock-out of *S. cerevisiae* reduced the level of O-mannosylation of antifreeze glycoprotein III to about 30% of the proteins and the residual mannosylated protein contains numerous mannose residues per protein, apparently also oligosaccharides (WO/2004/057007).

WO/2010/034708 reports no significant level of O-mannosylation of recombinant hydrophobin *Trichoderma* protein when expressed in pmt1 knock-out of *S. cerevisiae* host cell. Such O-mannosylation appears to be artificial yeast glycosylation of the original non-mannosylated filamentous fungal protein.

WO/2010/128143 further reports single chain antibody-albumin fusion construct in yeast *S. cerevisiae* pmt1 and/or pmt4 knock-out strains.

Pmt1, pmt2, and pmt3 single gene knock-outs, double, and triple knock-outs of *Aspergillus* species (*Aspergillus nidulans*, *Aspergillus fumigatus*, and/or *Aspergillus awamori*) are described in Goto et al, 2009 (Eukaryotic cell 2009, 8(10):1465); Mouyna et al, 2010 (Molecular Microbiology 2010, 76(5), 1205-1221); Zhou et al, 2007 (Eukaryotic cell 2007, 6(12):2260); Oka et al, 2004 (Microbiology 2004, 150, 1973-1982); Kriangkripipat et al, 2009; Fang et al, 2010 (Glycobiology, 2010, vol. 20 pp 542-552); and Oka et al, 2005 (Microbiology 2005, 151, 3657-3667).

Despite numerous reports on knock out of pmt homologues in filamentous fungi, there is no description of a filamentous fungal cell with reduced O-mannosylation and useful as a host cell for the production of recombinant glycoprotein.

In particular, Gorka-Niec et al (2008, Acta Biochimica Polonica, Vol. 55 No 2/2008, 251-259) reported the deletion of pmt1 gene in *Trichoderma reesei*. PMT1 protein showed the highest identity to Pmt4p of *S. cerevisiae* (51%) but functionally complement pmt2Δ *S. cerevisiae* mutant (Gorka-Niec et al, 2007, Biochimica et Biophysica Acta 1770, 2007, 774-780). However, the authors reported that disruption of the pmt1 gene caused a decrease of protein secretion but did not alter O- and N-glycosylation of secreted protein.

Zakrzewska et al (Curr Genet 2003 43: 11-16) further reported that *Trichoderma reesei* pmt1 gene did not functionally complement pmt4Δ *S. cerevisiae* mutant.

In fact, deletions of the PMT genes in yeasts or filamentous fungi appears to either result in no phenotype at all or lethality or severely impaired vital functions of the cells, which would not be suitable for recombinant production of heterologous proteins, especially mammalian glycoproteins. For this reason, alternative methods such as the use of pmt inhibitors have been proposed as an alternative to pmt knock out strains (WO2009/143041).

Thus, a need remains for improved filamentous fungal cells, such as *Trichoderma* fungus cells, that can stably produce heterologous proteins with no or reduced O-mannosylation, such as immunoglobulins, preferably at high levels of expression.

SUMMARY

The present invention relates to improved methods for producing proteins with no or reduced O-mannosylation in filamentous fungal expression systems, and more specifically, glycoproteins, such as antibodies or related immunoglobulins or fusion proteins which may be O-mannosylated when produced in filamentous fungal expression systems.

The present invention is based in part on the surprising discovery that filamentous fungal cells, such as *Trichoderma* cells, can be genetically modified to reduce or suppress 0-mannosylation activity, without adversely affecting viability and yield of produced glycoproteins.

Accordingly, in a first aspect, the invention relates to a PMT-deficient filamentous fungal cell comprising
a) a first mutation that reduces or eliminates an endogenous protease activity compared to a parental filamentous fungal cell which does not have said first mutation, and,
b) a second mutation in a PMT gene that reduces endogenous O-mannosyltransferase activity compared to a parental filamentous fungal cell which does not have said second mutation,
wherein said filamentous fungal cell is selected from the group consisting of *Trichoderma, Neurospora, Myceliophthora* and *Chrysosporium* cell.

In one embodiment, said PMT-deficient cell further expresses a heterologous protein containing serine and/or threonine residues. The expressed heterologous protein with serine and/or threonine residues has reduced O-mannosylation due to said mutation in said PMT gene. For example, the O-mannosylation level of the heterologous protein expressed in a PMT-deficient cell of the invention is at least 10%, 20%, 30%, 40%, 50%, 60%, 70%, 80% or at least 90% lower as compared to the O-mannosylation level of the heterologous protein when expressed in the parental filamentous fungal cell which does not have said second PMT-deficient mutation.

In another embodiment, said second mutation that reduces endogenous 0-mannosyltransferase activity is a deletion or a disruption of a PMT gene encoding an endogenous protein O-mannosyltransferase activity.

In another embodiment, said second PMT-deficient mutation in a PMT gene may be a mutation (such as a deletion or disruption) in either:
a) PMT1 gene comprising the polynucleotide of SEQ ID NO:1,
b) a functional homologous gene of PMT1 gene, which functional gene is capable of restoring parental O-mannosylation level by functional complementation when introduced into a *T. reesei* strain having a disruption in said PMT1 gene, or,
c) a polynucleotide encoding a polypeptide having at least 50%, at least 60%, at least 70%, at least 90%, or at least 95% identity with SEQ ID NO:2, said polypeptide having O-mannosyltransferase activity.

In another embodiment that may be combined with the precedent embodiments, said PMT-deficient cell has a third mutation that reduces or eliminates the level of expression of an ALG3 gene compared to the level of expression in a parental cell which does not have such third mutation. In a specific embodiment, said PMT-deficient cell further comprises a first polynucleotide encoding N-acetylglucosaminyltransferase I catalytic domain and a second polynucleotide encoding N-acetylglucosaminyltransferase II catalytic domain.

In another embodiment that may be combined with the preceding embodiments, said PMT-deficient cell further comprises one or more polynucleotides encoding a polypeptide selected from the group consisting of:
a) α1,2 mannosidase,
b) N-acetylglucosaminyltransferase I catalytic domain,
c) α mannosidase II, and
d) N-acetylglucosaminyltransferase II catalytic domain.

In another embodiment that may be combined with the preceding embodiments, said PMT-deficient cell further comprises one or more polynucleotides encoding a β1,4 galactosyltransferase and/or a fucosyltransferase.

In one specific embodiment, said PMT-deficient cell is a *Trichoderma* cell comprising at least a mutation that reduces or eliminates the protein O-mannosyltransferase activity of *Trichoderma* pmt1, and, optionally, further comprising mutations in at least one or more other PMT genes that reduces or eliminates the protein O-mannosyltransferase activity selected from the group consisting of pmt2 and pmt3.

In one embodiment that may be combined with the preceding embodiments, the PMT deficient cells comprise mutations that reduce or eliminate the activity of at least two, or at least three endogenous proteases. Typically, said cell may be a *Trichoderma* cell and may comprise mutations that reduce or eliminate the activity of
a) the three endogenous proteases pep1, tsp1 and slp1,
b) the three endogenous proteases gap1, slp1 and pep1,
c) three endogenous proteases selected from the group consisting of pep1, pep2, pep3, pep4, pep5, pep8, pep11, pep12, tsp1, slp1, slp2, slp3, slp7, gap1 and gap2,
d) three to six proteases selected from the group consisting of pep1, pep2, pep3, pep4, pep5, tsp1, slp1, slp2, slp3, gap1 and gap2, or,
e) seven to ten proteases selected from the group consisting of pep1, pep2, pep3, pep4, pep5, pep7, pep8, tsp1, slp1, slp2, slp3, slp5, slp6, slp7, slp8, tpp1, gap1 and gap2.

In one embodiment that may be combined with the precedent embodiments, the filamentous fungal cell of the invention does not comprise a deletion or disruption of an endogenous gene encoding a chaperone protein. In particular, said filamentous fungal cell of the invention expresses functional endogenous chaperone protein Protein Disulphide Isomerase (PDI).

In another aspect, the invention relates to a method for producing a protein having reduced O-mannosylation, comprising:
a) providing a PMT-deficient filamentous fungal cell, having a mutation in a PMT gene that reduces endogenous O-mannosyltransferase activity as compared to parental strain which does not have such mutation, and further comprising a polynucleotide encoding a protein with serine or threonine residue,
b) culturing said PMT-deficient filamentous fungal cell to produce said protein with reduced O-mannosylation,
wherein said filamentous fungal cell is selected from the group consisting of *Trichoderma, Neurospora, Myceliophthora* and *Chrysosporium* cell.

According to one specific embodiment of the method, said mutation in a PMT gene is a mutation, such as a deletion or disruption, in either:
a) PMT1 gene comprising the polynucleotide of SEQ ID NO:1,
b) a functional homologous gene of PMT1 gene, which gene is capable of restoring parental O-mannosylation level by functional complementation when introduced into a *T. reesei* strain having a disruption in said PMT1 gene, or,
c) a polynucleotide encoding a polypeptide having at least 50%, at least 60%, at least 70%, at least 90%, or at least 95% identity with SEQ ID NO:2, said polypeptide having protein O-mannosyltransferase activity.

In another embodiment of the method, said PMT-deficient cell is a *Trichoderma reesei* cell and said mutation is a deletion or a disruption of *T. reesei* PMT1 gene.

In other embodiments of the method, said PMT-deficient cell is a PMT-deficient cell of the invention as described above.

In a specific embodiment, said polynucleotide encoding a protein is a recombinant polynucleotide encoding a heterologous protein. Typically, said heterologous protein may be a mammalian protein selected from the group consisting of a) an immunoglobulin, such as IgG,
b) a light chain or heavy chain of an immunoglobulin,
c) a heavy chain or a light chain of an antibody,
d) a single chain antibody,
e) a camelid antibody,
f) a monomeric or multimeric single domain antibody,
g) a FAb-fragment, a FAb2-fragment, and,
h) their antigen-binding fragments.

In one embodiment of the method, that may be combined with the preceding embodiments, said polynucleotide encoding said protein further comprises a polynucleotide encoding CBH1 catalytic domain and linker as a carrier protein and/or cbh1 promoter.

In another embodiment, said polynucleotide encodes a protein with serine or threonine, which may be O-mannosylated in a PMT functional parental strain, and further comprising at least one N-glycan.

The invention also relates to a method for producing an antibody having reduced O-mannosylation, comprising:
a) providing a PMT-deficient filamentous fungal cell having
   i. a mutation that reduces endogenous protein O-mannosyltransferase activity as compared to parental strain which does not have such mutation and
   ii. a polynucleotide encoding a light chain antibody and a polynucleotide encoding a heavy chain antibody,
b) culturing the cell to produce said antibody, consisting of heavy and light chains, having reduced O-mannosylation,
wherein said filamentous fungal cell is selected from the group consisting of *Trichoderma*, *Neurospora*, *Myceliophthora* and *Chrysosporium* cell.

In a specific method for producing antibody, said PMT-deficient cell is a *Trichoderma reesei* cell and said mutation is a deletion or a disruption of *T. reesei* PMT1 gene.

In one embodiment of the method for producing antibody, at least 70%, 80%, 90%, 95%, or 100% of the produced antibody is not O-mannosylated.

The invention also relates to the protein composition or antibody composition obtainable or obtained by the methods of the invention as described above. In one embodiment, at least 70%, 80%, 90%, 95%, or 100% of the antibodies as obtained or obtainable the methods of the invention are not O-mannosylated.

In one specific embodiment, such protein (e.g. a glycoprotein) or antibody composition with reduced O-mannosylation comprises, as a major glycoform, either,
Manα3[Manα6(Manα3)Manα6]
   Manβ4GlcNAβ4GlcNAc (Man5 glycoform);
Manα6(Manα3)Manβ4GlcNAβ4GlcNAc (Man3 glycoform);
hybrid or complex type N-glycans such as glycoforms selected from the subgroup consisting of GlcNAc-Man3, G0, hybrid glycan, or GlcNAcMan5, or galactosylated derivatives, such as GalGlcNAcMan3, G1, G2; or, GalGlcNAcMan5 glycoform.

In one specific embodiment, when the core of the glycan consists of Man3, then the composition essentially lacks Man5 glycoforms.

In an embodiment that may be combined with one or more of the preceding embodiments less than 0.1%, 0.01%, 0.001% or 0% of the N-glycans and/or O-glycans of the protein composition comprises Neu5Gc and/or Galα-structure. In an embodiment that may be combined with the preceding embodiments, less than 0.1%, 0.01%, 0.001% or 0% of the N-glycans and/or O-glycans of the antibody composition comprises Neu5Gc and/or Galα-structure.

In an embodiment that may be combined with one or more of the preceding embodiments, less than 0.1%, 0.01%, 0.001%, or 0% of the N-glycan of the glycoprotein composition comprises core fucose structures. In an embodiment that may be combined with the preceding embodiments, less than 0.1%, 0.01%, 0.001%, or 0% of the N-glycan of the antibody composition comprises core fucose structures.

In an embodiment that may be combined with one or more of the preceding embodiments, less than 0.1%, 0.01%, 0.001%, or 0% of N-glycan of the glycoprotein composition comprises terminal galactose epitopes Galβ3/4GlcNAc. In an embodiment that may be combined with the preceding embodiments, less than 0.1%, 0.01%, 0.001%, or 0% of the N-glycan of the antibody composition comprises terminal galactose epitopes Galβ3/4GlcNAc.

In an embodiment that may be combined with one or more of the preceding embodiments, less than 1.0%, 0.5%, 0.1%, 0.01%, 0.001%, or 0% of the glycoprotein composition comprises glycation structures. In an embodiment that may be combined with the preceding embodiments, less than 1.0%, 0.5%, 0.1%, 0.01%, 0.001%, or 0% of the antibody composition comprises glycation structures.

In another embodiment that may be combined with one or more of the preceding embodiments, the glycoprotein composition, such as an antibody is devoid of one, two, three, four, five, or six of the structures selected from the group of Neu5Gc, terminal Galα3Galβ4GlcNAc, terminal Galβ4GlcNAc, terminal Galβ3GlcNAc, core linked fucose and glycation structures.

The invention also relates to a method of reducing O-mannosylation level of a recombinant glycoprotein composition produced in a filamentous fungal cell, for example, *Trichoderma* cell, typically, *Trichoderma reesei*, said method consisting of using a filamentous fungal cell having a mutation in a PMT gene wherein said PMT gene is either:
   i. PMT1 gene comprising the polynucleotide of SEQ ID NO:1,
   ii. a functional homologous gene of PMT1 gene, which gene is capable of restoring parental O-mannosylation level by functional complementation when introduced into a *T. reesei* strain having a disruption in said PMT1 gene, or,
   iii. a polynucleotide encoding a polypeptide having at least 50%, at least 60%, at least 70%, at least 90%, or at least 95% identity with SEQ ID NO:2, said polypeptide having protein O-mannosyltransferase activity.

DESCRIPTION OF THE FIGURES

FIG. 6 depicts a partial sequence alignment of the results of the PMT BLAST searches.

DETAILED DESCRIPTION

Definitions

Figure 1:
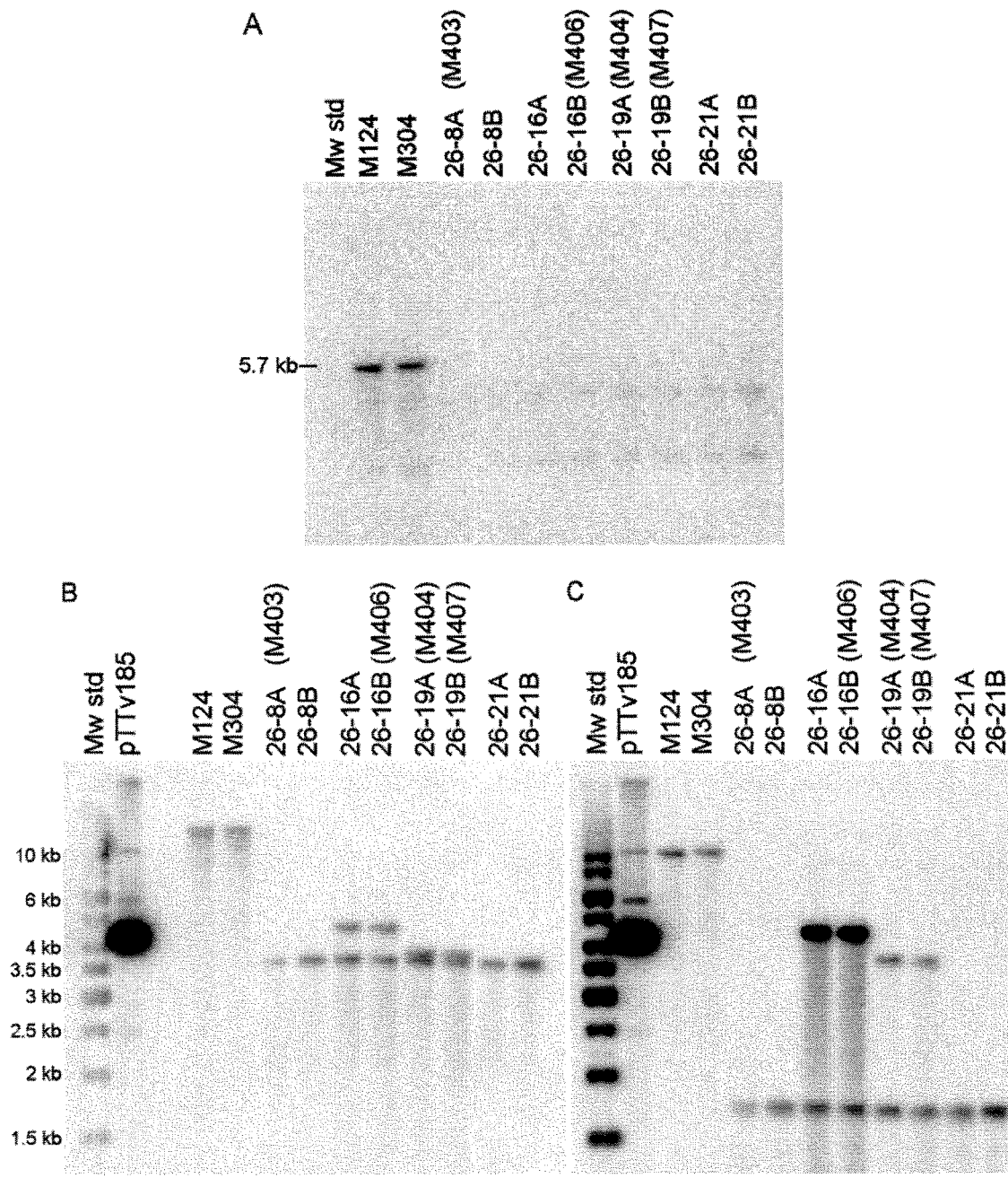
FIG. 1 depicts results for Southern analyses of *Trichoderma reesei* pmt1 deletion strains expressing antibody MAB01. A) A 5.7 kb signal is expected from parental strains M124 and M304 with pmt1 ORF probe after SpeI+XbaI digestion. No signal is expected from pure pmt1 deletion strains. B) A 3.5 kb signal is expected for pmt1 5'flank probe from deletion strains after SpeI+AscI digestion. C) A 1.7 kb signal is expected for pmt1 3'flank probe from deletion strains after AscI+XbaI digestions. AscI does not cut intact pmt1 locus in close distance, therefore signals of over 16 kb (B) and 10 kb (C) are expected from parental strains M124 or M304. A 4.1 kb signal is expected from PmeI digested plasmid pTTv185 used as a control in hybridisations with both flank probes (B, C).

As used herein, an "expression system" or a "host cell" refers to the cell that is genetically modified to enable the transcription, translation and proper folding of a polypeptide or a protein of interest, typically of mammalian protein.

The term "polynucleotide" or "oligonucleotide" or "nucleic acid" as used herein typically refers to a polymer of at least two nucleotides joined together by a phosphodiester bond and may consist of either ribonucleotides or deoxynucleotides or their derivatives that can be introduced into a host cell for genetic modification of such host cell. For example, a polynucleotide may encode a coding sequence of a protein, and/or comprise control or regulatory sequences of a coding sequence of a protein, such as enhancer or promoter sequences or terminator. A polynucleotide may for example comprise native coding sequence of a gene or their fragments, or variant sequences that have been optimized for optimal gene expression in a specific host cell (for example to take into account codon bias).

As used herein, the term, "optimized" with reference to a polynucleotide means that a polynucleotide has been altered to encode an amino acid sequence using codons that are preferred in the production cell or organism, for example, a filamentous fungal cell such as a *Trichoderma* cell. Heterologous nucleotide sequences that are transfected in a host cell are typically optimized to retain completely or as much as possible the amino acid sequence originally encoded by the original (not optimized) nucleotide sequence. The optimized sequences herein have been engineered to have codons that are preferred in the corresponding production cell or organism, for example the filamentous fungal cell.

The amino acid sequences encoded by optimized nucleotide sequences may also be referred to as optimized.

As used herein, a "peptide" or a "polypeptide" is an amino acid sequence including a plurality of consecutive polymerized amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide or a combination of more than one peptide or polypeptide assembled together by covalent or non-covalent bonds. Unless specified, the term "protein" may encompass one or more amino acid sequences with their post-translation modifications, and in particular with either O-mannosylation or N-glycan modifications.

As used herein, the term "glycoprotein" refers to a protein which comprises at least one N-linked glycan attached to at least one asparagine residue of a protein, or at least one mannose attached to at least one serine or threonine resulting in O-mannosylation.

The terms "O-mannosylation" or "O-mannosyltransferase activity" are used herein to refer to the covalent linkage of at least one mannose to one specific amino acid via one oxygen (typically from serine or threonine). O-mannosyltransferase protein typically adds mannose to hydroxyl groups such as hydroxyl of serine or threonine residues.

In particular, O-mannosyltransferase activity may refer to the specificity of 0-mannosyltransferase activity of fungal PMT gene encoding enzymes, and more specifically with the same specificity of *T. reesei* PMT1.

As used herein, "glycan" refers to an oligosaccharide chain that can be linked to a carrier such as an amino acid, peptide, polypeptide, lipid or a reducing end conjugate. In certain embodiments, the invention relates to N-linked glycans ("N-glycan") conjugated to a polypeptide N-glycosylation site such as -Asn-Xaa-Ser/Thr- by N-linkage to side-chain amide nitrogen of asparagine residue (Asn), where Xaa is any amino acid residue except Pro. The invention may further relate to glycans as part of dolichol-phospho-oligosaccharide (Dol-P-P-OS) precursor lipid structures, which are precursors of N-linked glycans in the endoplasmic reticulum of eukaryotic cells. The precursor oligosaccharides are linked from their reducing end to two phosphate residues on the dolichol lipid. For example, α3-mannosyltransferase Alg3 modifies the Dol-P-P-oligosaccharide precursor of N-glycans. Generally, the glycan structures described herein are terminal glycan structures, where the non-reducing residues are not modified by other monosaccharide residue or residues.

As used throughout the present disclosure, glycolipid and carbohydrate nomenclature is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 29). It is assumed that Gal (galactose), Glc (glucose), GlcNAc (N-acetylglucosamine), GalNAc (N-acetylgalactosamine), Man (mannose), and Neu5Ac are of the D-configuration, Fuc of the L-configuration, and all the monosaccharide units in the pyranose form (D-Galp, D-Glcp, D-GlcpNAc, D-GalpNAc, D-Manp, L-Fucp, D-Neup5Ac). The amine group is as defined for natural galactose and glucosamines on the 2-position of GalNAc or GlcNAc. Glycosidic linkages are shown partly in shorter and partly in longer nomenclature, the linkages of the sialic acid SA/Neu5X-residues α3 and α6 mean the same as α2-3 and α2-6, respectively, and for hexose monosaccharide residues α1-3, α1-6, ρ1-2, ρ1-3, β1-4, and ρ1-6 can be shortened as α3, α6, β2, β3, β4, and β6, respectively. Lactosamine refers to type II N-acetyllactosamine, Galβ4GlcNAc, and/or type I N-acetyllactosamine. Galβ3GlcNAc and sialic acid (SA) refer to N-acetylneuraminic acid (Neu5Ac), N-glycolylneuraminic acid (Neu5Gc), or any other natural sialic acid including derivatives of Neu5X. Sialic acid is referred to as NeuNX or Neu5X, where preferably X is Ac or Gc. Occasionally Neu5Ac/Gc/X may be referred to as NeuNAc/NeuNGc/NeuNX.

The sugars typically constituting N-glycans found in mammalian glycoprotein, include, without limitation, N-acetylglucosamine (abbreviated hereafter as "GlcNAc"), mannose (abbreviated hereafter as "Man"), glucose (abbreviated hereafter as "Glc"), galactose (abbreviated hereafter as "Gal"), and sialic acid (abbreviated hereafter as "Neu5Ac"). N-glycans share a common pentasaccharide referred to as the "core" structure $Man_3GlcNAc_2$ (Manα6 (Manα3)Manβ4GlcNAβ4GlcNAc, referred to as Man3). In some embodiments Man3 glycan or its derivative Manα6 (GlcNAcβ2Manα3)Manβ4GlcNAβ4GlcNAc is the major glycoform. When a fucose is attached to the core structure, preferably α6-linked to reducing end GlcNAc, the N-glycan or the core of N-glycan, may be represented as Man$_3$GlcNAc$_2$(Fuc). In an embodiment the major N-glycan is Manα3[Manα6(Manα3)Manα6] Manβ4GlcNAβ4GlcNAc (Man5).

Preferred hybrid type N-glycans comprise GlcNAcβ2Manα3[Manα6(Manα3)Manα6] Manβ4GlcNAβ4GlcNAc ("GlcNAcMan5"), or b4-galactosylated derivatives thereof Galβ4GlcNAcMan3, G1, G2, or GalGlcNAcMan5 glycoform.

A "complex N-glycan" refers to a N-glycan which has at least one GlcNAc residue, optionally by GlcNAcβ2-residue, on terminal 1,3 mannose arm of the core structure and at least one GlcNAc residue, optionally by GlcNAcβ2-residue, on terminal 1,6 mannose arm of the core structure.

Such complex N-glycans include, without limitation, GlcNAc$_2$Man$_3$GlcNAc$_2$ (also referred as G0 glycoform), Gal$_1$GlcNAc$_2$Man$_3$GlcNAc$_2$ (also referred as G1 glycoform), and Gal$_2$GlcNAc$_2$Man$_3$GlcNAc$_2$ (also referred as G2 glycoform), and their core fucosylated glycoforms FG0, FG1 and FG2, respectively GlcNAc$_2$Man$_3$GlcNAc$_2$(Fuc), Gal$_1$GlcNAc$_2$Man$_3$GlcNAc$_2$(Fuc), and Gal$_2$GlcNAc$_2$Man$_3$GlcNAc$_2$(Fuc).

"Increased" or "Reduced activity of an endogenous enzyme": The filamentous fungal cell may have increased or reduced levels of activity of various endogenous enzymes. A reduced level of activity may be provided by inhibiting the activity of the endogenous enzyme with an inhibitor, an antibody, or the like. In certain embodiments, the filamentous fungal cell is genetically modified in ways to increase or reduce activity of various endogenous enzymes. "Genetically modified" refers to any recombinant DNA or RNA method used to create a prokaryotic or eukaryotic host cell that expresses a polypeptide at elevated levels, at lowered levels, or in a mutated form. In other words, the host cell has been transfected, transformed, or transduced with a recombinant polynucleotide molecule, and thereby been altered so as to cause the cell to alter expression of a desired protein.

"Genetic modifications" which result in a decrease or deficiency in gene expression, in the function of the gene, or in the function of the gene product (i.e., the protein encoded by the gene) can be referred to as inactivation (complete or partial), knock-out, deletion, disruption, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete (disruption) or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action of proteins discussed herein generally refers to any genetic modification in the host cell in question, which results in decreased expression and/or functionality (biological activity) of the proteins and includes decreased activity of the proteins (e.g., decreased catalysis), increased inhibition or degradation of the proteins as well as a reduction or elimination of expression of the proteins. For example, the action or activity of a protein can be decreased by blocking or reducing the production of the protein, reducing protein action, or inhibiting the action of the protein. Combinations of some of these modifications are also possible. Blocking or reducing the production of a protein can include placing the gene encoding the protein under the control of a promoter that requires the presence of an inducing compound in the growth medium. By establishing conditions such that the inducer becomes depleted from the medium, the expression of the gene encoding the protein (and therefore, of protein synthesis) could be turned off. Blocking or reducing the action of a protein could also include using an excision technology approach similar to that described in U.S. Pat. No. 4,743, 546. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In general, according to the present invention, an increase or a decrease in a given characteristic of a mutant or modified protein (e.g., enzyme activity) is made with reference to the same characteristic of a parent (i.e., normal, not modified) protein that is derived from the same organism (from the same source or parent sequence), which is measured or established under the same or equivalent conditions. Similarly, an increase or decrease in a characteristic of a genetically modified host cell (e.g., expression and/or biological activity of a protein, or production of a product) is made with reference to the same characteristic of a wild-type host cell of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the host cell is measured, as well as the type of assay used, the host cell that is evaluated, etc. As discussed above, equivalent conditions are conditions (e.g., culture conditions) which are similar, but not necessarily identical (e.g., some conservative changes in conditions can be tolerated), and which do not substantially change the effect on cell growth or enzyme expression or biological activity as compared to a comparison made under the same conditions.

Preferably, a genetically modified host cell that has a genetic modification that increases or decreases (reduces) the activity of a given protein (e.g., an O-mannosyltransferase or protease) has an increase or decrease, respectively, in the activity or action (e.g., expression, production and/or biological activity) of the protein, as compared to the activity of the protein in a parent host cell (which does not have such genetic modification), of at least about 5%, and more preferably at least about 10%, 15%, 20%, 25%, 30%, 35%, 40%, 45%, 50%, 55 60%, 65%, 70%, 75 80%, 85 90%, 95%, or any percentage, in whole integers between 5% and 100% (e.g., 6%, 7%, 8%, etc.).

In another aspect of the invention, a genetically modified host cell that has a genetic modification that increases or decreases (reduces) the activity of a given protein (e.g., an O-mannosyltransferase or protease) has an increase or decrease, respectively, in the activity or action (e.g., expression, production and/or biological activity) of the protein, as compared to the activity of the wild-type protein in a parent host cell, of at least about 2-fold, and more preferably at least about 5-fold, 10-fold, 20-fold, 30-fold, 40-fold, 50-fold, 75-fold, 100-fold, 125-fold, 150-fold, or any whole integer increment starting from at least about 2-fold (e.g., 3-fold, 4-fold, 5-fold, 6-fold, etc.).

As used herein, the terms "identical" or percent "identity," in the context of two or more nucleic acid or amino acid sequences, refers to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8): 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. The BLASTN program (for nucleotide sequences) uses as defaults a wordlength (W) of 11, an expectation (E) or 10, M=5, N=-4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22): 10915-10919] alignments (B) of 50, expectation (E) of 10, M=5, N=-4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Functional variant" or "functional homologous gene" as used herein refers to a coding sequence or a protein having sequence similarity with a reference sequence, typically, at least 30%, 40%, 50%, 60%, 70%, 80%, 90% or 95% identity with the reference coding sequence or protein, and retaining substantially the same function as said reference coding sequence or protein. A functional variant may retain the same function but with reduced or increased activity. Functional variants include natural variants, for example, homologs from different species or artificial variants, resulting from the introduction of a mutation in the coding sequence. Functional variant may be a variant with only conservatively modified mutations.

"Conservatively modified mutations" as used herein include individual substitutions, deletions or additions to an encoded amino acid sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Filamentous Fungal Cells

As used herein, "filamentous fungal cells" include cells from all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). Filamentous fungal cells are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Preferably, the filamentous fungal cell is not adversely affected by the transduction of the necessary nucleic acid sequences, the subsequent expression of the proteins (e.g., mammalian proteins), or the resulting intermediates. General methods to disrupt genes of and cultivate filamentous fungal cells are disclosed, for example, for *Penicillium*, in Kopke et al. (2010) Appl Environ Microbiol. 76(14):4664-74. doi: 10.1128/AEM.00670-10, for *Aspergillus*, in Maruyama and Kitamoto (2011), Methods in Molecular Biology, vol. 765, DOI10.1007/978-1-61779-197-0_27; for *Neurospora*, in Collopy et al. (2010) Methods Mol Biol. 2010; 638:33-40. doi: 10.1007/978-1-60761-611-5_3; and for *Myceliophthora* or *Chrysosporium* PCT/NL2010/000045 and PCT/EP98/06496.

Examples of suitable filamentous fungal cells include, without limitation, cells from an *Acremonium, Aspergillus, Fusarium, Humicola, Mucor, Myceliophthora, Neurospora, Penicillium, Scytalidium, Thielavia, Tolypocladium*, or *Trichoderma/Hypocrea* strain.

In certain embodiments, the filamentous fungal cell is from a *Trichoderma* sp., *Acremonium, Aspergillus, Aureobasidium, Cryptococcus, Chrysosporium, Chrysosporium lucknowense, Filibasidium, Fusarium, Gibberella, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia*, or *Tolypocladium* strain.

In some embodiments, the filamentous fungal cell is a *Myceliophthora* or *Chrysosporium, Neurospora* or *Trichoderma* strain.

*Aspergillus* fungal cells of the present disclosure may include, without limitation, *Aspergillus aculeatus, Aspergillus awamori, Aspergillus clavatus, Aspergillus flavus, Aspergillus foetidus, Aspergillus fumigatus, Aspergillus japonicus, Aspergillus nidulans, Aspergillus niger, Aspergillus oryzae*, or *Aspergillus terreus*.

*Neurospora* fungal cells of the present disclosure may include, without limitation, *Neurospora crassa*.

*Myceliophthora* fungal cells of the present disclosure may include, without limitation, *Myceliophthora thermophila*.

In a preferred embodiment, the filamentous fungal cell is a *Trichoderma* fungal cell. *Trichoderma* fungal cells of the present disclosure may be derived from a wild-type *Trichoderma* strain or a mutant thereof. Examples of suitable *Trichoderma* fungal cells include, without limitation, *Trichoderma harzianum, Trichoderma koningii, Trichoderma longibrachiatum, Trichoderma reesei, Trichoderma atroviride, Trichoderma virens, Trichoderma viride*; and alternative sexual form thereof (i.e., *Hypocrea*).

In a more preferred embodiment, the filamentous fungal cell is a *Trichoderma reesei*, and for example, strains derived from ATCC 13631 (QM 6a), ATCC 24449 (radiation mutant 207 of QM 6a), ATCC 26921 (QM 9414; mutant of ATCC 24449), VTT-D-00775 (Selinheimo et al., FEBS J., 2006, 273: 4322-4335), Rut-C30 (ATCC 56765), RL-P37 (NRRL 15709) or *T. harzianum* isolate T3 (Wolffhechel, H., 1989).

The invention described herein relates to a PMT deficient filamentous fungal cell, for example selected from *Trichoderma, Neurospora, Myceliophthora* or a *Chrysosporium* cells, such as *Trichoderma reesei* fungal cell, comprising:
  a. at least a first mutation that reduces or eliminates an endogenous protease activity compared to the parental filamentous fungal cell which does not have said first mutation (i.e. a protease-deficient mutation), and,
  b. at least a second mutation in a PMT gene that reduces or eliminates an endogenous O-mannosyltransferase activity compared to a parental filamentous fungal cell which does not have said second mutation (i.e. a PMT-deficient mutation).

Proteases with Reduced Activity

It has been found that reducing protease activity enables to increase substantially the production of heterologous mammalian protein. Indeed, such proteases found in filamentous fungal cells that express a heterologous protein normally catalyse significant degradation of the expressed recombinant protein. Thus, by reducing the activity of proteases in filamentous fungal cells that express a heterologous protein, the stability of the expressed protein is increased, resulting in an increased level of production of the protein, and in some circumstances, improved quality of the produced protein (e.g., full-length instead of degraded).

Proteases include, without limitation, aspartic proteases, trypsin-like serine proteases, subtilisin proteases, glutamic proteases, and sedolisin proteases. Such proteases may be identified and isolated from filamentous fungal cells and tested to determine whether reduction in their activity affects the production of a recombinant polypeptide from the filamentous fungal cell. Methods for identifying and isolating proteases are well known in the art, and include, without limitation, affinity chromatography, zymogram assays, and gel electrophoresis. An identified protease may then be tested by deleting the gene encoding the identified protease from a filamentous fungal cell that expresses a recombinant polypeptide, such a heterologous or mammalian polypeptide, and determining whether the deletion results in a decrease in total protease activity of the cell, and an increase in the level of production of the expressed recombinant polypeptide. Methods for deleting genes, measuring total protease activity, and measuring levels of produced protein are well known in the art and include the methods described herein.

Aspartic Proteases

Aspartic proteases are enzymes that use an aspartate residue for hydrolysis of the peptide bonds in polypeptides and proteins. Typically, aspartic proteases contain two highly-conserved aspartate residues in their active site which are optimally active at acidic pH. Aspartic proteases from eukaryotic organisms such as *Trichoderma* fungi include pepsins, cathepsins, and renins. Such aspartic proteases have a two-domain structure, which is thought to arise from ancestral gene duplication. Consistent with such a duplication event, the overall fold of each domain is similar, though the sequences of the two domains have begun to diverge. Each domain contributes one of the catalytic aspartate residues. The active site is in a cleft formed by the two domains of the aspartic proteases. Eukaryotic aspartic proteases further include conserved disulfide bridges, which can assist in identification of the polypeptides as being aspartic acid proteases.

Nine aspartic proteases have been identified in *Trichoderma* fungal cells: pep1 (tre74156); pep2 (tre53961); pep3 (tre121133); pep4 (tre77579), pep5 (tre81004), and pep7 (tre58669), pep8 (tre122076), pep11 (121306), and pep12 (tre119876).

Examples of suitable aspartic proteases include, without limitation, *Trichoderma reesei* pep1 (SEQ ID NO: 22), *Trichoderma reesei* pep2 (SEQ ID NO: 18), *Trichoderma reesei* pep3 (SEQ ID NO: 19); *Trichoderma reesei* pep4 (SEQ ID NO: 20), *Trichoderma reesei* pep5 (SEQ ID NO: 21) and *Trichoderma reesei* pep7 (SEQ ID NO:23), *Trichoderma reesei* EGR48424 pep8 (SEQ ID NO:134), *Trichoderma reesei* EGR49498 pep11 (SEQ ID NO:135), *Trichoderma reesei* EGR52517 pep12 (SEQ ID NO:35), and homologs thereof. Examples of homologs of pep1, pep2, pep3, pep4, pep5, pep7, pep8, pep11 and pep12 proteases identified in other organisms are also described in PCT/EP/2013/050186, the content of which being incorporated by reference.

Trypsin-Like Serine Proteases

Trypsin-like serine proteases are enzymes with substrate specificity similar to that of trypsin. Trypsin-like serine proteases use a serine residue for hydrolysis of the peptide bonds in polypeptides and proteins. Typically, trypsin-like serine proteases cleave peptide bonds following a positively-charged amino acid residue. Trypsin-like serine proteases from eukaryotic organisms such as *Trichoderma* fungi include trypsin 1, trypsin 2, and mesotrypsin. Such trypsin-like serine proteases generally contain a catalytic triad of three amino acid residues (such as histidine, aspartate, and serine) that form a charge relay that serves to make the active site serine nucleophilic. Eukaryotic trypsin-like serine proteases further include an "oxyanion hole" formed by the backbone amide hydrogen atoms of glycine and serine, which can assist in identification of the polypeptides as being trypsin-like serine proteases.

One trypsin-like serine protease has been identified in *Trichoderma* fungal cells: tsp1 (tre73897). As discussed in PCT/EP/2013/050186, tsp1 has been demonstrated to have a significant impact on expression of recombinant glycoproteins, such as immunoglobulins.

Examples of suitable tsp1 proteases include, without limitation, *Trichoderma reesei* tsp1 (SEQ ID NO: 24) and homologs thereof. Examples of homologs of tsp1 proteases identified in other organisms are described in PCT/EP/2013/050186.

Subtilisin Proteases

Subtilisin proteases are enzymes with substrate specificity similar to that of subtilisin. Subtilisin proteases use a serine residue for hydrolysis of the peptide bonds in polypeptides and proteins. Generally, subtilisin proteases are serine proteases that contain a catalytic triad of the three amino acids aspartate, histidine, and serine. The arrangement of these catalytic residues is shared with the prototypical subtilisin from *Bacillus licheniformis*. Subtilisin proteases from eukaryotic organisms such as *Trichoderma* fungi include furin, MBTPS1, and TPP2. Eukaryotic trypsin-like serine proteases further include an aspartic acid residue in the oxyanion hole.

Seven subtilisin proteases have been identified in *Trichoderma* fungal cells: slp1 (tre51365); slp2 (tre123244); slp3 (tre123234); slp5 (tre64719), slp6 (tre121495), slp7 (tre123865), and slp8 (tre58698). Subtilisin protease slp7 resembles also sedolisin protease tpp1.

Examples of suitable slp proteases include, without limitation, *Trichoderma reesei* slp1 (SEQ ID NO: 25), slp2 (SEQ ID NO: 26); slp3 (SEQ ID NO: 27); slp5 (SEQ ID NO: 28), slp6 (SEQ ID NO: 29), slp7 (SEQ ID NO: 30), and slp8 (SEQ ID NO: 31), and homologs thereof. Examples of homologs of slp proteases identified in other organisms are described in in PCT/EP/2013/050186.

Glutamic Proteases

Glutamic proteases are enzymes that hydrolyse the peptide bonds in polypeptides and proteins. Glutamic proteases are insensitive to pepstatin A, and so are sometimes referred to as pepstatin insensitive acid proteases. While glutamic proteases were previously grouped with the aspartic proteases and often jointly referred to as acid proteases, it has been recently found that glutamic proteases have very different active site residues than aspartic proteases.

Two glutamic proteases have been identified in *Trichoderma* fungal cells: gap1 (tre69555) and gap2 (tre106661).

Examples of suitable gap proteases include, without limitation, *Trichoderma reesei* gap1 (SEQ ID NO: 32), *Trichoderma reesei* gap2 (SEQ ID NO: 33), and homologs thereof. Examples of homologs of gap proteases identified in other organisms are described in PCT/EP/2013/050186.

Sedolisin Proteases and Homologs of Proteases

Sedolisin proteases are enzymes that use a serine residue for hydrolysis of the peptide bonds in polypeptides and proteins. Sedolisin proteases generally contain a unique catalytic triad of serine, glutamate, and aspartate. Sedolisin proteases also contain an aspartate residue in the oxyanion hole. Sedolisin proteases from eukaryotic organisms such as *Trichoderma* fungi include tripeptidyl peptidase.

Examples of suitable tpp1 proteases include, without limitation, *Trichoderma reesei* tpp1 tre82623 (SEQ ID NO: 34) and homologs thereof. Examples of homologs of tpp1 proteases identified in other organisms are described in PCT/EP/2013/050186.

As used in reference to protease, the term "homolog" refers to a protein which has protease activity and exhibit sequence similarity with a known (reference) protease sequence. Homologs may be identified by any method known in the art, preferably, by using the BLAST tool to compare a reference sequence to a single second sequence or fragment of a sequence or to a database of sequences. As described in the "Definitions" section, BLAST will compare sequences based upon percent identity and similarity.

Preferably, a homologous protease has at least 30% identity with (optionally 30%, 40%, 45%, 50%, 55%, 60%, 65%, 70%, 75%, 80%, 85%, 90%, 95%, 99% or 100% identity over a specified region, or, when not specified, over the entire sequence), when compared to one of the protease sequences listed above, including *T. reesei* pep1, pep2, pep3, pep4, pep5, pep7, pep8, pep11, pep12, tsp1, slp1, slp2, slp3, slp5, slp6, slp7, slp8, tpp1, gap1 and gap2. Corresponding homologous proteases from *N. crassa* and *M. thermophila* are shown in SEQ ID NO: 136-169.

Reducing the Activity of Proteases in the Filamentous Fungal Cell of the Invention The filamentous fungal cells according to the invention have reduced activity of at least one endogenous protease, typically 2, 3, 4, 5 or more, in order to improve the stability and production of the protein with reduced O-mannosylation in said filamentous fungal cell, preferably in a PMT-deficient *Trichoderma* cell.

The activity of proteases found in filamentous fungal cells can be reduced by any method known to those of skill in the art. In some embodiments reduced activity of proteases is achieved by reducing the expression of the protease, for example, by promoter modification or RNAi.

In further embodiments, the reduced or eliminated expression of the proteases is the result of anti-sense polynucleotides or RNAi constructs that are specific for each of the genes encoding each of the proteases. In one embodiment, an RNAi construct is specific for a gene encoding an aspartic protease such as a pep-type protease, a trypsin-like serine proteases such as a tsp1, a glutamic protease such as a gap-type protease, a subtilisin protease such as a slp-type protease, or a sedolisin protease such as a tpp1 or a slp7 protease. In one embodiment, an RNAi construct is specific for the gene encoding a slp-type protease. In one embodiment, an RNAi construct is specific for the gene encoding slp2, slp3, slp5 or slp6. In one embodiment, an RNAi construct is specific for two or more proteases. In one embodiment, two or more proteases are any one of the pep-type proteases, any one of the trypsin-like serine proteasess, any one of the slp-type proteases, any one of the gap-type proteases and/or any one of the sedolisin proteases. In one embodiment, two or more proteases are slp2, slp3, slp5 and/or slp6. In one embodiment, RNAi construct comprises any one of the following nucleic acid sequences (see also PCT/EP/2013/050186).

| RNAi Target sequence |
|---|
| GCACACTTTCAAGATTGGC (SEQ ID NO: 15) |
| GTACGGTGTTGCCAAGAAG (SEQ ID NO: 16) |
| GTTGAGTACATCGAGCGCGACAGCATTGTGCACACCATGCTTCCCCTCGA<br>GTCCAAGGACAGCATCATCGTTGAGGACTCGTGCAACGGCGAGACGGAGA<br>AGCAGGCTCCCTGGGGTCTTGCCCGTATCTCTCACCGAGAGACGCTCAAC<br>TTTGGCTCCTTCAACAAGTACCTCTACACCGCTGATGGTGGTGAGGGTGT<br>TGATGCCTATGTCATTGACACCGGCACCAACATCGAGCACGTCGACTTTG<br>AGGGTCGTGCCAAGTGGGGCAAGACCATCCCTGCCGGCGATGAGGACGAG<br>GACGGCAACGGCCACGGCACTCACTGCTCTGGTACCGTTGCTGGTAAGAA<br>GTACGGTGTTGCCAAGAAGGCCCACGTCTACGCCGTCAAGGTGCTCCGAT<br>CCAACGGATCCGGCACCATGTCTGACGTCGTCAAGGGCGTCGAGTACG<br>(SEQ ID NO: 17) |

In other embodiments, reduced activity of proteases is achieved by modifying the gene encoding the protease. Examples of such modifications include, without limitation, a mutation, such as a deletion or disruption of the gene encoding said endogenous protease activity.

Accordingly, the invention relates to a filamentous fungal cell, such as a PMT-deficient *Trichoderma* cell, which has a first mutation that reduces or eliminates at least one endogenous protease activity compared to a parental filamentous fungal cell which does not have such protease deficient mutation, said filamentous fungal cell further comprising at least a second mutation in a PMT gene that reduces endogenous protein O-mannosyltransferase activity compared to a parental *Trichoderma* cell which does not have said second PMT-deficient mutation.

Deletion or disruption mutation includes without limitation knock-out mutation, a truncation mutation, a point mutation, a missense mutation, a substitution mutation, a frameshift mutation, an insertion mutation, a duplication mutation, an amplification mutation, a translocation mutation, or an inversion mutation, and that results in a reduction in the corresponding protease activity. Methods of generating at least one mutation in a protease encoding gene of interest are well known in the art and include, without limitation, random mutagenesis and screening, site-directed mutagenesis, PCR mutagenesis, insertional mutagenesis, chemical mutagenesis, and irradiation.

In certain embodiments, a portion of the protease encoding gene is modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, without limitation, a leader sequence, a propeptide sequence, a signal sequence, a transcription terminator, and a transcriptional activator.

Protease encoding genes that are present in filamentous fungal cells may also be modified by utilizing gene deletion techniques to eliminate or reduce expression of the gene. Gene deletion techniques enable the partial or complete removal of the gene thereby eliminating their expression. In such methods, deletion of the gene may be accomplished by homologous recombination using a plasmid that has been constructed to contiguously contain the 5' and 3' regions flanking the gene.

The protease encoding genes that are present in filamentous fungal cells may also be modified by introducing, substituting, and/or removing one or more nucleotides in the gene, or a control sequence thereof required for the transcription or translation of the gene. For example, nucleotides may be inserted or removed for the introduction of a stop codon, the removal of the start codon, or a frame-shift of the open reading frame. Such a modification may be accomplished by methods known in the art, including without limitation, site-directed mutagenesis and peR generated mutagenesis (see, for example, Botstein and Shortie, 1985, Science 229: 4719; Lo et al., 1985, Proceedings of the National Academy of Sciences USA 81: 2285; Higuchi et al., 1988, Nucleic Acids Research 16: 7351; Shimada, 1996, Meth. Mol. Bioi. 57: 157; Ho et al., 1989, Gene 77: 61; Horton et al., 1989, Gene 77: 61; and Sarkar and Sommer, 1990, BioTechniques 8: 404).

Additionally, protease encoding genes that are present in filamentous fungal cells may be modified by gene disruption techniques by inserting into the gene a disruptive nucleic acid construct containing a nucleic acid fragment homologous to the gene that will create a duplication of the region of homology and incorporate construct nucleic acid between the duplicated regions. Such a gene disruption can eliminate gene expression if the inserted construct separates the promoter of the gene from the coding region or interrupts the coding sequence such that a nonfunctional gene product results. A disrupting construct may be simply a selectable marker gene accompanied by 5' and 3' regions homologous to the gene. The selectable marker enables identification of transformants containing the disrupted gene.

Protease encoding genes that are present in filamentous fungal cells may also be modified by the process of gene conversion (see, for example, Iglesias and Trautner, 1983, Molecular General Genetics 189:5 73-76). For example, in the gene conversion a nucleotide sequence corresponding to the gene is mutagenized in vitro to produce a defective nucleotide sequence, which is then transformed into a *Trichoderma* strain to produce a defective gene. By homologous recombination, the defective nucleotide sequence replaces the endogenous gene. It may be desirable that the defective nucleotide sequence also contains a marker for selection of transformants containing the defective gene.

Protease encoding genes of the present disclosure that are present in filamentous fungal cells that express a recombinant polypeptide may also be modified by established anti-sense techniques using a nucleotide sequence complementary to the nucleotide sequence of the gene (see, for example, Parish and Stoker, 1997, FEMS Microbiology Letters 154: 151-157). In particular, expression of the gene by filamentous fungal cells may be reduced or inactivated by introducing a nucleotide sequence complementary to the nucleotide sequence of the gene, which may be transcribed in the strain and is capable of hybridizing to the mRNA produced in the cells. Under conditions allowing the complementary anti-sense nucleotide sequence to hybridize to the mRNA, the amount of protein translated is thus reduced or eliminated.

Protease encoding genes that are present in filamentous fungal cells may also be modified by random or specific mutagenesis using methods well known in the art, including without limitation, chemical mutagenesis (see, for example, Hopwood, The Isolation of Mutants in Methods in Microbiology (J. R. Norris and D. W. Ribbons, eds.) pp. 363-433, Academic Press, New York, 25 1970). Modification of the gene may be performed by subjecting filamentous fungal cells to mutagenesis and screening for mutant cells in which expression of the gene has been reduced or inactivated. The mutagenesis, which may be specific or random, may be performed, for example, by use of a suitable physical or chemical mutagenizing agent, use of a suitable oligonucleotide, subjecting the DNA sequence to peR generated mutagenesis, or any combination thereof. Examples of physical and chemical mutagenizing agents include, without limitation, ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the filamentous fungal cells, such as *Trichoderma* cells, to be mutagenized in the presence of the mutagenizing agent of choice under suitable conditions, and then selecting for mutants exhibiting reduced or no expression of the gene.

In certain embodiments, the at least one mutation or modification in a protease encoding gene of the present disclosure results in a modified protease that has no detectable protease activity. In other embodiments, the at least one modification in a protease encoding gene of the present disclosure results in a modified protease that has at least 25% less, at least 50% less, at least 75% less, at least 90%, at least 95%, or a higher percentage less protease activity compared to a corresponding non-modified protease.

The filamentous fungal cells or *Trichoderma* fungal cells of the present disclosure may have reduced or no detectable protease activity of at least three, or at least four proteases selected from the group consisting of pep1, pep2, pep3, pep4, pep5, pep8, pep11, pep12, tsp1, slp1, slp2, slp3, slp5, slp6, slp7, gap1 and gap2. In preferred embodiment, a filamentous fungal cell according to the invention is a PMT-deficient filamentous fungal cell which has a deletion or disruption in at least 3 or 4 endogenous proteases, resulting in no detectable activity for such deleted or disrupted endogenous proteases and further comprising another mutation in a PMT gene that reduces endogenous protein O-mannosyltransferase activity compared to a parental *Trichoderma* cell which does not have said mutation.

In certain embodiments, the PMT-deficient filamentous fungal cell or *Trichoderma* cell, has reduced or no detectable protease activity in pep1, tsp1, and slp1. In other embodiments, the PMT-deficient filamentous fungal cell or *Trichoderma* cell, has reduced or no detectable protease activity in gap1, slp1, and pep1. In certain embodiments, the PMT-deficient filamentous fungal cell or *Trichoderma* cell, has reduced or no detectable protease activity in slp2, pep1 and gap1. In certain embodiments, the PMT-deficient filamentous fungal cell or *Trichoderma* cell, has reduced or no detectable protease activity in slp2, pep1, gap1 and pep4. In certain embodiments, the PMT-deficient filamentous fungal cell or *Trichoderma* cell, has reduced or no detectable protease activity in slp2, pep1, gap1, pep4 and slp1. In certain embodiments, the PMT-deficient filamentous fungal cell or *Trichoderma* cell, has reduced or no detectable protease activity in slp2, pep1, gap1, pep4, slp1, and slp3. In certain embodiments, the PMT-deficient filamentous fungal cell or *Trichoderma* cell, has reduced or no detectable protease activity in slp2, pep1, gap1, pep4, slp1, slp3, and pep3. In certain embodiments, the PMT-deficient filamentous fungal cell or *Trichoderma* cell, has reduced or no detectable protease activity in slp2, pep1, gap1, pep4, slp1, slp3, pep3 and pep2. In certain embodiments, the PMT-deficient filamentous fungal cell or *Trichoderma* cell, has reduced or no detectable protease activity in slp2, pep1, gap1, pep4, slp1, slp3, pep3, pep2 and pep5. In certain embodiments, the PMT-deficient filamentous fungal cell or *Trichoderma* cell, has reduced or no detectable protease activity in slp2, pep1, gap1, pep4, slp1, slp3, pep3, pep2, pep5 and tsp1. In certain embodiments, the PMT-deficient filamentous fungal cell or *Trichoderma* cell, has reduced or no detectable protease activity in slp2, pep1, gap1, pep4, slp1, slp3, pep3, pep2, pep5, tsp1 and slp7. In certain embodiments, the PMT-deficient filamentous fungal cell or *Trichoderma* cell, has reduced or no detectable protease activity in slp2, pep1, gap1, pep4, slp1, slp3, pep3, pep2, pep5, tsp1, slp7 and slp8. In certain embodiments, the PMT-deficient filamentous fungal cell or *Trichoderma* cell, has reduced or no detectable protease activity in slp2, pep1, gap1, pep4, slp1, slp3, pep3, pep2, pep5, tsp1, slp7, slp8 and gap2. In certain embodiments, the PMT-deficient filamentous fungal cell or *Trichoderma* cell, has reduced or no detectable protease activity in at least three endogenous proteases selected from the group consisting of pep1, pep2, pep3, pep4, pep5, pep8, pep11, pep12, tsp1, slp2, slp3, slp7, gap1 and gap2. In certain embodiments, the PMT-deficient filamentous fungal cell or *Trichoderma* cell, has reduced or no detectable protease activity in at least three to six endogenous proteases selected from the group consisting of pep1, pep2, pep3, pep4, pep5, tsp1, slp1, slp2, slp3, gap1 and gap2. In certain embodiments, the PMT-deficient filamentous fungal cell or *Trichoderma* cell, has reduced or no detectable protease activity in at least seven to ten endogenous proteases selected from the group consisting of pep1, pep2, pep3, pep4, pep5, pep7, pep8, tsp1, slp1, slp2, slp3, slp5, slp6, slp7, slp8, tpp1, gap1 and gap2.

In one embodiment that may be combined with the precedent embodiments, the filamentous fungal cell of the invention does not comprise a deletion or disruption of an endogenous gene encoding a chaperone protein. In particular, said filamentous fungal cell of the invention expresses functional endogenous chaperone protein Protein Disulphide Isomerase (PDI).

Endogenous O-Mannosyltransferase in Filamentous Fungal Cells

O-mannosyltransferases are encoded by pmt genes in yeasts and filamentous fungi, which can be divided into three subfamilies, based on sequence homologies: PMT1, PMT2 and PMT4.

For example, in yeast *S. cerevisiae*, 7 different PMTs have been characterized: ScPMT1, ScPMT5 and ScPMT7 belong to the PMT1 subfamily. ScPMT2, ScPMT3 and ScPMT6 belong to the PMT2 subfamily and ScPMT4 belongs to the PMT4 subfamily. Such O-mannosyltransferases and their coding sequences may be identified and isolated from filamentous fungal cells and tested to determine whether reduction in their activity enables the reduction of O-mannosylation on secreted O-mannosylated recombinant protein preferably not affecting the production of such recombinant polypeptide from the filamentous fungal cell. Methods for identifying and isolating PMTs are well known in the art. An identified O-mannosyltransferase may then be tested by deleting the gene encoding the identified O-mannosyltransferase from a filamentous fungal cell that expresses a recombinant O-mannosylated protein, such a heterologous or mammalian 0-mannosylated protein, and determining whether the deletion results in a decrease in total O-mannosyltransferase activity of the cell, preferably not affecting the level of production of the expressed recombinant protein. Methods for deleting genes and measuring levels of produced protein are well known in the art and include the methods described herein.

Three O-mannosyltransferases have been identified in *Trichoderma* fungal cells: pmt1, pmt2 and pmt3, belonging respectively based on sequence homologies to the PMT4, PMT1 and PMT2 subfamily.

Figure 5:
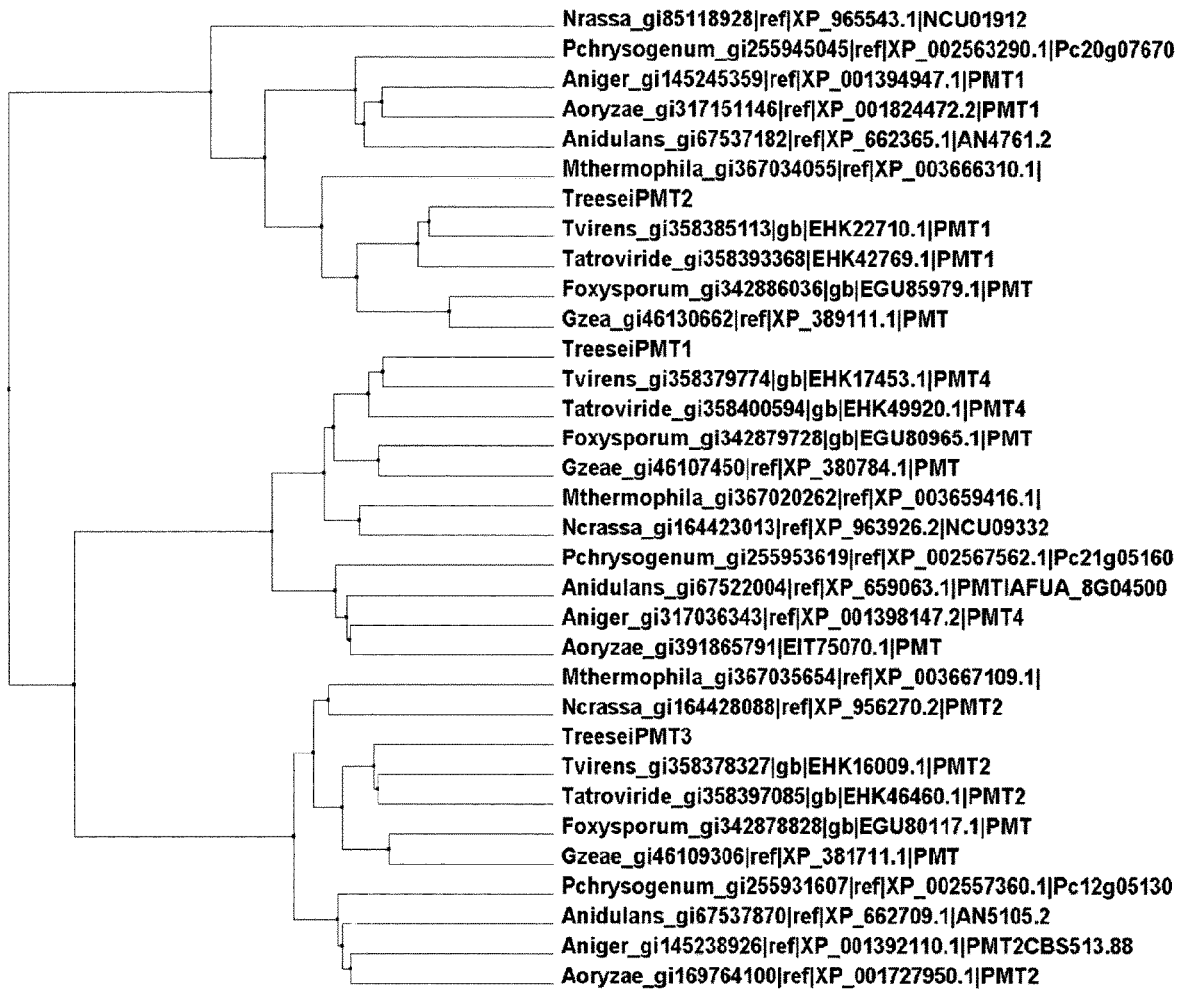
FIG. 5 depicts a phylogeny of PMTs of selected filamentous fungi.

Examples of suitable O-mannosyltransferase include, without limitation, *Trichoderma reesei* pmt1 (SEQ ID NO: 2), *Trichoderma reesei* pmt2 (SEQ ID NO: 3), *Trichoderma reesei* pmt3 (SEQ ID NO: 4) and homologs thereof. FIG. 5 shows phylogeny of pmt homologs in selected filamentous fungi and FIG. 6 shows an alignment of pmt1 conserved domains among different species.

In a preferred embodiment, said PMT-deficient filamentous fungal cell, e.g., a *Trichoderma* cell, has at least one mutation in a PMT gene selected from the group consisting of:
 a) PMT1 gene comprising the polynucleotide of SEQ ID NO:1,
 b) a functional homologous gene of PMT1 gene, which functional homologous gene is capable of restoring parental O-mannosylation level by functional complementation when introduced into a *T. reesei* strain having a disruption in said PMT1 gene, and,
 c) a polynucleotide encoding a polypeptide having at least 50%, at least 60%, at least 70%, at least 90%, or at least 95% identity with SEQ ID NO:2, said polypeptide having protein O-mannosyltransferase activity.

More preferably, said PMT-deficient filamentous fungal cell, e.g., a *Trichoderma* cell, has at least one mutation in a PMT gene which
 a) has a polynucleotide encoding a polypeptide having at least 50%, at least 60%, at least 70%, at least 90%, or at least 95% identity with SEQ ID NO:2, and,
 b) is capable of restoring, at least 50%, preferably about 100% of parental O-mannosylation level by functional complementation when introduced into a *T. reesei* strain having a disruption in a *T. reesei* PMT1 gene.

Methods for disrupting PMT1 gene in *T. reesei* are disclosed in the Examples below.

Sequences of homologs of pmt1 in filamentous fungi can be found in the databases using sequence alignment search tools, such as BLAST algorithm. It includes without limitation, *A. oryzae* gi391865791, EIT75070.1 (SEQ ID NO:5), *A. niger* gi317036343, XP_001398147.2 (SEQ ID NO:6), *A. nidulans* gi67522004, XP_659063.1 (SEQ ID NO:7), *T. virens* gi358379774, EHK17453.1 (SEQ ID NO:8), *T. atroviride* gi358400594, EHK49920.1 (SEQ ID NO:9), *F. oxysporum* gi342879728, EGU80965.1 (SEQ ID NO:10), *G. zeae* gi46107450, XP_380784.1 (SEQ ID NO:11), *M. thermophila* gi367020262, XP_003659416.1 (SEQ ID NO:12), *N. crassa* gi164423013, XP_963926.2 (SEQ ID NO:13), and *P. chrysogenum* gi255953619, XP_002567562.1 (SEQ ID NO:14).

Reducing Endogenous Protein O-Mannosyltransferase Activity in Filamentous Fungal Cell of the Invention The PMT-deficient filamentous fungal cells according to the invention have reduced activity of at least one O-mannosyltransferase activity, in order to reduce or decrease 0-mannosylation in said filamentous fungal cell, preferably *Trichoderma* cell.

The activity of said O-mannosyltransferases found in filamentous fungal cells can be reduced by any method known to those of skill in the art. In some embodiments reduced activity of O-mannosyltransferases is achieved by reducing the expression of the O-mannosyltransferases, for example, by promoter modification or RNAi.

In other embodiments, reduced activity of O-mannosyltransferases is achieved by modifying the gene encoding the O-mannosyltransferase. Examples of such modifications include, without limitation, a mutation, such as a deletion or disruption of the gene encoding said endogenous O-mannosyltransferase activity.

Deletion or disruption mutation can be performed as described in the above sections, in particular in relation to deletion or disruption of genes encoding proteases. These includes without limitation knock-out mutation, a truncation mutation, a point mutation, a missense mutation, a substitution mutation, a frameshift mutation, an insertion mutation, a duplication mutation, an amplification mutation, a translocation mutation, or an inversion mutation, and that results in a reduction in the corresponding O-mannosyltransferase activity.

In certain embodiments, the mutation or modification in an O-mannosyltransferase (PMT) encoding gene of the present disclosure results in a modified O-mannosyltransferase that has no detectable O-mannosyltransferase activity. In other embodiments, the at least one modification in a O-mannosyltransferase encoding gene of the present disclosure results in a modified O-mannosyltransferase that has at least 25% less, at least 50% less, at least 75% less, at least 90%, at least 95%, or a higher percentage less O-mannosyltransferase activity compared to a corresponding non-modified O-mannosyltransferase.

In preferred embodiment, a mutation that reduces endogenous protein O-mannosyltransferase activity in a PMT-deficient filamentous fungal cell, e.g. *Trichoderma* cell, is a PMT-deficient cell which has a deletion or disruption of a PMT gene encoding said O-mannosyltransferase activity, resulting in no detectable expression for such deleted or disrupted PMT gene.

One specific embodiment of the present invention is a PMT-deficient *Trichoderma reesei* cell, comprising
 a. at least a first mutation that reduces an endogenous protease activity compared to a parental *Trichoderma* cell which does not have said first mutation, and,
 b. at least a disruption or deletion of PMT1 gene of *T. reesei*.
 c. optionally, said cell further express a heterologous protein with serine or threonine, which has reduced O-mannosylation due to said mutation in said PMT gene.

The reduction (or decrease) of O-mannosyltransferase activity may be determined by comparing the O-mannosylation level of a heterologous protein in PMT-deficient filamentous fungal cell according to the invention, with the O-mannosylation level of a heterologous protein in the parental cell which does not have said PMT-deficient mutation.

In specific embodiments, the PMT-deficient filamentous fungal cell according to the invention expresses a heterologous protein which has reduced O-mannosylation due to said mutation in said PMT gene and the O-mannosylation level on the expressed heterologous protein is at least 20%, 40%, 50%, 60%, 70%, 80%, or 90% lower than the O-mannosylation level of the heterologous protein when expressed in the parental filamentous fungal cell which does not have said second PMT-deficient mutation.

O-mannosylation level may also be determined as mole % of O-mannosylated polypeptide per total polypeptide as produced by the host cell of the invention. Analytical methods, such as MALDI TOF MS analysis may be used to determine O-mannosylation level as described in detail in the Example 1 below, section entitled "Analyses of Dpmt1 strains M403, M404, M406 and M407. In brief, a polypeptide as produced by the PMT-deficient filamentous fungal cell is purified to determine its O-mannoslyation level. Non O-mannosylated, and O-mannosylated structure of the polypeptide are separated and quantified by MALDI-TOF MS analysis. For example, the quantification of 0-mannosylation level may be performed by determining area values or intensity of the different peaks of MALDI-TOF MS spectrum. An O-mannosylation level of 5% as determined by such method, using area values or intensity, reflects that about 95% (mol %) of the analysed polypeptides in the composition are not O-mannosylatedIn specific embodiments, the PMT-deficient filamentous fungal cell expresses a heterologous protein which has reduced O-mannosylation due to said mutation in said PMT gene, and the O-mannosylation level on the expressed heterologous protein (for example, as defined above by determining area or intensity values of MALDI TOF MS spectrum peaks) is reduced to less than 25%, 20%, 17%, 15%, 13%, 12%, 11%, 10%, 9%, 8%, 7%, 6%, 5%, 4%, 3%, 2%, or 1%, or 0.5% (as mole % of mannose residues per polypeptide chain).

In an embodiment, the heterologous protein with reduced O-mannosylation is selected from the group consisting of:
a) an immunoglobulin, such as IgG,
b) a light chain or heavy chain of an immunoglobulin,
c) a heavy chain or a light chain of an antibody,
d) a single chain antibody,
e) a camelid antibody,
f) a monomeric or multimeric single domain antibody,
g) a FAb-fragment, a FAb2-fragment, and,
h) their antigen-binding fragments.

In a specific embodiment, a mutation that reduces endogenous O-mannosyltransferase activity is a deletion or a disruption of a PMT gene encoding said engogenous protein O-mannosyltransferase activity. For example in *Trichoderma* cell, a mutation that reduces endogenous O-mannosyltransferase activity is a deletion or a disruption of a PMT1 gene.

Filamentous Fungal Cell for Producing Glycoproteins with Reduced O-Mannosylation and Mammalian-Like N-Glycans The filamentous fungal cells according to the present invention may be useful in particular for producing heterologous glycoproteins with reduced O-mannosylation and mammalian-like N-glycans, such as complex N-glycans.

Accordingly, in one aspect, the filamentous fungal cell is further genetically modified to produce a mammalian-like N-glycan, thereby enabling in vivo production of glycoprotein with no or reduced O-mannosylation and with mammalian-like N-glycan as major glycoforms.

In certain embodiments, this aspect includes methods of producing glycoproteins with mammalian-like N-glycans in a *Trichoderma* cell.

In certain embodiment, the glycoprotein comprises, as a major glycoform, the mammalian-like N-glycan having the formula [(Galβ4)$_x$GlcNAcβ2]$_z$Manα3([(Galβ4)$_y$GlcNAcβ2]$_w$Manα6)Man{β4GlcNAcβGlcNAc, where ( ) defines a branch in the structure, where [ ] or { } define a part of the glycan structure either present or absent in a linear sequence, and where x, y, z and w are 0 or 1, independently. In an embodiment w and z are 1.

In certain embodiments, the glycoprotein comprises, as a major glycoform, mammalian-like N-glycan selected from the group consisting of:
i. Manα3[Manα6(Manα3)Manα6]Manβ4GlcNAβ4GlcNAc (Man5 glycoform);
ii. GlcNAcβ2Manα3[Manα6(Manα3)Manα6]Manβ4GlcNAβ4GlcNAc (GlcNAcMan5 glycoform);
iii. Manα6(Manα3)Manβ4GlcNAβ4GlcNAc (Man3 glycoform);
iv. Manα6(GlcNAcβ2Manα3)Manβ4GlcNAβ4GlcNAc (GlcNAcMan3) or,
v. complex type N-glycans selected from the G0, G1, or G2 glycoform.

In an embodiment, the glycoprotein composition with mammalian-like N-glycans, preferably produced by an alg3 knock-out strain, include glycoforms that essentially lack or are devoid of glycans Manα3[Manα6(Manα3)Manα6]Manβ4GlcNAβ4GlcNAc (Man5). In specific embodiments, the filamentous fungal cell produces glycoproteins with, as major glycoform, the trimannosyl N-glycan structure Manα3[Manα6]Manβ4GlcNAcβ4GlcNAc. In other embodiments, the filamentous fungal cell produces glycoproteins with, as major glycoform, the G0 N-glycan structure GlcNAcβ2Manα3[GlcNAcβ2Manα6]Manβ4GlcNAcβ4GlcNAc.

In certain embodiments, the PMT-deficient filamentous fungal cell of the invention produces glycoprotein composition with a mixture of different N-glycans.

In some embodiments, Man3GlcNAc2 N-glycan (i.e. Manα3[Manα6]Manβ4GlcNAcβ4GlcNAc) represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, GlcNAc2Man3 N-glycan (for example G0 GlcNAcβ2Manα3[GlcNAcβ2Manα6]Manβ4GlcNAcβ4GlcNAc) represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, GalGlcNAc2Man3GlcNAc2 N-glycan (for example G1 N-glycan) represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, Gal2GlcNAc2Man3GlcNAc2 N-glycan (for example G2 N-glycan) represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, complex type N-glycan represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, hybrid type N-glycan represents at least 10%, at least 20%, at least at least 30%, at least 40%, at least 50%, at least 60%, at least 70%, at least 80%, at least 90% or more of total (mol %) neutral N-glycans of a heterologous protein with reduced O-mannosylation, as expressed in a filamentous fungal cells of the invention.

In other embodiments, less than 0.5%, 0.1%, 0.05%, or less than 0.01% of the N-glycan of the glycoprotein composition produced by the host cell of the invention, comprises galactose. In certain embodiments, none of N-glycans comprise galactose.

The Neu5Gc and Galα- (non-reducing end terminal Galα3Galβ4GlcNAc) structures are known xenoantigenic (animal derived) modifications of antibodies which are produced in animal cells such as CHO cells. The structures may be antigenic and, thus, harmful even at low concentrations. The filamentous fungi of the present invention lack biosynthetic pathways to produce the terminal Neu5Gc and Galα-structures. In an embodiment that may be combined with the preceding embodiments less than 0.1%, 0.01%, 0.001% or 0% of the N-glycans and/or O-glycans of the glycoprotein composition comprises Neu5Gc and/or Galα-structure. In an embodiment that may be combined with the preceding embodiments, less than 0.1%, 0.01%, 0.001% or 0% of the N-glycans and/or O-glycans of the antibody composition comprises Neu5Gc and/or Galα-structure.

The filamentous fungal cells of the present invention lack genes to produce fucosylated heterologous proteins. In an embodiment that may be combined with the preceding embodiments, less than 0.1%, 0.01%, 0.001%, or 0% of the N-glycan of the glycoprotein composition comprises core fucose structures. In an embodiment that may be combined with the preceding embodiments, less than 0.1%, 0.01%, 0.001%, or 0% of the N-glycan of the antibody composition comprises core fucose structures.

The terminal Galβ4GlcNAc structure of N-glycan of mammalian cell produced glycans affects bioactivity of antibodies and Galβ3GlcNAc may be xenoantigen structure from plant cell produced proteins. In an embodiment that may be combined with one or more of the preceding embodiments, less than 0.1%, 0.01%, 0.001%, or 0% of N-glycan of the glycoprotein composition comprises terminal galactose epitopes Galβ3/4GlcNAc. In an embodiment that may be combined with one or more of the preceding embodiments, less than 0.1%, 0.01%, 0.001%, or 0% of the N-glycan of the antibody composition comprises terminal galactose epitopes Galβ3/4GlcNAc.

Glycation is a common post-translational modification of proteins, resulting from the chemical reaction between reducing sugars such as glucose and the primary amino groups on protein. Glycation occurs typically in neutral or slightly alkaline pH in cell cultures conditions, for example, when producing antibodies in CHO cells and analysing them (see, for example, Zhang et al. (2008) Unveiling a glycation hot spot in a recombinant humanized monoclonal antibody. Anal Chem. 80(7):2379-2390). As filamentous fungi of the present invention are typically cultured in acidic pH, occurrence of glycation is reduced. In an embodiment that may be combined with the preceding embodiments, less than 1.0%, 0.5%, 0.1%, 0.01%, 0.001%, or 0% of the glycoprotein composition comprises glycation structures. In an embodiment that may be combined with the preceding embodiments, less than 1.0%, 0.5%, 0.1%, 0.01%, 0.001%, or 0% of the antibody composition comprises glycation structures.

In one embodiment, the glycoprotein composition, such as an antibody is devoid of one, two, three, four, five, or six of the structures selected from the group of Neu5Gc, terminal Galα3Galβ4GlcNAc, terminal Galβ4GlcNAc, terminal Galβ3GlcNAc, core linked fucose and glycation structures.

In certain embodiments, such glycoprotein protein with mammalian-like N-glycan and reduced O-mannosylation, as produced in the filamentous fungal cell of the invention, is a therapeutic protein. Therapeutic proteins may include immunoglobulin, or a protein fusion comprising a Fc fragment or other therapeutic glycoproteins, such as antibodies, erythropoietins, interferons, growth hormones, albumins or serum albumin, enzymes, or blood-clotting factors and may be useful in the treatment of humans or animals. For example, the glycoproteins with mammalian-like N-glycan and reduced O-mannosylation as produced by the filamentous fungal cell according to the invention may be a therapeutic glycoprotein such as rituximab.

Methods for producing glycoproteins with mammalian-like N-glycans in filamentous fungal cells are also described for example in WO2012/069593.

In one aspect, the filamentous fungal cell according to the invention as described above, is further genetically modified to mimic the traditional pathway of mammalian cells, starting from Man5 N-glycans as acceptor substrate for GnTI, and followed sequentially by GnT1, mannosidase II and GnTII reaction steps (hereafter referred as the "traditional pathway" for producing G0 glycoforms). In one variant, a single recombinant enzyme comprising the catalytic domains of GnTI and GnTII, is used.

Alternatively, in a second aspect, the filamentous fungal cell according to the invention as described above is further genetically modified to have alg3 reduced expression, allowing the production of core $Man_3GlcNAc_2$ N-glycans, as acceptor substrate for GnTI and GnTII subsequent reactions and bypassing the need for mannosidase a1,2 or mannosidase II enzymes (the reduced "alg3" pathway). In one variant, a single recombinant enzyme comprising the catalytic domains of GnTI and GnTII, is used.

In such embodiments for mimicking the traditional pathway for producing glycoproteins with mammalian-like N-glycans, a $Man_5$ expressing filamentous fungal cell, such as *T. reesei* strain, may be transformed with a GnTI or a GnTII/GnTI fusion enzyme using random integration or by targeted integration to a known site known not to affect Man5 glycosylation. Strains that synthesise GlcNAcMan5 N-glycan for production of proteins having hybrid type glycan(s) are selected. The selected strains are further transformed with a catalytic domain of a mannosidase II-type mannosidase capable of cleaving Man5 structures to generate GlcNAcMan3 for production of proteins having the corresponding GlcNAcMan3 glycoform or their derivative(s). In certain embodiments, mannosidase II-type enzymes belong to glycoside hydrolase family 38 (cazy.org/GH38_all.html). Characterized enzymes include enzymes listed in cazy.org/GH38_characterized.html. Especially useful enzymes are Golgi-type enzymes that cleaving glycoproteins, such as those of subfamily α-mannosidase II (Man2A1; ManA2). Examples of such enzymes include human enzyme AAC50302, *D. melanogaster* enzyme (Van den Elsen J. M. et al (2001) EMBO J. 20: 3008-3017), those with the 3D structure according to PDB-reference 1HTY, and others referenced with the catalytic domain in PDB. For cytoplasmic expression, the catalytic domain of the mannosidase is typically fused with an N-terminal targeting peptide (for example as disclosed in the above Section) or expressed with endogenous animal or plant Golgi targeting structures of animal or plant mannosidase II enzymes. After transformation with the catalytic domain of a mannosidase II-type mannosidase, strains are selected that produce GlcNAcMan3 (if GnTI is expressed) or strains are selected that effectively produce GlcNAc2Man3 (if a fusion of GnTI and GnTII is expressed). For strains producing GlcNAcMan3, such strains are further transformed with a polynucleotide encoding a catalytic domain of GnTII and transformant strains that are capable of producing GlcNAc2Man3GlcNAc2 are selected.

In such embodiment for mimicking the traditional pathway, the filamentous fungal cell is a PMT-deficient filamentous fungal cell as defined in previous sections, and further comprising one or more polynucleotides encoding a polypeptide selected from the group consisting of:

i) α1,2 mannosidase,
ii) N-acetylglucosaminyltransferase I catalytic domain,
iii) a mannosidase II,
iv) N-acetylglucosaminyltransferase II catalytic domain,
v) β1,4 galactosyltransferase, and,
vi) fucosyltransferase.

In embodiments using the reduced alg3 pathway, the filamentous fungal cell, such as a *Trichoderma* cell, has a reduced level of activity of a dolichyl-P-Man:Man(5)GlcNAc(2)-PP-dolichyl mannosyltransferase compared to the level of activity in a parent host cell. Dolichyl-P-Man:Man(5)GlcNAc(2)-PP-dolichyl mannosyltransferase (EC 2.4.1.130) transfers an alpha-D-mannosyl residue from dolichyl-phosphate D-mannose into a membrane lipid-linked oligosaccharide. Typically, the dolichyl-P-Man:Man(5)GlcNAc(2)-PP-dolichyl mannosyltransferase enzyme is encoded by an alg3 gene. In certain embodiments, the filamentous fungal cell for producing glycoproteins with mammalian-like N-glycans has a reduced level of expression of an alg3 gene compared to the level of expression in a parent strain.

More preferably, the filamentous fungal cell comprises a mutation of alg3. The ALG3 gene may be mutated by any means known in the art, such as point mutations or deletion of the entire alg3 gene. For example, the function of the alg3 protein is reduced or eliminated by the mutation of alg3. In certain embodiments, the alg3 gene is disrupted or deleted from the filamentous fungal cell, such as *Trichoderma* cell. In certain embodiments, the filamentous fungal cell is a *T. reesei* cell. SEQ ID NOs: 36 and 37 provide, the nucleic acid and amino acid sequences of the alg3 gene in *T. reesei*, respectively. In an embodiment the filamentous fungal cell is used for the production of a glycoprotein, wherein the glycan(s) comprise or consist of Manα3[Manα6]Manβ4GlcNAcβ4GlcNAc, and/or a non-reducing end elongated variant thereof.

In certain embodiments, the filamentous fungal cell has a reduced level of activity of an alpha-1,6-mannosyltransferase compared to the level of activity in a parent strain. Alpha-1,6-mannosyltransferase (EC 2.4.1.232) transfers an alpha-D-mannosyl residue from GDP-mannose into a protein-linked oligosaccharide, forming an elongation initiating alpha-(1→6)-D-mannosyl-D-mannose linkage in the Golgi apparatus. Typically, the alpha-1,6-mannosyltransferase enzyme is encoded by an och1 gene. In certain embodiments, the filamentous fungal cell has a reduced level of expression of an och1 gene compared to the level of expression in a parent filamentous fungal cell. In certain embodiments, the och1 gene is deleted from the filamentous fungal cell.

The filamentous fungal cells used in the methods of producing glycoprotein with mammalian-like N-glycans may further contain a polynucleotide encoding an N-acetylglucosaminyltransferase I catalytic domain (GnTI) that catalyzes the transfer of N-acetylglucosamine to a terminal Manα3 and a polynucleotide encoding an N-acetylglucosaminyltransferase II catalytic domain (GnTII), that catalyses N-acetylglucosamine to a terminal Manα6 residue of an acceptor glycan to produce a complex N-glycan. In one embodiment, said polynucleotides encoding GnTI and GnTII are linked so as to produce a single protein fusion comprising both catalytic domains of GnTI and GnTII.

As disclosed herein, N-acetylglucosaminyltransferase I (GlcNAc-TI; GnTI; EC 2.4.1.101) catalyzes the reaction UDP-N-acetyl-D-glucosamine+3-(alpha-D-mannosyl)-beta-D-mannosyl-R<=>UDP+3-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase I catalytic domain is any portion of an N-acetylglucosaminyltransferase I enzyme that is capable of catalyzing this reaction. GnTI enzymes are listed in the CAZy database in the glycosyltransferase family 13 (cazy.org/GT13_all). Enzymatically characterized species includes *A. thaliana* AAR78757.1 (U.S. Pat. No. 6,653,459), *C. elegans* AAD03023.1 (Chen S. et al J. Biol. Chem 1999; 274(1): 288-97), *D. melanogaster* AAF57454.1 (Sarkar & Schachter Biol Chem. 2001 February; 382(2):209-17); *C. griseus* AAC52872.1 (Puthalakath H. et al J. Biol. Chem 1996 271(44):27818-22); *H. sapiens* AAA52563.1 (Kumar R. et al Proc Natl Acad Sci USA. 1990 December; 87(24):9948-52); *M. auratus* AAD04130.1 (Opat As et al Biochem J. 1998 Dec. 15; 336 (Pt 3):593-8), (including an example of deactivating mutant), Rabbit, *O. cuniculus* AAA31493.1 (Sarkar M et al. Proc Natl Acad Sci USA. 1991 Jan. 1; 88(1):234-8). Amino acid sequences for N-acetylglucosaminyltransferase I enzymes from various organisms are described for example in PCT/EP2011/070956. Additional examples of characterized active enzymes can be found at cazy.org/GT13_characterized. The 3D structure of the catalytic domain of rabbit GnTI was defined by X-ray crystallography in Unligil U M et al. EMBO J. 2000 Oct. 16; 19(20):5269-80. The Protein Data Bank (PDB) structures for GnTI are 1FO8, 1 FO9, 1FOA, 2AM3, 2AM4, 2AM5, and 2APC. In certain embodiments, the N-acetylglucosaminyltransferase I catalytic domain is from the human N-acetylglucosaminyltransferase I enzyme (SEQ ID NO: 38) or variants thereof. In certain embodiments, the N-acetylglucosaminyltransferase I catalytic domain contains a sequence that is at least 70%, at least 75%, at least 80%, at least 85%, at least 90%, at least 95%, at least 96%, at least 97%, at least 98%, at least 99%, or 100% identical to amino acid residues 84-445 of SEQ ID NO: 38. In some embodiments, a shorter sequence can be used as a catalytic domain (e.g. amino acid residues 105-445 of the human enzyme or amino acid residues 107-447 of the rabbit enzyme; Sarkar et al. (1998) Glycoconjugate J 15:193-197). Additional sequences that can be used as the GnTI catalytic domain include amino acid residues from about amino acid 30 to 445 of the human enzyme or any C-terminal stem domain starting between amino acid residue 30 to 105 and continuing to about amino acid 445 of the human enzyme, or corresponding homologous sequence of another GnTI or a catalytically active variant or mutant thereof. The catalytic domain may include N-terminal parts of the enzyme such as all or part of the stem domain, the transmembrane domain, or the cytoplasmic domain.

As disclosed herein, N-acetylglucosaminyltransferase II (GlcNAc-TII; GnTII; EC 2.4.1.143) catalyzes the reaction UDP-N-acetyl-D-glucosamine+6-(alpha-D-mannosyl)-beta-D-mannosyl-R<=>UDP+6-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase II catalytic domain is any portion of an N-acetylglucosaminyltransferase II enzyme that is capable of catalyzing this reaction. Amino acid sequences for N-acetylglucosaminyltransferase II enzymes from various organisms are listed in WO2012069593. In certain embodiments, the N-acetylglucosaminyltransferase II catalytic domain is from the human N-acetylglucosaminyltransferase II enzyme (SEQ ID NO: 39) or variants thereof. Additional GnTII species are listed in the CAZy database in the glycosyltransferase family 16 (cazy.org/GT16_all). Enzymatically characterized species include GnTII of *C. elegans, D. melanogaster, Homo sapiens* (NP_002399.1), *Rattus norvegicus, Sus scrofa* (cazy.org/GT16_characterized). In certain embodiments, the N-acetylglucosaminyltransferase II catalytic domain contains a sequence that is at least 70%, at least 75%, at least 80%, at least 85%, at least 90%, at least 95%, at least 96%, at least 97%, at least 98%, at least 99%, or 100% identical to amino acid residues from about 30 to about 447 of SEQ ID NO: 39. The catalytic domain may include N-terminal parts of the enzyme such as all or part of the stem domain, the transmembrane domain, or the cytoplasmic domain.

In embodiments where the filamentous fungal cell contains a fusion protein of the invention, the fusion protein may further contain a spacer in between the N-acetylglucosaminyltransferase I catalytic domain and the N-acetylglucosaminyltransferase II catalytic domain. In certain embodiments, the spacer is an EGIV spacer, a 2×G4S spacer, a 3×G4S spacer, or a CBHI spacer. In other embodiments, the spacer contains a sequence from a stem domain.

For ER/Golgi expression the N-acetylglucosaminyltransferase I and/or N-acetylglucosaminyltransferase II catalytic domain is typically fused with a targeting peptide or a part of an ER or early Golgi protein, or expressed with an endogenous ER targeting structures of an animal or plant N-acetylglucosaminyltransferase enzyme. In certain preferred embodiments, the N-acetylglucosaminyltransferase I and/or N-acetylglucosaminyltransferase II catalytic domain contains any of the targeting peptides of the invention as described in the section entitled "Targeting sequences". Preferably, the targeting peptide is linked to the N-terminal end of the catalytic domain. In some embodiments, the targeting peptide contains any of the stem domains of the invention as described in the section entitled "Targeting sequences". In certain preferred embodiments, the targeting peptide is a Kre2/Mnt1 targeting peptide. In other embodiments, the targeting peptide further contains a transmembrane domain linked to the N-terminal end of the stem domain or a cytoplasmic domain linked to the N-terminal end of the stem domain. In embodiments where the targeting peptide further contains a transmembrane domain, the targeting peptide may further contain a cytoplasmic domain linked to the N-terminal end of the transmembrane domain.

The filamentous fungal cells may also contain a polynucleotide encoding a UDP-GlcNAc transporter. The polynucleotide encoding the UDP-GlcNAc transporter may be endogenous (i.e., naturally present) in the host cell, or it may be heterologous to the filamentous fungal cell.

In certain embodiments, the filamentous fungal cell may further contain a polynucleotide encoding a α-1,2-mannosidase. The polynucleotide encoding the α-1,2-mannosidase may be endogenous in the host cell, or it may be heterologous to the host cell. Heterologous polynucleotides are especially useful for a host cell expressing high-mannose glycans transferred from the Golgi to the ER without effective exo-α-2-mannosidase cleavage. The α-1,2-mannosidase may be a mannosidase I type enzyme belonging to the glycoside hydrolase family 47 (cazy.org/GH47_all.html). In certain embodiments the α-1,2-mannosidase is an enzyme listed at cazy.org/GH47_characterized.html. In particular, the α-1,2-mannosidase may be an ER-type enzyme that cleaves glycoproteins such as enzymes in the subfamily of ER α-mannosidase I EC 3.2.1.113 enzymes. Examples of such enzymes include human α-2-mannosidase 1B (AAC26169), a combination of mammalian ER mannosidases, or a filamentous fungal enzyme such as α-1,2-mannosidase (MDS1) (*T. reesei* AAF34579; Maras M et al J Biotech. 77, 2000, 255, or Trire 45717). For ER expression, the catalytic domain of the mannosidase is typically fused with a targeting peptide, such as HDEL, KDEL, or part of an ER or early Golgi protein, or expressed with an endogenous ER targeting structures of an animal or plant mannosidase I enzyme.

In certain embodiments, the filamentous fungal cell may also further contain a polynucleotide encoding a galactosyltransferase. Galactosyltransferases transfer β-linked galactosyl residues to terminal N-acetylglucosaminyl residue. In certain embodiments the galactosyltransferase is a β-1,4-galactosyltransferase. Generally, β-1,4-galactosyltransferases belong to the CAZy glycosyltransferase family 7 (cazy.org/GT7_all.html) and include β-N-acetylglucosaminyl-glycopeptide β-1,4-galactosyltransferase (EC 2.4.1.38), which is also known as N-acetylactosamine synthase (EC 2.4.1.90). Useful subfamilies include β4-GalT1, β4-GalT-II, -III, -IV, -V, and -VI, such as mammalian or human β4-GalT1 or β4GalT-II, -III, -IV, -V, and -VI or any combinations thereof. β4-GalT1, β4-GalTII, or β4-GalTIII are especially useful for galactosylation of terminal GlcNAcβ2-structures on N-glycans such as GlcNAcMan3, GlcNAc2Man3, or GlcNAcMan5 (Guo S. et al. Glycobiology 2001, 11:813-20). The three-dimensional structure of the catalytic region is known (e.g. (2006) J. Mol. Biol. 357: 1619-1633), and the structure has been represented in the PDB database with code 2FYD. The CAZy database includes examples of certain enzymes. Characterized enzymes are also listed in the CAZy database at cazy.org/GT7_characterized.html. Examples of useful β4GalT enzymes include β4GalT1, e.g. bovine *Bos taurus* enzyme AAA30534.1 (Shaper N. L. et al Proc. Natl. Acad. Sci. U.S.A. 83 (6), 1573-1577 (1986)), human enzyme (Guo S. et al. Glycobiology 2001, 11:813-20), and *Mus musculus* enzyme AAA37297 (Shaper, N. L. et al. 1998 J. Biol. Chem. 263 (21), 10420-10428); β4GalTII enzymes such as human β4GalTII BAA75819.1, Chinese hamster *Cricetulus griseus* AAM77195, *Mus musculus* enzyme BAA34385, and Japanese Medaka fish *Oryzias latipes* BAH36754; and β4GalTIII enzymes such as human β4GalTIII BAA75820.1, Chinese hamster *Cricetulus griseus* AAM77196 and *Mus musculus* enzyme AAF22221.

The galactosyltransferase may be expressed in the plasma membrane of the host cell. A heterologous targeting peptide, such as a Kre2 peptide described in Schwientek J. Biol. Chem 1996 3398, may be used. Promoters that may be used for expression of the galactosyltransferase include constitutive promoters such as gpd, promoters of endogenous glycosylation enzymes and glycosyltransferases such as mannosyltransferases that synthesize N-glycans in the Golgi or ER, and inducible promoters of high-yield endogenous proteins such as the cbh1 promoter.

In certain embodiments of the invention where the filamentous fungal cell contains a polynucleotide encoding a galactosyltransferase, the filamentous fungal cell also contains a polynucleotide encoding a UDP-Gal 4 epimerase and/or UDP-Gal transporter. In certain embodiments of the invention where the filamentous fungal cell contains a polynucleotide encoding a galactosyltransferase, lactose may be used as the carbon source instead of glucose when culturing the host cell. The culture medium may be between pH 4.5 and 7.0 or between 5.0 and 6.5. In certain embodiments of the invention where the filamentous fungal cell contains a polynucleotide encoding a galactosyltransferase and a polynucleotide encoding a UDP-Gal 4 epimerase and/or UDP-Gal transporter, a divalent cation such as Mn2+, Ca2+ or Mg2+ may be added to the cell culture medium.

Accordingly, in certain embodiments, the filamentous fungal cell of the invention, for example, selected among *Neurospora, Trichoderma, Myceliophthora* or *Chrysosporium* cell, and more preferably *Trichoderma reesei* cell, may comprise the following features:
a) a mutation in at least one endogenous protease that reduces or eliminates the activity of said endogenous protease, preferably the protease activity of two or three or more endogenous proteases is reduced, for example, pep1, tsp1, gap1 and/or slp1 proteases, in order to improve production or stability of a heterologous protein to be produced,
b) a mutation in a PMT gene, for example *T. reesei* pmt1 gene, that reduces or eliminates endogenous O-mannosyltransferase activity compared to a parental *Trichoderma* cell which does not have said second mutation,
c) a polynucleotide encoding a protein having at least one serine or threonine, preferably a heterologous glycoprotein, such as an immunoglobulin, an antibody, or a protein fusion comprising Fc fragment of an immunoglobulin.
d) optionally, a deletion or disruption of the alg3 gene,
e) optionally, a polynucleotide encoding N-acetylglucosaminyltransferase I catalytic domain and a polynucleotide encoding N-acetylglucosaminyltransferase II catalytic domain,
f) optionally, a polynucleotide encoding β1,4 galactosyltransferase,
g) optionally, a polynucleotide or polynucleotides encoding UDP-Gal 4 epimerase and/or transporter.

Targeting Sequences

In certain embodiments, recombinant enzymes, such as α1,2 mannosidases, GnTI, or other glycosyltransferases introduced into the filamentous fungal cells, include a targeting peptide linked to the catalytic domains. The term "linked" as used herein means that two polymers of amino acid residues in the case of a polypeptide or two polymers of nucleotides in the case of a polynucleotide are either coupled directly adjacent to each other or are within the same polypeptide or polynucleotide but are separated by intervening amino acid residues or nucleotides. A "targeting peptide", as used herein, refers to any number of consecutive amino acid residues of the recombinant protein that are capable of localizing the recombinant protein to the endoplasmic reticulum (ER) or Golgi apparatus (Golgi) within the host cell. The targeting peptide may be N-terminal or C-terminal to the catalytic domains. In certain embodiments, the targeting peptide is N-terminal to the catalytic domains. In certain embodiments, the targeting peptide provides binding to an ER or Golgi component, such as to a mannosidase II enzyme. In other embodiments, the targeting peptide provides direct binding to the ER or Golgi membrane.

Components of the targeting peptide may come from any enzyme that normally resides in the ER or Golgi apparatus. Such enzymes include mannosidases, mannosyltransferases, glycosyltransferases, Type 2 Golgi proteins, and MNN2, MNN4, MNN6, MNN9, MNN10, MNS1, KRE2, VAN1, and OCH1 enzymes. Such enzymes may come from a yeast or fungal species such as those of *Acremonium, Aspergillus, Aureobasidium, Cryptococcus, Chrysosporium, Chrysosporium lucknowense, Filobasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium,* and *Trichoderma*. Sequences for such enzymes can be found in the GenBank sequence database.

In certain embodiments the targeting peptide comes from the same enzyme and organism as one of the catalytic domains of the recombinant protein. For example, if the recombinant protein includes a human GnTII catalytic domain, the targeting peptide of the recombinant protein is from the human GnTII enzyme. In other embodiments, the targeting peptide may come from a different enzyme and/or organism as the catalytic domains of the recombinant protein.

Examples of various targeting peptides for use in targeting proteins to the ER or Golgi that may be used for targeting the recombinant enzymes, include: Kre2/Mnt1 N-terminal peptide fused to galactosyltransferase (Schwientek, J B C 1996, 3398), HDEL for localization of mannosidase to ER of yeast cells to produce Man5 (Chiba, J B C 1998, 26298-304; Callewaert, FEBS Lett 2001, 173-178), OCH1 targeting peptide fused to GnTI catalytic domain (Yoshida et al, Glycobiology 1999, 53-8), yeast N-terminal peptide of Mns1 fused to α2-mannosidase (Martinet et al, Biotech Lett 1998, 1171), N-terminal portion of Kre2 linked to catalytic domain of GnTI or β4GalT (Vervecken, Appl. Environ Microb 2004, 2639-46), various approaches reviewed in Wildt and Gerngross (Nature Rev Biotech 2005, 119), full-length GnTI in *Aspergillus nidulans* (Kalsner et al, Glycocon. J 1995, 360-370), full-length GnTI in *Aspergillus oryzae* (Kasajima et al, Biosci Biotech Biochem 2006, 2662-8), portion of yeast Sec12 localization structure fused to *C. elegans* GnTI in *Aspergillus* (Kainz et al 2008), N-terminal portion of yeast Mnn9 fused to human GnTI in *Aspergillus* (Kainz et al 2008), N-terminal portion of *Aspergillus* Mnn10 fused to human GnTI (Kainz et al, Appl. Environ Microb 2008, 1076-86), and full-length human GnTI in *T. reesei* (Maras et al, FEBS Lett 1999, 365-70).

In certain embodiments the targeting peptide is an N-terminal portion of the Mnt1/Kre2 targeting peptide having the amino acid sequence of SEQ ID NO: 40 (for example encoded by the polynucleotide of SEQ ID NO:41). In certain embodiments, the targeting peptide is selected from human GNT2, KRE2, KRE2-like, Och1, Anp1, Van1 as shown in the Table 1 below:

TABLE 1

Amino acid sequence of targeting peptides

| Protein | TreID | Amino acid sequence |
|---|---|---|
| human GNT2 | — | MRFRIYKRKVLILTLVVAACGFVLWSSNGRQ RKNEALAPPLLDAEPARGAGGRGGDHP (SEQ ID NO: 42) |
| KRE2 | 21576 | MASTNARYVRYLLIAFFTILVFYFVSNSKYE GVDLNKGTFTAPDSTKTTPK (SEQ ID NO: 43) |
| KRE2-like | 69211 | MAIARPVRALGGLAAILWCFFLYQLLRPSSS NYSPGDRYINFERDPNLDPTG (SEQ ID NO: 44) |
| Och1 | 65646 | MLNPRRALIAAAFILTVFFLISRSHNSESAS TS (SEQ ID NO: 45) |
| Anp1 | 82551 | MMPRHHSSGFSNGYPRADTFEISPHRFQPRA TLPPHRKRKRTAIRVGIAVVVILVLVLWFGQ PRSVASLISLGILSGYDDLKLE (SEQ ID NO: 46) |

TABLE 1-continued

Amino acid sequence of targeting peptides

| Protein | TreID | Amino acid sequence |
|---|---|---|
| Van1 | 81211 | MLLPKGGLDWRSARAQIPPTRALWNAVTRTR FILLVGITGLILLLWRGVSTSASE (SEQ ID NO: 47) |

Further examples of sequences that may be used for targeting peptides include the targeting sequences as described in WO2012/069593.

Uncharacterized sequences may be tested for use as targeting peptides by expressing enzymes of the glycosylation pathway in a host cell, where one of the enzymes contains the uncharacterized sequence as the sole targeting peptide, and measuring the glycans produced in view of the cytoplasmic localization of glycan biosynthesis (e.g. as in Schwientek JBC 1996 3398), or by expressing a fluorescent reporter protein fused with the targeting peptide, and analysing the localization of the protein in the Golgi by immunofluorescence or by fractionating the cytoplasmic membranes of the Golgi and measuring the location of the protein.

Methods for Producing a Protein Having Reduced O-Mannosylation

The filamentous fungal cells as described above are useful in methods for producing a protein having reduced O-mannosylation.

Accordingly, in another aspect, the invention relates to a method for producing a protein having reduced O-mannosylation, comprising:
 a) providing a PMT-deficient *Trichoderma* cell having a mutation in a PMT gene that reduces endogenous protein O-mannosyltransferase activity as compared to parental strain which does not have such mutation, and further comprising a polynucleotide encoding a protein with serine or threonine, which may be O-mannosylated,
 b) culturing said PMT-deficient *Trichoderma* cell to produce said protein having reduced O-mannosylation.

In such method, the produced protein has reduced O-mannosylation due to said mutation in said PMT gene as described in the previous sections. The PMT-deficient *Trichoderma* cell may optionally have reduced endogenous protease activity as described in the previous sections.

The filamentous fungal cells and methods of the invention are useful for the production of protein with serine or threonine which may be O-mannosylated. For example, it is particularly useful for the production of protein which are O-mannosylated when produced in a parental PMT-functional filamentous fungal host cell, for example, in at least one *Trichoderma* cell which is wild type for PMT1 gene, such as SEQ ID NO:1.

In methods of the invention, certain growth media include, for example, common commercially-prepared media such as Luria-Bertani (LB) broth, Sabouraud Dextrose (SD) broth or Yeast medium (YM) broth. Other defined or synthetic growth media may also be used and the appropriate medium for growth of the particular host cell will be known by someone skilled in the art of microbiology or fermentation science. Culture medium typically has the *Trichoderma reesei* minimal medium (Penttila et al., 1987, Gene 61, 155-164) as a basis, supplemented with substances inducing the production promoter such as lactose, cellulose, spent grain or sophorose. Temperature ranges and other conditions suitable for growth are known in the art (see, e.g., Bailey and Ollis 1986). In certain embodiments the pH of cell culture is between 3.5 and 7.5, between 4.0 and 7.0, between 4.5 and 6.5, between 5 and 5.5, or at 5.5. In certain embodiments, to produce an antibody the filamentous fungal cell or *Trichoderma* fungal cell is cultured at a pH range selected from 4.7 to 6.5; pH 4.8 to 6.0; pH 4.9 to 5.9; and pH 5.0 to 5.8.

In some embodiments, the protein which may be O-mannosylated is a heterologous protein, preferably a mammalian protein. In other embodiments, the heterologous protein is a non-mammalian protein.

In certain embodiments, the protein which may be O-mannosylated is a glycoprotein with N-glycan posttranslational modifications.

In certain embodiments, a mammalian protein which may be O-mannosylated is selected from an immunoglobulin, immunoglobulin or antibody heavy or light chain, a monoclonal antibody, a Fab fragment, an F(ab')2 antibody fragment, a single chain antibody, a monomeric or multimeric single domain antibody, a camelid antibody, or their antigen-binding fragments.

A fragment of a protein, as used herein, consists of at least 10, 20, 30, 40, 50, 60, 70, 80, 90, 100 consecutive amino acids of a reference protein.

As used herein, an "immunoglobulin" refers to a multimeric protein containing a heavy chain and a light chain covalently coupled together and capable of specifically combining with antigen. Immunoglobulin molecules are a large family of molecules that include several types of molecules such as IgM, IgD, IgG, IgA, and IgE.

As used herein, an "antibody" refers to intact immunoglobulin molecules, as well as fragments thereof which are capable of binding an antigen. These include hybrid (chimeric) antibody molecules (see, e.g., Winter et al. Nature 349:293-99225, 1991; and U.S. Pat. No. 4,816,567 226); F(ab')2 molecules; non-covalent heterodimers; dimeric and trimeric antibody fragment constructs; humanized antibody molecules (see e.g., Riechmann et al. Nature 332, 323-27, 1988; Verhoeyan et al. Science 239, 1534-36, 1988; and GB 2,276,169); and any functional fragments obtained from such molecules, as well as antibodies obtained through non-conventional processes such as phage display or transgenic mice. Preferably, the antibodies are classical antibodies with Fc region. Methods of manufacturing antibodies are well known in the art.

In further embodiments, the yield of the mammalian glycoprotein is at least 0.5, at least 1, at least 2, at least 3, at least 4, or at least 5 grams per liter.

In certain embodiments, the mammalian glycoprotein is an antibody, optionally, IgG1, IgG2, IgG3, or IgG4. In further embodiments, the yield of the antibody is at least 0.5, at least 1, at least 2, at least 3, at least 4, or at least 5 grams per liter. In further embodiments, the mammalian glycoprotein is an antibody, and the antibody contains at least 70%, at least 80%, at least 90%, at least 95%, or at least 98% of a natural antibody C-terminus and N-terminus without additional amino acid residues. In other embodiments, the mammalian glycoprotein is an antibody, and the antibody contains at least 70%, at least 80%, at least 90%, at least 95%, or at least 98% of a natural antibody C-terminus and N-terminus that do not lack any C-terminal or N-terminal amino acid residues.

In certain embodiments where the mammalian glycoprotein is purified from cell culture, the culture containing the mammalian glycoprotein contains polypeptide fragments that make up a mass percentage that is less than 50%, less than 40%, less than 30%, less than 20%, or less than 10% of the mass of the produced polypeptides. In certain preferred embodiments, the mammalian glycoprotein is an antibody, and the polypeptide fragments are heavy chain fragments and/or light chain fragments. In other embodiments, where the mammalian glycoprotein is an antibody and the antibody purified from cell culture, the culture containing the antibody contains free heavy chains and/or free light chains that make up a mass percentage that is less than 50%, less than 40%, less than 30%, less than 20%, or less than 10% of the mass of the produced antibody. Methods of determining the mass percentage of polypeptide fragments are well known in the art and include, measuring signal intensity from an SDS-gel.

In certain embodiments, where the protein with reduced O-mannosylation, e.g. an antibody, is purified from cell culture, the culture contains at least 70%, 80%, 90%, 95% or 100% of the proteins that is not O-mannosylated (mol %, as determined for example by MALDI TOF MS analysis, and measuring area or intensity of peaks as described in the Example 1 below).

In certain embodiments where the protein with at least one serine or threonine residue which may be O-mannosylated is purified from cell culture, and where the strain is a *Trichoderma* cell genetically engineered to produce complex N-glycans, the culture further comprises at least 5%, 10%, 15%, 20%, 25%, 30% of secreted complex neutral N-glycans (mol %) compared to total secreted neutral N-glycans (as measured for example as described in WO2012069593).

In other embodiments, the heterologous protein with reduced O-mannosylation, for example, the antibody, comprises the trimannosyl N-glycan structure Manα3[Manα6]Manβ4GlcNAcβ4GlcNAc. In some embodiments, the Manα3[Manα6]Manβ4GlcNAcβ4GlcNAc structure represents at least 20%, 30%; 40%, 50%; 60%, 70%, 80% (mol %) or more, of the total N-glycans of the heterologous protein with reduced O-mannosylation. In other embodiments, the heterologous protein with reduced O-mannosylation comprises the G0 N-glycan structure GlcNAcβ2Manα3[GlcNAcβ2Manα6]Manβ4GlcNAcβ4GlcNAc. In other embodiments, the non-fucosylated G0 glycoform structure represents at least 20%, 30%; 40%, 50%; 60%, 70%, 80% (mol %) or more, of the total N-glycans of the heterologous protein with reduced O-mannosylation. In other embodiments, galactosylated N-glycans represents less (mol %) than 0.5%, 0.1%, 0.05%, 0.01% of total N-glycans of the culture, and/or of the heterologous protein with reduced O-mannosylation, for example an antibody. In certain embodiments, the culture or the heterologous protein, for example an antibody, comprises no galactosylated N-glycans.

In certain embodiments, the heterologous (purified) protein is an antibody, a light chain antibody, a heavy chain antibody or a Fab, that comprises Man3, GlcNAcMan3, Man5, GlcNAcMan5, G0, core G0, G1, or G2 N-glycan structure as major glycoform and less than 35%, 20%, 17%, 15%, 13%, 12%, 11%, 10%, 9%, 8%, 7%, 6%, 5%, 4%, 3%, 2%, or 1%, or less than 0.5% of O-mannosylation level (as mole % as determined for example by MALDI TOF MS analysis, and measuring area or intensity of peaks as described in Example 1).

In a specific embodiment, the invention therefore relates to a method for producing an antibody having reduced O-mannosylation, comprising:

a. providing a PMT-deficient *Trichoderma* cell having
  i. a mutation that reduces endogenous protein O-mannosyltransferase activity as compared to parental strain which does not have such mutation and
  ii. a polynucleotide encoding a light chain antibody and a polynucleotide encoding a heavy chain antibody,
b. culturing the cell to produce said antibody, consisting of heavy and light chains, having reduced O-mannosylation.

In such specific embodiments of the methods related to the production of antibody, at least 70%, 80%, 90%, 95%, 97%, 98%, 99% or 100% of the produced antibody is not O-mannosylated (mol %, as determined for example by MALDI TOF MS analysis, and measuring area or intensity of peaks as described in Example 1.

In certain embodiments of any of the disclosed methods, the method includes the further step of providing one or more, two or more, three or more, four or more, or five or more protease inhibitors. In certain embodiments, the protease inhibitors are peptides that are co-expressed with the mammalian polypeptide. In other embodiments, the inhibitors inhibit at least two, at least three, or at least four proteases from a protease family selected from aspartic proteases, trypsin-like serine proteases, subtilisin proteases, and glutamic proteases.

In certain embodiments of any of the disclosed methods, the filamentous fungal cell or *Trichoderma* fungal cell also contains a carrier protein. As used herein, a "carrier protein" is portion of a protein that is endogenous to and highly secreted by a filamentous fungal cell or *Trichoderma* fungal cell. Suitable carrier proteins include, without limitation, those of *T. reesei* mannanase I (Man5A, or MANI), *T. reesei* cellobiohydrolase II (Cel6A, or CBHII) (see, e.g., Paloheimo et al Appl. Environ. Microbiol. 2003 December; 69(12): 7073-7082) or *T. reesei* cellobiohydrolase I (CBHI). In some embodiments, the carrier protein is CBH1. In other embodiments, the carrier protein is a truncated *T. reesei* CBH1 protein that includes the CBH1 core region and part of the CBH1 linker region. In some embodiments, a carrier such as a cellobiohydrolase or its fragment is fused to an antibody light chain and/or an antibody heavy chain. In some embodiments, a carrier-antibody fusion polypeptide comprises a Kex2 cleavage site. In certain embodiments, Kex2, or other carrier cleaving enzyme, is endogenous to a filamentous fungal cell. In certain embodiments, carrier cleaving protease is heterologous to the filamentous fungal cell, for example, another Kex2 protein derived from yeast or a TEV protease. In certain embodiments, carrier cleaving enzyme is overexpressed. In certain embodiments, the carrier consists of about 469 to 478 amino acids of N-terminal part of the *T. reesei* CBH1 protein GenBank accession No. EGR44817.1.

In certain embodiments, the filamentous fungal cell of the invention overexpress KEX2 protease. In an embodiment the heterologous protein is expressed as fusion construct comprising an endogenous fungal polypeptide, a protease site such as a Kex2 cleavage site, and the heterologous protein such as an antibody heavy and/or light chain. Useful 2-7 amino acids combinations preceding Kex2 cleavage site have been described, for example, in Mikosch et al. (1996) J. Biotechnol. 52:97-106; Goller et al. (1998) Appl Environ Microbiol. 64:3202-3208; Spencer et al. (1998) Eur. J. Biochem. 258:107-112; Jalving et al. (2000) Appl. Environ. Microbiol. 66:363-368; Ward et al. (2004) Appl. Environ. Microbiol. 70:2567-2576; Ahn et al. (2004) Appl. Microbiol. Biotechnol. 64:833-839; Paloheimo et al. (2007) Appl Environ Microbiol. 73:3215-3224; Paloheimo et al. (2003)

Appl Environ Microbiol. 69:7073-7082; and Margolles-Clark et al. (1996) Eur J Biochem. 237:553-560.

The invention further relates to the protein composition, for example the antibody composition, obtainable or obtained by the method as disclosed above.

In specific embodiment, such antibody composition obtainable or obtained by the methods of the invention, comprises at least 70%, 80%, 90%, 95%, or 100% of the antibodies that are not O-mannosylated (mol %, as determined for example by MALDI TOF MS analysis, and measuring area or intensity of peaks as described in Example 1). In other specific embodiments, such antibody composition further comprises as 50%, 60%, 70% or 80% (mole % neutral N-glycan), of the following glycoform:
 (i) Manα3[Manα6(Manα3)Manα6] Manβ4GlcNAβ4GlcNAc (Man5 glycoform);
 (ii) GlcNAcβ2Manα3[Manα6(Manα3)Manα6] Manβ4GlcNAβ4GlcNAc, or β4-galactosylated variant thereof;
 (iii) Manα6(Manα3)Manβ4GlcNAβ4GlcNAc;
 (iv) Manα6(GlcNAcβ2Manα3) Manβ4GlcNAβ4GlcNAc, or β4-galactosylated variant thereof: or,
 (v) complex type N-glycans selected from the G0, G1 or G2 glycoform.

In some embodiments the N-glycan glycoform according to iii-v comprises less than 15%, 10%, 7%, 5%, 3%, 1% or 0.5% or is devoid of Man5 glycan as defined in i) above.

The invention also relates to a method of reducing O-mannosylation level of a recombinant glycoprotein composition produced in a *Trichoderma* cell, said method consisting of using a *Trichoderma* cell having a mutation in a PMT gene wherein said PMT gene is either:
 a. PMT1 gene comprising the polynucleotide of SEQ ID NO:1,
 b. a functional homologous gene of PMT1 gene, which gene is capable of restoring parental O-mannosylation level by functional complementation when introduced into a *T. reesei* strain having a disruption in said PMT1 gene, or,
 c. a polynucleotide encoding a polypeptide having at least 50%, at least 60%, at least 70%, at least 90%, or at least 95% identity with SEQ ID NO:2, said polypeptide having protein O-mannosyltransferase activity.

In one specific embodiment of such method, said *Trichoderma* cell is *Trichoderma reesei*.

In another specific embodiment of such method, said recombinant glycoprotein comprises at least a light chain antibody or its fragments comprising at least one serine or threonine residue and with at least one N-glycan.

EXAMPLES

As more specifically exemplified in Example 2, after deletion of pmt1, almost 95% of purified mAb and 70% of Fab molecules no longer contained any O-mannose residues. In contrast, as exemplified in Examples 3 to 4, O-mannosylation level analysis performed on pmt2 and pmt3 deletion strains did not exhibit any appreciable reduction in O-mannosylation. Together with the titer and growth analysis set forth in Example 2, these results demonstrate that filamentous fungal cells, such as *Trichoderma* cells, can be genetically modified to reduce or suppress O-mannosylation activity, without adversely affecting viability and yield of produced glycoproteins. As such, pmt1 is identified a valuable target to reduce O-mannosylation of secreted proteins and to improve product quality of biopharmaceuticals produced by *Trichoderma reesei*.

Example 1: Pmt1 Deletion in a *Trichoderma reesei* Strain

This example demonstrates that pmt1 is a valuable target to reduce O-mannosylation of secreted proteins and to improve product quality of biopharmaceuticals produced by *Trichoderma reesei*.

Generation of Pmt1 Deletion Plasmids

Three different deletion plasmids (pTTv36, pTTv124, pTTv185) were constructed for deletion of the protein O-mannosyltransferase gene pmt1 (TreID75421). All the plasmids contain the same 5' and 3' flanking regions for correct integration to the pmt1 locus. The difference between the three plasmids is the marker used in the selection; pTTv36 contains a gene encoding acetamidase of *Aspergillus nidulans* (amdS), pTTv124 contains a loopout version (blaster cassette) of the amdS marker and pTTv185 a loopout version (blaster cassette) of a gene encoding orotidine-5'-monophosphate (OMP) decarboxylase of *T. reesei* (pyr4).

The third deletion construct, pTTv185, for the protein O-mannosyltransferase gene pmt1 (TreID75421) was designed to enable removal of the selection marker from the *Trichoderma reesei* genome after successful integration and thereby recycling of the selection marker for subsequent transformations. In this approach, the recycling of the marker, i.e. removal of pyr4 gene from the deletion construct, resembles so called blaster cassettes developed for yeasts (Hartl, L. and Seiboth, B., 2005, Curr Genet 48:204-211; and Alani, E. et al., 1987, Genetics 116:541-545). Similar blaster cassettes have also been developed for filamentous fungi including *Hypocrea jecorina* (anamorph: *T. reesei*) (Hartl, L. and Seiboth, B., 2005, Curr Genet 48:204-211).

The TreID number refers to the identification number of a particular protease gene from the Joint Genome Institute *Trichoderma reesei* v2.0 genome database. Primers for construction of deletion plasmids were designed either manually or using Primer3 software (Primer3 website, Rozen and Skaletsky (2000) *Bioinformatics Methods and Protocols: Methods in Molecular Biology*. Humana Press, Totowa, N.J., pp 365-386).

The principle of the blaster cassette using pyr4 as the marker gene is as follows: pyr4, encoding orotidine-5'-monophosphate (OMP) decarboxylase of *T. reesei* (Smith, J. L., et al., 1991, Current Genetics 19:27-33) is needed for uridine synthesis. Strains deficient for OMP decarboxylase activity are unable to grow on minimal medium without uridine supplementation (i.e. are uridine auxotrophs). The utilisation of 5-fluoroorotic acid (5-FOA) in generation of mutant strains lacking OMP decarboxylase activity (pyr4⁻ strains) is based on the conversion of 5-FOA to a toxic intermediate 5-fluoro-UMP by OMP decarboxylase. Therefore, cells which have a mutated pyr4 gene are resistant to 5-FOA, but in addition are also auxotrophic for uridine. The 5-FOA resistance can in principle result also from a mutation in another gene (pyr2, orotate phosphoribosyltransferase), and therefore the spontaneous mutants obtained with this selection need to be verified for the pyr4⁻ genotype by complementing the mutant with the pyr4 gene. Once mutated, the pyr4 gene can be used as an auxotrophic selection marker in *T. reesei*. In our blaster cassette pyr4 is followed by a 310 bp direct repeat of pyr4 5' untranslated region (5'UTR) and surrounded by 5' and 3' flanking regions of the gene to be deleted. Integration of the deletion cassette is selected via the pyr4 function. Removal of the pyr4 marker is then forced in the presence of 5-FOA by recombination between the two homologous regions (direct repeat of 5'UTR) resulting in looping out of the selection marker and enabling the utilisation of the same blaster cassette (pyr4 loopout) in successive rounds of gene deletions. After looping out, only the 310 bp sequence of 5'UTR remains in the locus.

Thus, the pyr4 selection marker and the 5' direct repeat (DR) fragment (310 bp of pyr4 5'UTR) were produced by PCR using plasmid containing a genomic copy of *T. reesei* pyr4 as a template. Both fragments contained 40 bp overlapping sequences needed to clone the plasmid with the loopout cassette using homologous recombination in yeast (see below). To enable possible additional cloning steps, an AscI digestion site was placed between the pyr4 marker and the 5' direct repeat and NotI sites to surround the complete blaster cassette.

1100 bp of 5' and 1000 bp of 3' flanking regions were selected as the basis of the pmt1 deletion plasmids. The flanking region fragments were produced by PCR using a *T. reesei* wild type strain QM6a (ATCC13631) as the template. For the yeast homologous recombination system used in cloning (see below), overlapping sequences for the vector and the selection marker were placed to the appropriate PCR-primers. To enable marker switch in the construct, NotI restriction sites were introduced between the flanking regions and the selection marker. PmeI restriction sites were placed between the vector and the flanking regions for removal of vector sequence prior to transformation into *T. reesei*. Vector backbone pRS426 was digested with restriction enzymes (EcoRI and XhoI).

First deletion plasmid for pmt1 (plasmid pTTv36, Table 2) used amdS, a gene encoding acetamidase of *Aspergillus nidulans*, as the marker. The marker cassette was digested from an existing plasmid pHHO1 with NotI. All fragments used in cloning were separated with agarose gel electrophoresis and correct fragments were isolated from the gel with a gel extraction kit (Qiagen) using standard laboratory methods.

To construct the first deletion plasmid pTTv36, the vector backbone and the appropriate marker and flanking region fragments were transformed into *Saccharomyces cerevisiae* (strain H3488/FY834). The yeast transformation protocol was based on the method for homologous yeast recombination described in the *Neurospora* knockouts workshop material of Colot and Collopy, (Dartmouth *Neurospora* genome protocols website), and the Gietz laboratory protocol (University of Manitoba, Gietz laboratory website). The plasmid DNA from the yeast transformants was rescued by transformation into *Escherichia coli*. A few clones were cultivated, plasmid DNA was isolated and digested to screen for correct recombination using standard laboratory methods. A few clones with correct insert sizes were sequenced and stored.

To clone the second pmt1 deletion plasmid (pTTv124, Table 2), the amdS marker was removed from the deletion plasmid pTTv36 with NotI digestion and replaced by another variant of the blaster cassette, amdS loopout cassette containing the amdS selection marker gene, followed by AscI restriction site and a 300 bp direct repeat of amdS 5'UTR. The amdS blaster cassette functions in a similar manner to the pyr4 blaster cassette. The clones containing the amdS blaster cassette are able to grow on acetamide as sole nitrogen source. On medium containing 5-fluoroacetamide (5-FAA) a functional amdS gene will convert 5-FAA to a toxic fluoroacetate and therefore, in the presence of 5-FAA, removal of amdS gene is beneficial to the fungus. Removal of amdS blaster cassette is enhanced via the 300 bp DRs in the cassette like in the pyr4 blaster cassette, which enables the amdS gene to loop out via single crossover between the two DRs. Resulting clones are resistant to 5-FAA and unable to grow on acetamide as the sole nitrogen source.

The fragments needed for the amdS blaster cassette were produced by PCR using a plasmid p3SR2 (Hynes M. J. et al, 1983, Mol. Cell. Biol. 3:1430-1439) containing a genomic copy of the amdS gene as the template. For the yeast homologous recombination system used in cloning (see above), overlapping sequences were placed to the appropriate PCR-primers. To enable marker switch in the construct, NotI restriction sites were kept between the flanking regions and the blaster cassette. Additional restriction sites FseI and AsiSI were introduced to the 5' end of amdS and an AscI site between amdS and amdS 5'DR. The plasmid pTTv124 was constructed using the yeast recombination system described above. The plasmid DNA from the yeast transformants was rescued by transformation into *Escherichia coli*. A few clones were cultivated, plasmid DNA was isolated and digested to screen for correct recombination using standard laboratory methods. A few clones with correct insert sizes were sequenced and stored.

To clone the third pmt1 deletion plasmid (pTTv185, Table 2), the amdS marker was removed from the deletion plasmid pTTv36 with NotI digestion and replaced by the pyr4 blaster cassette described above. The pyr4 blaster cassette was obtained from another plasmid with NotI digestion, ligated to NotI cut pTTv36 and transformed into *E. coli* using standard laboratory methods. A few transformants were cultivated, plasmid DNA isolated and digested to screen for correct ligation and orientation of the pyr4 blaster cassette using standard laboratory methods. One clone with correct insert size and orientation was sequenced and stored.

These deletion plasmids for pmt1 (pTTv36, pTTv124 and pTTv185) result in 2465 bp deletion in the pmt1 locus and cover the complete coding sequence of PMT1.

TABLE 2

Primers for generating deletion plasmids pTTv36, pTTv124 and pTTv185 for protein O-mannosyltransferase 1 (pmt1, TreID75421)

Deletion plasmid pTTv36 for pmt1 (TreID75421), vector backbone pRS426

| Primer | Sequence |
|---|---|
| 75421_5'F | CGATTAAGTTGGGTAACGCCAGGGTTTTCCCAGTCACGACGGTTT AAACGCTGCAGGGCGTACAGAACT (SEQ ID NO: 48) |
| 75421_5'R | ATCTCTCAAAGGAAGAATCCCTTCAGGGTTGCGTTTCCAGTGCGG CCGCGGCTCTAAAATGCTTCACAG (SEQ ID NO: 49) |

TABLE 2-continued

Primers for generating deletion plasmids pTTv36, pTTv124 and pTTv185 for protein O-mannosyltransferase 1 (pmt1, TreID75421)

| | |
|---|---|
| 75421_3'F | CGGTTCTCATCTGGGCTTGCTCGGTCCTGGCGTAGATCTAGCGG CCGCACGATGATGATGACAGCCAG (SEQ ID NO: 50) |
| 75421_3'R | GTGGAATTGTGAGCGGATAACAATTTCACACAGGAAACAGCGTTT AAACCGTCCAGCTCCCGCAGCGCC (SEQ ID NO: 51) |

Deletion plasmid pTTv124 for pmt1 (TreID75421), vector backbone pTTv36

| | |
|---|---|
| T282_75421_amds_5for | ATCGCTAACTGCTTTCTCTTCTGTGAAGCATTTTAGAGCCGCGGC CGCGGCCGGCCGCGATCGCCTAGATCTACGCCAGGACCG (SEQ ID NO: 52) |
| T283_amds_3rev_loop | CGGTCCTGGCGTAGATCTAGGGCGCGCCACTGGAAACGCAACC CTGAA (SEQ ID NO: 53) |
| T284_amds_loop_5for | TTCAGGGTTGCGTTTCCAGTGGCGCGCCCTAGATCTACGCCAGG ACCG (SEQ ID NO: 54) |
| T287_75421_loop_3rev | AGCATCATGACCGCCCCCTTCTGGCTGTCATCATCATCGTGCGG CCGCGATTATTGCACAAGCAGCGA (SEQ ID NO: 55) |

Deletion plasmid pTTv185 for pmt1 (TreID75421), vector backbone pTTv36

| Primer | Sequence |
|---|---|
| no new primers, pTTv36 digested with NotI and ligated with pyr4-loopout fragment obtained from another plasmid | |

Generation of Pmt1 Deletion Strains M403, M404, M406 and M407

To generate a pyr4 negative target strain suitable for the deletion of pmt1 using plasmid pTTv185, the MAB01 antibody producing strain M304 was subjected to selection in the presence of 5-fluoro-orotic acid in order to select for strains containing impaired pyr4 genes. The generation of the strain M304 is described in the International Patent Application No. PCT/EP2013/05012. *T. reesei* strain M304 comprises MAB01 light chain fused to *T. reesei* truncated CBH1 carrier with NVISKR Kex2 cleavage sequence, MAB01 heavy chain fused to *T. reesei* truncated CBH1 carrier with AXE1 [DGETVVKR] Kex2 cleavage sequence, Δpep1Δtsp1Δslp1, and overexpresses *T. reesei* KEX2.

Spores of M304 were spread onto minimal medium plates containing 20 g/l glucose, 2 g/l proteose peptone, 5 mM uridine and 1.5 g/l 5-FOA, pH 4.8. Some 5-FOA resistant colonies were streaked after 5-7 days onto plates described above with 1 ml/l Triton X-100 supplementation. A few clones were further purified to single cell clones via consecutive purification platings: a small piece of mycelia was picked to 0.8% NaCl—0.025% Tween 20-20% glycerol, suspended thoroughly by vortexing and filtrated through a cotton-filled pipette tip. Purified clones were sporulated on plates containing 39 g/l potato dextrose agarose. These clones were tested for uridine auxotrophy by plating spores onto minimal medium plates (20 g/l glucose, 1 ml/l Triton X-100, pH 4.8) with and without 5 mM uridine supplementation. No growth was observed on plates without uridine indicating the selected clones were putative pyr4⁻. Clones were stored for future use and one of them was designated with strain number M317.

Pmt1 was deleted from M317 (pyr4⁻ of the strain M304) using the pmt1 deletion cassette from plasmid pTTv185 described above. To remove the vector sequence, plasmid pTTv185 (Δpmt1-pyr4) was digested with PmeI+XbaI and the correct fragment was purified from an agarose gel using QIAquick Gel Extraction Kit (Qiagen). Approximately 5 μg of the pmt1 deletion cassette was used to transform strain M317. Preparation of protoplasts and transformation for pyr4 selection were carried out essentially according to methods in Penttila et al. (1987, Gene 61:155-164) and Gruber et al (1990, *Curr. Genet.* 18:71-76).

100 colonies were picked as selective streaks. 40 transformants were screened by PCR using the primers in Table 3 for the correct integration of the deletion cassette using standard laboratory methods. 12 putative deletion clones were purified to single cell clones. Purified clones were rescreened for integration and for deletion of pmt1 ORF using primers on Table 5. Four clones (in duplicate) were pure disruptants (i.e. no signal with ORF primers).

TABLE 3

Primers for screening integration of deletion cassette pTTv185 and for deletion of protein O-mannosyltransferase 1 (pmt1, TreID75421) from M317.

| Primer | Sequence |
|---|---|
| T296_75421_5int | TATGGCTTTAGATGGGGACA (SEQ ID NO: 56) |
| T027_Pyr4_orf_start_rev | TGCGTCGCCGTCTCGCTCCT (SEQ ID NO: 57) |
| T061_pyr4_orf_screen_2F | TTAGGCGACCTCTTTTTCCA (SEQ ID NO: 58) |

TABLE 3-continued

Primers for screening integration of deletion cassette pTTv185 and for deletion of protein O-mannosyltransferase 1 (pmt1, TreID75421) from M317.

| Primer | Sequence |
|---|---|
| T297_75421_3int | CCTGTATCGTCCTGTTCC (SEQ ID NO: 59) |
| T359_pmt1_orf_for | GCGCCTGTCGAGTCGGCATT (SEQ ID NO: 60) |
| T360_pmt1_orf_rev | CACCGGCCATGCTCTTGCCA (SEQ ID NO: 61) |
| T756_pmt1_orf_for2 | CAAGGTGCCCTATGTCGC (SEQ ID NO: 62) |
| T757_pmt1_orf_rev2 | GATCGGGTCAGGACGGAA (SEQ ID NO: 63) |

Deletion of pmt1 was verified by Southern analyses. DNA for Southern analyses was extracted with Easy-DNA kit for genomic DNA isolation (Invitrogen) essentially according to the manufacturer's instructions.

Southern analyses were essentially performed according to the protocol for homologous hybridizations in Sambrook et al. (1989, Molecular Cloning: A laboratory manual. 2$^{nd}$ Ed., Cold Spring Harbor Laboratory Press) using radioactive labeling ($^{32}$P-dCTP) and DecaLabel Plus kit (Fermentas). Southern digestion schemes were designed using Geneious Pro software (Geneious website). Fragments for probes were produced by PCR using the primers listed in Table 4 using a *T. reesei* wild type strain QM6a (ATCC13631) as the template. PCR products were separated with agarose gel electrophoresis and correct fragments were isolated from the gel with a gel extraction kit (Qiagen) using standard laboratory methods.

TABLE 4

Primers for production of probe fragments used in Southern analyses of protein O-mannosyltransferase 1 (pmt1, TreID75421) deletion strains.

| Primer | Sequence |
|---|---|
| T635_pmt1_5f_for | AGCCTGTCTGAGGGACGG (SEQ ID NO: 64) |
| T636_pmt1_5f_rev | CAAGGTCGAGATTCGGCA (SEQ ID NO: 65) |
| T637_pmt1_3f_for | CAGAAGGGGGCGGTCAT (SEQ ID NO: 66) |
| T638_pmt1_3f_rev | GTCCCAGCTCCCGCTCT (SEQ ID NO: 67) |
| T359_pmt1_orf_for | GCGCCTGTCGAGTCGGCATT (SEQ ID NO: 68) |
| T360_pmt1_orf_rev | CACCGGCCATGCTCTTGCCA (SEQ ID NO: 69) |

None of the clones hybridised with pmt1 ORF probe (FIG. 1A) indicating successful deletion of pmt1. Analyses using 5' and 3' flank probes revealed that four of the clones were single integrants (FIGS. 1B and 1C; 26-8A and B, 26-21A and B). Four clones gave additional signals and thus indicated multiple integration of the deletion cassette. Four pure clones (with and without additional copies of the deletion cassette) have been stored for future use (M403; 26-8A, M404; 26-19A, M406; 26-168 and M407; 26-198).

Example 2 Analyses of ΔPmt1 Strains M403, M404, M406 and M407

Shake flask cultivation of *T. reesei* M304 and eight pmt1 deletion strains (26-8A (M403), 26-8B, 26-16A, 26-16B (M406), 26-19A (M404), 26-19B (M407), 26-21A, 26-21B) was carried out in *Trichoderma* minimal medium with 40 g/l lactose, 20 g/l spent grain extract, 100 mM PIPPS, 9 g/l casamino acids, pH 5.5 at +28° C., 200 rpm. Samples were collected on days 3, 5, 7 and 10 by vacuum filtration. Supernatant samples were stored to −20° C. (antibody and glycan analyses) or used in pH determinations. Mycelia for cell dry weight determinations were rinsed once with DDIW and dried at +100° C. for 20-24 h. Mycelia for genomic DNA extraction were rinsed once with DDIW and stored to −20° C.

O-mannosylation status analysis was performed to shake flask cultivations of *T. reesei* M304, eight pmt1 disruptants (pTTv185: 26-8A, 26-8B, 26-16A, 26-16B, 26-19A, 26-19B, 26-21A, 26-21B). All were cultivated in TrMM—40 g/l lactose—20 g/l SGE—100 mM PIPPS—9 g/l casamino acids, pH 5.5 at +28° C. and samples were taken on time point days 3, 5, 7 and 10.

MAB01 antibody from each sample from day 7 was purified from supernatants using Protein G HP MultiTrap 96-well plate (GE Healthcare) according to manufacturer's instructions. The antibody was eluted with 0.1 M citrate buffer, pH 2.6 and neutralized with 2 M Tris, pH 9. The concentration was determined via UV absorbance in spectrophotometer against MAB01 standard curve. For O-mannosylation analysis, 10 μg of protein was incubated in 6 M Guanidinium HCl for 30 minutes at +60° C. after which 5 μl of fresh 0.1 M DTT was added and incubated again as above. The samples were purified using Poros R1 96-well plate and the resulting light chains were analysed using MALDI-TOF MS. All were made as duplicates.

Figure 2:
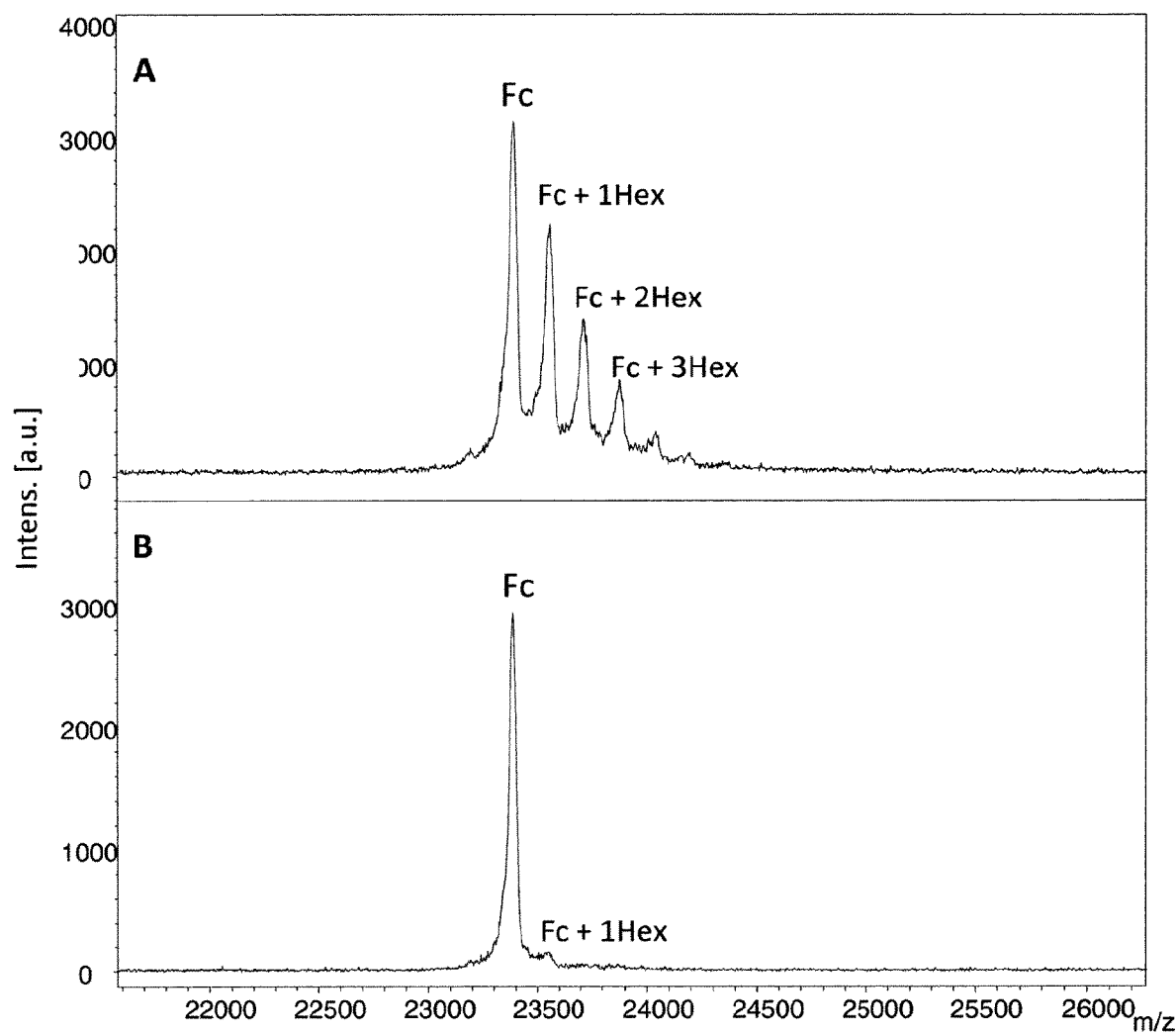
FIG. 2 depicts a spectra of light chain of flask cultured parental *T. reesei* strain M317 (pyr4⁻ of M304) (A) and Δpmt1 disruptant clone 26-8A (B), day 7.

In flask cultures the O-mannosylation status in pmt1 disruptants was remarkably changed; all Δpmt1 disruptants looked the same—nearly complete loss of O-mannosylation in MAB01 LC (FIG. 2: Spectra of light chain of flask cultured parental *T. reesei* strain M317 (pyr4⁻ of M304) (A) and Δpmt1 disruptant clone 26-8A (B), day 7).

Fermentation of Δpmt1 Strain M403

Fermentation was carried out with Δpmt1 strain M403 (clone 26-8A; pTTv185 in M317). Fermentation culture medium contained 30 g/l glucose, 60 g/l lactose, 60 g/l whole spent grain at pH 5.5. Lactose feed was started after glucose exhaustion. Growth temperature was shifted from +28° C. to +22° C. after glucose exhaustion. Samples were collected by vacuum filtration. Supernatant samples were stored to −20° C.

Figure 3:
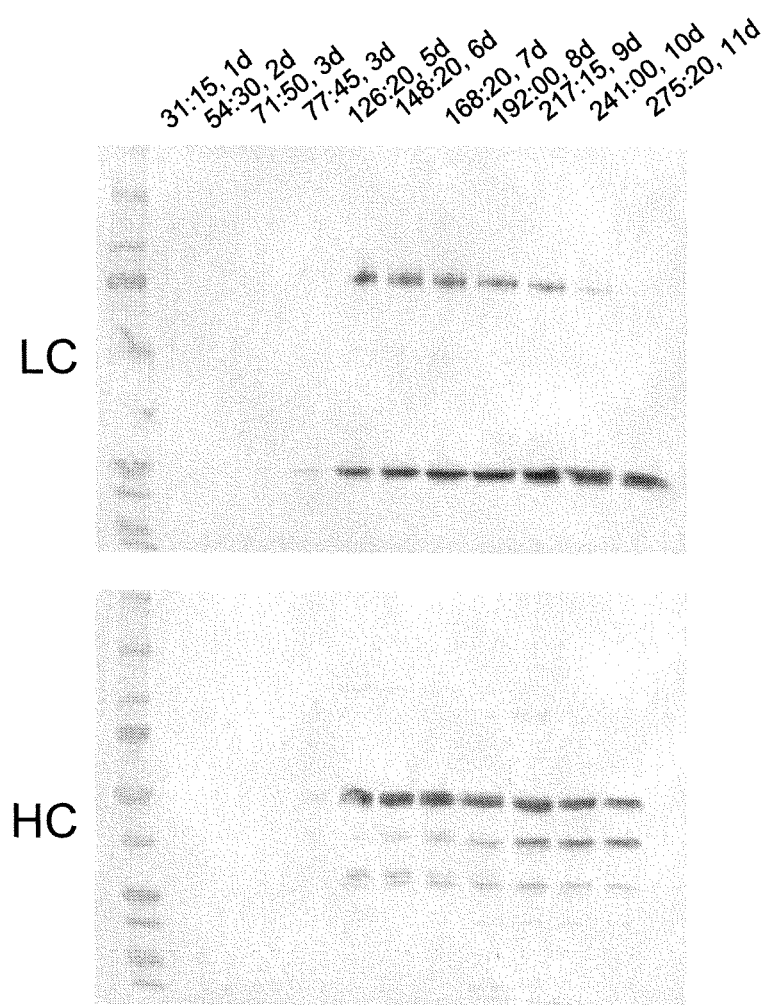
FIG. 3 depicts results for Western analyses of *Trichoderma reesei* pmt1 deletion strain M403 from fed-batch fermentation. Upper panel: MAB01 light chain, lower panel: MAB01 heavy chain. 0.1 µl of supernatant was loaded on each lane.

In FIG. 3 is shown the Western analyses of supernatant samples. MAB01 heavy and light chains were detected from supernatant after day three. Despite the deletion of pmt1, that could also reduce O-mannosylation of the linker and thus aid KEX2 cleavage, substantial amount of light chain remains attached to the carrier in the early days of the fermentation. At later stages, the cleavage is more complete but the yield may be affected by the degradation of the heavy chain. Results on antibody titres (Table 7 below) indicate fairly steady expression between days 7 to 10. In this fermentation the pmt1 deletion strain produced approximately equal antibody levels as the parental strain. Higher titres were obtained when the same strain was fermented using a different fermenter.

Figure 4:
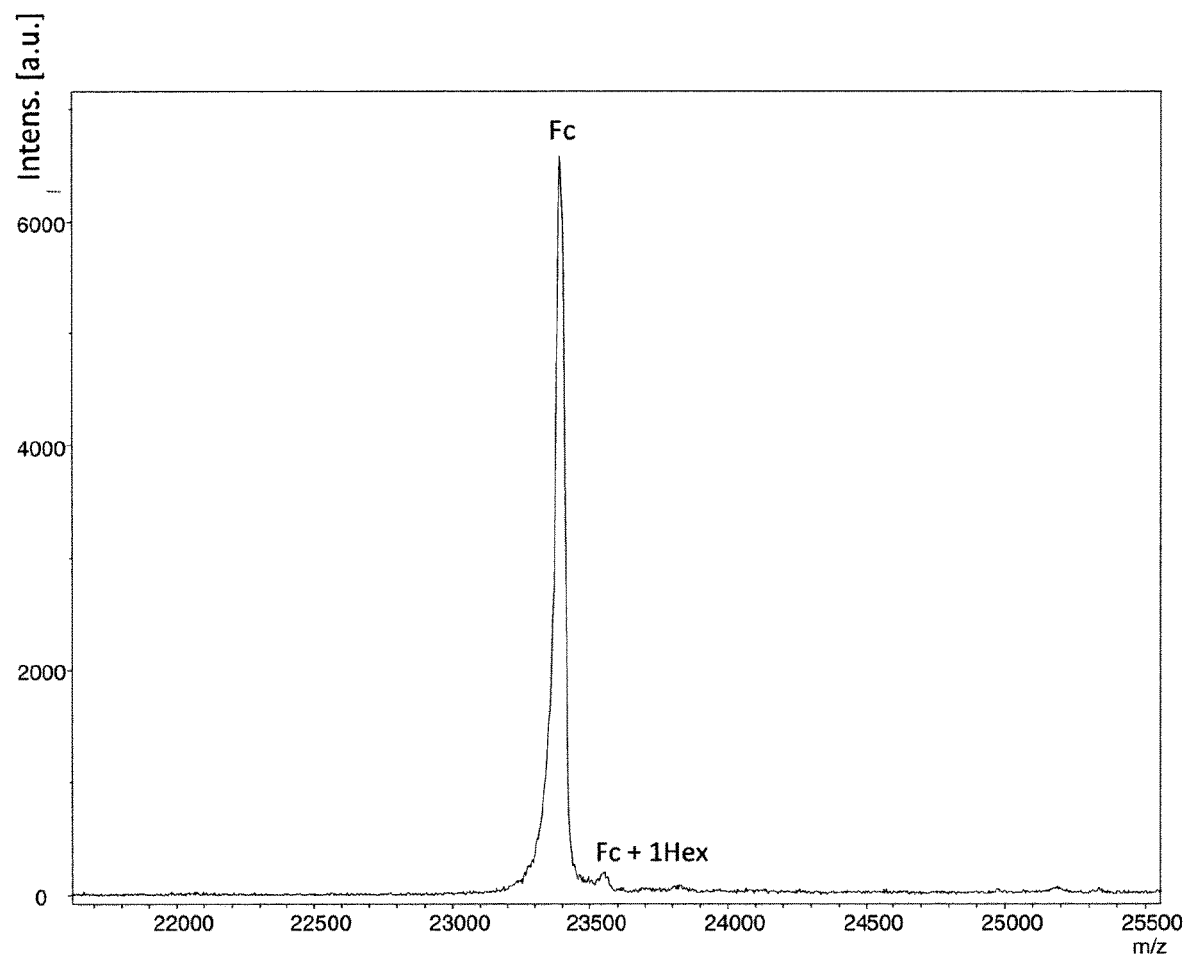
FIG. 4 depicts a spectrum of light chain of fermenter cultured *T. reesei* strain M403 (pmt1 deletion strain of MAB01 antibody producing strain, clone 26-8A), day 7.

M403 (clone 26-8A) was cultivated in fermenter in TrMM, 30 g/l glucose, 60 g/l lactose, 60 g/l spent grain, pH 5.5 with lactose feed. Samples were harvested on days 2, 3 and 5-11. O-mannosylation level analysis was performed as to flask cultures. The O-mannosylation status was greatly decreased also in fermenter culture (FIG. 4, Table 5).

The O-mannosylation level was calculated from average of area and intensity (Table 5). Area (Table 6) seems to give more commonly higher rate of non-O-glycosylated LC than intensity (Table 7). In all time points the O-mannosylation level was below 5%.

TABLE 7

The percentages of intensity values of three parallel samples from fermenter cultured M403 from day 7.

|  | Intensity average | Std |
|---|---|---|
| LC | 96.3 | 0.57 |
| LC + Hex | 3.7 | 0.57 |

No negative effects of strain growth characteristic and secretion capacity were observed. The strain M403 grew well and produced increased amount of antibody in function of time in fermenter culture. The best titer was obtained from day 10 (Table 8). On day 11 the titer is decreased.

TABLE 8

Titers from fermenter cultured MAB01 producing strain M403. The antibody was purified using Protein G 96-well plate.

| Time point | Days cultured | Titer g/l |
|---|---|---|
| 54:30 hours | 2 | 0.04 |
| 71:50 hours | 3 | 0.04 |
| 77:45 hours | 3 | 0.07 |
| 126:20 hours | 5 | 0.91 |
| 148:20 hours | 6 | 1.23 |
| 168:20 hours | 7 | 1.47 |
| 192:00 hours | 8 | 1.50 |
| 217:15 hours | 9 | 1.35 |
| 241:00 hours | 10 | 1.52 |
| 275:20 hours | 11 | 1.06 |

Deletion of pmt1 diminished dramatically MAB01 O-mannosylation; the amount of O-mannosylated LC was ~61% in parental strain, 3% in the best Δpmt1 clone in shake flask culture and practically 0% in fermenter culture in time point day 9.

Deletion of Pmt1 in a Fab Expressing *Trichoderma reesei* Strain

The pmt1 disruption cassette (pmt1 amdS) was released from its backbone vector pTTv124 described above by restriction digestion and purified through gel extraction.

TABLE 5

O-mannosylation status of T. reesei strain M403 (pmt1 deletion strain of MAB01 antibody producing strain, clone 26-8A) from fermenter culture. Percentages calculated from area and intensity of single charged signals. In time point d 9 both samples gave 100% to LC, LC + Hex1 being practically absent.

|  | 3 d | 5 d | | 6 d | | 7 d | | d 8 | d 9 | d 10 | | d 11 | |
|---|---|---|---|---|---|---|---|---|---|---|---|---|---|
|  | Average | Average | Std | Average | Std | Average | Std | Average | Average | Average | Std | Average | Std |
| LC | 95.8 | 96.8 | 0.30 | 97.5 | 0.29 | 97.4 | 0.36 | 97.3 | 100.0 | 96.6 | 0.2 | 95.5 | 0.11 |
| LC + Hex | 4.2 | 3.2 | 0.30 | 2.5 | 0.29 | 2.6 | 0.36 | 2.7 | 0.0 | 3.4 | 0.2 | 4.5 | 0.11 |

TABLE 6

The percentages of area values of three parallel samples from fermenter cultured M403 from day 7.

|  | Area average | Std |
|---|---|---|
| LC | 98.5 | 0.15 |
| LC + Hex | 1.5 | 0.15 |

Using protoplast transformation the deletion cassette was introduced to *T. reesei* strains M304 (3-fold protease deletion strain expressing MAB01) and M307 (4-fold protease deletion strain Δpep1 Δtsp1 Δslp1 Δgap1, also described in PCT/EP2013/050126 that has been transformed to express a Fab). Transformants were plated to acetamidase selective medium (minimal medium containing acetamide as the sole carbon source).

Transformants were screened by PCR for homologous integration of the acetamidase marker to the pmt1 locus using a forward primer outside the 5' flanking region fragment of the construct and the reverse primer inside the AmdS selection marker (5' integration) as well as a forward primer inside the AmdS selection marker and a reverse primer outside the 3' flanking region fragment (3' integration). Three independent transformants of each transformation (MAB01 and Fab expressing strains), which gave PCR results displaying correct integration of the construct to the pmt1 locus were selected for single spore purification to obtain uninuclear clones. Proper integration of the disruption cassette was reconfirmed by PCR using the same primer combinations as described above and the absence of the pmt1 gene was verified by using a primer combination targeted to the pmt1 open reading frame. Correct integration of the disruption cassette was additionally verified for all clones applying Southern hybridization. Digested genomic DNA of the three clones as well as the parental strain were probed against the 5' and 3' flanks of the pmt1 gene to confirm modification of the pmt1 locus as expected. Furthermore, the blotted DNA was hybridized with a probe specific to the pmt1 open reading frame in order to substantiate the absence of pmt1.

MAB01 and Fab Expression for O-Mannosylation Analysis

To evaluate the impact of pmt1 deletion on O-mannosylation levels of mAb and Fab molecules, strains were grown in batch fermentations for 7 days, in media containing 2% yeast extract, 4% cellulose, 4% cellobiose, 2% sorbose, 5 g/L KH2PO4, and 5 g/L (NH4)2SO4. Culture pH was controlled at pH 5.5 (adjusted with NH4OH). The starting temperature was 30° C., which was shifted to 22° C. after 48 hours. mAb fermentations (strains M304, M403, M406 and M407) were carried out in 4 parallel 2 L glas reactor vessels (DASGIP) with a culture volume of 1 L and the Fab fermentation (TR090#5) was done in a 15 L steel tank reactor (Infors) with a culture volume of 6 L. Fab strains (TR090#5, TR090#3, TR090#17) were additionally cultured in shake flasks for 4 days at 28° C. Main media components were 1% yeast extract, 2% cellobiose, 1% sorbose, 15 g/L KH2PO4 and 5 g/L (NH4)2SO4 and the pH was uncontrolled (pH drops from 5.5 to <3 during a time course of cultivation). Culture supernatant samples were taken during the course of the runs and stored at −20° C. Samples were collected daily from the whole course of these cultivations, and production levels were analyzed by affinity liquid chromatography. Samples with maximum production levels were subject to purification and further O-mannosylation analysis.

Analysis of O-Mannosylation on Fab and mAb

O-mannosylation was analyzed on mAb and Fab molecules expressed from both, the pmt1 deletion and parental strains. The mAb and Fab was purified from culture supernatants using Lambda Select Sure and CaptureSelect Fab Lambda (BAC) affinity chromatography resin, respectively, applying conditions as described by the manufactures protocols. Both purified molecules including, the purified mAb and Fab were subjected to RP-LC-QTOF-MS either as intact and/or reduced/alkylated samples.

For intact analysis, an equivalent of 20 µg protein was injected onto the column. For reduced/alkylated analyses of mAb, an equivalent of 100 µg protein was deglycosylated using PNGase-F enzyme, reduced using DTT and alkylated using iodoacetamide prior to LC-MS analysis. For reduced/alkylated analyses of Fab, an equivalent of 100 µg protein was reduced with DTT and alkylated with iodoacetamide prior to LC-MS analysis. 6 µg of the reduced/alkylated sample were injected onto the column. Reversed-phase chromatographic separation was carried out on a 2.1×150 mm Zorbax C3 column packed with 5 µm particles, 300 Å pore size the eluents were: eluent A 0.1% TFA in water and eluent B 0.1% TFA in 70% IPA, 20% ACN, 10% water. The column was heated at 75° C. and the flow rate was 200 µL/min. The gradient used for the sample separation is shown in Table 9.

TABLE 9

HPLC gradient used for intact and reduced/alkylated samples

| Time | % B | Flow (mL/min) |
|------|------|---------------|
| 0 | 10 | 0.1 |
| 0.1 | 10 | 0.2 |
| 2 | 10 | 0.2 |
| 4 | 28 | 0.2 |
| 30 | 36.4 | 0.2 |
| 31 | 100 | 0.2 |
| 34 | 100 | 0.2 |
| 35 | 10 | 0.2 |
| 40 | 10 | 0.2 |

The HPLC was directly coupled with a Q-TOF Ultima mass spectrometer (Waters, Manchester, UK). The ESI-TOF mass spectrometer was set to run in positive ion mode. The data evaluation of intact and reduced/alkylated analyses was performed using MassLynx analysis software (Waters, Manchester, UK). The deconvolution of the averaged mass spectra from the main UV signals was carried out using the MaxEnt algorithm, a part of the MassLynx analysis software (Waters, Manchester, UK). The deconvolution parameters were the following: "max numbers of iterations" are 8; resolution is 0.1 Da/channel; Uniform Gaussian—width at half height is 1 Da for intact and 0.5 for the reduced chains and minimum intensity ratios are left 30% and right 30%. The estimated level of O-mannosylation (%) was determined using the peak signal height after deconvolution. The observed O-mannosylation levels (%) of mAbs and Fabs from independent pmt1 deletion strains are compared to the ones of the respective parental wild-type strains in Tables 10 and 11.

TABLE 10

O-mannosylation level [%] of Fabs from different strains

| | Strain | | | |
|---|---|---|---|---|
| Sample | Parental M307 | TR090#5 | TR090#3 | TR090#17 |
| Intact Fab | 70.1 | 34.2 | 34.3 | 34.7 |
| LC | 58.8 | 10.4 | 10.1 | 10.8 |
| HC | 42.9 | 26.1 | 25.9 | 25.8 |

TABLE 11

O-mannosylation level [%] of MAB01 from different pmt1 deficient strains M403, M406 and M407. Parental strain is M304

| | Strain in yeast extract medium | | | |
|---|---|---|---|---|
| Sample | Parental | M403 | M406 | M407 |
| LC | 50.7 | 5.7 | 5.8 | 5.8 |
| HC | 4.8 | Not detected | Not detected | Not detected |

The O-mannosylation level was found to be 70% on intact Fab derived from the parental strain and reduced to ~34% in all three pmt1 deletion strains. The transfer of mannoses was more efficiently diminished on the Fab light chains (10% of residual O-mannosylation on light chains obtained from pmt1 deletion strains vs. 59% for the parental strain), as compared to the heavy chains, for which it decreased from 43% to ~26%.

The O-mannosylation level was found to be 50% on the light chain of mAb derived from parental strains and reduced to 5.7-5.8% in all three pmt1 deletion strains. The O-mannosylation level was found to be 4.8% on the heavy chain of mAb derived from parental strains and was completely reduced (below the limit of detection by LC-MS) in all three pmt1 deletion strains.

In conclusion, after deletion of pmt1, almost 95% of purified mAb and 70% of Fab molecules did no longer contain any O-mannose residues. Therefore, pmt1 is a valuable target to reduce O-mannosylation of secreted proteins and to improve product quality of biopharmaceuticals produced by *Trichoderma reesei*.

Example 3: Pmt2 Deletion in a *Trichoderma reesei* Strain

Generation of Pmt2 Deletion Plasmids

Three different deletion plasmids (pTTv34, pTTv122, pTTv186) were constructed for deletion of the protein O-mannosyltransferase gene pmt2 (TreID22005). All the plasmids contain the same 5' and 3' flanking regions for correct integration to the pmt2 locus. The difference between the three plasmids is the marker used in the selection; pTTv34 contains a gene encoding acetamidase of *Aspergillus nidulans* (amdS), pTTv122 contains a loopout version (blaster cassette) of the amdS marker and pTTv186 a loopout version (blaster cassette) of a gene encoding orotidine-5'-monophosphate (OMP) decarboxylase of *T. reesei* (pyr4).

1100 bp of 5' and 1000 bp of 3' flanking regions were selected as the basis of the second protein O-mannosyltransferase gene, pmt2 (TreID22005), deletion plasmids. The construction of the first plasmid for this gene was carried out essentially as described for pmt1 in Example 1. As for pmt1, the first deletion plasmid for pmt2 (plasmid pTTv34, Table 12) used amdS, a gene encoding acetamidase of *Aspergillus nidulans*, as the selection marker.

Like for pmt1 in Example 1, to clone the second deletion plasmid, pTTv122 (Table 12), the amdS marker was removed from the deletion plasmid pTTv34 with NotI digestion and replaced by amdS blaster cassette for which the fragments were produced by PCR (see Example 1 above for details). The plasmid pTTv122 was constructed using the yeast recombination system described in Example 1. The plasmid DNA from the yeast transformants was rescued by transformation into *Escherichia coli*. A few clones were cultivated, plasmid DNA was isolated and digested to screen for correct recombination using standard laboratory methods. A few clones with correct insert sizes were sequenced and stored.

The third deletion plasmid for pmt2, pTTv186 (Table 12) was cloned like the third plasmid for pmt1; the amdS blaster cassette was removed from the deletion plasmid pTTv122 with NotI digestion and replaced by the pyr4 blaster cassette described in Example 1. The pyr4 blaster cassette was obtained from another plasmid with NotI digestion, ligated to NotI cut pTTv122 and transformed into *E. coli* using standard laboratory methods. A few transformants were cultivated, plasmid DNA isolated and digested to screen for correct ligation and orientation of the pyr4 blaster cassette using standard laboratory methods. One clone with correct insert size and orientation was sequenced and stored. These deletion plasmids for pmt2 (pTTv34, pTTv122 and pTTv186, Table 12) result in 3186 bp deletion in the pmt2 locus and cover the complete coding sequence of PMT2.

TABLE 12

Primers for generating deletion plasmids pTTv34, pTTv122 and pTTv186 for protein O-mannosyltransferase 2 (pmt2, TreID22005).

| Deletion plasmid pTTv34 for pmt2 (TreID22005), vector backbone pRS426 | |
|---|---|
| Primer | Sequence |
| 22005_5'F | CGATTAAGTTGGGTAACGCCAGGGTTTTCCCAGTCACGACGGTTTAAACGTTTCAGGTACCAACACCTG (SEQ ID NO: 70) |
| 22005_5'R | ATCTCTCAAAGGAAGAATCCCTTCAGGGTTGCGTTTCCAGTGCGGCCGCGGCGAAGAGTCTGGCGGGGA (SEQ ID NO: 71) |
| 22005_3'F | CGGTTCTCATCTGGGCTTGCTCGGTCCTGGCGTAGATCTAGCGGCCGCAAGAGGATGGGGGTAAAGCT (SEQ ID NO: 72) |
| 22005_3'R | GTGGAATTGTGAGCGGATAACAATTTCACACAGGAAACAGCGTTTAAACGAGGAGGACTCGTGAGTTAT (SEQ ID NO: 73) |
| Deletion plasmid pTTv122 for pmt2 (TreID22005), vector backbone pTTv34 | |
| T280_22005_amds_5for | GCGCCCTTCCGCCTCGACAATCCCCGCCAGACTCTTCGCCGCGGCCGCGGCCGGCCGCGATCGCCTAGATCTACGCCAGGACCG (SEQ ID NO: 74) |
| T283_amds_3rev_loop | CGGTCCTGGCGTAGATCTAGGGCGCGCCACTGGAAACGCAACCCTGAA (SEQ ID NO: 75) |
| T284_amds_loop_5for | TTCAGGGTTGCGTTTCCAGTGGCGCGCCCTAGATCTACGCCAGGACCG (SEQ ID NO: 76) |

TABLE 12-continued

Primers for generating deletion plasmids pTTv34, pTTv122 and pTTv186 for protein O-mannosyltransferase 2 (pmt2, TreID22005).

| | |
|---|---|
| T285_22005_loop_3rev | GAGCTGGCCAGAAAAGACCAAGCTTTACCCCCATCCTCTTGCG GCCGCGATTATTGCACAAGCAGCGA (SEQ ID NO: 77) |

Deletion plasmid pTTv186 for pmt2 (TreID22005), vector backbone pTTv122

| Primer | Sequence |
|---|---|
| no new primers, pTTv122 digested with NotI and ligated with pyr4-loopout fragment from another plasmid | |

Generation of Pmt2 Deletion Strains M338, M339 and M340

To remove vector sequence plasmid pTTv122 (Δpmt2-amdS) was digested with PmeI+XbaI and the 5.2 kb fragment purified from agarose gel using QIAquick Gel Extraction Kit (Qiagen). Approximately 5 μg of the pmt2 deletion cassette was used to transform the strain M124 (M124 strain is described in WO2012/069593). Protoplast preparation and transformation were carried out essentially according to Penttilä et al., 1987, Gene 61:155-164 and Gruber et al, 1990, Current Genetics 18:71-76 for amdS selection.

120 colonies were picked as selective streaks. 10 transformants were screened by PCR using the primers in Table 13 for the correct integration of the deletion cassette using standard laboratory methods. Five putative deletion clones were purified to single cell clones. Purified clones (two parallel from each) were rescreened for correct integration and for deletion of pmt2 ORF (primers on Table 13). Five clones were selected for Southern analyses.

TABLE 13

Primers for screening integration of deletion cassette pTTv122 and for deletion of protein O-mannosyltransferase 2 (pmt2, TreID22005) from M124.

| Primer | Sequence |
|---|---|
| T288_22005_5int | ACGAGTTGTTTCGTGTACCG (SEQ ID NO: 78) |
| T020_Amds_rev2 | CTTTCCATTCATCAGGGATGG (SEQ ID NO: 79) |
| T021_amds_end_fwd | GGAGACTCAGTGAAGAGAGG (SEQ ID NO: 80) |
| T289_22005_3int | ATGTTGCAGTTGCGAAAG (SEQ ID NO: 81) |
| T290_22005_5orf | CCCTCGTCGCAGAAAAGATG (SEQ ID NO: 82) |
| T291_22005_3orf | AGCCTCCTTGGGAACCTCAG (SEQ ID NO: 83) |

Deletion of pmt2 was verified by Southern analyses. DNA for Southern analyses was extracted with Easy-DNA kit for genomic DNA isolation (Invitrogen) essentially according to the manufacturer's instructions.

Southern analyses were essentially performed as described in Example 1. Fragments for probes were produced by PCR using the primers listed in Table 14 using a *T. reesei* strain M124 as the template for the ORF probe and plasmid pTTv122 for the 5' and 3' flank probes. PCR products were separated with agarose gel electrophoresis and correct fragments were isolated from the gel with a gel extraction kit (Qiagen) using standard laboratory methods.

TABLE 14

Primers for production of probe fragments used in Southern analyses of protein O-mannosyltransferase 2 (pmt2, TreID22005) deletion strains.

| Primer | Sequence |
|---|---|
| T639_22005 5' flank probe F | CTTAGTGCGGCTGGAGGGCG (SEQ ID NO: 84) |
| T640_22005 5' flank probe R | GGCCGGTTCGTGCAACTGGA (SEQ ID NO: 85) |
| T641_22005 3' flank probe F | GGCCGCAAGAGGATGGGGGT (SEQ ID NO: 86) |
| T642_22005 3' flank probe R | TCGGGCCAGCTGAAGCACAAC (SEQ ID NO: 87) |
| T643_22005 orf 5' probe | TTGAGGAACGGCTGCCTGCG (SEQ ID NO: 88) |
| T644_22005 orf 3' probe | CGATGGCTCCGTCATCCGCC (SEQ ID NO: 89) |

Three of the clones did not hybridise with pmt2 ORF probe (Data not shown) indicating successful deletion of pmt2. Analyses using 5' and 3' flank probes revealed that the same three clones were single integrants (Data not shown). The two other clones (19-35A and 19-40B) gave signals corresponding to parental strain M124. Three pure clones have been stored for future use (M338; 19-7B, M339; 19-22B and M340; 19-39B).

Analyses of Δpmt2 Strains M338, M339 and M340

Shake flask cultivation of T. reesei strain M124 and the pmt2 deletion strains (19-7B/M338, 19-22B/M339 and 19-39B/M340) was carried out in Trichoderma minimal medium with 40 g/l lactose, 20 g/l spent grain extract, 100 mM PIPPS, pH 5.5 with and without 1 M sorbitol as osmotic stabiliser at +28° C., 200 rpm. Samples were collected on days 3, 5 and 7 by vacuum filtration. Supernatant samples were stored to −20° C. (antibody and glycan analyses) or used in pH determinations. Mycelia for cell dry weight determinations were rinsed once with DDIW and dried at +100° C. for 20-24 h. Mycelia for genomic DNA extraction were rinsed once with DDIW and stored to −20° C.

Generation of Pmt2 Deletion Strains M452, M453 and M454

Generation of M317 is described in Example 1 above.

To remove vector sequence plasmid pTTv186 (Δpmt2-pyr4) was digested with PmeI+XbaI and the 4.1 kb fragment purified from agarose gel using QIAquick Gel Extraction Kit (Qiagen). Approximately 5 μg of the pmt2 deletion cassette was used to transform M317.

Protoplast preparation and transformation were carried out essentially according to Penttilä et al., 1987, Gene 61:155-164 and Gruber et al, 1990, Current Genetics 18:71-76 for pyr4 selection.

100 colonies were picked as selective streaks. 20 transformants were screened by PCR using the primers in Table 15 for the correct integration of the deletion cassette using standard laboratory methods. Nine putative deletion clones were purified to single cell clones. Purified clones were rescreened for 5' integration and for deletion of pmt2 ORF (primers on Table 14). Three clones were pure deletants (i.e. no signal with ORF primers).

TABLE 15

Primers for screening integration of deletion cassette pTTv186 and for deletion of protein O-mannosyltransferase 2 (pmt2, TreID22005) from M317.

| Primer | Sequence |
| --- | --- |
| T288_22005_5int | ACGAGTTGTTTCGTGTACCG (SEQ ID NO: 90) |
| T027_Pyr4_orf_start_rev | TGCGTCGCCGTCTCGCTCCT (SEQ ID NO: 91) |
| T061_pyr4_orf_screen_2F | TTAGGCGACCTCTTTTTCCA (SEQ ID NO: 92) |
| T289_22005_3int | ATGTTGCAGTTGCGAAAG (SEQ ID NO: 93) |
| T290_22005_5orf | CCCTCGTCGCAGAAAAGATG (SEQ ID NO: 94) |
| T291_22005_3orf | AGCCTCCTTGGGAACCTCAG (SEQ ID NO: 95) |

Deletion of pmt2 was verified by Southern analyses. DNA for Southern analyses was extracted with Easy-DNA kit for genomic DNA isolation (Invitrogen) essentially according to the manufacturer's instructions.

Southern analyses were essentially performed as described in Example 1. Fragments for probes were produced by PCR using the primers listed in Table 16 using a T. reesei wild type strain QM6a (ATCC13631) as the template for pmt2 ORF probe and plasmid pTTv186 for 5' and 3' flank probes. PCR products were separated with agarose gel electrophoresis and correct fragments were isolated from the gel with a gel extraction kit (Qiagen) using standard laboratory methods.

TABLE 16

Primers for production of probe fragments used in Southern analyses of protein O-mannosyltransferase 2 (pmt2, TreID22005) deletion clones.

| Primer | Sequence |
| --- | --- |
| T639_22005 5' flank probe F | CTTAGTGCGGCTGGAGGGCG (SEQ ID NO: 96) |
| T640_22005 5' flank probe R | GGCCGGTTCGTGCAACTGGA (SEQ ID NO: 97) |
| T641_22005 3' flank probe F | GGCCGCAAGAGGATGGGGT (SEQ ID NO: 98) |
| T642_22005 3' flank probe R | TCGGGCCAGCTGAAGCACAAC (SEQ ID NO: 99) |
| T290_22005_5orf | CCCTCGTCGCAGAAAAGATG (SEQ ID NO: 100) |
| T291_22005_3orf | AGCCTCCTTGGGAACCTCAG (SEQ ID NO: 101) |

None of the clones hybridised with pmt2 ORF probe (Data not shown) indicating successful deletion of pmt2. Analyses using 5' and 3' flank probes revealed that two of the clones were single integrants (Data not shown). One clone gave additional signal from the 3'flank probing (Data not shown) and thus indicated partial or multiple integration of the deletion cassette. Three pure clones (with and without additional copies of the deletion cassette) have been stored for future use (M452; 27-10A, M453; 27-17A and M454: 27-18B).

Analyses of Δpmt2 Strains M452, M453 and M454

Shake flask cultivation of *T. reesei* strain M304 and three pmt2 deletion strains (27-10A/M452, 27-17A/M453 and 27-18B/M454) was carried out in *Trichoderma* minimal medium with 40 g/l lactose, 20 g/l spent grain extract, 100 mM PIPPS, 9 g/l casamino acids, pH 5.5 at +28° C., 200 rpm. Samples were collected on days 3, 5, 7 and 10 by vacuum filtration. Supernatant samples were stored to −20° C. (antibody and glycan analyses) or used in pH determinations. Mycelia for cell dry weight determinations were rinsed once with DDIW and dried at +100° C. for 20-24 h. Mycelia for genomic DNA extraction were rinsed once with DDIW and stored to −20° C.

O-mannosylation level analysis was performed to pmt2 deletion strains as to flask cultures of pmt1 deletion strains. No difference was observed in O-mannosylation compared to parental strain M304.

Example 4: Pmt3 Deletion in a *Trichoderma reesei* Strain

Generation of Pmt3 Deletion Plasmids

Three different deletion plasmids (pTTv35, pTTv123, pTTv187) were constructed for deletion of the protein O-mannosyltransferase gene pmt3 (TreID22527). All the plasmids contain the same 5' and 3' flanking regions for correct integration to the pmt3 locus. The difference between the three plasmids is the marker used in the selection; pTTv35 contains a gene encoding acetamidase of *Aspergillus nidulans* (amdS), pTTv123 contains a loopout version (blaster cassette) of the amdS marker and pTTv187 a loopout version (blaster cassette) of a gene encoding orotidine-5'-monophosphate (OMP) decarboxylase of *T. reesei* (pyr4).

1100 bp of 5' and 1000 bp of 3' flanking regions were selected as the basis of the third protein O-mannosyltransferase gene, pmt3 (TreID22527), deletion plasmids. The construction of the first plasmid for this gene was carried out essentially as described for pmt1 in Example 1. As for pmt1, the first deletion plasmid for pmt3 (plasmid pTTv35, Table 17) used amdS, a gene encoding acetamidase of *Aspergillus nidulans*, as the selection marker.

Like for pmt1 in Example 1, to clone the second deletion plasmid, pTTv123 (Table 16), the amdS marker was removed from the deletion plasmid pTTv35 with NotI digestion and replaced by amdS blaster cassette for which the fragments were produced by PCR (see Example 1 above for details). The plasmid pTTv123 was constructed using the yeast recombination system described in Example 1. The plasmid DNA from the yeast transformants was rescued by transformation into *Escherichia coli*. A few clones were cultivated, plasmid DNA was isolated and digested to screen for correct recombination using standard laboratory methods. A few clones with correct insert sizes were sequenced and stored.

The third deletion plasmid for pmt3, pTTv187 (Table 17) was cloned like the third plasmid for pmt1; the amdS blaster cassette was removed from the deletion plasmid pTTv123 with NotI digestion and replaced by the pyr4 blaster cassette described in Example 1. The pyr4 blaster cassette was obtained from another plasmid with NotI digestion, ligated to NotI cut pTTv123 and transformed into *E. coli* using standard laboratory methods. A few transformants were cultivated, plasmid DNA isolated and digested to screen for correct ligation and orientation of the pyr4 blaster cassette using standard laboratory methods. One clone with correct insert size and orientation was sequenced and stored. These deletion plasmids for pmt3 (pTTv35, pTTv123 and pTTv187, Table 17) result in 2495 bp deletion in the pmt3 locus and cover the complete coding sequence of PMT3.

TABLE 17

Primers for generating deletion plasmids pTTv35, pTTv123 and pTTv187 for protein O-mannosyltransferase 3 (pmt3, TreID22527).

Deletion plasmid pTTv35 for pmt3 (TreID22527), vector backbone pRS426

| Primer | Sequence |
| --- | --- |
| 22527_5'F | CGATTAAGTTGGGTAACGCCAGGGTTTTCCCAGTCACGAC GGTTTAAACGTGTTTAAATTTGATGAGGC (SEQ ID NO: 102) |
| 22527_5'R | ATCTCTCAAAGGAAGAATCCCTTCAGGGTTGCGTTTCCAGT GCGGCCGCGGTCTCAGAGACAGCCTTCT (SEQ ID NO: 103) |
| 22527_3'F | CGGTTCTCATCTGGGCTTGCTCGGTCCTGGCGTAGATCTA GCGGCCGCACTCGGCTTCTTTGTCCGAG (SEQ ID NO: 104) |
| 22527_3'R | GTGGAATTGTGAGCGGATAACAATTTCACACAGGAAACAG CGTTTAAACTCCTCGTCGGCAACAAGGCC (SEQ ID NO: 105) |

Deletion plasmid pTTv123 for pmt3 (TreID22527), vector backbone pTTv35

| | |
| --- | --- |
| T281_22527_amds_5for | GCAGATCTGGGGGAGGAATCAGAAGGCTGTCTCTGAGACC GCGGCCGCGGCCGGCCGCGATCGCCTAGATCTACGCCAG GACCG (SEQ ID NO: 106) |
| T283_amds_3rev_loop | CGGTCCTGGCGTAGATCTAGGGCGCGCCACTGGAAACGC AACCCTGAA (SEQ ID NO: 107) |

TABLE 17-continued

Primers for generating deletion plasmids pTTv35, pTTv123 and pTTv187 for protein O-mannosyltransferase 3 (pmt3, TreID22527).

| | |
|---|---|
| T284_amds_loop_5for | TTCAGGGTTGCGTTTCCAGTGGCGCGCCCTAGATCTACGC CAGGACCG (SEQ ID NO: 108) |
| T286_22527_loop_3rev | AAAGTGGGCGAGCTGAGATACTCGGACAAAGAAGCCGAGT GCGGCCGCGATTATTGCACAAGCAGCGA (SEQ ID NO: 109) |

Deletion plasmid pTTv187 for pmt3 (TreID22527), vector backbone pTTv123

| Primer | Sequence |
|---|---|
| no new primers, pTTv123 digested with NotI and ligated with pyr4-loopout fragment from another plasmid. | |

Generation of pmt3 Deletion Strains M341 and M342

To remove vector sequence plasmid pTTv123 (Δpmt3-amdS) was digested with PmeI+XbaI and the 5.2 kb fragment purified from agarose gel using QIAquick Gel Extraction Kit (Qiagen). Approximately 5 µg of the pmt3 deletion cassette was used to transform the strain M124. Protoplast preparation and transformation were carried out essentially according to Penttilä et al., 1987, Gene 61:155-164 and Gruber et al, 1990, Current Genetics 18:71-76 for amdS selection.

120 colonies were picked as selective streaks. 10 transformants were screened by PCR using the primers in Table 18 for the correct integration of the deletion cassette using standard laboratory methods. Three putative deletion clones were purified to single cell clones. Purified clones (three parallel from each) were rescreened for correct integration and for deletion of pmt3 ORF (primers on Table 18). Three clones were selected for Southern analyses.

TABLE 18

Primers for screening integration of deletion cassette pTTv123 and for deletion of protein O-mannosyltransferase 3 (pmt3, TreID22527) from M124.

| Primer | Sequence |
|---|---|
| T292_22527_5int | ACGGGAGATCTCGGAAAA (SEQ ID NO: 110) |
| T020_Amds_rev2 | CTTTCCATTCATCAGGGATGG (SEQ ID NO: 111) |
| T021_amds_end_fwd | GGAGACTCAGTGAAGAGAGG (SEQ ID NO: 112) |
| T293_22527_3int | ATGAAGCTCAGCCTGTGG (SEQ ID NO: 113) |
| T294_22527_5orf | GGGGACGGCTTGAGGAAG (SEQ ID NO: 114) |
| T295_22527_3orf | CTGCTTGCTGCTTCCAGTCA (SEQ ID NO: 115) |

Deletion of pmt3 was verified by Southern analyses. DNA for Southern analyses was extracted with Easy-DNA kit for genomic DNA isolation (Invitrogen) essentially according to the manufacturer's instructions.

Southern analyses were essentially performed as described in Example 1. Fragments for probes were produced by PCR using the primers listed in Table 19 using a T. reesei strain M124 as the template for the ORF probe and plasmid pTTv123 for the 5' and 3' flank probes. PCR products were separated with agarose gel electrophoresis and correct fragments were isolated from the gel with a gel extraction kit (Qiagen) using standard laboratory methods.

TABLE 19

Primers for production of probe fragments used in Southern analyses of protein O-mannosyltransferase 3 (pmt3, TreID22527) deletion strains.

| Primer | Sequence |
|---|---|
| T645_22527 5' flank probe F | TGGCAGATGCCGAAAGGCGG (SEQ ID NO: 116) |
| T646_22527 5' flank probe R | TGGCAACCAGCTGTGGCTCC (SEQ ID NO: 117) |
| T647_22527 3' flank probe F | CGGCCGCACTCGGCTTCTTT (SEQ ID NO: 118) |
| T648_22527 3' flank probe R | GAGTGGGCTAGGCGCAACGG (SEQ ID NO: 119) |
| T649_22527 orf 5' probe | GGATCGGCCACTGCCACCAC (SEQ ID NO: 120) |
| T650_22527 orf 3' probe | GCCCACTTCTCTGCGCGTGT (SEQ ID NO: 121) |

Two of the clones did not hybridise with pmt3 ORF probe (Data not shown) indicating successful deletion of pmt3. Analyses using 5' and 3' flank probes revealed that the same two clones were single integrants (Data not shown). One clone (20-32C) gave signals corresponding to parental strain M124. Two clones have been stored for future use (M341; 20-34C and M342; 20-35B).

Analyses of Δpmt3 Strains M341 and M342

Shake flask cultivation of T. reesei strain M124 and the pmt3 deletion strains (20-34C/M341 and 20-35B/M342) was carried out in Trichoderma minimal medium with 40 g/l lactose, 20 g/l spent grain extract, 100 mM PIPPS, pH 5.5 with and without 1 M sorbitol as osmotic stabiliser at +28° C., 200 rpm. Samples were collected on days 3, 5 and 7 by vacuum filtration. Supernatant samples were stored to −20° C. (antibody and glycan analyses) or used in pH determinations. Mycelia for cell dry weight determinations were rinsed once with DDIW and dried at +100° C. for 20-24 h. Mycelia for genomic DNA extraction were rinsed once with DDIW and stored to −20° C.

Generation of Pmt3 Deletion Strains M522 and M523

Generation of M317 is described in Example 1 above.

To remove vector sequence plasmid pTTv187 (Δpmt3-pyr4) was digested with PmeI+XbaI and the 4.1 kb fragment purified from agarose gel using QIAquick Gel Extraction Kit (Qiagen). Approximately 5 μg of the pmt3 deletion cassette was used to transform M317. Protoplast preparation and transformation were carried out essentially according to Penttila et al., 1987, Gene 61:155-164 and Gruber et al, 1990, Current Genetics 18:71-76 for pyr4 selection.

200 colonies were picked as selective streaks. 59 transformants were screened by PCR using the primers in Table 20 for the correct integration of the deletion cassette using standard laboratory methods. Three putative deletion clones were purified to single cell clones. Purified clones were rescreened for correct integration and for deletion of pmt3 ORF (primers on Table 19). Two clones (several parallels) were pure deletants (i.e. no signal with ORF primers).

TABLE 20

Primers for screening integration of deletion cassette pTTv187 and for deletion of protein O-mannosyltransferase 3 (pmt3, TreID22527) from M317.

| Primer | Sequence |
| --- | --- |
| T292_22527_5int | ACGGGAGATCTCGGAAAA (SEQ ID NO: 122) |
| T026_Pyr4_orf_5rev2 | CCATGAGCTTGAACAGGTAA (SEQ ID NO: 123) |
| T061_pyr4_orf_screen_2F | TTAGGCGACCTCTTTTTCCA (SEQ ID NO: 124) |
| T293_22527_3int | ATGAAGCTCAGCCTGTGG (SEQ ID NO: 125) |
| T649_22527 orf 5' probe | GGATCGGCCACTGCCACCAC (SEQ ID NO: 126) |
| T650_22527 orf 3' probe | GCCCACTTCTCTGCGCGTGT (SEQ ID NO: 127) |

Deletion of pmt3 was verified by Southern analyses. DNA for Southern analyses was extracted with Easy-DNA kit for genomic DNA isolation (Invitrogen) essentially according to the manufacturer's instructions.

Southern analyses were essentially performed as described in Example 1. Fragments for probes were produced by PCR using the primers listed in Table 21 using a *T. reesei* wild type strain QM6a (ATCC13631) as the template for the ORF probe and plasmid pTTv187 for the 5' and 3' flank probes. PCR products were separated with agarose gel electrophoresis and correct fragments were isolated from the gel with a gel extraction kit (Qiagen) using standard laboratory methods.

TABLE 21

Primers for production of probe fragments used in Southern analyses of protein O-mannosyltransferase 3 (pmt3, TreID22527) deletion strains.

| Primer | Sequence |
| --- | --- |
| T645_22527 5' flank probe F | TGGCAGATGCCGAAAGGCGG (SEQ ID NO: 128) |
| T646_22527 5' flank probe R | TGGCAACCAGCTGTGGCTCC (SEQ ID NO: 129) |

TABLE 21-continued

Primers for production of probe fragments used in Southern analyses of protein O-mannosyltransferase 3 (pmt3, TreID22527) deletion strains.

| Primer | Sequence |
| --- | --- |
| T647_22527 3' flank probe F | CGGCCGCACTCGGCTTCTTT (SEQ ID NO: 130) |
| T648_22527 3' flank probe R | GAGTGGGCTAGGCGCAACGG (SEQ ID NO: 131) |
| T874_pmt3_orf_f3 | CTCTGCGCGTGTTGTGG (SEQ ID NO: 132) |
| T875_pmt3_orf_r3 | TAAGGGTGCGGATTCGG (SEQ ID NO: 133) |

Eight of the clones did not hybridise with pmt3 ORF probe (Data not shown) indicating successful deletion of pmt3. One clone (33-37K) hybridised with pmt3 ORF probe even though the signal size did not correspond to those from parental strains suggesting rearrangement in the pmt3 locus. Analyses using 5' and 3' flank probes revealed that the eight Δpmt3 clones were single integrants (Data not shown). One clone (33-37K) gave incorrect or additional signals suggesting rearrangements in the pmt3 locus and multiple integrations of the deletion cassette. Two pure clones have been stored for future use (M522; 33-34A and M523; 33-188A-a).

Analyses of Δpmt3 Strains M522 and M523

24-well plate cultivation of *T. reesei* strain M304 and eight pmt3 deletion strains (33-34S/M522, 33-34T, 33-34U, 33-34Ö, 33-188A-a/M523, 33-188B-a, 33-188C-a and 33-188D-a) was carried out in *Trichoderma* minimal medium with 40 g/l lactose, 20 g/l spent grain extract, 100 mM PIPPS, 9 g/l casamino acids, pH 5.5 at +28° C., 800 rpm with humidity control. Samples were collected on days 3, 5 and 6 by centrifugation. Supernatant samples were stored to −20° C. Mycelia for cell dry weight determinations were rinsed once with DDIW and dried at +100° C. for 20-24 h. Mycelia for genomic DNA extraction were rinsed twice with DDIW and stored to −20° C.

O-mannosylation level analysis was performed to pmt3 deletion strains as to flask cultures of pmt1 deletion strains. No difference was observed in O-mannosylation compared to parental strain M304.

Example 5—Pmt Homologs

*T. reesei* pmt homologs were identified from other organisms.

BLAST searches were conducted using the National Center for Biotechnology Information (NCBI) non-redundant amino acid database using the *Trichoderma reesei* PMT amino acid sequences as queries. Sequence hits from the BLAST searches were aligned using the ClustalW2 alignment tool provided by EBI. Phylogenetic trees were generated using average distance with BLOSUM62 after aligning the sequences in the Clustal Omega alignment tool.

A phylogenetic tree and a partial sequence alignment of the results of the PMT BLAST searches are depicted in FIGS. 5 and 6, respectively.

The invention claimed is:

1. A Protein O-mannosyltransferase 1 (PMT1)-deficient filamentous fungal cell comprising
   a) a first mutation in a gene encoding an endogenous protease that eliminates an endogenous protease activity as compared to a parental filamentous fungal cell which does not have said first mutation, said endogenous protease being selected among aspartic proteases, trypsin-like serine proteases, subtilisin proteases, glutamic proteases and sedolisin proteases;
   b) a second mutation in a PMT1 gene that reduces endogenous O-mannosyltransferase activity compared to a parental filamentous fungal cell which does not have said second mutation, wherein the reduced endogenous O-mannosyltransferase activity results from a deletion or a disruption of a PMT1 gene encoding a polypeptide of SEQ ID NO:2 or SEQ ID NO:12;
   c) a third mutation that eliminates the level of expression of an dolichyl-P-Man:Man(5)GlcNAc(2)-PP-dolichyl mannosyltransferase (ALG3) gene compared to the level of expression in a parental cell which does not have such third mutation;

d) a first polynucleotide encoding a N-acetylglucosaminyltransferase I catalytic domain and a second polynucleotide encoding a N-acetylglucosaminyltransferase II catalytic domain, e) a polynucleotide encoding a β1,4 galactosyltransferase; and f) a polynucleotide encoding a mammalian antibody comprising a heavy chain and a light chain;

wherein:

the mammalian antibody is secreted by the PMT1-deficient filamentous fungal cell upon expression of the polynucleotide encoding the mammalian antibody;

said antibody comprising reduced O-mannosylation on the light chain, said reduced O-mannosylation being less than about 10% that of a light chain secreted by said parental filamentous fungal cell which does not have said second mutation, O-mannosylation being defined as mole % of mannose residues per polypeptide chain;

said antibody comprising core G0 N-glycan structure as the major glycoform; and, said filamentous fungal cell is a *Trichoderma* or *Myceliophthora* cell.

2. The PMT1-deficient filamentous fungal cell of claim 1, further comprising one or more polynucleotides encoding a polypeptide selected from the group consisting of:

a) α1,2 mannosidase;
b) α mannosidase II; and,
c) fucosyltransferase.

3. The PMT1-deficient filamentous fungal cell of claim 1, wherein said cell is a *Trichoderma* cell comprising a mutation that reduces or eliminates the protein O-mannosyltransferase activity of *Trichoderma* pmt1.

4. The PMT1-deficient filamentous fungal cell of claim 1, wherein said cell is a *Trichoderma* cell, for example *Trichoderma reesei*, and said cell comprises mutations that reduce or eliminate the activity of a) the three endogenous proteases pep1, tsp1 and slp1;
b) the three endogenous proteases gap1, slp1 and pep1;
c) the three endogenous proteases selected from the group consisting of pep1, pep2, pep3, pep4, pep5, pep8, pep11, pep12, tsp1, slp1, slp2, slp3, slp7, gap1 and gap2;
d) three to six proteases selected from the group consisting of pep1, pep2, pep3, pep4, pep5, tsp1, slp1, slp2, slp3, gap1 and gap2; or
e) seven to ten proteases selected from the group consisting of pep1, pep2, pep3, pep4, pep5, pep7, pep8, tsp1, slp1, slp2, slp3, slp5, slp6, slp7, slp8, tpp1, gap1 and gap2.

5. The PMT1-deficient filamentous fungal cell of claim 1, wherein the O-mannosylation level on the expressed light chain of the antibody is reduced to 0%.

6. The PMT1-deficient filamentous fungal cell of claim 1, wherein the polynucleotide encoding a β1,4 galactosyltransferase is a human β1,4 galactosyltransferase.

* * * * *

SEQUENCE LISTING

<160> NUMBER OF SEQ ID NOS: 197

<210> SEQ ID NO 1
<211> LENGTH: 2322
<212> TYPE: DNA
<213> ORGANISM: Trichoderma reesei

<400> SEQUENCE: 1

| | | | | | | |
|---|---|---|---|---|---|---|
| atggctcgaa | gtccaacgcc | gcagggcagc | ctgcgacagc | ggaacgttgc | gtccaagcag | 60 |
| gcgcctgtcg | agtcggcatt | cgttcccgag | gtcgagctcg | acaagctctc | caaggccgct | 120 |
| ctgtcgtcgc | gccgaaacat | ccagagaggc | gagctcgagc | acaagcttgc | cctgacgctg | 180 |
| gtgacgatcc | tcggctttgt | cacgcgattc | tggggcatca | gccaccccga | cgaggtcgtc | 240 |
| tttgacgagg | tgcattttgg | aaagttcgcc | tcctactacc | tccagcgaac | ctacttcttc | 300 |
| gacgtccacc | cccctttcgc | caagctgctc | ttcgccttcg | ttggctggct | ggttggctac | 360 |
| gacggtcact | ccacttcgcga | caacattggc | gactcctacg | tggccaacaa | ggtgccctat | 420 |
| gtcgccttcc | gagccttgcc | cgccttcctc | ggcgcattga | ctgtgtcggt | cacataccct | 480 |
| atcatgtggg | agtctggcta | tagtgtgccg | gcttgccttg | tcgcgaccgg | cctgatcctc | 540 |
| ctggacaatg | cgcacattgg | ccagacccgc | ctcattctgc | tcgacgccac | cctggtgctc | 600 |
| gccatggcct | gcagtctctt | gttctacatc | aagttctaca | agctgcggca | cgagcccttt | 660 |
| agccgcaagt | ggtggaagtg | gctcatcctg | accggctttg | cgctgtcgtg | cgacatctcg | 720 |
| accaagtatg | tcggtctctt | tgcctttgtc | accattggct | ccgccgtcat | cattgatctg | 780 |
| tgggatcttt | tggatatcaa | gcgccgctat | ggagccatca | gcatgccaga | gtttggaaag | 840 |
| cactttgcag | cccgcgcctt | tggcctcatc | atcttgccct | tcctcttcta | cctcttctgg | 900 |
| ttccaggtgc | acttttccgt | cctgacccga | tccggtcccg | cgacgacttt | catgactccc | 960 |
| gagttccagg | agacgttgag | cgacaacgtc | atgctggcaa | cgccgtcga | catccagtac | 1020 |
| tacgatacca | tcaccatcag | gcacaaggag | accaaggcgt | atcttcacag | ccacaccgac | 1080 |
| acctaccctc | tgcgatatga | cgacggccgc | atctccagcc | aaggccaaca | ggtcaccggc | 1140 |
| taccccacga | acgacaccaa | caactactgg | cagatcctcc | ctgccgacaa | tgaccagaag | 1200 |
| ctcggccgta | acgttaagaa | tcaagacttg | gtgcgacttc | gacacattgt | cacggacaag | 1260 |
| atcctgctct | cccatgatgt | cgcctcgccc | tactacccta | ccaaccagga | gttcacctgt | 1320 |
| gtgaccccg | aggaagcatt | cggcgagcgc | caaaacgaca | ctctgttcga | gatccggatt | 1380 |
| gagggaggca | agaccggcca | ggacttcaag | accgttgcca | gccacttcaa | gctcattcac | 1440 |
| ttccccagca | aggtggccat | gtggactcat | accacgcccc | ttcccgagtg | ggcctacagg | 1500 |
| cagcaggaaa | tcaacggcaa | caagcaaatc | actcccagct | ccaacgtctg | gattgccgaa | 1560 |
| gacattcctt | cgctcccgga | agacgacgct | cgccgccaca | aggagcagcg | caaggtcaag | 1620 |
| tcgctgccgt | tcctccgcaa | gtggtttgag | ctgcagaggt | ccatgttcta | ccacaacaac | 1680 |
| aagctgacca | gcagccaccc | ctactccagc | cagccctacc | actggccatt | cctcctccgc | 1740 |
| ggagtgagct | tctggacgca | gaatgacaca | cgccagcaaa | tctactttgt | gggcaacccc | 1800 |
| atcggctggt | ggcttgccag | cagtctgctg | gctgtgtttg | ccggcatcat | ggagctgat | 1860 |
| caggtctcgc | tgcgccgagg | catcgatgct | ctggatcacc | gcacccgctc | ccgactgtac | 1920 |
| aactctaccg | gcttcttctt | ccttgcctgg | gccaccccact | acttcccctt | tttcctcatg | 1980 |
| ggtcgtcagc | tgttcttgca | tcactacttg | cctgcccatt | tggcgtcctg | cctggtcacg | 2040 |
| ggctccctcg | tcgagttcat | ctttaacacg | gacccggcag | acgaggagcc | ttcgcgatcc | 2100 |

```
aaaaacccca aggctactgg tcctcggaga cacatcacgg ctcgcgagcg gtttgctggc      2160
aagagcatgg ccggtgcctg gatcgcttgc tttgtgattc tcgctgccgc cgcggctagc      2220
tggtacttct tcttgccgtt gacgtatggc taccccggac tgtctgttga ggaggttctc      2280
aggagaaagt ggcttggata tgatcttcac tttgccaagt ag                         2322
```

<210> SEQ ID NO 2
<211> LENGTH: 773
<212> TYPE: PRT
<213> ORGANISM: Trichoderma reesei

<400> SEQUENCE: 2

```
Met Ala Arg Ser Pro Thr Pro Gln Gly Ser Leu Arg Gln Arg Asn Val
1               5                   10                  15

Ala Ser Lys Gln Ala Pro Val Glu Ser Ala Phe Val Pro Glu Val Glu
            20                  25                  30

Leu Asp Lys Leu Ser Lys Ala Ala Leu Ser Ser Arg Arg Asn Ile Gln
        35                  40                  45

Arg Gly Glu Leu Glu His Lys Leu Ala Leu Thr Leu Val Thr Ile Leu
    50                  55                  60

Gly Phe Val Thr Arg Phe Trp Gly Ile Ser His Pro Asp Glu Val Val
65                  70                  75                  80

Phe Asp Glu Val His Phe Gly Lys Phe Ala Ser Tyr Tyr Leu Gln Arg
                85                  90                  95

Thr Tyr Phe Phe Asp Val His Pro Pro Phe Ala Lys Leu Leu Phe Ala
            100                 105                 110

Phe Val Gly Trp Leu Val Gly Tyr Asp Gly His Phe His Phe Asp Asn
        115                 120                 125

Ile Gly Asp Ser Tyr Val Ala Asn Lys Val Pro Tyr Val Ala Phe Arg
    130                 135                 140

Ala Leu Pro Ala Phe Leu Gly Ala Leu Thr Val Ser Val Thr Tyr Leu
145                 150                 155                 160

Ile Met Trp Glu Ser Gly Tyr Ser Val Pro Ala Cys Leu Val Ala Thr
                165                 170                 175

Gly Leu Ile Leu Leu Asp Asn Ala His Ile Gly Gln Thr Arg Leu Ile
            180                 185                 190

Leu Leu Asp Ala Thr Leu Val Leu Ala Met Ala Cys Ser Leu Leu Phe
        195                 200                 205

Tyr Ile Lys Phe Tyr Lys Leu Arg His Glu Pro Phe Ser Arg Lys Trp
    210                 215                 220

Trp Lys Trp Leu Ile Leu Thr Gly Phe Ala Leu Ser Cys Asp Ile Ser
225                 230                 235                 240

Thr Lys Tyr Val Gly Leu Phe Ala Phe Val Thr Ile Gly Ser Ala Val
                245                 250                 255

Ile Ile Asp Leu Trp Asp Leu Leu Asp Ile Lys Arg Arg Tyr Gly Ala
            260                 265                 270

Ile Ser Met Pro Glu Phe Gly Lys His Phe Ala Ala Arg Ala Phe Gly
        275                 280                 285

Leu Ile Ile Leu Pro Phe Leu Phe Tyr Leu Phe Trp Phe Gln Val His
    290                 295                 300

Phe Ser Val Leu Thr Arg Ser Gly Pro Gly Asp Asp Phe Met Thr Pro
305                 310                 315                 320

Glu Phe Gln Glu Thr Leu Ser Asp Asn Val Met Leu Ala Ser Ala Val
                325                 330                 335
```

```
Asp Ile Gln Tyr Tyr Asp Thr Ile Thr Ile Arg His Lys Glu Thr Lys
            340                 345                 350

Ala Tyr Leu His Ser His Thr Asp Thr Tyr Pro Leu Arg Tyr Asp Asp
            355                 360                 365

Gly Arg Ile Ser Ser Gln Gly Gln Gln Val Thr Gly Tyr Pro His Asn
        370                 375                 380

Asp Thr Asn Asn Tyr Trp Gln Ile Leu Pro Ala Asp Asn Asp Gln Lys
385                 390                 395                 400

Leu Gly Arg Asn Val Lys Asn Gln Asp Leu Val Arg Leu Arg His Ile
                405                 410                 415

Val Thr Asp Lys Ile Leu Leu Ser His Asp Val Ala Ser Pro Tyr Tyr
            420                 425                 430

Pro Thr Asn Gln Glu Phe Thr Cys Val Thr Pro Glu Glu Ala Phe Gly
            435                 440                 445

Glu Arg Gln Asn Asp Thr Leu Phe Glu Ile Arg Ile Glu Gly Gly Lys
            450                 455                 460

Thr Gly Gln Asp Phe Lys Thr Val Ala Ser His Phe Lys Leu Ile His
465                 470                 475                 480

Phe Pro Ser Lys Val Ala Met Trp Thr His Thr Thr Pro Leu Pro Glu
                485                 490                 495

Trp Ala Tyr Arg Gln Gln Glu Ile Asn Gly Asn Lys Gln Ile Thr Pro
            500                 505                 510

Ser Ser Asn Val Trp Ile Ala Glu Asp Ile Pro Ser Leu Pro Glu Asp
            515                 520                 525

Asp Ala Arg Arg His Lys Glu Gln Arg Lys Val Lys Ser Leu Pro Phe
            530                 535                 540

Leu Arg Lys Trp Phe Glu Leu Gln Arg Ser Met Phe Tyr His Asn Asn
545                 550                 555                 560

Lys Leu Thr Ser Ser His Pro Tyr Ser Gln Pro Tyr His Trp Pro
                565                 570                 575

Phe Leu Leu Arg Gly Val Ser Phe Trp Thr Gln Asn Asp Thr Arg Gln
            580                 585                 590

Gln Ile Tyr Phe Val Gly Asn Pro Ile Gly Trp Trp Leu Ala Ser Ser
            595                 600                 605

Leu Leu Ala Val Phe Ala Gly Ile Ile Gly Ala Asp Gln Val Ser Leu
            610                 615                 620

Arg Arg Gly Ile Asp Ala Leu Asp His Arg Thr Arg Ser Arg Leu Tyr
625                 630                 635                 640

Asn Ser Thr Gly Phe Phe Leu Ala Trp Ala Thr His Tyr Phe Pro
                645                 650                 655

Phe Phe Leu Met Gly Arg Gln Leu Phe Leu His His Tyr Leu Pro Ala
            660                 665                 670

His Leu Ala Ser Cys Leu Val Thr Gly Ser Leu Val Glu Phe Ile Phe
            675                 680                 685

Asn Thr Asp Pro Ala Asp Glu Glu Pro Ser Arg Ser Lys Asn Pro Lys
            690                 695                 700

Ala Thr Gly Pro Arg Arg His Ile Thr Ala Arg Glu Arg Phe Ala Gly
705                 710                 715                 720

Lys Ser Met Ala Gly Ala Trp Ile Ala Cys Phe Val Ile Leu Ala Ala
                725                 730                 735

Ala Ala Ala Ser Trp Tyr Phe Phe Leu Pro Leu Thr Tyr Gly Tyr Pro
            740                 745                 750
```

Gly Leu Ser Val Glu Glu Val Leu Arg Arg Lys Trp Leu Gly Tyr Asp
            755                 760                 765

Leu His Phe Ala Lys
        770

<210> SEQ ID NO 3
<211> LENGTH: 944
<212> TYPE: PRT
<213> ORGANISM: Trichoderma reesei

<400> SEQUENCE: 3

Met Ala Lys Ala Thr Ala Arg Gly Arg Ser Pro Gln Pro Pro Leu Val
1               5                   10                  15

Ala Glu Lys Met Pro Val Ala Val Thr Ala Pro Val Ala Ser Ser Lys
            20                  25                  30

Ser Lys Ala Ala Lys Lys Asn Ser Ser Tyr Arg Ser Asp Gly Val Ala
        35                  40                  45

Asp Asn Asp Val Phe Leu Leu Pro Gly Ala Asp Tyr Val Ala Ala Leu
    50                  55                  60

Gly Val Thr Val Leu Ala Thr Ile Val Arg Leu Phe Lys Ile Tyr Thr
65              70                  75                  80

Pro Thr Ser Val Val Phe Asp Glu Val His Phe Gly Phe Ala Ser
                85                  90                  95

Lys Tyr Ile Lys Gly Arg Phe Met Asp Val His Pro Pro Leu Ala
            100                 105                 110

Lys Met Leu Ile Ala Leu Thr Gly Trp Leu Ala Gly Phe Asp Gly Asn
        115                 120                 125

Phe Asp Phe Lys Asp Ile Gly Lys Asp Tyr Leu Glu Pro Gly Val Pro
    130                 135                 140

Tyr Val Ala Met Arg Met Phe Pro Ala Val Cys Gly Ile Leu Leu Ala
145                 150                 155                 160

Pro Phe Met Phe Phe Thr Leu Lys Ala Val Gly Cys Arg Thr Thr Thr
                165                 170                 175

Ala Ile Leu Gly Ala Ser Phe Ile Ile Phe Glu Asn Gly Leu Leu Thr
            180                 185                 190

Gln Ala Arg Leu Ile Leu Leu Asp Ser Pro Leu Val Ala Ala Thr Ala
        195                 200                 205

Phe Thr Ala Met Ser Phe Asn Cys Phe Thr Asn Gln His Glu Gln Gly
    210                 215                 220

Pro Asp Lys Ala Phe Ser Leu Ser Trp Trp Phe Trp Leu Ala Met Thr
225                 230                 235                 240

Gly Leu Gly Leu Gly Ile Thr Ser Ser Ile Lys Trp Val Gly Leu Phe
                245                 250                 255

Thr Ile Ala Trp Val Gly Ser Leu Thr Leu Val Gln Leu Trp Val Leu
            260                 265                 270

Leu Gly Asp Ser Lys Asn Val Ser Met Arg Leu Trp Phe Lys His Phe
        275                 280                 285

Met Ala Arg Val Phe Cys Leu Ile Ile Ile Pro Leu Thr Phe Tyr Leu
    290                 295                 300

Ser Met Phe Ala Ile His Phe Leu Cys Leu Thr Asn Pro Gly Glu Gly
305                 310                 315                 320

Asp Gly Phe Met Ser Ser Glu Phe Gln Ala Thr Leu Asn Ser Lys Gly
                325                 330                 335

Met Lys Asp Val Pro Ala Asp Val Val Phe Gly Ser Arg Val Thr Ile
            340                 345                 350

-continued

```
Arg His Val Asn Thr Gln Gly Gly Tyr Leu His Ser His Pro Leu Met
        355                 360                 365
Tyr Pro Thr Gly Ser Leu Gln Gln Ile Thr Leu Tyr Pro His Lys
    370                 375                 380
Asp Glu Asn Asn Ile Trp Ile Met Glu Asn Gln Thr Gln Pro Leu Gly
385                 390                 395                 400
Val Asp Gly Gln Pro Ile Asn Gly Thr Glu Ala Trp Asp Ala Leu Pro
                405                 410                 415
Glu Val His His Val Asp Gly Ser Val Ile Arg Leu Tyr His Lys
            420                 425                 430
Pro Thr Phe Arg Arg Leu His Ser His Asp Val Arg Pro Val Thr
        435                 440                 445
Glu Ala Glu Trp Gln Asn Glu Val Ser Ala Tyr Gly Tyr Glu Gly Phe
    450                 455                 460
Glu Gly Asp Ala Asn Asp Leu Phe Arg Val Glu Ile Val Lys Lys Gln
465                 470                 475                 480
Ser Lys Gly Pro Leu Ala Lys Glu Arg Leu Arg Thr Ile Glu Thr Lys
                485                 490                 495
Phe Arg Leu Ile His Val Met Thr Gly Cys Ala Leu Phe Ser His Lys
                500                 505                 510
Val Lys Leu Pro Glu Trp Ala Ser Glu Gln Gln Glu Val Thr Cys Ala
        515                 520                 525
Arg Gly Gly Ser Leu Pro Asn Ser Ile Trp Tyr Ile Glu Tyr Asn Glu
    530                 535                 540
His Pro Leu Leu Gly Asp Asp Val Glu Lys Val Asn Tyr Ala Asn Pro
545                 550                 555                 560
Gly Phe Phe Gly Lys Phe Trp Glu Leu His Lys Val Met Trp Lys Thr
                565                 570                 575
Asn Ala Gly Leu Thr Asp Ser His Ala Trp Asp Ser Arg Pro Pro Ser
            580                 585                 590
Trp Pro Ile Leu Arg Arg Gly Ile Asn Phe Trp Gly Lys His His Met
        595                 600                 605
Gln Val Tyr Leu Leu Gly Asn Pro Phe Ile Trp Trp Ser Ser Thr Ala
    610                 615                 620
Ala Val Ala Ile Trp Val Ile Phe Lys Gly Val Ala Ile Leu Arg Trp
625                 630                 635                 640
Gln Arg Gly Cys Asn Asp Tyr Ala Ser Ser Thr Phe Lys Arg Phe Asp
                645                 650                 655
Tyr Glu Ile Gly Thr Ser Val Leu Gly Trp Ala Leu His Tyr Phe Pro
            660                 665                 670
Phe Tyr Leu Met Glu Arg Gln Leu Phe Leu His His Tyr Phe Pro Ala
        675                 680                 685
Leu Tyr Phe Ala Ile Leu Ala Leu Cys Gln Met Phe Asp Phe Ala Thr
    690                 695                 700
Val Arg Ile Pro Ala Ala Leu Gly Tyr Arg Ser Thr Leu Ile Asn Arg
705                 710                 715                 720
Val Gly Thr Val Ser Leu Leu Val Ile Ser Ala Ala Val Phe Thr Leu
                725                 730                 735
Phe Ala Pro Leu Ala Tyr Gly Thr Pro Trp Thr Lys Ala Glu Cys Asn
            740                 745                 750
Arg Val Lys Leu Phe Asp Lys Trp Asp Phe Asp Cys Asn Thr Phe Leu
        755                 760                 765
```

-continued

```
Asp Asp Tyr Lys Ser Tyr Thr Leu Thr Ser Leu Ala Pro Ser Ser Ile
770             775                 780

Ala Pro Ser Pro Pro Ala Ala Asn Val Pro Val Val Asn Gln Glu Gln
785             790                 795                 800

Lys Pro Leu Ala Lys Gln Pro Glu Pro Val Ile Ser Gln Ala Ala Val
            805                 810                 815

Pro Gln Glu Pro Gln Ile Leu Ser Lys Glu Lys Ile Glu Tyr Arg
            820                 825                 830

Asp Gln Asp Gly Asn Leu Leu Asn Asp Glu Gln Val Lys Ala Leu Gln
            835                 840                 845

Gly Lys Val Glu Phe Lys Thr Lys Tyr Glu Thr Lys Thr Arg Val Val
850                 855                 860

Asp Ala Gln Gly His Glu Ile Pro Val Pro Glu Gly Gly Trp Pro Asp
865             870                 875                 880

Asp Met Ile Ala Gly Val Ala Pro Pro His Pro Asp Val Glu Gly Val
                885                 890                 895

Asp Lys Glu Thr Pro Lys Val Glu Ser Ala Glu Val Pro Lys Glu Ala
            900                 905                 910

Ala Ala Ser Arg Asp Gly Glu Val Glu Ala Glu Asn Leu Lys Ala Lys
            915                 920                 925

Pro Ala Ser Glu Gly Gln Glu Val Glu Ala Thr Val Gln Glu Glu Leu
930                 935                 940

<210> SEQ ID NO 4
<211> LENGTH: 740
<212> TYPE: PRT
<213> ORGANISM: Trichoderma reesei

<400> SEQUENCE: 4

Met Ala Ala Asp Lys Ala Ala Leu Ala Ser Gly Ala Asp Leu Gly Asp
1               5                   10                  15

Gly Leu Arg Lys Arg Gln Ala Ala Ser Gln Ala Val Pro Ser Phe Ile
            20                  25                  30

Pro Ala Gln Thr Glu Asp Thr Lys Lys Leu Ala Lys Lys Asp Lys Thr
        35                  40                  45

Phe Val Gln Val Leu Ala Asp Trp Glu Ser Val Leu Ala Pro Leu Ile
50                  55                  60

Phe Thr Ala Val Ala Ile Phe Thr Arg Leu Tyr Lys Ile Gly Leu Ser
65                  70                  75                  80

Asn Ile Val Thr Trp Asp Glu Ala His Phe Gly Lys Phe Gly Ser Tyr
                85                  90                  95

Tyr Ile Lys His Glu Tyr Tyr Phe Asp Val His Pro Pro Leu Gly Lys
            100                 105                 110

Met Leu Val Gly Leu Ser Gly Val Leu Ala Gly Tyr Asn Gly Ser Phe
        115                 120                 125

Glu Phe Lys Ser Gly Glu Gln Tyr Pro Glu Asp Val Asn Tyr Thr Phe
    130                 135                 140

Met Arg Ala Phe Asn Ala Ala Phe Gly Ile Ala Cys Ile Pro Met Ala
145                 150                 155                 160

Tyr Phe Thr Ala Lys Glu Leu Lys Leu Thr Arg Pro Ala Val Trp Phe
                165                 170                 175

Val Thr Leu Met Val Leu Cys Glu Asn Ser Tyr Thr Thr Ile Ser Arg
            180                 185                 190

Phe Ile Leu Leu Asp Ser Met Leu Leu Cys Gly Thr Phe Ala Thr Thr
        195                 200                 205
```

```
Leu Cys Trp Ala Lys Phe His Asn Gln Arg His Asn Ser Phe Glu Pro
    210                 215                 220

Glu Trp Phe Phe Trp Leu Phe Met Thr Gly Leu Ser Ile Gly Cys Val
225                 230                 235                 240

Cys Ser Val Lys Leu Val Gly Leu Phe Val Thr Ala Leu Val Gly Leu
                245                 250                 255

Tyr Thr Ile Glu Asp Leu Trp Arg Lys Tyr Gly Asp Arg Lys Met Pro
            260                 265                 270

Ile Pro Val Leu Ala Ala His Phe Ser Ala Arg Val Val Gly Leu Ile
        275                 280                 285

Ile Val Pro Phe Leu Ile Tyr Met Leu Ser Phe Ala Leu His Phe Ala
    290                 295                 300

Ile Leu Asp His Ser Gly Pro Asp Ala Gln Met Ser Ser Leu Phe
305                 310                 315                 320

Gln Ala Asn Leu Lys Gly Thr Glu Val Gly Lys Asn Ser Pro Leu Glu
                325                 330                 335

Ile Ala Leu Gly Ser Arg Ala Thr Ile Lys Asn Met Gly Tyr Gly Gly
            340                 345                 350

Gly Leu Leu His Ser His Val Gln Thr Tyr Pro Glu Gly Ser Gly Gln
        355                 360                 365

Gln Gln Val Thr Cys Tyr His His Lys Asp Ala Asn Asn Asp Trp Phe
    370                 375                 380

Phe Tyr Pro Asn Arg His Glu Pro Asp Tyr Asp Pro Glu Gly Glu Leu
385                 390                 395                 400

Arg Phe Ile Gly Asp Gly Ser Val Ile Arg Leu Ile His Ala Gln Thr
                405                 410                 415

Gly Arg Asn Leu His Ser His Asp Ile Asp Ala Pro Ile Thr Lys Ser
            420                 425                 430

His Arg Glu Val Ser Ser Tyr Gly Asn Leu Thr Val Gly Asp Glu Lys
        435                 440                 445

Asp His Trp Lys Ile Glu Val Val Arg Asp Ala Ala Ser Arg Asp Arg
    450                 455                 460

Ser Arg Ile Arg Thr Leu Thr Thr Ala Phe Arg Leu Lys His Thr Val
465                 470                 475                 480

Leu Gly Cys Tyr Leu Arg Ala Gly Asn Val Asn Leu Pro Gln Trp Gly
                485                 490                 495

Phe Lys Gln Ile Glu Val Thr Cys Asp Lys Gln Asn Asn Pro Arg Asp
            500                 505                 510

Thr Tyr Thr His Trp Asn Val Glu Ala His Trp Asn Asp Arg Leu Pro
        515                 520                 525

Pro Ser Asp Pro Gly Val Tyr Lys Ser Pro Phe Ile His Asp Phe Ile
    530                 535                 540

His Leu Asn Val Ala Met Met Thr Ser Asn Asn Ala Leu Val Pro Asp
545                 550                 555                 560

Pro Asp Lys Gln Asp Asp Leu Ala Ser Gln Trp Gln Trp Pro Ile
                565                 570                 575

Leu His Val Gly Leu Arg Met Cys Ser Trp Asp Asp Asn Ile Val Lys
            580                 585                 590

Tyr Phe Leu Leu Gly Asn Pro Phe Val Tyr Trp Ala Ser Thr Ala Ser
        595                 600                 605

Leu Gly Ala Val Ala Leu Val Ile Ala Trp Tyr Val Val Arg Trp Gln
    610                 615                 620
```

-continued

```
Arg Gly Phe Lys Glu Leu Ser Asn Ser Glu Val Asp Gln Ile His Tyr
625                 630                 635                 640

Ala Gly Ile Tyr Pro Val Ile Gly Trp Phe Leu His Tyr Leu Pro Phe
            645                 650                 655

Val Ile Met Ala Arg Val Thr Tyr Val His His Tyr Tyr Pro Ala Leu
                660                 665                 670

Tyr Phe Ala Ile Leu Ser Leu Gly Phe Leu Val Asp Trp Val Leu Arg
            675                 680                 685

Asn Arg Ala Ala Val Val Gln Gly Val Ala Tyr Gly Ile Leu Tyr Thr
        690                 695                 700

Val Val Ile Gly Leu Tyr Ile Leu Phe Met Pro Ile Cys Trp Gly Met
705                 710                 715                 720

Thr Gly Ser Ser Lys Gln Tyr Ser Tyr Leu Lys Trp Phe Asp Asn Trp
                725                 730                 735

Arg Ile Ser Asp
            740

<210> SEQ ID NO 5
<211> LENGTH: 775
<212> TYPE: PRT
<213> ORGANISM: Aspergillus oryzae

<400> SEQUENCE: 5

Met Ser Gln Ser Pro Ser Pro Ser Leu Arg Lys Arg Gly Gly Lys Lys
1               5                   10                  15

Glu Ala Ser Pro Gly Pro Ser Glu Val Ser Ser Pro Tyr Pro Thr Asn
            20                  25                  30

Gln Gly Ala Thr Pro Lys Pro Gln Ser Glu Trp Asp Tyr Arg Leu Ala
        35                  40                  45

Ile Thr Val Leu Thr Val Leu Ala Phe Ile Thr Arg Phe Tyr Arg Ile
    50                  55                  60

Ser Tyr Pro Asp Glu Val Val Phe Asp Glu Val His Phe Gly Lys Phe
65                  70                  75                  80

Ala Ser Tyr Tyr Leu Gln Arg Thr Tyr Phe Phe Asp Val His Pro Pro
                85                  90                  95

Phe Gly Lys Leu Leu Phe Ala Ala Val Gly Trp Leu Ile Gly Tyr Asp
            100                 105                 110

Gly His Phe Leu Phe Glu Asn Ile Gly Asp Ser Tyr Ile Asp Asn Lys
        115                 120                 125

Val Pro Tyr Val Ala Phe Arg Ala Leu Pro Ala Thr Leu Gly Ala Leu
    130                 135                 140

Thr Val Pro Val Val Phe Leu Ile Met Trp Glu Ser Gly Tyr Ser Leu
145                 150                 155                 160

Pro Ala Cys Val Leu Ala Ala Gly Leu Val Leu Phe Asp Asn Ala His
                165                 170                 175

Ile Gly Glu Asp Arg Leu Ile Leu Leu Asp Ala Thr Leu Val Ile Thr
            180                 185                 190

Met Ala Leu Ser Ile Leu Cys Tyr Val Arg Phe Tyr Lys Leu Arg His
        195                 200                 205

Glu Pro Phe Gly Arg Lys Trp Trp Lys Trp Leu Leu Leu Thr Gly Val
    210                 215                 220

Ser Leu Ser Cys Val Ile Ser Thr Lys Tyr Val Gly Val Phe Thr Phe
225                 230                 235                 240

Val Thr Ile Gly Ala Ala Val Met Val Asp Leu Trp Asn Leu Leu Asp
                245                 250                 255
```

-continued

Ile Arg Arg Pro Ala Gly Ala Leu Ser Met Met Glu Trp Thr Lys His
            260                 265                 270

Phe Ala Ala Arg Gly Phe Ala Leu Ile Val Val Pro Phe Phe Tyr
        275                 280                 285

Leu Phe Trp Phe Gln Val His Phe Ala Ile Leu Thr Arg Ser Gly Pro
    290                 295                 300

Gly Asp Asp Phe Met Thr Pro Glu Phe Gln Glu Thr Leu Ser Asp Asn
305                 310                 315                 320

Ala Leu Ala Ala Glu Ser Ile Gly Ile Gln Tyr Tyr Asp Ala Ile Thr
                325                 330                 335

Ile Arg His Lys Asp Thr Lys Val Phe Leu His Ser His Trp Glu Arg
                340                 345                 350

Tyr Pro Leu Arg Tyr Asp Asp Gly Arg Ile Ser Ser Gln Gly Gln Gln
        355                 360                 365

Val Thr Gly Tyr Pro Phe Asn Asp Thr Asn Asn Gln Trp Gln Ile Leu
    370                 375                 380

Pro Thr Val Pro Leu Glu Asp Asn Glu Gly Gln Gly His Ser Val Lys
385                 390                 395                 400

Asn Gly Asp Leu Val Gln Leu Leu His Leu Gly Thr Asp Ser Ile Leu
                405                 410                 415

Leu Thr His Asp Val Ala Ser Pro Phe Tyr Pro Thr Asn Gln Glu Phe
                420                 425                 430

Thr Thr Val Thr Lys Asp Val Ala Ser Gly Glu Arg His Asn Glu Thr
        435                 440                 445

Leu Phe Glu Ile Lys Ile Glu Asn Gly Lys Ala Gly Gln Glu Phe Arg
    450                 455                 460

Thr Leu Ser Ser His Phe Lys Leu Ile His Tyr Pro Thr Arg Val Ala
465                 470                 475                 480

Met Trp Thr His Thr Thr Pro Leu Pro Glu Trp Gly Phe Lys Gln Ala
                485                 490                 495

Glu Ile Asn Gly Asn Lys Asn Val Leu Gln Thr Ser Asn Leu Trp Tyr
                500                 505                 510

Ala Glu Ser Ile Glu Ser Leu Glu Glu Asp Ser Pro Arg Lys Gln Lys
        515                 520                 525

Glu Glu Arg Lys Val Lys Gln Leu Pro Phe Leu Arg Lys Tyr Leu Glu
    530                 535                 540

Leu Gln Arg Ala Met Phe Phe His Asn Asn Ala Leu Thr Ser Ser His
545                 550                 555                 560

Pro Tyr Ala Ser Glu Pro Phe Gln Trp Pro Phe Leu Leu Arg Gly Val
                565                 570                 575

Ser Phe Trp Thr Lys Asn Asp Thr Arg Glu Gln Ile Tyr Phe Leu Gly
                580                 585                 590

Asn Pro Ile Gly Trp Trp Ile Ala Ser Ser Leu Leu Ala Val Phe Ala
        595                 600                 605

Gly Val Ile Gly Ala Asp Gln Leu Ser Leu Arg Arg Gly Val Asp Ala
    610                 615                 620

Val Glu Glu Ile Trp Gly Pro Gly Ala Arg Ser Arg Leu Tyr Asn Ser
625                 630                 635                 640

Thr Gly Phe Leu Phe Leu Cys Trp Gly Ala His Tyr Phe Pro Phe Trp
                645                 650                 655

Leu Met Gly Arg Gln Arg Phe Leu His His Tyr Leu Pro Ala His Leu
                660                 665                 670

```
Ala Ser Cys Leu Val Thr Gly Ala Leu Ile Glu Phe Ile Phe Asn Leu
            675                 680                 685

Gln Pro Val Gln Ala Val Ile Asp Ser Glu Val Asp Pro Ser Gly Lys
        690                 695                 700

Ser Lys Ser Ile Arg Pro Arg His Phe Val Thr Ala Lys Glu Arg Met
705                 710                 715                 720

Ser Arg Lys Ser Leu Val Ala Cys Trp Ile Ala Thr Leu Ser Ile Leu
                725                 730                 735

Ala Val Thr Val Trp Gly Phe Trp Phe Tyr Ala Pro Leu Thr Tyr Gly
            740                 745                 750

Thr Pro Gly Leu Asp Val Ala Gly Val Asn Ala Arg Arg Trp Leu Gly
        755                 760                 765

Tyr Asp Leu His Phe Ala Lys
770                 775

<210> SEQ ID NO 6
<211> LENGTH: 775
<212> TYPE: PRT
<213> ORGANISM: Aspergillus niger

<400> SEQUENCE: 6

Met Ser Ser Ser Pro Ser Ser Leu Arg Lys Arg Gly Gly Lys Lys
1               5                   10                  15

Glu Ser Thr Pro Val Pro Ala Asp Asn Phe Ser Pro Leu Ser Lys
            20                  25                  30

Ala Ser Ala Pro Arg Ser Glu Trp Asp Tyr Trp Leu Ala Ile Ser Ile
            35                  40                  45

Leu Thr Val Leu Ala Phe Val Thr Arg Phe Tyr Lys Ile Ser Tyr Pro
    50                  55                  60

Asn Glu Val Val Phe Asp Glu Val His Phe Gly Lys Phe Ala Ser Tyr
65                  70                  75                  80

Tyr Leu Gln Arg Thr Tyr Phe Phe Asp Val His Pro Pro Phe Gly Lys
                85                  90                  95

Leu Leu Phe Ala Phe Met Gly Trp Leu Val Gly Tyr Asp Gly His Phe
            100                 105                 110

Leu Phe Asp Asn Ile Gly Asp Ser Tyr Ile Glu His Gln Val Pro Tyr
        115                 120                 125

Val Ala Leu Arg Ala Met Pro Ala Thr Leu Gly Ala Leu Thr Val Pro
    130                 135                 140

Val Val Phe Leu Ile Met Trp Glu Ser Gly Tyr Ser Leu Pro Ala Cys
145                 150                 155                 160

Val Leu Ser Ala Gly Leu Val Leu Phe Asp Asn Ala His Ile Gly Glu
                165                 170                 175

Asp Arg Leu Ile Leu Leu Asp Ala Ser Leu Val Leu Thr Met Ala Leu
            180                 185                 190

Ser Ile Leu Cys Tyr Ile Arg Phe Tyr Lys Leu Arg His Glu Ala Phe
        195                 200                 205

Gly Arg Lys Trp Trp Lys Trp Leu Leu Leu Thr Gly Val Ser Leu Ser
    210                 215                 220

Cys Val Ile Ser Thr Lys Tyr Val Gly Val Phe Thr Phe Val Thr Ile
225                 230                 235                 240

Gly Ser Ala Val Met Val Asp Leu Trp Asn Leu Leu Asp Ile Arg Arg
                245                 250                 255

Arg Gly Gly Ala Leu Thr Met Phe Gln Trp Gly Gln His Phe Val Ala
            260                 265                 270
```

```
Arg Ala Phe Ala Leu Ile Ile Val Pro Phe Phe Tyr Leu Phe Trp
        275                 280                 285
Phe Gln Val His Phe Ala Ile Leu Thr Arg Ser Gly Pro Gly Asp Asp
    290                 295                 300
Phe Met Thr Pro Glu Phe Gln Glu Thr Leu Ser Asp Asn Val Leu Ser
305                 310                 315                 320
Ala Gln Ser Ile Gly Ile Glu Tyr Tyr Asp Thr Ile Thr Met Lys His
                325                 330                 335
Lys Asp Thr Lys Val Tyr Leu His Ser His Leu Glu Arg Tyr Pro Leu
                340                 345                 350
Arg Tyr Asp Asp Gly Arg Ile Ser Ser Gln Gly Gln Gln Val Thr Gly
            355                 360                 365
Tyr Pro Tyr Asn Asp Thr Asn Asn Gln Trp Gln Ile Ile Pro Thr Val
    370                 375                 380
Pro Leu Asp Val Thr Asp Thr Ser Gly His Lys Val Arg Asn Gly Asp
385                 390                 395                 400
Val Val Gln Leu Arg His Met Gly Thr Asp Thr Ile Leu Leu Thr His
                405                 410                 415
Asp Val Ala Ser Pro Tyr Tyr Pro Thr Asn Gln Glu Phe Thr Thr Val
            420                 425                 430
Ser His Glu Val Ala Asn Gly Asp Arg His Asn Asp Thr Leu Phe Glu
    435                 440                 445
Ile Lys Ile Glu Asn Gly Lys Pro His Gln Glu Phe Arg Thr Leu Ser
450                 455                 460
Ser His Phe Lys Leu Ile His Met Pro Thr Arg Val Ala Met Trp Thr
465                 470                 475                 480
His Thr Thr Pro Leu Pro Asp Trp Ala Phe Lys Gln Ala Glu Ile Asn
                485                 490                 495
Gly Asn Lys Asn Ile Leu Gln Thr Ser Asn Leu Trp Phe Val Glu Ser
            500                 505                 510
Ile Glu Ser Leu Glu Glu Asp Ser Pro Arg Leu Val Lys Glu Glu Arg
    515                 520                 525
Gln Val Lys His Leu Pro Phe Arg Lys Tyr Leu Glu Leu Gln Arg
530                 535                 540
Ala Met Phe Phe His Asn Asn Ala Leu Thr Ser Ser His Pro Tyr Ala
545                 550                 555                 560
Ser Glu Pro Phe Gln Trp Pro Phe Leu Leu Arg Gly Val Ser Phe Trp
                565                 570                 575
Thr Lys Asn Asp Thr Arg Glu Gln Ile Tyr Phe Leu Gly Asn Pro Val
            580                 585                 590
Gly Trp Trp Ile Ala Ser Ser Leu Leu Ala Val Phe Ala Gly Val Ile
    595                 600                 605
Gly Ala Asp Gln Leu Ser Leu Arg Arg Gly Val Asp Ala Val Glu Glu
610                 615                 620
Ile Trp Gly Gln Gly Ser Arg Ser Arg Leu Tyr Asn Ser Met Gly Phe
625                 630                 635                 640
Leu Phe Leu Cys Trp Ala Ala His Tyr Phe Pro Phe Trp Leu Met Gly
                645                 650                 655
Arg Gln Arg Phe Leu His His Tyr Leu Pro Ala His Leu Ala Ser Ala
            660                 665                 670
Leu Val Ala Gly Ala Leu Ile Glu Phe Ile Phe Asn Leu Glu Pro Leu
    675                 680                 685
```

```
Ser Val Ile Gln Arg Val Arg Ser Glu Asp Pro Ser Gly Lys Ala
    690             695             700

Lys Ala Ser Ala Ser Val Gly Arg Phe Val Thr Ala Lys Glu Arg Met
705                 710                 715                 720

Gly Thr Lys Ser Leu Leu Ala Gly Trp Ile Ala Thr Leu Val Ile Leu
                725                 730                 735

Ala Gly Thr Ile Tyr Gly Phe Val Phe Tyr Ala Pro Leu Thr Tyr Gly
                740                 745                 750

Thr Pro Gly Leu Asp Val Pro Gly Ile Leu Ala Arg Lys Trp Leu Gly
                755                 760                 765

Tyr Asp Leu His Phe Ala Lys
770                 775

<210> SEQ ID NO 7
<211> LENGTH: 773
<212> TYPE: PRT
<213> ORGANISM: Aspergillus nidulans

<400> SEQUENCE: 7

Met Ser Ser Ser Pro Ser Leu Arg Lys Arg Gly Gly Lys Arg Glu Asp
1               5                   10                  15

Thr Pro Val Pro Ser Asp Arg Ser Phe Ala Pro Ser Ala Ser Gln Leu
            20                  25                  30

Gly Ala Ala Ser Arg Ser Ser Glu Trp Asp Tyr Arg Leu Ala Ile Thr
        35                  40                  45

Ile Leu Thr Val Leu Ala Phe Ile Thr Arg Phe Tyr Lys Ile Ser Tyr
    50                  55                  60

Pro Asp Gln Val Val Phe Asp Glu Val His Phe Gly Lys Phe Ala Ser
65                  70                  75                  80

Tyr Tyr Leu Arg Arg Thr Tyr Phe Phe Asp Val His Pro Pro Phe Ala
                85                  90                  95

Lys Leu Leu Leu Ala Phe Thr Gly Trp Leu Val Gly Tyr Asp Gly His
                100                 105                 110

Phe Leu Phe Glu Asn Ile Gly Asp Ser Tyr Ile Asp Asn Lys Val Pro
            115                 120                 125

Tyr Val Ala Leu Arg Ala Met Pro Ala Val Leu Gly Ala Leu Thr Ile
    130                 135                 140

Pro Val Val Phe Leu Ile Met Trp Glu Ser Gly Tyr Ser Leu Pro Ala
145                 150                 155                 160

Cys Val Leu Ala Ser Gly Leu Val Leu Phe Asp Asn Ala His Val Gly
                165                 170                 175

Glu Asp Arg Leu Ile Leu Leu Asp Ser Thr Leu Val Ile Thr Met Ala
                180                 185                 190

Leu Ser Ile Leu Cys Tyr Ile Arg Phe Tyr Lys Leu Arg His Glu Pro
            195                 200                 205

Phe Gly Arg Lys Trp Trp Lys Trp Leu Leu Leu Thr Gly Val Ser Leu
    210                 215                 220

Ser Cys Val Ile Ser Thr Lys Tyr Val Gly Val Phe Thr Phe Val Thr
225                 230                 235                 240

Ile Gly Ser Ala Val Met Val Asp Leu Trp Asn Leu Leu Asp Ile Arg
                245                 250                 255

Arg Gln Gly Gly Ala Leu Thr Met Phe Glu Trp Thr Lys His Phe Ala
                260                 265                 270

Ala Arg Phe Phe Ser Leu Ile Val Val Pro Phe Phe Phe Tyr Leu Phe
            275                 280                 285
```

-continued

```
Trp Phe Gln Val His Phe Ala Ile Leu Thr His Ser Gly Pro Gly Asp
            290                 295                 300

Asp Phe Met Thr Pro Ala Phe Gln Glu Thr Leu Ser Asp Asn Ala Met
305                 310                 315                 320

Ala Ala Gln Ser Val Ser Ile Glu Tyr Phe Asp Thr Ile Thr Met Arg
                325                 330                 335

His Lys Asp Thr Lys Val Phe Leu His Ser His Ser Asp Thr Tyr Pro
            340                 345                 350

Leu Arg Tyr Asp Asp Gly Arg Ile Ser Ser Gln Gly Gln Gln Val Thr
        355                 360                 365

Gly Tyr Pro Tyr Asn Asp Thr Asn Asn His Trp Gln Ile Ile Pro Thr
    370                 375                 380

Val Pro Leu Asp Glu Thr Asp Glu Lys Ser Arg Lys Val Arg Asn Gly
385                 390                 395                 400

Asp Ile Val Gln Leu Arg His Val Ala Thr Asp Thr Ile Leu Leu Thr
                405                 410                 415

His Asp Val Ala Ser Pro Tyr Tyr Pro Thr Asn Gln Glu Phe Thr Thr
            420                 425                 430

Val Ser His Glu Leu Ala Asp Gly Lys Arg His Asn Asp Thr Leu Phe
        435                 440                 445

Glu Ile Arg Val Glu His Gly Lys Ser Lys Gln Glu Phe Arg Thr Leu
    450                 455                 460

Ser Ser Gln Phe Lys Leu Val His Val Pro Thr Lys Val Ala Met Trp
465                 470                 475                 480

Thr His Thr Thr Pro Leu Pro Asp Trp Ala Tyr Lys Gln Ala Glu Ile
                485                 490                 495

Asn Gly Asn Lys Asn Val Leu Gln Ser Ser Asn Ile Trp Tyr Val Glu
            500                 505                 510

Ala Ile Glu Ser Leu Glu Glu Asp Ser Pro Arg Leu Lys Lys Glu Glu
        515                 520                 525

Arg Lys Val Lys His Leu Pro Phe Trp Arg Lys Tyr Ile Glu Leu Gln
    530                 535                 540

Arg Ala Met Phe Phe His Asn Asn Ala Leu Thr Ser Ser His Pro Tyr
545                 550                 555                 560

Ala Ser Glu Pro Phe Gln Trp Pro Phe Leu Leu Arg Gly Val Ser Phe
                565                 570                 575

Trp Thr Lys Ser Asp Thr Arg Glu Gln Ile Tyr Phe Leu Gly Asn Pro
            580                 585                 590

Val Gly Trp Trp Ile Ser Ser Leu Leu Ala Val Phe Ala Gly Val
        595                 600                 605

Ile Gly Ala Asp Gln Leu Ser Leu Arg Arg Gly Val Asp Ala Val Glu
    610                 615                 620

Glu Ile Trp Gly Pro Gly Ser Arg Ser Arg Leu Tyr Asn Ser Thr Gly
625                 630                 635                 640

Phe Leu Phe Leu Cys Trp Ala Ala His Tyr Phe Pro Phe Trp Leu Met
                645                 650                 655

Gly Arg Gln Arg Phe Leu His His Tyr Leu Pro Ala His Val Ala Ser
            660                 665                 670

Ala Leu Val Thr Gly Ala Leu Ile Glu Phe Ile Phe Asn Ile Gln Pro
        675                 680                 685

Ile Ser Val Pro Ala Thr Ile Pro Val Ala Ala Asp Asp Pro Thr Gly
    690                 695                 700
```

```
Lys Gly Lys Thr Arg Arg Phe Val Thr Ala Arg Glu Arg Met Gly Val
705                 710                 715                 720

Lys Ser Ile Val Ala Gly Trp Ile Ala Ser Leu Thr Ile Leu Ala Ala
            725                 730                 735

Thr Ile Trp Gly Phe Trp Phe Phe Ala Pro Leu Thr Tyr Gly Thr Pro
            740                 745                 750

Gly Leu Asp Val Ala Gln Val Asn Ala Arg Lys Trp Leu Gly Tyr Asp
            755                 760                 765

Leu His Phe Ala Lys
            770

<210> SEQ ID NO 8
<211> LENGTH: 774
<212> TYPE: PRT
<213> ORGANISM: Trichoderma virens

<400> SEQUENCE: 8

Met Ala Arg Thr Pro Thr Pro Gln Pro Pro Ser Leu Arg Gln Arg Asn
1               5                   10                  15

Val Ala Ser Lys Gln Pro Val Ser Glu Ala Thr Phe Ala Pro Glu Val
            20                  25                  30

Glu Leu Asp Lys Leu Ser Lys Ala Ala Ser Ser Arg Gln Asn Ile
        35                  40                  45

Gln Arg Gly Glu Thr Glu His Arg Val Ala Leu Thr Leu Val Thr Ile
    50                  55                  60

Leu Gly Phe Val Thr Arg Phe Trp Gly Ile Ser His Pro Asp Glu Val
65                  70                  75                  80

Val Phe Asp Glu Val His Phe Gly Lys Phe Ala Ser Tyr Tyr Leu Gln
                85                  90                  95

Arg Thr Tyr Phe Phe Asp Val His Pro Pro Phe Ala Lys Leu Leu Phe
                100                 105                 110

Ala Phe Val Gly Trp Leu Val Gly Tyr Asp Gly His Phe His Phe Glu
            115                 120                 125

Asn Ile Gly Asp Ser Tyr Ile Ala Asn Lys Val Pro Tyr Val Ala Phe
130                 135                 140

Arg Ala Leu Pro Ala Phe Leu Gly Ala Leu Thr Val Ser Val Thr Tyr
145                 150                 155                 160

Leu Ile Met Trp Glu Ser Gly Tyr Ser Val Pro Ala Cys Leu Val Ala
                165                 170                 175

Thr Gly Leu Ile Leu Leu Asp Asn Ala His Ile Gly Gln Thr Arg Leu
            180                 185                 190

Ile Leu Leu Asp Ala Thr Leu Val Leu Ala Met Ala Cys Ser Leu Leu
        195                 200                 205

Phe Tyr Ile Lys Phe Tyr Lys Leu Arg His Glu Pro Phe Ser Arg Lys
    210                 215                 220

Trp Trp Lys Trp Leu Val Leu Thr Gly Phe Ala Leu Ser Cys Asp Ile
225                 230                 235                 240

Ser Thr Lys Tyr Val Gly Leu Phe Ala Phe Val Thr Ile Gly Ser Ala
                245                 250                 255

Val Ile Ile Asp Leu Trp Glu Leu Asp Ile Arg Arg Pro Gly Gly
            260                 265                 270

Ala Ile Ser Leu Pro Leu Phe Gly Lys His Phe Ala Ala Arg Ala Val
        275                 280                 285

Gly Leu Ile Ile Leu Pro Phe Leu Phe Tyr Leu Phe Trp Phe Gln Val
    290                 295                 300
```

```
His Phe Ala Val Leu Thr Arg Ser Gly Pro Gly Asp Asp Phe Met Ser
305                 310                 315                 320

Pro Glu Phe Gln Glu Thr Leu Ser Asp Asn Val Met Leu Ala Ser Ala
            325                 330                 335

Val Asp Ile Gln Tyr Tyr Asp Thr Ile Thr Ile Arg His Lys Glu Thr
            340                 345                 350

Lys Ala Tyr Leu His Ser His Leu Asp Thr Tyr Pro Leu Arg Tyr Asp
            355                 360                 365

Asp Gly Arg Ile Ser Ser Gln Gly Gln Gln Val Thr Gly Tyr Pro His
370                 375                 380

Asn Asp Thr Asn Asn Tyr Trp Gln Ile Ile Pro Ala Ser Asn Asp Gln
385                 390                 395                 400

Lys Leu Gly Arg Ile Val Arg Asn Gln Glu Leu Val Arg Leu Arg His
                405                 410                 415

Ile Val Thr Asp Lys Ile Leu Leu Ser His Asp Val Ala Ser Pro Tyr
                420                 425                 430

Tyr Pro Thr Asn Gln Glu Phe Thr Ala Val Ser Ala Glu Glu Ala Tyr
            435                 440                 445

Gly Asp Arg Leu Asn Asp Thr Leu Phe Glu Ile Arg Ile Glu Gly Gly
450                 455                 460

Lys Pro Asn Gln Asp Phe Lys Thr Ile Ala Ser His Phe Lys Leu Ile
465                 470                 475                 480

His Phe Pro Ser Lys Val Ala Met Trp Thr His Thr Pro Leu Pro
                485                 490                 495

Glu Trp Ala Tyr Arg Gln Gln Glu Ile Asn Gly Asn Lys Gln Ile Thr
                500                 505                 510

Pro Ser Ser Asn Val Trp Ile Ala Glu Asp Ile Pro Ser Leu Pro Glu
            515                 520                 525

Asp His Ser Arg Arg Gln Lys Glu Glu Arg Lys Val Lys Ser Leu Pro
530                 535                 540

Phe Leu Arg Lys Trp Phe Glu Leu Gln Arg Ser Met Phe Tyr His Asn
545                 550                 555                 560

Asn Lys Leu Thr Ser Ser His Pro Tyr Ser Ser Gln Pro Tyr His Trp
                565                 570                 575

Pro Phe Leu Leu Arg Gly Val Ser Phe Trp Thr Gln Asn Asp Thr Arg
            580                 585                 590

Gln Gln Ile Tyr Phe Val Gly Asn Pro Ile Gly Trp Trp Leu Ala Ser
            595                 600                 605

Gly Leu Leu Ala Val Phe Ala Gly Ile Ile Gly Ala Asp Gln Val Ser
            610                 615                 620

Leu Arg Arg Gly Ile Asp Ala Leu Asp His Arg Thr Arg Ser Arg Leu
625                 630                 635                 640

Tyr Asn Ser Thr Gly Phe Phe Trp Leu Ala Trp Ala Thr His Tyr Phe
                645                 650                 655

Pro Phe Phe Leu Met Gly Arg Gln Leu Phe Leu His His Tyr Leu Pro
            660                 665                 670

Ala His Leu Ala Ser Cys Leu Val Thr Gly Ser Leu Val Glu Phe Ile
            675                 680                 685

Phe Asn Thr Asp Pro Ala Asp Glu Glu Pro Ser Arg Ala Thr Asn Pro
            690                 695                 700

Arg Ala Ser Gly Pro Lys Arg His Ile Thr Ala Arg Glu Arg Phe Ala
705                 710                 715                 720
```

```
Gly Lys Ser Met Ala Gly Ala Trp Ile Ala Cys Phe Val Ile Leu Thr
            725                 730                 735

Val Ala Ala Ala Ser Trp Tyr Phe Phe Leu Pro Leu Thr Tyr Gly Tyr
            740                 745                 750

Pro Gly Leu Ser Val Asp Glu Val Asn Arg Arg Lys Trp Leu Gly Tyr
            755                 760                 765

Asp Leu His Phe Ala Lys
            770

<210> SEQ ID NO 9
<211> LENGTH: 771
<212> TYPE: PRT
<213> ORGANISM: Trichoderma atroviride

<400> SEQUENCE: 9

Met Ala Arg Ala Ser Thr Pro Gln Gly Ser Leu Arg Gln Arg Gly Val
1               5                   10                  15

Ala Ser Lys Gln Thr Leu Ser Glu Ser Thr Phe Ala Pro Glu Val Glu
            20                  25                  30

Leu Asp Lys Leu Ser Lys Ala Ala Ser Ser Arg Gln Asn Val Gln
            35                  40                  45

Arg Gly Glu Ile Glu His Lys Ile Ala Leu Thr Leu Val Thr Ile Leu
        50                  55                  60

Gly Phe Val Thr Arg Phe Trp Gly Ile Ser His Pro Asp Glu Val Val
65                  70                  75                  80

Phe Asp Glu Val His Phe Gly Lys Phe Ala Ser Tyr Tyr Leu Gln Arg
                85                  90                  95

Thr Tyr Phe Phe Asp Val His Pro Phe Ala Lys Leu Leu Phe Ala
            100                 105                 110

Phe Val Gly Trp Leu Val Gly Tyr Asp Gly His Phe His Phe Glu Asn
            115                 120                 125

Ile Gly Asp Ser Tyr Val Ala Asn Lys Val Pro Tyr Val Ala Phe Arg
        130                 135                 140

Ala Leu Pro Ala Val Leu Gly Ala Leu Thr Val Ser Val Thr Tyr Leu
145                 150                 155                 160

Ile Met Trp Glu Ser Gly Tyr Ser Leu Pro Ala Cys Leu Val Ala Thr
                165                 170                 175

Gly Leu Ile Leu Leu Asp Asn Ala His Ile Gly Gln Thr Arg Leu Ile
            180                 185                 190

Leu Leu Asp Ala Thr Leu Val Leu Ala Met Ala Cys Ser Leu Leu Phe
            195                 200                 205

Tyr Ile Lys Phe Tyr Lys Leu Arg His Glu Ala Phe Ser Arg Lys Trp
        210                 215                 220

Trp Lys Trp Leu Ile Leu Thr Gly Phe Ala Leu Ser Cys Asp Ile Ser
225                 230                 235                 240

Thr Lys Tyr Val Gly Leu Phe Ala Phe Val Thr Ile Gly Ser Ala Val
                245                 250                 255

Ile Ile Asp Leu Trp Asp Leu Leu Asp Ile Lys Arg Arg Asn Gly Ala
            260                 265                 270

Ile Ser Leu Gln Leu Phe Gly Lys His Phe Ala Ala Arg Ala Ile Gly
            275                 280                 285

Leu Ile Val Leu Pro Phe Leu Phe Tyr Leu Phe Trp Phe Gln Val His
        290                 295                 300

Phe Ala Val Leu Thr Arg Ser Gly Pro Gly Asp Asp Phe Met Thr Pro
305                 310                 315                 320
```

```
Glu Phe Gln Glu Thr Leu Ser Asp Asn Val Met Leu Ala Asn Ala Val
                325                 330                 335

Asp Ile His Tyr Tyr Asp Tyr Ile Thr Ile Arg His Lys Glu Thr Lys
            340                 345                 350

Ala Tyr Leu His Ser His Pro Asp Thr Tyr Pro Leu Arg Tyr Asp Asp
        355                 360                 365

Gly Arg Ile Ser Ser Gln Gly Gln Gln Ile Thr Gly Tyr Pro His Asn
    370                 375                 380

Asp Thr Asn Asn Tyr Trp Gln Val Leu Pro Ser Asp Asn Val His Asn
385                 390                 395                 400

Thr Glu Arg Ile Val Arg Asn Phe Asp Leu Val Arg Leu Arg His Ile
                405                 410                 415

Val Thr Asp Lys Ile Leu Leu Ser His Asp Val Ala Ser Pro Tyr Phe
            420                 425                 430

Pro Thr Asn Gln Glu Phe Thr Ala Val Thr Ser Glu Glu Ala Phe Gly
        435                 440                 445

Glu Arg Gln Asn Asp Thr Leu Phe Glu Ile Arg Val Glu Thr Ala Lys
    450                 455                 460

Val Gly Ala Glu Phe Lys Thr Val Ala Ser His Phe Lys Leu Val His
465                 470                 475                 480

Phe Pro Ser Lys Val Ala Met Trp Thr His Thr Thr Pro Leu Pro Glu
                485                 490                 495

Trp Gly Tyr Lys Gln Gln Glu Ile Asn Gly Asn Lys Gln Val Thr Val
            500                 505                 510

Ser Ser Asn Met Trp Ile Ala Glu Asp Ile Pro Ser Leu Pro Gln Asp
        515                 520                 525

Asp Ala Arg Arg Gln Lys Glu Gln Arg Gln Val Lys Ser Leu Pro Phe
    530                 535                 540

Leu Arg Lys Trp Phe Glu Leu Gln Arg Ser Met Phe Tyr His Asn Asn
545                 550                 555                 560

Lys Leu Thr Ser Ser His Pro Tyr Ser Ser Gln Pro Tyr His Trp Pro
                565                 570                 575

Phe Leu Leu Arg Gly Val Ser Phe Trp Thr Gln Asn Asp Thr Arg Gln
            580                 585                 590

Gln Ile Tyr Phe Val Gly Asn Pro Ile Gly Trp Trp Ile Thr Ser Ser
        595                 600                 605

Leu Leu Ala Val Phe Ala Gly Ile Ile Ala Ala Asp Gln Ile Ser Leu
    610                 615                 620

Arg Arg Asn Ile Asp Ala Leu Asp His Arg Thr Arg Ser Arg Leu Tyr
625                 630                 635                 640

Asn Ser Thr Gly Phe Phe Trp Leu Ala Trp Ala Thr His Tyr Phe Pro
                645                 650                 655

Phe Tyr Leu Met Gly Arg Gln Leu Phe Leu His His Tyr Leu Pro Ala
            660                 665                 670

His Leu Ala Ser Cys Leu Val Thr Gly Ala Leu Val Glu Phe Ile Phe
        675                 680                 685

Asn Ser Asp Ala Val Glu Glu Glu Ser Ser Lys Ser Gly Asn Arg Ser
    690                 695                 700

Ser Pro Lys Arg His Val Thr Ala Arg Glu Arg Phe Ala Gly Lys Ser
705                 710                 715                 720

Met Leu Gly Ala Trp Ile Ala Cys Gly Val Ile Leu Ser Ala Ala Ala
                725                 730                 735
```

```
Ala Cys Trp Tyr Phe Phe Leu Pro Leu Thr Tyr Gly Tyr Pro Gly Leu
            740                 745                 750

Ser Val Glu Glu Val Val Arg Arg Lys Trp Leu Gly Tyr Asp Leu His
    755                 760                 765

Phe Ala Lys
    770

<210> SEQ ID NO 10
<211> LENGTH: 770
<212> TYPE: PRT
<213> ORGANISM: Fusarium oxysporum

<400> SEQUENCE: 10

Met Ala Arg Ser Ser Thr Pro Gln Gly Ser Leu Arg Gln Arg Gly Ala
1               5                   10                  15

Pro Ser Lys Lys Pro Phe Glu Glu Asp Ser Phe Asp Pro Asn Ile Glu
            20                  25                  30

Leu Asp Lys Leu Ala Lys Ala Gly Ala Gln Arg Ala Ala Ala Gln Ser
        35                  40                  45

Glu Thr Glu Tyr Lys Ile Gly Leu Phe Leu Ile Thr Ile Leu Ser Phe
50                  55                  60

Val Thr Arg Phe Trp Gly Ile Ser His Pro Asn Glu Val Val Phe Asp
65                  70                  75                  80

Glu Val His Phe Gly Lys Phe Ala Ser Tyr Tyr Leu Glu Arg Thr Tyr
                85                  90                  95

Phe Phe Asp Val His Pro Pro Phe Gly Lys Leu Leu Phe Ala Phe Val
            100                 105                 110

Gly Trp Leu Val Gly Tyr Asp Gly Asn Phe His Phe Glu Asn Ile Gly
        115                 120                 125

Asp Ser Tyr Ile Ala Asn Lys Val Pro Tyr Val Ala Tyr Arg Ala Leu
130                 135                 140

Pro Ala Thr Leu Gly Ala Leu Thr Val Ser Val Thr Tyr Leu Ile Met
145                 150                 155                 160

Trp Glu Ser Gly Tyr Ser Leu Pro Ala Cys Ile Leu Ala Ala Gly Leu
                165                 170                 175

Val Leu Leu Asp Asn Ala His Ile Gly Gln Thr Arg Leu Ile Leu Leu
            180                 185                 190

Asp Ala Thr Leu Val Leu Ala Met Ala Cys Ser Leu Leu Phe Tyr Ile
        195                 200                 205

Lys Trp Tyr Lys Leu Arg His Glu Pro Phe Ser Arg Lys Trp Trp Lys
210                 215                 220

Trp Leu Ile Leu Thr Gly Phe Ala Leu Ser Cys Asp Ile Ser Val Lys
225                 230                 235                 240

Tyr Val Gly Val Phe Ala Phe Val Thr Ile Gly Ser Ala Val Val Ile
                245                 250                 255

Asp Leu Trp Asp Leu Leu Asn Ile Asn Arg Pro Gly Gly Ala Ile Ser
            260                 265                 270

Leu Gln Glu Phe Thr Lys His Phe Ala Ala Arg Ala Phe Gly Leu Ile
        275                 280                 285

Ile Met Pro Phe Leu Phe Tyr Leu Phe Trp Phe Gln Val His Phe Ala
290                 295                 300

Val Leu Tyr Arg Ser Gly Pro Gly Asp Asp Phe Met Thr Pro Glu Phe
305                 310                 315                 320

Gln Glu Thr Leu Ser Asp Asn Val Met Leu Ala Asn Ser Ile Asp Ile
                325                 330                 335
```

```
Gln Tyr Tyr Asp Gln Ile Thr Ile Arg His Lys Glu Thr Lys Thr Tyr
            340                 345                 350

Leu His Ser His Glu Asp Arg Tyr Pro Leu Arg Tyr Asp Asp Gly Arg
            355                 360                 365

Val Ser Ser Gln Gly Gln Gln Ile Thr Gly Tyr Pro Tyr Asn Asp Thr
370                 375                 380

Asn Asn Tyr Trp Glu Ile Leu Pro Ala Asn Asn Asp Lys Gln Ile Gly
385                 390                 395                 400

Arg Ile Val Lys Asn His Glu Leu Val Arg Leu Arg His Val Gly Thr
                405                 410                 415

Asp Lys Ile Leu Leu Ser His Asp Val Ala Ser Pro Tyr Tyr Pro Thr
            420                 425                 430

Asn Gln Glu Phe Thr Ala Val Thr Pro Glu Glu Ala Phe Gly Lys Arg
            435                 440                 445

Glu Lys Asp Thr Leu Phe Glu Val Arg Ile Glu His Gly Lys Lys Asn
        450                 455                 460

Gln Asn Phe Lys Thr Val Ala Gly His Phe Lys Leu Ile His Asn Pro
465                 470                 475                 480

Ser Lys Val Ala Met Trp Thr His Thr Lys Pro Leu Pro Glu Trp Gly
            485                 490                 495

Tyr Lys Gln Gln Glu Ile Asn Gly Asn Lys Gln Ile Ala Pro Ser Ser
        500                 505                 510

Asn Val Trp Ile Ala Glu Asp Ile Pro Ser Leu Pro Ala Asp His Pro
        515                 520                 525

Arg Arg Gln Lys Pro Glu Arg Lys Val Lys Ser Leu Pro Phe Leu Gln
        530                 535                 540

Lys Trp Phe Glu Leu Gln Arg Ala Met Phe Tyr His Asn Ser Lys Leu
545                 550                 555                 560

Thr Ser Ser His Pro Tyr Ala Ser His Pro Tyr Gln Trp Pro Phe Leu
            565                 570                 575

Leu Arg Gly Val Ser Phe Trp Thr Gln Ser Glu Thr Arg Gln Gln Ile
            580                 585                 590

Tyr Phe Leu Gly Asn Pro Ile Gly Trp Trp Leu Ala Ser Ser Leu Leu
            595                 600                 605

Ala Val Tyr Ala Gly Ile Leu Leu Ala Asp Gln Val Ser Leu Arg Arg
            610                 615                 620

Gly Val Asp Ala Leu Asp Arg Arg Thr Arg Ser Arg Leu Tyr Asn Ser
625                 630                 635                 640

Thr Gly Phe Phe Phe Leu Ala Trp Ala Thr His Tyr Phe Pro Phe Phe
                645                 650                 655

Leu Met Gly Arg Gln Leu Phe Leu His His Tyr Leu Pro Ala His Leu
            660                 665                 670

Ala Ser Cys Leu Val Ala Gly Ala Leu Leu Glu Phe Ile Phe Asn Ser
        675                 680                 685

Glu Ala Pro Glu Glu Val Thr Ile Lys Asp Lys Lys Gly Pro Val Ser
            690                 695                 700

Pro Arg His His Val Thr Ala Arg Glu Arg Phe Ala Gly Gln Ser Met
705                 710                 715                 720

Leu Gly Ala Trp Ile Ala Cys Gly Val Ile Leu Ser Leu Ile Ile Ala
                725                 730                 735

Gly Trp Tyr Phe Phe Leu Pro Leu Thr Tyr Gly Tyr Pro Gly Leu Ser
            740                 745                 750
```

```
Val Asp Ala Ile Leu Arg Arg Lys Trp Leu Gly Tyr Asp Leu His Phe
            755                 760                 765
Ala Lys
    770

<210> SEQ ID NO 11
<211> LENGTH: 788
<212> TYPE: PRT
<213> ORGANISM: Gibberella zeae

<400> SEQUENCE: 11

Met Ala Arg Ser Ser Pro Ser Gln Gly Ser Leu Arg Gln Arg Gly
1               5                   10                  15

Ala Pro Ser Lys Lys Pro Ser Glu Glu Ser Phe Asn Pro Asn Pro Glu
                20                  25                  30

Leu Asp Lys Leu Ala Lys Ala Gly Ala Gln Arg Ala Ala Ala Gln Ser
            35                  40                  45

Glu Thr Glu His Lys Ile Gly Leu Ala Val Ile Thr Ile Leu Ser Phe
    50                  55                  60

Val Thr Arg Phe Trp Gly Ile Ser His Pro Asn Glu Val Val Phe Asp
65                  70                  75                  80

Glu Val His Phe Gly Lys Phe Ala Ser Tyr Tyr Leu Glu Arg Thr Tyr
                85                  90                  95

Phe Phe Asp Val His Pro Pro Phe Gly Lys Leu Leu Phe Ala Phe Val
            100                 105                 110

Gly Trp Leu Val Gly Tyr Asp Gly His Phe His Phe Asp Asn Ile Gly
        115                 120                 125

Asp Ser Tyr Ile Ala Asn Lys Ile Pro Tyr Val Ala Phe Arg Ala Leu
    130                 135                 140

Pro Ala Thr Leu Gly Ala Leu Thr Val Ala Val Thr Tyr Leu Ile Met
145                 150                 155                 160

Trp Glu Ser Gly Tyr Ser Leu Pro Ala Cys Val Leu Ala Ala Gly Leu
                165                 170                 175

Leu Leu Leu Asp Asn Ala His Ile Gly Gln Thr Arg Leu Ile Leu Leu
            180                 185                 190

Asp Ala Thr Leu Val Leu Ala Met Ala Cys Ser Leu Leu Phe Tyr Ile
        195                 200                 205

Lys Trp Tyr Lys Leu Arg His Glu Pro Phe Ser Arg Lys Trp Trp Lys
    210                 215                 220

Trp Leu Ile Leu Thr Gly Phe Ala Leu Ser Cys Asp Ile Ser Val Lys
225                 230                 235                 240

Tyr Val Gly Val Phe Ala Phe Val Thr Ile Gly Cys Ala Val Val Ile
                245                 250                 255

Asp Leu Trp Asp Leu Leu Asn Ile Asn Arg Pro Gly Gly Ala Ile Ser
            260                 265                 270

Met Gln Glu Phe Gly Lys His Phe Ala Ala Arg Ala Phe Gly Leu Ile
        275                 280                 285

Val Leu Pro Phe Leu Phe Tyr Leu Phe Trp Phe Gln Val His Phe Ala
    290                 295                 300

Val Leu Tyr Arg Ser Gly Pro Gly Asp Asp Phe Met Thr Pro Glu Phe
305                 310                 315                 320

Gln Glu Thr Leu Ser Asp Asn Val Met Leu Ala Asn Ala Ile Asp Ile
                325                 330                 335

Gln Tyr Tyr Asp Ser Ile Thr Ile Arg His Lys Glu Thr Lys Thr Tyr
            340                 345                 350
```

```
Leu His Ser His Glu Asp Arg Tyr Pro Leu Arg Tyr Asp Asp Gly Arg
            355                 360                 365

Val Ser Ser Gln Gly Gln Gln Ile Thr Gly Tyr Pro Tyr Asn Asp Thr
        370                 375                 380

Asn Asn Tyr Trp Glu Ile Trp Pro Ala Asp Asn Asn Lys Thr Pro Gly
385                 390                 395                 400

Arg Ile Val Lys Asn His Asp Leu Val Arg Leu Arg His Val Gly Thr
                405                 410                 415

Asp Lys Ile Leu Leu Ser His Asp Val Ala Ser Pro Tyr Tyr Pro Thr
                420                 425                 430

Asn Gln Glu Phe Thr Ala Val Thr Pro Glu Glu Ala Leu Gly Lys Arg
            435                 440                 445

Glu Lys Glu Thr Leu Phe Glu Val Arg Leu Glu His Gly Lys Lys Asn
        450                 455                 460

Gln Asn Phe Lys Ser Val Ala Gly His Phe Lys Leu Ile His Asn Pro
465                 470                 475                 480

Ser Lys Val Ala Met Trp Thr His Thr Lys Pro Leu Pro Glu Trp Gly
                485                 490                 495

Tyr Lys Gln Gln Glu Ile Asn Gly Asn Lys Gln Ile Ala Pro Ser Ser
            500                 505                 510

Asn Val Trp Ile Ala Glu Asp Ile Ala Ser Leu Glu Ala Asp His Pro
        515                 520                 525

Arg Arg Gln Lys Pro Glu Arg Lys Val Lys Ser Leu Pro Phe Leu Gln
530                 535                 540

Lys Trp Phe Glu Leu Gln Arg Ala Met Phe Tyr His Asn Ser Lys Leu
545                 550                 555                 560

Thr Ser Ser His Pro Tyr Ala Ser His Pro Tyr Gln Trp Pro Phe Leu
                565                 570                 575

Leu Arg Gly Val Ser Phe Trp Thr Gln Ser Glu Thr Arg Gln Gln Ile
            580                 585                 590

Tyr Phe Leu Gly Asn Pro Val Gly Trp Trp Leu Ala Ser Ser Leu Leu
        595                 600                 605

Ala Val Tyr Ala Gly Ile Leu Leu Ala Asp Gln Val Ser Leu Arg Arg
        610                 615                 620

Gly Ile Asp Ala Leu Asp Arg Arg Lys Leu Met Leu Gln Ser Gln Leu
625                 630                 635                 640

Met Asn Pro Thr Leu Thr Asn Ser Lys Gly Thr Arg Ser Arg Leu Tyr
                645                 650                 655

Asn Ser Thr Gly Phe Phe Leu Ala Trp Ala Thr His Tyr Phe Pro
            660                 665                 670

Phe Phe Leu Met Gly Arg Gln Leu Phe Leu His His Tyr Leu Pro Ala
            675                 680                 685

His Leu Ala Ser Cys Leu Val Ala Gly Ala Leu Leu Glu Phe Ile Phe
        690                 695                 700

Asn Ser Glu Pro Ala Glu Glu Ile Thr Ile Lys Asp Lys Lys Gly Pro
705                 710                 715                 720

Val Ser Pro Arg His His Val Thr Ala Arg Glu Arg Phe Ser Gly Gln
                725                 730                 735

Ser Met Ala Ser Ala Trp Ile Ala Cys Gly Val Val Leu Ala Leu Val
            740                 745                 750

Val Ala Gly Trp Tyr Phe Phe Leu Pro Leu Thr Tyr Gly Tyr Pro Gly
        755                 760                 765
```

```
Leu Ser Val Glu Ala Ile Leu Arg Arg Lys Trp Leu Gly Tyr Asp Leu
    770                 775                 780

His Phe Ala Lys
785

<210> SEQ ID NO 12
<211> LENGTH: 775
<212> TYPE: PRT
<213> ORGANISM: Myceliophthora thermophila

<400> SEQUENCE: 12

Met Ala Ser Thr Ser Thr Pro Gln Gly Thr Leu Arg Gln Arg Asn Val
1               5                   10                  15

Gly Val Ser Thr Lys Lys Pro Lys Asp Gly Ala Ser Ser Asp Val Glu
            20                  25                  30

Leu Asp Lys Leu Val Lys Ala Ala Glu Lys Ser Ser Lys Asn Ser
        35                  40                  45

Glu Arg Asp Phe Lys Val Val Phe Val Val Met Thr Ala Leu Ala Phe
    50                  55                  60

Leu Thr Arg Phe Trp Gly Ile Ser His Pro Asn Glu Val Val Phe Asp
65                  70                  75                  80

Glu Val His Phe Gly Lys Phe Ala Ser Tyr Tyr Leu Glu Arg Thr Tyr
                85                  90                  95

Phe Phe Asp Val His Pro Pro Leu Gly Lys Leu Leu Phe Ala Phe Met
            100                 105                 110

Gly Trp Leu Val Gly Tyr Asp Gly His Phe His Phe Glu Asn Ile Gly
        115                 120                 125

Asp Ser Tyr Ile Val Asn Lys Val Pro Tyr Val Ala Phe Arg Ser Leu
    130                 135                 140

Pro Ala Ile Leu Gly Ala Leu Thr Val Ser Val Thr Tyr Leu Ile Met
145                 150                 155                 160

Trp Glu Ser Gly Tyr Ser Leu Pro Ala Cys Ile Ile Ala Ala Gly Leu
                165                 170                 175

Ile Leu Leu Asp Asn Ala His Ile Gly Gln Thr Arg Leu Ile Leu Leu
            180                 185                 190

Asp Ala Thr Leu Val Phe Ala Met Ala Cys Ser Leu Leu Cys Tyr Ile
        195                 200                 205

Lys Phe Tyr Lys Leu Arg His Glu Pro Phe Ser Arg Lys Trp Trp Lys
    210                 215                 220

Trp Leu Ile Leu Thr Gly Phe Ala Leu Ser Cys Asp Ile Ser Thr Lys
225                 230                 235                 240

Tyr Val Gly Leu Phe Ala Phe Ile Thr Ile Gly Ser Ala Val Val Ile
                245                 250                 255

Asp Leu Trp Asp Leu Leu Asp Ile Lys Arg Pro Gly Gly Ala Leu Thr
            260                 265                 270

Leu Ala Glu Phe Gly Lys His Phe Ala Ala Arg Ala Phe Gly Leu Ile
        275                 280                 285

Ile Met Pro Phe Leu Phe Tyr Leu Phe Trp Phe Gln Val His Phe Ser
    290                 295                 300

Ile Leu Thr Arg Ser Gly Pro Gly Asp Asp Phe Met Thr Pro Glu Phe
305                 310                 315                 320

Gln Glu Thr Leu Ser Asp Asn Ile Met Leu Ala Asn Ala Val Thr Ile
                325                 330                 335

Asp Tyr Tyr Asp Thr Ile Leu Ile Lys His Lys Glu Thr Lys Val Tyr
            340                 345                 350
```

```
Leu His Ser His Pro Asp Arg Tyr Pro Leu Arg Tyr Asp Asp Gly Arg
            355                 360                 365

Val Ser Ser Gln Gly Gln Val Thr Gly Tyr Pro Phe Asn Asp Thr
        370                 375                 380

Asn Asn Tyr Trp Gln Ile Leu Pro Gly Gly Ala Asp Asp Gln Lys Leu
385                 390                 395                 400

Gly Arg His Val Arg Asn His Asp Leu Val Arg Leu Arg His Leu Gly
                405                 410                 415

Thr Asp Thr Ile Leu Leu Ser His Asp Val Ala Ser Pro Tyr Tyr Pro
            420                 425                 430

Thr Asn Gln Glu Phe Thr Thr Val Ser Ile Ala Asp Ala Tyr Gly Glu
            435                 440                 445

Arg Ala Ala Asp Thr Leu Phe Glu Ile Arg Ile Glu His Gly Lys Asp
        450                 455                 460

Gly Gln Glu Phe Lys Ser Val Ser Ser His Phe Lys Leu Ile His Asn
465                 470                 475                 480

Pro Ser Lys Val Ala Met Trp Thr His Pro Lys Pro Leu Pro Asp Trp
                485                 490                 495

Gly Tyr Lys Gln Gln Glu Ile Asn Gly Asn Lys Gln Ile Ala Pro Ser
            500                 505                 510

Ser Asn Val Trp Leu Val Glu Asp Ile Val Ser Leu Pro Pro Asp His
            515                 520                 525

Lys Arg Arg Glu Lys Pro Glu Arg Lys Val Lys Thr Leu Pro Phe Leu
        530                 535                 540

Arg Lys Trp Phe Glu Leu Gln Arg Ser Met Phe Trp His Asn Asn Gln
545                 550                 555                 560

Leu Thr Ala Ser His Pro Tyr Ala Ser Leu Pro Tyr Gln Trp Pro Phe
                565                 570                 575

Leu Leu Arg Gly Val Ser Phe Trp Thr Gln Asn Glu Thr Arg Gln Gln
            580                 585                 590

Ile Tyr Phe Leu Gly Asn Pro Val Gly Trp Trp Ile Ala Ser Ser Val
        595                 600                 605

Leu Ala Ile Tyr Ala Gly Ile Val Leu Ala Asp Gln Phe Ser Leu Arg
        610                 615                 620

Arg Gly Ile Asp Ala Leu Asp His Arg Ser Arg Ser Arg Leu Tyr Asn
625                 630                 635                 640

Ser Thr Gly Phe Phe Phe Leu Ala Trp Ala Thr His Tyr Phe Pro Phe
                645                 650                 655

Tyr Val Met Gly Arg Gln Leu Phe Leu His His Tyr Leu Pro Ala His
                660                 665                 670

Leu Ala Ser Ala Leu Val Thr Gly Ala Ile Val Glu Phe Ile Phe Ala
            675                 680                 685

Gln Asp Ser Leu Glu His Glu Val Ala Tyr Gln Ala Ala Lys Ala Gly
        690                 695                 700

Lys Lys Thr Gly Val Gln Lys Arg His Leu Ser Ala Arg Glu Arg Phe
705                 710                 715                 720

Ala Gly Gln Ser Met Val Ala Ser Trp Ile Ala Thr Val Ile Leu
                725                 730                 735

Ile Ala Val Ala Ala Ser Trp Tyr Phe Phe Leu Pro Leu Thr Tyr Gly
                740                 745                 750

Tyr Pro Gly Leu Ser Val Asp Gln Val Leu Arg Arg Lys Trp Leu Gly
            755                 760                 765
```

```
<210> SEQ ID NO 13
<211> LENGTH: 774
<212> TYPE: PRT
<213> ORGANISM: Neurospora crassa

<400> SEQUENCE: 13

Met Ala Ser Thr Thr Ala Thr Pro Glu Ala Thr Leu Arg Gln Arg Asn
1               5                   10                  15

Val Pro Ala Ser Ser Lys Lys Ala Lys Asn Gly Val Ser Ser Asp Val
            20                  25                  30

Glu Thr Asp Lys Val Pro Asp Ala Val Ala Pro Ala Lys Ser Gly Ser
        35                  40                  45

Glu Leu Glu Tyr Lys Leu Ala Leu Ile Leu Ile Thr Gly Leu Ala Phe
    50                  55                  60

Leu Thr Arg Phe Trp Gly Ile Ser His Pro Asp Glu Val Val Phe Asp
65                  70                  75                  80

Glu Val His Phe Gly Lys Phe Ala Ser Tyr Tyr Leu Glu Arg Thr Tyr
                85                  90                  95

Phe Phe Asp Val His Pro Pro Phe Gly Lys Leu Leu Phe Ala Phe Met
            100                 105                 110

Gly Trp Leu Val Gly Tyr Asp Gly His Phe His Phe Glu Asn Ile Gly
        115                 120                 125

Asp Ser Tyr Ile Arg Asn Lys Val Pro Tyr Val Ala Phe Arg Ser Leu
    130                 135                 140

Pro Ala Ile Leu Gly Ala Leu Thr Val Ser Val Val Tyr Met Ile Met
145                 150                 155                 160

Trp Glu Ser Gly Tyr Ser Leu Pro Ala Cys Leu Ile Ala Ala Gly Leu
                165                 170                 175

Val Leu Leu Asp Asn Ala His Ile Gly Gln Thr Arg Leu Ile Leu Leu
            180                 185                 190

Asp Ala Thr Leu Val Phe Ala Met Ala Cys Ser Leu Leu Cys Tyr Ile
        195                 200                 205

Lys Phe His Lys Leu Arg His Glu Pro Phe Ser Arg Lys Trp Trp Lys
    210                 215                 220

Trp Leu Ile Leu Thr Gly Phe Ala Leu Ser Cys Asp Ile Ser Thr Lys
225                 230                 235                 240

Tyr Val Gly Leu Phe Ala Phe Ile Thr Ile Gly Ser Ala Val Cys Ile
                245                 250                 255

Asp Leu Trp Asp Leu Leu Asp Ile Lys Arg Pro Gly Gly Ala Leu Thr
            260                 265                 270

Leu Pro Gln Phe Gly Lys His Phe Ala Ala Arg Ala Phe Gly Leu Ile
        275                 280                 285

Ile Met Pro Phe Ile Phe Tyr Leu Phe Trp Phe Gln Val His Phe Ser
    290                 295                 300

Ile Leu Thr Arg Ser Gly Pro Gly Asp Asp Phe Met Thr Pro Glu Phe
305                 310                 315                 320

Gln Glu Thr Leu Ser Asp Asn Ile Met Leu Ala Asn Ala Val Thr Ile
                325                 330                 335

Asp Tyr Tyr Asp Thr Ile Ser Ile Arg His Lys Glu Thr Lys Ala Tyr
            340                 345                 350

Leu His Ser His Pro Asp Lys Tyr Pro Leu Arg Tyr Asp Asp Gly Arg
        355                 360                 365
```

```
Val Ser Ser Gln Gly Gln Gln Val Thr Gly Tyr Pro Phe Asn Asp Thr
    370                 375                 380

Asn Asn Tyr Trp Gln Ile Leu Pro Pro Gly Pro Asp Asp Gln Lys Leu
385                 390                 395                 400

Gly His Pro Ile Lys Asn His Asp Leu Val Arg Leu Arg His Ile Val
                405                 410                 415

Thr Asp Thr Ile Leu Leu Ser His Asp Val Ala Ser Pro Tyr Tyr Pro
            420                 425                 430

Thr Asn Gln Glu Phe Thr Thr Val Ser Ile Gly Asp Ala Tyr Gly Asp
        435                 440                 445

Arg Ala Ala Asp Thr Leu Phe Glu Ile Arg Ile Glu His Gly Lys Ala
    450                 455                 460

Asn Gln Glu Phe Lys Ser Ile Ser Ser His Phe Lys Leu Ile His Asn
465                 470                 475                 480

Pro Ser Lys Val Ala Met Trp Thr His Ser Lys Pro Leu Pro Glu Trp
                485                 490                 495

Gly His Lys Gln Gln Glu Ile Asn Gly Asn Lys Gln Leu Ala Gln Ser
            500                 505                 510

Ser Asn Val Trp Leu Val Glu Asp Ile Val Ser Leu Pro Ala Asp His
        515                 520                 525

Ala Arg Arg Glu Lys Pro Glu Lys Lys Val Lys Thr Leu Pro Phe Leu
    530                 535                 540

Arg Lys Trp Phe Glu Leu Gln Arg Ser Met Phe Trp His Asn Asn Gln
545                 550                 555                 560

Leu Thr Ser Ser His Pro Tyr Ala Ser Leu Pro Tyr Gln Trp Pro Phe
                565                 570                 575

Leu Leu Arg Gly Val Ser Phe Trp Thr Gln Asn Asp Thr Arg Gln Gln
            580                 585                 590

Ile Tyr Phe Leu Gly Asn Pro Ile Gly Trp Trp Leu Ala Ser Ser Val
        595                 600                 605

Leu Ala Ile Tyr Ala Gly Ile Ile Leu Ala Asp Gln Phe Ser Leu Arg
    610                 615                 620

Arg Gly Leu Asp Ala Met Asp Arg Arg Thr Arg Ser Arg Leu Tyr Asn
625                 630                 635                 640

Ser Thr Gly Phe Phe Phe Leu Ala Trp Ala Thr His Tyr Phe Pro Phe
                645                 650                 655

Phe Val Met Gly Arg Gln Leu Phe Leu His His Tyr Leu Pro Ala His
            660                 665                 670

Leu Ala Ser Ala Leu Val Thr Gly Ser Val Val Glu Phe Leu Phe Ser
        675                 680                 685

Thr Asp Ser Ala Glu Pro Glu Tyr Gln Pro Ser Lys Ser Gly Lys Lys
    690                 695                 700

Val Ala Pro Thr Thr Lys Arg Arg Leu Ser Ala Arg Glu Arg Leu Ala
705                 710                 715                 720

Gly Gln Ser Met Ala Gly Ala Trp Ile Ala Thr Ala Val Ile Met Val
                725                 730                 735

Leu Val Ala Phe Gly Trp Tyr Phe Phe Leu Pro Leu Thr Tyr Gly Tyr
            740                 745                 750

Pro Gly Leu Thr Ala Pro Glu Val Asn Arg Arg Lys Trp Leu Gly Tyr
        755                 760                 765

Asp Leu His Phe Ala Lys
    770
```

```
<210> SEQ ID NO 14
<211> LENGTH: 776
<212> TYPE: PRT
<213> ORGANISM: Penicillium chrysogenum

<400> SEQUENCE: 14

Met Ser Ser Pro Ser Pro Ser Leu Arg Lys Arg Gly Gly Lys Lys Asp
1               5                   10                  15

Val Tyr Thr Ala Leu Pro Ser Asp Asp Thr Ser Thr Pro Val Ser Val
                20                  25                  30

Pro Val Lys Gln Lys Ser Glu Trp Asp Tyr Trp Leu Ala Ile Val Ile
            35                  40                  45

Leu Thr Leu Leu Ala Phe Ala Thr Arg Phe Tyr Arg Leu Asp Tyr Pro
    50                  55                  60

Asn Glu Val Val Phe Asp Glu Val His Phe Gly Lys Phe Ala Ser Tyr
65                  70                  75                  80

Tyr Leu Gln Arg Thr Tyr Phe Phe Asp Val His Pro Pro Phe Gly Lys
                85                  90                  95

Leu Leu Phe Ala Leu Met Gly Trp Leu Val Gly Phe Asp Gly Ser Phe
            100                 105                 110

Leu Phe Glu Asn Ile Gly Asp Ser Tyr Ile Glu Asn Asn Val Pro Tyr
        115                 120                 125

Leu Ser Leu Arg Ala Met Pro Ala Thr Leu Gly Ala Leu Thr Ile Pro
    130                 135                 140

Val Val Phe Leu Ile Met Trp Glu Ser Gly Tyr Ser Leu Pro Ala Cys
145                 150                 155                 160

Val Leu Ser Ala Gly Leu Met Val Phe Asp Asn Ala His Val Gly Glu
                165                 170                 175

Asp Arg Leu Ile Leu Leu Asp Ala Thr Leu Val Leu Ser Met Ala Leu
            180                 185                 190

Ser Ile Leu Cys Tyr Val Arg Phe Tyr Lys Leu Arg His Gln Pro Phe
        195                 200                 205

Gly Arg Lys Trp Trp Lys Trp Leu Leu Leu Thr Gly Phe Cys Met Ser
    210                 215                 220

Cys Val Ile Ser Thr Lys Tyr Val Gly Phe Phe Thr Phe Val Thr Ile
225                 230                 235                 240

Gly Ala Ala Val Leu Ile Asp Leu Trp Asn Leu Leu Asp Ile Asn Arg
                245                 250                 255

Glu Gln Gly Ala Leu Ser Met Ile Ser Trp Gly Lys His Phe Ile Ala
            260                 265                 270

Arg Ala Val Gly Leu Val Ile Ile Pro Phe Met Phe Tyr Leu Phe Trp
        275                 280                 285

Phe Gln Val His Phe Ala Ile Leu Asn Arg Ser Gly Pro Gly Asp Asp
    290                 295                 300

Phe Met Thr Pro Glu Phe Gln Glu Thr Leu Ser Asp Asn Gln Met Thr
305                 310                 315                 320

Ala Gln Ser Val Gly Ile Gln Tyr Phe Asp Thr Ile Thr Met Arg His
                325                 330                 335

Lys Asp Thr Lys Val Phe Leu His Ser His Trp Asp Lys Tyr Pro Leu
            340                 345                 350

Arg Tyr Asp Asp Gly Arg Ile Ser Ser Gln Gly Gln Val Thr Gly
        355                 360                 365

Tyr Pro His Asn Asp Thr Asn Asn Gln Trp Gln Ile Leu Pro Ala Glu
    370                 375                 380
```

Pro Leu Ala Asp Ser Ser Glu Pro Lys Ser Val Arg Asn Gly Asp Ile
385                 390                 395                 400

Ile Gln Leu Arg His Ile Gly Thr Glu Ser Tyr Leu Leu Thr His Asp
            405                 410                 415

Val Ala Ser Pro Phe Phe Pro Thr Asn Gln Glu Phe Thr Thr Val Ser
        420                 425                 430

Gln Glu Leu Ala Asp Gly Glu Arg His Asn Asp Thr Leu Phe Glu Leu
    435                 440                 445

Lys Ile Glu Ser Gly Lys Thr Ala Gln Glu Phe Arg Thr Leu Ala Ser
450                 455                 460

Leu Phe Lys Leu Val His Val Pro Thr Arg Val Ala Leu Trp Thr His
465                 470                 475                 480

Thr Thr Pro Leu Pro Glu Trp Gly Tyr Lys Gln Ala Glu Ile Asn Gly
                485                 490                 495

Asn Lys Asn Ile Leu Gln Ser Ser Asn Met Trp Tyr Val Glu Asn Ile
            500                 505                 510

Glu Asn Leu Ala Glu Asp Ser Pro Arg Leu Val Lys Glu Arg Lys
        515                 520                 525

Val Lys Thr Leu Pro Phe Leu Arg Lys Tyr Phe Glu Leu Gln Gly Ala
530                 535                 540

Met Phe His His Asn Asn Ala Leu Thr Ser Ser His Pro Tyr Ala Thr
545                 550                 555                 560

Glu Pro Phe Gln Trp Pro Phe Leu Leu Arg Gly Val Ser Phe Trp Thr
                565                 570                 575

Lys Asn Asp Thr Arg Glu Gln Ile Tyr Phe Leu Gly Asn Pro Ile Gly
            580                 585                 590

Trp Trp Ile Ala Ser Ser Ile Leu Ala Val Phe Ala Gly Val Val Gly
        595                 600                 605

Ala Asp Gln Leu Ser Leu Arg Arg Gly Val Asp Ala Leu Glu Glu Ile
    610                 615                 620

Trp Gly Pro Gly Thr Arg Ser Arg Leu Tyr Asn Ser Thr Gly Phe Leu
625                 630                 635                 640

Phe Leu Cys Trp Ala Ala His Tyr Phe Pro Phe Trp Leu Met Gly Arg
                645                 650                 655

Gln Arg Phe Leu His His Tyr Leu Pro Ser His Leu Ala Ser Thr Met
            660                 665                 670

Val Cys Gly Ala Leu Ile Glu Phe Ile Phe Asn Leu Gln Pro Leu Asp
        675                 680                 685

Pro Arg Thr Ala Leu Pro Pro Val Asp Asp Pro Ser Gly Lys Ser Lys
    690                 695                 700

Ala Arg Ser Leu Ser Ser Leu Arg Arg Phe Ile Thr Ala Lys Glu Arg
705                 710                 715                 720

Met Gly Cys Arg Ser Leu Ile Ala Gly Trp Ile Ala Thr Leu Ile Ile
                725                 730                 735

Leu Ala Ala Thr Ile Trp Gly Phe Ile Phe Tyr Ala Pro Leu Thr Tyr
            740                 745                 750

Gly Thr Pro Gly Leu Asp Val Ala Gly Val Asn Ala Arg Lys Trp Leu
        755                 760                 765

Asn Tyr Asp Leu His Phe Ala Lys
770                 775

<210> SEQ ID NO 15
<211> LENGTH: 19

-continued

<212> TYPE: DNA
<213> ORGANISM: Trichoderma reesei

<400> SEQUENCE: 15
gcacactttc aagattggc                                               19

<210> SEQ ID NO 16
<211> LENGTH: 19
<212> TYPE: DNA
<213> ORGANISM: Trichoderma reesei

<400> SEQUENCE: 16
gtacggtgtt gccaagaag                                               19

<210> SEQ ID NO 17
<211> LENGTH: 448
<212> TYPE: DNA
<213> ORGANISM: Trichoderma reesei

<400> SEQUENCE: 17
gttgagtaca tcgagcgcga cagcattgtg cacaccatgc ttcccctcga gtccaaggac    60
agcatcatcg ttgaggactc gtgcaacggc gagacggaga agcaggctcc ctggggtctt   120
gcccgtatct ctcaccgaga gacgctcaac tttggctcct tcaacaagta cctctacacc   180
gctgatggtg gtgagggtgt tgatgcctat gtcattgaca ccggcaccaa catcgagcac   240
gtcgactttg agggtcgtgc caagtggggc aagaccatcc ctgccggcga tgaggacgag   300
gacggcaacg gccacggcac tcactgctct ggtaccgttg ctggtaagaa gtacggtgtt   360
gccaagaagg cccacgtcta cgccgtcaag gtgctccgat ccaacggatc cggcaccatg   420
tctgacgtcg tcaagggcgt cgagtacg                                     448

<210> SEQ ID NO 18
<211> LENGTH: 399
<212> TYPE: PRT
<213> ORGANISM: Trichoderma reesei

<400> SEQUENCE: 18

Met Gln Pro Ser Phe Gly Ser Phe Leu Val Thr Val Leu Ser Ala Ser
1               5                   10                  15

Met Ala Ala Gly Ser Val Ile Pro Ser Thr Asn Ala Asn Pro Gly Ser
            20                  25                  30

Phe Glu Ile Lys Arg Ser Ala Asn Lys Ala Phe Thr Gly Arg Asn Gly
        35                  40                  45

Pro Leu Ala Leu Ala Arg Thr Tyr Ala Lys Tyr Gly Val Glu Val Pro
    50                  55                  60

Lys Thr Leu Val Asp Ala Ile Gln Leu Val Lys Ser Ile Gln Leu Ala
65                  70                  75                  80

Lys Arg Asp Ser Ala Thr Val Thr Ala Thr Pro Asp His Asp Asp Ile
            85                  90                  95

Glu Tyr Leu Val Pro Val Lys Ile Gly Thr Pro Gln Thr Leu Asn
            100                 105                 110

Leu Asp Phe Asp Thr Gly Ser Ser Asp Leu Trp Val Phe Ser Ser Asp
        115                 120                 125

Val Asp Pro Thr Ser Ser Gln Gly His Asp Ile Tyr Thr Pro Ser Lys
    130                 135                 140

Ser Thr Ser Ser Lys Lys Leu Glu Gly Ala Ser Trp Asn Ile Thr Tyr
145                 150                 155                 160

```
Gly Asp Arg Ser Ser Ser Gly Asp Val Tyr His Asp Ile Val Ser
            165                 170                 175

Val Gly Asn Leu Thr Val Lys Ser Gln Ala Val Glu Ser Ala Arg Asn
        180                 185                 190

Val Ser Ala Gln Phe Thr Gln Gly Asn Asn Asp Gly Leu Val Gly Leu
    195                 200                 205

Ala Phe Ser Ser Ile Asn Thr Val Lys Pro Thr Pro Gln Lys Thr Trp
210                 215                 220

Tyr Asp Asn Ile Val Gly Ser Leu Asp Ser Pro Val Phe Val Ala Asp
225                 230                 235                 240

Leu Arg His Asp Thr Pro Gly Ser Tyr His Phe Gly Ser Ile Pro Ser
            245                 250                 255

Glu Ala Ser Lys Ala Phe Tyr Ala Pro Ile Asp Asn Ser Lys Gly Phe
        260                 265                 270

Trp Gln Phe Ser Thr Ser Ser Asn Ile Ser Gly Gln Phe Asn Ala Val
    275                 280                 285

Ala Asp Thr Gly Thr Thr Leu Leu Leu Ala Ser Asp Asp Leu Val Lys
290                 295                 300

Ala Tyr Tyr Ala Lys Val Gln Gly Ala Arg Val Asn Val Phe Leu Gly
305                 310                 315                 320

Gly Tyr Val Phe Asn Cys Thr Thr Gln Leu Pro Asp Phe Thr Phe Thr
            325                 330                 335

Val Gly Glu Gly Asn Ile Thr Val Pro Gly Thr Leu Ile Asn Tyr Ser
        340                 345                 350

Glu Ala Gly Asn Gly Gln Cys Phe Gly Gly Ile Gln Pro Ser Gly Gly
    355                 360                 365

Leu Pro Phe Ala Ile Phe Gly Asp Ile Ala Leu Lys Ala Ala Tyr Val
370                 375                 380

Ile Phe Asp Ser Gly Asn Lys Gln Val Gly Trp Ala Gln Lys Lys
385                 390                 395

<210> SEQ ID NO 19
<211> LENGTH: 452
<212> TYPE: PRT
<213> ORGANISM: Trichoderma reesei

<400> SEQUENCE: 19

Met Glu Ala Ile Leu Gln Ala Gln Ala Lys Phe Arg Leu Asp Arg Gly
1               5                   10                  15

Leu Gln Lys Ile Thr Ala Val Arg Asn Lys Asn Tyr Lys Arg His Gly
            20                  25                  30

Pro Lys Ser Tyr Val Tyr Leu Leu Asn Arg Phe Gly Phe Glu Pro Thr
        35                  40                  45

Lys Pro Gly Pro Tyr Phe Gln Gln His Arg Ile His Gln Arg Gly Leu
    50                  55                  60

Ala His Pro Asp Phe Lys Ala Val Gly Gly Arg Val Thr Arg Gln
65                  70                  75                  80

Lys Val Leu Ala Lys Lys Val Lys Glu Asp Gly Thr Val Asp Ala Gly
            85                  90                  95

Gly Ser Lys Thr Gly Glu Val Asp Ala Glu Asp Gln Gln Asn Asp Ser
        100                 105                 110

Glu Tyr Leu Cys Glu Val Thr Ile Gly Thr Pro Gly Gln Lys Leu Met
    115                 120                 125

Leu Asp Phe Asp Thr Gly Ser Ser Asp Leu Trp Val Phe Ser Thr Glu
130                 135                 140
```

Leu Ser Lys His Leu Gln Glu Asn His Ala Ile Phe Asp Pro Lys Lys
145                 150                 155                 160

Ser Ser Thr Phe Lys Pro Leu Lys Asp Gln Thr Trp Gln Ile Ser Tyr
            165                 170                 175

Gly Asp Gly Ser Ser Ala Ser Gly Thr Cys Gly Ser Asp Thr Val Thr
        180                 185                 190

Leu Gly Gly Leu Ser Ile Lys Asn Gln Thr Ile Glu Leu Ala Ser Lys
        195                 200                 205

Leu Ala Pro Gln Phe Ala Gln Gly Thr Gly Asp Gly Leu Leu Gly Leu
    210                 215                 220

Ala Trp Pro Gln Ile Asn Thr Val Gln Thr Asp Gly Arg Pro Thr Pro
225                 230                 235                 240

Ala Asn Thr Pro Val Ala Asn Met Ile Gln Gln Asp Ile Pro Ser
                245                 250                 255

Asp Ala Gln Leu Phe Thr Ala Ala Phe Tyr Ser Glu Arg Asp Glu Asn
            260                 265                 270

Ala Glu Ser Phe Tyr Thr Phe Gly Tyr Ile Asp Gln Asp Leu Val Ser
            275                 280                 285

Ala Ser Gly Gln Glu Ile Ala Trp Thr Asp Val Asp Asn Ser Gln Gly
        290                 295                 300

Phe Trp Met Phe Pro Ser Thr Lys Thr Ile Asn Gly Lys Asp Ile
305                 310                 315                 320

Ser Gln Glu Gly Asn Thr Ala Ile Ala Asp Thr Gly Thr Thr Leu Ala
                325                 330                 335

Leu Val Ser Asp Glu Val Cys Glu Ala Leu Tyr Lys Ala Ile Pro Gly
            340                 345                 350

Ala Lys Tyr Asp Asp Asn Gln Gln Gly Tyr Val Phe Pro Ile Asn Thr
        355                 360                 365

Asp Ala Ser Ser Leu Pro Glu Leu Lys Val Ser Val Gly Asn Thr Gln
    370                 375                 380

Phe Val Ile Gln Pro Glu Asp Leu Ala Phe Ala Pro Ala Asp Asp Ser
385                 390                 395                 400

Asn Trp Tyr Gly Gly Val Gln Ser Arg Gly Ser Asn Pro Phe Asp Ile
                405                 410                 415

Leu Gly Asp Val Phe Leu Lys Ser Val Tyr Ala Ile Phe Asp Gln Gly
            420                 425                 430

Asn Gln Arg Phe Gly Ala Val Pro Lys Ile Gln Ala Lys Gln Asn Leu
        435                 440                 445

Gln Pro Pro Gln
    450

<210> SEQ ID NO 20
<211> LENGTH: 395
<212> TYPE: PRT
<213> ORGANISM: Trichoderma reesei

<400> SEQUENCE: 20

Met Lys Ser Ala Leu Leu Ala Ala Ala Leu Val Gly Ser Ala Gln
1               5                   10                  15

Ala Gly Ile His Lys Met Lys Leu Gln Lys Val Ser Leu Glu Gln Gln
                20                  25                  30

Leu Glu Gly Ser Ser Ile Glu Ala His Val Gln Gln Leu Gly Gln Lys
            35                  40                  45

Tyr Met Gly Val Arg Pro Thr Ser Arg Ala Glu Val Met Phe Asn Asp

```
             50                  55                  60
Lys Pro Pro Lys Val Gln Gly Gly His Pro Val Pro Val Thr Asn Phe
 65                  70                  75                  80

Met Asn Ala Gln Tyr Phe Ser Glu Ile Thr Ile Gly Thr Pro Pro Gln
                 85                  90                  95

Ser Phe Lys Val Val Leu Asp Thr Gly Ser Ser Asn Leu Trp Val Pro
                100                 105                 110

Ser Gln Ser Cys Asn Ser Ile Ala Cys Phe Leu His Ser Thr Tyr Asp
                115                 120                 125

Ser Ser Ser Ser Ser Thr Tyr Lys Pro Asn Gly Ser Asp Phe Glu Ile
            130                 135                 140

His Tyr Gly Ser Gly Ser Leu Thr Gly Phe Ile Ser Asn Asp Val Val
145                 150                 155                 160

Thr Ile Gly Asp Leu Lys Ile Lys Gly Gln Asp Phe Ala Glu Ala Thr
                165                 170                 175

Ser Glu Pro Gly Leu Ala Phe Ala Phe Gly Arg Phe Asp Gly Ile Leu
                180                 185                 190

Gly Leu Gly Tyr Asp Thr Ile Ser Val Asn Gly Ile Val Pro Pro Phe
            195                 200                 205

Tyr Gln Met Val Asn Gln Lys Leu Ile Asp Glu Pro Val Phe Ala Phe
210                 215                 220

Tyr Leu Gly Ser Ser Asp Glu Gly Ser Glu Ala Val Phe Gly Gly Val
225                 230                 235                 240

Asp Asp Ala His Tyr Glu Gly Lys Ile Glu Tyr Ile Pro Leu Arg Arg
                245                 250                 255

Lys Ala Tyr Trp Glu Val Asp Leu Asp Ser Ile Ala Phe Gly Asp Glu
                260                 265                 270

Val Ala Glu Leu Glu Asn Thr Gly Ala Ile Leu Asp Thr Gly Thr Ser
            275                 280                 285

Leu Asn Val Leu Pro Ser Gly Leu Ala Glu Leu Leu Asn Ala Glu Ile
            290                 295                 300

Gly Ala Lys Lys Gly Phe Gly Gly Gln Tyr Thr Val Asp Cys Ser Lys
305                 310                 315                 320

Arg Asp Ser Leu Pro Asp Ile Thr Phe Ser Leu Ala Gly Ser Lys Tyr
                325                 330                 335

Ser Leu Pro Ala Ser Asp Tyr Ile Ile Glu Met Ser Gly Asn Cys Ile
                340                 345                 350

Ser Ser Phe Gln Gly Met Asp Phe Pro Glu Pro Val Gly Pro Leu Val
            355                 360                 365

Ile Leu Gly Asp Ala Phe Leu Arg Arg Tyr Tyr Ser Val Tyr Asp Leu
            370                 375                 380

Gly Arg Asp Ala Val Gly Leu Ala Lys Ala Lys
385                 390                 395

<210> SEQ ID NO 21
<211> LENGTH: 426
<212> TYPE: PRT
<213> ORGANISM: Trichoderma reesei

<400> SEQUENCE: 21

Met Lys Phe His Ala Ala Ala Leu Thr Leu Ala Cys Leu Ala Ser Ser
 1               5                  10                  15

Ala Ser Ala Gly Val Ala Gln Pro Arg Ala Asp Glu Val Glu Ser Ala
                20                  25                  30
```

-continued

```
Glu Gln Gly Lys Thr Phe Ser Leu Glu Gln Ile Pro Asn Glu Arg Tyr
             35                  40                  45

Lys Gly Asn Ile Pro Ala Ala Tyr Ile Ser Ala Leu Ala Lys Tyr Ser
 50                  55                  60

Pro Thr Ile Pro Asp Lys Ile Lys His Ala Ile Glu Ile Asn Pro Asp
 65                  70                  75                  80

Leu His Arg Lys Phe Ser Lys Leu Ile Asn Ala Gly Asn Met Thr Gly
                 85                  90                  95

Thr Ala Val Ala Ser Pro Pro Gly Ala Asp Ala Glu Tyr Val Leu
            100                 105                 110

Pro Val Lys Ile Gly Thr Pro Pro Gln Thr Leu Pro Leu Asn Leu Asp
            115                 120                 125

Thr Gly Ser Ser Asp Leu Trp Val Ile Ser Thr Asp Thr Tyr Pro Pro
130                 135                 140

Gln Val Gln Gly Gln Thr Arg Tyr Asn Val Ser Ala Ser Thr Thr Ala
145                 150                 155                 160

Gln Arg Leu Ile Gly Glu Ser Trp Val Ile Arg Tyr Gly Asp Gly Ser
                165                 170                 175

Ser Ala Asn Gly Ile Val Tyr Lys Asp Arg Val Gln Ile Gly Asn Thr
                180                 185                 190

Phe Phe Asn Gln Gln Ala Val Glu Ser Ala Val Asn Ile Ser Asn Glu
195                 200                 205

Ile Ser Asp Asp Ser Phe Ser Ser Gly Leu Leu Gly Ala Ala Ser Ser
            210                 215                 220

Ala Ala Asn Thr Val Arg Pro Asp Arg Gln Thr Thr Tyr Leu Glu Asn
225                 230                 235                 240

Ile Lys Ser Gln Leu Ala Arg Pro Val Phe Thr Ala Asn Leu Lys Lys
                245                 250                 255

Gly Lys Pro Gly Asn Tyr Asn Phe Gly Tyr Ile Asn Gly Ser Glu Tyr
                260                 265                 270

Ile Gly Pro Ile Gln Tyr Ala Ala Ile Asn Pro Ser Ser Pro Leu Trp
            275                 280                 285

Glu Val Ser Val Ser Gly Tyr Arg Val Gly Ser Asn Asp Thr Lys Tyr
290                 295                 300

Val Pro Arg Val Trp Asn Ala Ile Ala Asp Thr Gly Thr Thr Leu Leu
305                 310                 315                 320

Leu Val Pro Asn Asp Ile Val Ser Ala Tyr Tyr Ala Gln Val Lys Gly
                325                 330                 335

Ser Thr Phe Ser Asn Asp Val Gly Met Met Leu Val Pro Cys Ala Ala
                340                 345                 350

Thr Leu Pro Asp Phe Ala Phe Gly Leu Gly Asn Tyr Arg Gly Val Ile
            355                 360                 365

Pro Gly Ser Tyr Ile Asn Tyr Gly Arg Met Asn Lys Thr Tyr Cys Tyr
370                 375                 380

Gly Gly Ile Gln Ser Ser Glu Asp Ala Pro Phe Ala Val Leu Gly Asp
385                 390                 395                 400

Ile Ala Leu Lys Ala Gln Phe Val Val Phe Asp Met Gly Asn Lys Val
                405                 410                 415

Val Gly Phe Ala Asn Lys Asn Thr Asn Val
                420                 425

<210> SEQ ID NO 22
<211> LENGTH: 407
<212> TYPE: PRT
```

<213> ORGANISM: Trichoderma reesei

<400> SEQUENCE: 22

```
Met Gln Thr Phe Gly Ala Phe Leu Val Ser Phe Leu Ala Ala Ser Gly
 1               5                  10                  15
Leu Ala Ala Leu Pro Thr Glu Gly Gln Lys Thr Ala Ser Val Glu
             20                  25                  30
Val Gln Tyr Asn Lys Asn Tyr Val Pro His Gly Pro Thr Ala Leu Phe
         35                  40                  45
Lys Ala Lys Arg Lys Tyr Gly Ala Pro Ile Ser Asp Asn Leu Lys Ser
     50                  55                  60
Leu Val Ala Ala Arg Gln Ala Lys Gln Ala Leu Ala Lys Arg Gln Thr
 65                  70                  75                  80
Gly Ser Ala Pro Asn His Pro Ser Asp Ser Ala Asp Ser Glu Tyr Ile
                 85                  90                  95
Thr Ser Val Ser Ile Gly Thr Pro Ala Gln Val Leu Pro Leu Asp Phe
            100                 105                 110
Asp Thr Gly Ser Ser Asp Leu Trp Val Phe Ser Ser Glu Thr Pro Lys
        115                 120                 125
Ser Ser Ala Thr Gly His Ala Ile Tyr Thr Pro Ser Lys Ser Ser Thr
    130                 135                 140
Ser Lys Lys Val Ser Gly Ala Ser Trp Ser Ile Ser Tyr Gly Asp Gly
145                 150                 155                 160
Ser Ser Ser Ser Gly Asp Val Tyr Thr Asp Lys Val Thr Ile Gly Gly
                165                 170                 175
Phe Ser Val Asn Thr Gln Gly Val Glu Ser Ala Thr Arg Val Ser Thr
            180                 185                 190
Glu Phe Val Gln Asp Thr Val Ile Ser Gly Leu Val Gly Leu Ala Phe
        195                 200                 205
Asp Ser Gly Asn Gln Val Arg Pro His Pro Gln Lys Thr Trp Phe Ser
    210                 215                 220
Asn Ala Ala Ser Ser Leu Ala Glu Pro Leu Phe Thr Ala Asp Leu Arg
225                 230                 235                 240
His Gly Gln Asn Gly Ser Tyr Asn Phe Gly Tyr Ile Asp Thr Ser Val
                245                 250                 255
Ala Lys Gly Pro Val Ala Tyr Thr Pro Val Asp Asn Ser Gln Gly Phe
            260                 265                 270
Trp Glu Phe Thr Ala Ser Gly Tyr Ser Val Gly Gly Lys Leu Asn
        275                 280                 285
Arg Asn Ser Ile Asp Gly Ile Ala Asp Thr Gly Thr Thr Leu Leu Leu
    290                 295                 300
Leu Asp Asp Asn Val Val Asp Ala Tyr Tyr Ala Asn Val Gln Ser Ala
305                 310                 315                 320
Gln Tyr Asp Asn Gln Gln Glu Gly Val Val Phe Asp Cys Asp Glu Asp
                325                 330                 335
Leu Pro Ser Phe Ser Phe Gly Val Gly Ser Ser Thr Ile Thr Ile Pro
            340                 345                 350
Gly Asp Leu Leu Asn Leu Thr Pro Leu Glu Glu Gly Ser Ser Thr Cys
        355                 360                 365
Phe Gly Gly Leu Gln Ser Ser Ser Gly Ile Gly Ile Asn Ile Phe Gly
    370                 375                 380
Asp Val Ala Leu Lys Ala Ala Leu Val Val Phe Asp Leu Gly Asn Glu
385                 390                 395                 400
```

Arg Leu Gly Trp Ala Gln Lys
            405

<210> SEQ ID NO 23
<211> LENGTH: 446
<212> TYPE: PRT
<213> ORGANISM: Trichoderma reesei

<400> SEQUENCE: 23

Met Thr Leu Pro Val Pro Leu Arg Glu His Asp Leu Pro Phe Leu Lys
1               5                   10                  15

Glu Lys Arg Lys Leu Pro Ala Asp Ile Pro Ser Gly Thr Tyr Thr
            20                  25                  30

Leu Pro Ile Ile His Ala Arg Arg Pro Lys Leu Ala Ser Arg Ala Ile
            35                  40                  45

Glu Val Gln Val Glu Asn Arg Ser Asp Val Ser Tyr Tyr Ala Gln Leu
        50                  55                  60

Asn Ile Gly Thr Pro Pro Gln Thr Val Tyr Ala Gln Ile Asp Thr Gly
65                  70                  75                  80

Ser Phe Glu Leu Trp Val Asn Pro Asn Cys Ser Asn Val Gln Ser Ala
                85                  90                  95

Asp Gln Arg Phe Cys Arg Ala Ile Gly Phe Tyr Asp Pro Ser Ser Ser
            100                 105                 110

Ser Thr Ala Asp Val Thr Ser Gln Ser Ala Arg Leu Arg Tyr Gly Ile
        115                 120                 125

Gly Ser Ala Asp Val Thr Tyr Val His Asp Thr Ile Ser Leu Pro Gly
    130                 135                 140

Ser Gly Ser Gly Ser Lys Ala Met Lys Ala Val Gln Phe Gly Val Ala
145                 150                 155                 160

Asp Thr Ser Val Asp Glu Phe Ser Gly Ile Leu Gly Leu Gly Ala Gly
                165                 170                 175

Asn Gly Ile Asn Thr Glu Tyr Pro Asn Phe Val Asp Glu Leu Ala Ala
            180                 185                 190

Gln Gly Val Thr Ala Thr Lys Ala Phe Ser Leu Ala Leu Gly Ser Lys
        195                 200                 205

Ala Glu Glu Glu Gly Val Ile Ile Phe Gly Gly Val Asp Thr Ala Lys
    210                 215                 220

Phe His Gly Glu Leu Ala His Leu Pro Ile Val Pro Ala Asp Asp Ser
225                 230                 235                 240

Pro Asp Gly Val Ala Arg Tyr Trp Val Lys Met Lys Ser Ile Ser Leu
                245                 250                 255

Thr Pro Pro Pro Pro Ser Ser Ser Gly Ser Thr Asp Asp Asn Asn Asn
            260                 265                 270

Lys Pro Val Ala Phe Pro Gln Thr Ser Met Thr Val Phe Leu Asp Ser
        275                 280                 285

Gly Ser Thr Leu Thr Leu Leu Pro Pro Ala Leu Val Arg Gln Ile Ala
    290                 295                 300

Ser Ala Leu Gly Ser Thr Gln Thr Asp Glu Ser Gly Phe Phe Val Val
305                 310                 315                 320

Asp Cys Ala Leu Ala Ser Gln Asp Gly Thr Ile Asp Phe Glu Phe Asp
                325                 330                 335

Gly Val Thr Ile Arg Val Pro Tyr Ala Glu Met Ile Arg Gln Val Ser
            340                 345                 350

Thr Leu Pro Pro His Cys Tyr Leu Gly Met Met Gly Ser Thr Gln Phe
        355                 360                 365

Ala Leu Leu Gly Asp Thr Phe Leu Arg Ser Ala Tyr Ala Val Phe Asp
        370                 375                 380

Leu Thr Ser Asn Val Val His Leu Ala Pro Tyr Ala Asn Cys Gly Thr
385                 390                 395                 400

Asn Val Lys Ser Ile Thr Ser Thr Ser Ser Leu Ser Asn Leu Val Gly
            405                 410                 415

Thr Cys Asn Asp Pro Ser Lys Pro Ser Ser Pro Ser Pro Ser Gln
        420                 425                 430

Thr Pro Ser Ala Ser Pro Ser Ser Thr Ala Thr Gln Lys Ala
        435                 440                 445

<210> SEQ ID NO 24
<211> LENGTH: 259
<212> TYPE: PRT
<213> ORGANISM: Trichoderma reesei

<400> SEQUENCE: 24

Met Ala Pro Ala Ser Gln Val Val Ser Ala Leu Met Leu Pro Ala Leu
1               5                   10                  15

Ala Leu Gly Ala Ala Ile Gln Pro Arg Gly Ala Asp Ile Val Gly Gly
            20                  25                  30

Thr Ala Ala Ser Leu Gly Glu Phe Pro Tyr Ile Val Ser Leu Gln Asn
        35                  40                  45

Pro Asn Gln Gly Gly His Phe Cys Gly Gly Val Leu Val Asn Ala Asn
    50                  55                  60

Thr Val Val Thr Ala Ala His Cys Ser Val Val Tyr Pro Ala Ser Gln
65                  70                  75                  80

Ile Arg Val Arg Ala Gly Thr Leu Thr Trp Asn Ser Gly Thr Leu
                85                  90                  95

Val Gly Val Ser Gln Ile Ile Val Asn Pro Ser Tyr Asn Asp Arg Thr
            100                 105                 110

Thr Asp Phe Asp Val Ala Val Trp His Leu Ser Ser Pro Ile Arg Glu
        115                 120                 125

Ser Ser Thr Ile Gly Tyr Ala Thr Leu Pro Ala Gln Gly Ser Asp Pro
    130                 135                 140

Val Ala Gly Ser Thr Val Thr Thr Ala Gly Trp Gly Thr Thr Ser Glu
145                 150                 155                 160

Asn Ser Asn Ser Ile Pro Ser Arg Leu Asn Lys Val Ser Val Pro Val
                165                 170                 175

Val Ala Arg Ser Thr Cys Gln Ala Asp Tyr Arg Ser Gln Gly Leu Ser
            180                 185                 190

Val Thr Asn Asn Met Phe Cys Ala Gly Leu Thr Gln Gly Gly Lys Asp
        195                 200                 205

Ser Cys Ser Gly Asp Ser Gly Gly Pro Ile Val Asp Ala Asn Gly Val
    210                 215                 220

Leu Gln Gly Val Val Ser Trp Gly Ile Gly Cys Ala Glu Ala Gly Phe
225                 230                 235                 240

Pro Gly Val Tyr Thr Arg Ile Gly Asn Phe Val Asn Tyr Ile Asn Gln
                245                 250                 255

Asn Leu Ala

<210> SEQ ID NO 25
<211> LENGTH: 882
<212> TYPE: PRT
<213> ORGANISM: Trichoderma reesei

<400> SEQUENCE: 25

```
Met Val Arg Ser Ala Leu Phe Val Ser Leu Leu Ala Thr Phe Ser Gly
1               5                   10                  15

Val Ile Ala Arg Val Ser Gly His Gly Ser Lys Ile Val Pro Gly Ala
            20                  25                  30

Tyr Ile Phe Glu Phe Glu Asp Ser Gln Asp Thr Ala Asp Phe Tyr Lys
        35                  40                  45

Lys Leu Asn Gly Glu Gly Ser Thr Arg Leu Lys Phe Asp Tyr Lys Leu
    50                  55                  60

Phe Lys Gly Val Ser Val Gln Leu Lys Asp Leu Asp Asn His Glu Ala
65                  70                  75                  80

Lys Ala Gln Gln Met Ala Gln Leu Pro Ala Val Lys Asn Val Trp Pro
                85                  90                  95

Val Thr Leu Ile Asp Ala Pro Asn Pro Lys Val Glu Trp Val Ala Gly
            100                 105                 110

Ser Thr Ala Pro Thr Leu Glu Ser Arg Ala Ile Lys Lys Pro Pro Ile
        115                 120                 125

Pro Asn Asp Ser Ser Asp Phe Pro Thr His Gln Met Thr Gln Ile Asp
    130                 135                 140

Lys Leu Arg Ala Lys Gly Tyr Thr Gly Lys Gly Val Arg Val Ala Val
145                 150                 155                 160

Ile Asp Thr Gly Ile Asp Tyr Thr His Pro Ala Leu Gly Gly Cys Phe
                165                 170                 175

Gly Arg Gly Cys Leu Val Ser Phe Gly Thr Asp Leu Val Gly Asp Asp
            180                 185                 190

Tyr Thr Gly Phe Asn Thr Pro Val Pro Asp Asp Pro Val Asp Cys
        195                 200                 205

Ala Gly His Gly Ser His Val Ala Gly Ile Ile Ala Ala Gln Glu Asn
    210                 215                 220

Pro Tyr Gly Phe Thr Gly Gly Ala Pro Asp Val Thr Leu Gly Ala Tyr
225                 230                 235                 240

Arg Val Phe Gly Cys Asp Gly Gln Ala Gly Asn Asp Val Leu Ile Ser
                245                 250                 255

Ala Tyr Asn Gln Ala Phe Glu Asp Gly Ala Gln Ile Ile Thr Ala Ser
            260                 265                 270

Ile Gly Gly Pro Ser Gly Trp Ala Glu Glu Pro Trp Ala Val Ala Val
        275                 280                 285

Thr Arg Ile Val Glu Ala Gly Val Pro Cys Thr Val Ser Ala Gly Asn
    290                 295                 300

Glu Gly Asp Ser Gly Leu Phe Phe Ala Ser Thr Ala Ala Asn Gly Lys
305                 310                 315                 320

Lys Val Ile Ala Val Ala Ser Val Asp Asn Glu Asn Ile Pro Ser Val
                325                 330                 335

Leu Ser Val Ala Ser Tyr Lys Ile Asp Ser Gly Ala Ala Gln Asp Phe
            340                 345                 350

Gly Tyr Val Ser Ser Lys Ala Trp Asp Gly Val Ser Lys Pro Leu
        355                 360                 365

Tyr Ala Val Ser Phe Asp Thr Ile Pro Asp Asp Gly Cys Ser Pro
    370                 375                 380

Leu Pro Asp Ser Thr Pro Asp Leu Ser Asp Tyr Ile Val Leu Val Arg
385                 390                 395                 400

Arg Gly Thr Cys Thr Phe Val Gln Lys Ala Gln Asn Val Ala Ala Lys
```

```
            405                 410                 415
Gly Ala Lys Tyr Leu Leu Tyr Tyr Asn Asn Ile Pro Gly Ala Leu Ala
            420                 425                 430
Val Asp Val Ser Ala Val Pro Glu Ile Glu Ala Val Gly Met Val Asp
            435                 440                 445
Asp Lys Thr Gly Ala Thr Trp Ile Ala Ala Leu Lys Asp Gly Lys Thr
            450                 455                 460
Val Thr Leu Thr Leu Thr Asp Pro Ile Glu Ser Glu Lys Gln Ile Gln
465                 470                 475                 480
Phe Ser Asp Asn Pro Thr Thr Gly Gly Ala Leu Ser Gly Tyr Thr Thr
            485                 490                 495
Trp Gly Pro Thr Trp Glu Leu Asp Val Lys Pro Gln Ile Ser Ser Pro
            500                 505                 510
Gly Gly Asn Ile Leu Ser Thr Tyr Pro Val Ala Leu Gly Gly Tyr Ala
            515                 520                 525
Thr Leu Ser Gly Thr Ser Met Ala Cys Pro Leu Thr Ala Ala Ala Val
            530                 535                 540
Ala Leu Ile Gly Gln Ala Arg Gly Thr Phe Asp Pro Ala Leu Ile Asp
545                 550                 555                 560
Asn Leu Leu Ala Thr Thr Ala Asn Pro Gln Leu Phe Asn Asp Gly Glu
            565                 570                 575
Lys Phe Tyr Asp Phe Leu Ala Pro Val Pro Gln Gln Gly Gly Gly Leu
            580                 585                 590
Ile Gln Ala Tyr Asp Ala Ala Phe Ala Thr Thr Leu Leu Ser Pro Ser
            595                 600                 605
Ser Leu Ser Phe Asn Asp Thr Asp His Phe Ile Lys Lys Lys Gln Ile
            610                 615                 620
Thr Leu Lys Asn Thr Ser Lys Gln Arg Val Thr Tyr Lys Leu Asn His
625                 630                 635                 640
Val Pro Thr Asn Thr Phe Tyr Thr Leu Ala Pro Gly Asn Gly Tyr Pro
            645                 650                 655
Ala Pro Phe Pro Asn Asp Ala Val Ala Ala His Ala Asn Leu Lys Phe
            660                 665                 670
Asn Leu Gln Gln Val Thr Leu Pro Ala Gly Arg Ser Ile Thr Val Asp
            675                 680                 685
Val Phe Pro Thr Pro Arg Asp Val Asp Ala Lys Arg Leu Ala Leu
            690                 695                 700
Trp Ser Gly Tyr Ile Thr Val Asn Gly Thr Asp Gly Thr Ser Leu Ser
705                 710                 715                 720
Val Pro Tyr Gln Gly Leu Thr Gly Ser Leu His Lys Gln Lys Val Leu
            725                 730                 735
Tyr Pro Glu Asp Ser Trp Ile Ala Asp Ser Thr Asp Glu Ser Leu Ala
            740                 745                 750
Pro Val Glu Asn Gly Thr Val Phe Thr Ile Pro Ala Pro Gly Asn Ala
            755                 760                 765
Gly Pro Asp Asp Lys Leu Pro Ser Leu Val Val Ser Pro Ala Leu Gly
            770                 775                 780
Ser Arg Tyr Val Arg Val Asp Leu Val Leu Ser Ala Pro Pro His
785                 790                 795                 800
Gly Thr Lys Leu Lys Thr Val Lys Phe Leu Asp Thr Thr Ser Ile Gly
            805                 810                 815
Gln Pro Ala Gly Ser Pro Leu Leu Trp Ile Ser Arg Gly Ala Asn Pro
            820                 825                 830
```

```
Ile Ala Trp Thr Gly Glu Leu Ser Asp Asn Lys Phe Ala Pro Pro Gly
        835                 840                 845

Thr Tyr Lys Ala Val Phe His Ala Leu Arg Ile Phe Gly Asn Glu Lys
850                 855                 860

Lys Lys Glu Asp Trp Asp Val Ser Glu Ser Pro Ala Phe Thr Ile Lys
865                 870                 875                 880

Tyr Ala

<210> SEQ ID NO 26
<211> LENGTH: 541
<212> TYPE: PRT
<213> ORGANISM: Trichoderma reesei

<400> SEQUENCE: 26

Met Arg Ser Val Val Ala Leu Ser Met Ala Ala Val Ala Gln Ala Ser
1               5                   10                  15

Thr Phe Gln Ile Gly Thr Ile His Glu Lys Ser Ala Pro Val Leu Ser
            20                  25                  30

Asn Val Glu Ala Asn Ala Ile Pro Asp Ala Tyr Ile Ile Lys Phe Lys
        35                  40                  45

Asp His Val Gly Glu Asp Ala Ser Lys His His Asp Trp Ile Gln
    50                  55                  60

Ser Ile His Thr Asn Val Glu Gln Glu Arg Leu Glu Leu Arg Lys Arg
65                  70                  75                  80

Ser Asn Val Phe Gly Ala Asp Asp Val Phe Asp Gly Leu Lys His Thr
                85                  90                  95

Phe Lys Ile Gly Asp Gly Phe Lys Gly Tyr Ala Gly His Phe His Glu
            100                 105                 110

Ser Val Ile Glu Gln Val Arg Asn His Pro Asp Val Glu Tyr Ile Glu
        115                 120                 125

Arg Asp Ser Ile Val His Thr Met Leu Pro Leu Glu Ser Lys Asp Ser
    130                 135                 140

Ile Ile Val Glu Asp Ser Cys Asn Gly Glu Thr Glu Lys Gln Ala Pro
145                 150                 155                 160

Trp Gly Leu Ala Arg Ile Ser His Arg Glu Thr Leu Asn Phe Gly Ser
                165                 170                 175

Phe Asn Lys Tyr Leu Tyr Thr Ala Asp Gly Gly Glu Gly Val Asp Ala
            180                 185                 190

Tyr Val Ile Asp Thr Gly Thr Asn Ile Glu His Val Asp Phe Glu Gly
        195                 200                 205

Arg Ala Lys Trp Gly Lys Thr Ile Pro Ala Gly Asp Glu Asp Glu Asp
    210                 215                 220

Gly Asn Gly His Gly Thr His Cys Ser Gly Thr Val Ala Gly Lys Lys
225                 230                 235                 240

Tyr Gly Val Ala Lys Lys Ala His Val Tyr Ala Val Lys Val Leu Arg
                245                 250                 255

Ser Asn Gly Ser Gly Thr Met Ser Asp Val Val Lys Gly Val Glu Tyr
            260                 265                 270

Ala Ala Leu Ser His Ile Glu Gln Val Lys Ala Lys Lys Gly Lys
        275                 280                 285

Arg Lys Gly Phe Lys Gly Ser Val Ala Asn Met Ser Leu Gly Gly Gly
    290                 295                 300

Lys Thr Gln Ala Leu Asp Ala Ala Val Asn Ala Ala Val Arg Ala Gly
305                 310                 315                 320
```

```
Val His Phe Ala Val Ala Ala Gly Asn Asp Asn Ala Asp Ala Cys Asn
                325                 330                 335

Tyr Ser Pro Ala Ala Ala Thr Glu Pro Leu Thr Val Gly Ala Ser Ala
            340                 345                 350

Leu Asp Asp Ser Arg Ala Tyr Phe Ser Asn Tyr Gly Lys Cys Thr Asp
        355                 360                 365

Ile Phe Ala Pro Gly Leu Ser Ile Gln Ser Thr Trp Ile Gly Ser Lys
    370                 375                 380

Tyr Ala Val Asn Thr Ile Ser Gly Thr Ser Met Ala Ser Pro His Ile
385                 390                 395                 400

Cys Gly Leu Leu Ala Tyr Tyr Leu Ser Leu Gln Pro Ala Gly Asp Ser
                405                 410                 415

Glu Phe Ala Val Ala Pro Ile Thr Pro Lys Lys Leu Lys Glu Ser Val
            420                 425                 430

Ile Ser Val Ala Thr Lys Asn Ala Leu Ser Asp Leu Pro Asp Ser Asp
        435                 440                 445

Thr Pro Asn Leu Leu Ala Trp Asn Gly Gly Cys Ser Asn Phe Ser
    450                 455                 460

Gln Ile Val Glu Ala Gly Ser Tyr Thr Val Lys Pro Lys Gln Asn Lys
465                 470                 475                 480

Gln Ala Lys Leu Pro Ser Thr Ile Glu Leu Glu Glu Ala Ile Glu
                485                 490                 495

Gly Asp Phe Glu Val Val Ser Gly Glu Ile Val Lys Gly Ala Lys Ser
            500                 505                 510

Phe Gly Ser Lys Ala Glu Lys Phe Ala Lys Lys Ile His Asp Leu Val
        515                 520                 525

Glu Glu Glu Ile Glu Glu Phe Ile Ser Glu Leu Ser Glu
    530                 535                 540
```

<210> SEQ ID NO 27
<211> LENGTH: 391
<212> TYPE: PRT
<213> ORGANISM: Trichoderma reesei

<400> SEQUENCE: 27

```
Met Arg Leu Ser Val Leu Leu Ser Val Leu Pro Leu Val Leu Ala Ala
1               5                   10                  15

Pro Ala Ile Glu Lys Arg Ala Glu Pro Ala Pro Leu Leu Val Pro Thr
            20                  25                  30

Thr Lys His Gly Leu Val Ala Asp Lys Tyr Ile Val Lys Phe Lys Asp
        35                  40                  45

Gly Ser Ser Leu Gln Ala Val Asp Glu Ala Ile Ser Gly Leu Val Ser
    50                  55                  60

Asn Ala Asp His Val Tyr Gln His Val Phe Arg Gly Phe Ala Ala Thr
65                  70                  75                  80

Leu Asp Lys Glu Thr Leu Glu Ala Leu Arg Asn His Pro Glu Val Asp
                85                  90                  95

Tyr Ile Glu Gln Asp Ala Val Val Lys Ile Asn Ala Tyr Val Ser Gln
            100                 105                 110

Thr Gly Ala Pro Trp Gly Leu Gly Arg Ile Ser His Lys Ala Arg Gly
        115                 120                 125

Ser Thr Thr Tyr Val Tyr Asp Asp Ser Ala Gly Ala Gly Thr Cys Ser
    130                 135                 140

Tyr Val Ile Asp Thr Gly Val Asp Ala Thr His Pro Asp Phe Glu Gly
```

```
                145                 150                 155                 160
Arg Ala Thr Leu Leu Arg Ser Phe Val Ser Gly Gln Asn Thr Asp Gly
                    165                 170                 175

Asn Gly His Gly Thr His Val Ser Gly Thr Ile Gly Ser Arg Thr Tyr
                180                 185                 190

Gly Val Ala Lys Lys Thr Gln Ile Tyr Gly Val Lys Val Leu Asp Asn
                195                 200                 205

Ser Gly Ser Gly Ser Phe Ser Thr Val Ile Ala Gly Met Asp Tyr Val
            210                 215                 220

Ala Ser Asp Ser Gln Thr Arg Asn Cys Pro Asn Gly Ser Val Ala Asn
225                 230                 235                 240

Met Ser Leu Gly Gly Gly Tyr Thr Ala Ser Val Asn Gln Ala Ala Ala
                245                 250                 255

Arg Leu Ile Gln Ala Gly Val Phe Leu Ala Val Ala Ala Gly Asn Asp
                260                 265                 270

Gly Val Asp Ala Arg Asn Thr Ser Pro Ala Ser Glu Pro Thr Val Cys
            275                 280                 285

Thr Val Gly Ala Ser Thr Ser Ser Asp Ala Arg Ala Ser Phe Ser Asn
290                 295                 300

Tyr Gly Ser Val Val Asp Ile Phe Ala Pro Gly Gln Asp Ile Leu Ser
305                 310                 315                 320

Thr Trp Pro Asn Arg Gln Thr Asn Thr Ile Ser Gly Thr Ser Met Ala
                325                 330                 335

Thr Pro His Ile Val Gly Leu Gly Ala Tyr Leu Ala Gly Leu Glu Gly
                340                 345                 350

Phe Ser Asp Pro Gln Ala Leu Cys Ala Arg Ile Gln Ser Leu Ala Asn
            355                 360                 365

Arg Asn Leu Leu Ser Gly Ile Pro Ser Gly Thr Ile Asn Ala Ile Ala
            370                 375                 380

Phe Asn Gly Asn Pro Ser Gly
385                 390

<210> SEQ ID NO 28
<211> LENGTH: 387
<212> TYPE: PRT
<213> ORGANISM: Tricochoderma reesei

<400> SEQUENCE: 28

Met Gly Leu Val Thr Asn Pro Phe Ala Lys Asn Ile Ile Pro Asn Arg
1               5                   10                  15

Tyr Ile Val Val Tyr Asn Asn Ser Phe Gly Glu Glu Ala Ile Ser Ala
                20                  25                  30

Lys Gln Ala Gln Phe Ala Ala Lys Ile Ala Lys Arg Asn Leu Gly Lys
            35                  40                  45

Arg Gly Leu Phe Gly Asn Glu Leu Ser Thr Ala Ile His Ser Phe Ser
        50                  55                  60

Met His Thr Trp Arg Ala Met Ala Leu Asp Ala Asp Ile Met Ile
65                  70                  75                  80

Lys Asp Ile Phe Asp Ala Glu Glu Val Ala Tyr Ile Glu Ala Asp Thr
                85                  90                  95

Lys Val Gln His Ala Ala Leu Val Ala Gln Thr Asn Ala Ala Pro Gly
            100                 105                 110

Leu Ile Arg Leu Ser Asn Lys Ala Val Gly Gly Gln Asn Tyr Ile Phe
        115                 120                 125
```

```
Asp Asn Ser Ala Gly Ser Asn Ile Thr Ala Tyr Val Val Asp Thr Gly
    130                 135                 140

Ile Arg Ile Thr His Ser Glu Phe Glu Gly Arg Ala Thr Phe Gly Ala
145                 150                 155                 160

Asn Phe Val Asn Asp Asp Thr Asp Glu Asn Gly His Gly Ser His Val
                165                 170                 175

Ala Gly Thr Ile Gly Gly Ala Thr Phe Gly Val Ala Lys Asn Val Glu
            180                 185                 190

Leu Val Ala Val Lys Val Leu Asp Ala Asp Gly Ser Gly Ser Asn Ser
        195                 200                 205

Gly Val Leu Asn Gly Met Gln Phe Val Val Asn Asp Val Gln Ala Lys
    210                 215                 220

Lys Arg Ser Gly Lys Ala Val Met Asn Met Ser Leu Gly Gly Ser Phe
225                 230                 235                 240

Ser Thr Ala Val Asn Asn Ala Ile Thr Ala Leu Thr Asn Ala Gly Ile
                245                 250                 255

Val Pro Val Ala Ala Gly Asn Glu Asn Gln Asp Thr Ala Asn Thr
            260                 265                 270

Ser Pro Gly Ser Ala Pro Gln Ala Ile Thr Val Gly Ala Ile Asp Ala
        275                 280                 285

Thr Thr Asp Ile Arg Ala Gly Phe Ser Asn Phe Gly Thr Gly Val Asp
    290                 295                 300

Ile Tyr Ala Pro Gly Val Asp Val Leu Ser Val Gly Ile Lys Ser Asp
305                 310                 315                 320

Ile Asp Thr Ala Val Leu Ser Gly Thr Ser Met Ala Ser Pro His Val
                325                 330                 335

Ala Gly Leu Ala Ala Tyr Leu Met Ala Leu Glu Gly Val Ser Asn Val
            340                 345                 350

Asp Asp Val Ser Asn Leu Ile Lys Asn Leu Ala Ala Lys Thr Gly Ala
        355                 360                 365

Ala Val Lys Gln Asn Ile Ala Gly Thr Thr Ser Leu Ile Ala Asn Asn
    370                 375                 380

Gly Asn Phe
385

<210> SEQ ID NO 29
<211> LENGTH: 409
<212> TYPE: PRT
<213> ORGANISM: Trichoderma reesei

<400> SEQUENCE: 29

Met Ala Ser Leu Arg Arg Leu Ala Leu Tyr Leu Gly Ala Leu Leu Pro
1               5                   10                  15

Ala Val Leu Ala Ala Pro Ala Val Asn Tyr Lys Leu Pro Glu Ala Val
            20                  25                  30

Pro Asn Lys Phe Ile Val Thr Leu Lys Asp Gly Ala Ser Val Asp Thr
        35                  40                  45

Asp Ser His Leu Thr Trp Val Lys Asp Leu His Arg Ser Leu Gly
    50                  55                  60

Lys Arg Ser Thr Ala Gly Val Glu Lys Thr Tyr Asn Ile Asp Ser Trp
65                  70                  75                  80

Asn Ala Tyr Ala Gly Glu Phe Asp Glu Thr Val Lys Gln Ile Lys
                85                  90                  95

Ala Asn Pro Asp Val Ala Ser Val Glu Pro Asp Tyr Ile Met Trp Leu
            100                 105                 110
```

-continued

Ser Asp Ile Val Glu Asp Lys Arg Ala Leu Thr Thr Gln Thr Gly Ala
115                 120                 125

Pro Trp Gly Leu Gly Thr Val Ser His Arg Thr Pro Gly Ser Thr Ser
130                 135                 140

Tyr Ile Tyr Asp Thr Ser Ala Gly Ser Gly Thr Phe Ala Tyr Val Val
145                 150                 155                 160

Asp Ser Gly Ile Asn Ile Ala His Gln Gln Phe Gly Gly Arg Ala Ser
            165                 170                 175

Leu Gly Tyr Asn Ala Ala Gly Gly Asp His Val Asp Thr Leu Gly His
            180                 185                 190

Gly Thr His Val Ser Gly Thr Ile Gly Gly Ser Thr Tyr Gly Val Ala
            195                 200                 205

Lys Gln Ala Ser Leu Ile Ser Val Lys Val Phe Gln Gly Asn Ser Ala
210                 215                 220

Ser Thr Ser Val Ile Leu Asp Gly Tyr Asn Trp Ala Val Asn Asp Ile
225                 230                 235                 240

Val Ser Arg Asn Arg Ala Ser Lys Ser Ala Ile Asn Met Ser Leu Gly
            245                 250                 255

Gly Pro Ala Ser Ser Thr Trp Ala Thr Ala Ile Asn Ala Ala Phe Asn
            260                 265                 270

Lys Gly Val Leu Thr Ile Val Ala Ala Gly Asn Gly Asp Ala Leu Gly
            275                 280                 285

Asn Pro Gln Pro Val Ser Ser Thr Ser Pro Ala Asn Val Pro Asn Ala
            290                 295                 300

Ile Thr Val Ala Ala Leu Asp Ile Asn Trp Arg Thr Ala Ser Phe Thr
305                 310                 315                 320

Asn Tyr Gly Ala Gly Val Asp Val Phe Ala Pro Gly Val Asn Ile Leu
            325                 330                 335

Ser Ser Trp Ile Gly Ser Asn Thr Ala Thr Asn Thr Ile Ser Gly Thr
            340                 345                 350

Ser Met Ala Thr Pro His Val Val Gly Leu Ala Leu Tyr Leu Gln Ala
            355                 360                 365

Leu Glu Gly Leu Ser Thr Pro Thr Ala Val Thr Asn Arg Ile Lys Ala
370                 375                 380

Leu Ala Thr Thr Gly Arg Val Thr Gly Ser Leu Asn Gly Ser Pro Asn
385                 390                 395                 400

Thr Leu Ile Phe Asn Gly Asn Ser Ala
            405

<210> SEQ ID NO 30
<211> LENGTH: 555
<212> TYPE: PRT
<213> ORGANISM: Trichoderma reesei

<400> SEQUENCE: 30

Met Arg Ala Cys Leu Leu Phe Leu Gly Ile Thr Ala Leu Ala Thr Ala
1               5                   10                  15

Ile Pro Ala Leu Lys Pro Pro His Gly Ser Pro Asp Arg Ala His Thr
            20                  25                  30

Thr Gln Leu Ala Lys Val Ser Ile Ala Leu Gln Pro Glu Cys Arg Glu
            35                  40                  45

Leu Leu Glu Gln Ala Leu His His Leu Ser Asp Pro Ser Ser Pro Arg
50                  55                  60

Tyr Gly Arg Tyr Leu Gly Arg Glu Glu Ala Lys Ala Leu Leu Arg Pro

```
            65                  70                  75                  80
Arg Arg Glu Ala Thr Ala Ala Val Lys Arg Trp Leu Ala Arg Ala Gly
                    85                  90                  95

Val Pro Ala His Asp Val Leu Thr Asp Gly Gln Phe Ile His Val Arg
            100                 105                 110

Thr Leu Ala Glu Lys Ala Gln Ala Leu Leu Gly Phe Glu Tyr Asn Ser
            115                 120                 125

Thr Leu Gly Ser Gln Thr Ile Ala Ile Ser Thr Leu Pro Gly Lys Ile
            130                 135                 140

Arg Lys His Val Met Thr Val Gln Tyr Val Pro Leu Trp Thr Glu Ala
145                 150                 155                 160

Asp Trp Glu Glu Cys Lys Thr Ile Ile Thr Pro Ser Cys Leu Lys Arg
                    165                 170                 175

Leu Tyr His Val Asp Ser Tyr Arg Ala Lys Tyr Glu Ser Ser Ser Leu
                    180                 185                 190

Phe Gly Ile Val Gly Phe Ser Gly Gln Ala Ala Gln His Asp Glu Leu
            195                 200                 205

Asp Lys Phe Leu His Asp Phe Ala Pro Tyr Ser Thr Asn Ala Asn Phe
            210                 215                 220

Ser Ile Glu Ser Val Asn Gly Gly Gln Ser Pro Gln Gly Met Asn Glu
225                 230                 235                 240

Pro Ala Ser Glu Ala Asn Gly Asp Val Gln Tyr Ala Val Ala Met Gly
                    245                 250                 255

Tyr His Val Pro Val Arg Tyr Tyr Ala Val Gly Gly Glu Asn His Asp
                    260                 265                 270

Ile Ile Pro Asp Leu Asp Leu Val Asp Thr Thr Glu Glu Tyr Leu Glu
            275                 280                 285

Pro Phe Leu Glu Phe Ala Ser His Leu Leu Asp Leu Asp Asp Asp Glu
            290                 295                 300

Leu Pro Arg Val Val Ser Ile Ser Tyr Gly Ala Asn Glu Gln Leu Phe
305                 310                 315                 320

Pro Arg Ser Tyr Ala His Gln Val Cys Asp Met Phe Gly Gln Leu Gly
                    325                 330                 335

Ala Arg Gly Val Ser Ile Val Val Ala Ala Gly Asp Leu Gly Pro Gly
                    340                 345                 350

Val Ser Cys Gln Ser Asn Asp Gly Ser Ala Arg Pro Lys Phe Ile Pro
            355                 360                 365

Ser Phe Pro Ala Thr Cys Pro Tyr Val Thr Ser Val Gly Ser Thr Arg
            370                 375                 380

Gly Ile Met Pro Glu Val Ala Ala Ser Phe Ser Ser Gly Gly Phe Ser
385                 390                 395                 400

Asp Tyr Phe Ala Arg Pro Ala Trp Gln Asp Arg Ala Val Gly Ala Tyr
                    405                 410                 415

Leu Gly Ala His Gly Glu Glu Trp Glu Gly Phe Tyr Asn Pro Ala Gly
                    420                 425                 430

Arg Gly Phe Pro Asp Val Ala Ala Gln Gly Val Asn Phe Arg Phe Arg
            435                 440                 445

Ala His Gly Asn Glu Ser Leu Ser Ser Gly Thr Ser Leu Ser Ser Pro
            450                 455                 460

Val Phe Ala Ala Leu Ile Ala Leu Leu Asn Asp His Arg Ser Lys Ser
465                 470                 475                 480

Gly Met Pro Pro Met Gly Phe Leu Asn Pro Trp Ile Tyr Thr Val Gly
                    485                 490                 495
```

```
Ser His Ala Phe Thr Asp Ile Ile Glu Ala Arg Ser Glu Gly Cys Pro
            500                 505                 510

Gly Gln Ser Val Glu Tyr Leu Ala Ser Pro Tyr Ile Pro Asn Ala Gly
        515                 520                 525

Trp Ser Ala Val Pro Gly Trp Asp Pro Val Thr Gly Trp Gly Thr Pro
    530                 535                 540

Leu Phe Asp Arg Met Leu Asn Leu Ser Leu Val
545                 550                 555

<210> SEQ ID NO 31
<211> LENGTH: 388
<212> TYPE: PRT
<213> ORGANISM: Trichoderma reesei

<400> SEQUENCE: 31

Met Ala Trp Leu Lys Lys Leu Ala Leu Val Leu Leu Ala Ile Val Pro
1               5                   10                  15

Tyr Ala Thr Ala Ser Pro Ala Leu Ser Pro Arg Ser Arg Glu Ile Leu
            20                  25                  30

Ser Leu Glu Asp Leu Glu Ser Glu Asp Lys Tyr Val Ile Gly Leu Lys
        35                  40                  45

Gln Gly Leu Ser Pro Thr Asp Leu Lys Lys His Leu Leu Arg Val Ser
    50                  55                  60

Ala Val Gln Tyr Arg Asn Lys Asn Ser Thr Phe Glu Gly Gly Thr Gly
65                  70                  75                  80

Val Lys Arg Thr Tyr Ala Ile Gly Asp Tyr Arg Ala Tyr Thr Ala Val
                85                  90                  95

Leu Asp Arg Asp Thr Val Arg Glu Ile Trp Asn Asp Thr Leu Glu Lys
            100                 105                 110

Pro Pro Trp Gly Leu Ala Thr Leu Ser Asn Lys Lys Pro His Gly Phe
        115                 120                 125

Leu Tyr Arg Tyr Asp Lys Ser Ala Gly Glu Gly Thr Phe Ala Tyr Val
    130                 135                 140

Leu Asp Thr Gly Ile Asn Ser Lys His Val Asp Phe Glu Gly Arg Ala
145                 150                 155                 160

Tyr Met Gly Phe Ser Pro Pro Lys Thr Glu Pro Thr Asp Ile Asn Gly
                165                 170                 175

His Gly Thr His Val Ala Gly Ile Ile Gly Gly Lys Thr Phe Gly Val
            180                 185                 190

Ala Lys Lys Thr Gln Leu Ile Gly Val Lys Val Phe Leu Asp Asp Glu
        195                 200                 205

Ala Thr Thr Ser Thr Leu Met Glu Gly Leu Glu Trp Ala Val Asn Asp
    210                 215                 220

Ile Thr Thr Lys Gly Arg Gln Gly Arg Ser Val Ile Asn Met Ser Leu
225                 230                 235                 240

Gly Gly Pro Tyr Ser Gln Ala Leu Asn Asp Ala Ile His Ile Ala
                245                 250                 255

Asp Met Gly Ile Leu Pro Val Ala Ala Ala Gly Asn Lys Gly Ile Pro
            260                 265                 270

Ala Thr Phe Ile Ser Pro Ala Ser Ala Asp Lys Ala Met Thr Val Gly
        275                 280                 285

Ala Ile Asn Ser Asp Trp Gln Glu Thr Asn Phe Ser Asn Phe Gly Pro
    290                 295                 300

Gln Val Asn Ile Leu Ala Pro Gly Glu Asp Val Leu Ser Ala Tyr Val
```

```
                         305                 310                 315                 320
Ser Thr Asn Thr Ala Thr Arg Val Leu Ser Gly Thr Ser Met Ala Ala
                    325                 330                 335

Pro His Val Ala Gly Leu Ala Leu Tyr Leu Met Ala Leu Glu Glu Phe
                340                 345                 350

Asp Ser Thr Gln Lys Leu Thr Asp Arg Ile Leu Gln Leu Gly Met Lys
            355                 360                 365

Asn Lys Val Val Asn Leu Met Thr Asp Ser Pro Asn Leu Ile Ile His
        370                 375                 380

Asn Asn Val Lys
385

<210> SEQ ID NO 32
<211> LENGTH: 256
<212> TYPE: PRT
<213> ORGANISM: Trichoderma reesei

<400> SEQUENCE: 32

Met Phe Ile Ala Gly Val Ala Leu Ser Ala Leu Leu Cys Ala Asp Thr
1               5                   10                  15

Val Leu Ala Gly Val Ala Gln Asp Arg Gly Leu Ala Ala Arg Leu Ala
            20                  25                  30

Arg Arg Ala Gly Arg Arg Ser Ala Pro Phe Arg Asn Asp Thr Ser His
        35                  40                  45

Ala Thr Val Gln Ser Asn Trp Gly Gly Ala Ile Leu Glu Gly Ser Gly
    50                  55                  60

Phe Thr Ala Ala Ser Ala Thr Val Asn Val Pro Arg Gly Gly Gly Gly
65                  70                  75                  80

Ser Asn Ala Ala Gly Ser Ala Trp Val Gly Ile Asp Gly Ala Ser Cys
                85                  90                  95

Gln Thr Ala Ile Leu Gln Thr Gly Phe Asp Trp Tyr Gly Asp Gly Thr
            100                 105                 110

Tyr Asp Ala Trp Tyr Glu Trp Tyr Pro Glu Phe Ala Ala Asp Phe Ser
        115                 120                 125

Gly Ile Asp Ile Arg Gln Gly Asp Gln Ile Ala Met Ser Val Val Ala
    130                 135                 140

Thr Ser Leu Thr Gly Gly Ser Ala Thr Leu Glu Asn Leu Ser Thr Gly
145                 150                 155                 160

Gln Lys Val Thr Gln Asn Phe Asn Arg Val Thr Ala Gly Ser Leu Cys
                165                 170                 175

Glu Thr Ser Ala Glu Phe Ile Ile Glu Asp Phe Glu Cys Asn Ser
            180                 185                 190

Asn Gly Ser Asn Cys Gln Pro Val Pro Phe Ala Ser Phe Ser Pro Ala
        195                 200                 205

Ile Thr Phe Ser Ser Ala Thr Ala Thr Arg Ser Gly Arg Ser Val Ser
    210                 215                 220

Leu Ser Gly Ala Glu Ile Thr Glu Val Ile Val Asn Asn Gln Asp Leu
225                 230                 235                 240

Thr Arg Cys Ser Val Ser Gly Ser Ser Thr Leu Thr Cys Ser Tyr Val
                245                 250                 255

<210> SEQ ID NO 33
<211> LENGTH: 236
<212> TYPE: PRT
<213> ORGANISM: Trichoderma reesei
```

```
<400> SEQUENCE: 33

Met Asp Ala Ile Arg Ala Arg Ser Ala Ala Arg Arg Ser Asn Arg Phe
1               5                   10                  15

Gln Ala Gly Ser Ser Lys Asn Val Asn Gly Thr Ala Asp Val Glu Ser
                20                  25                  30

Thr Asn Trp Ala Gly Ala Ala Ile Thr Thr Ser Gly Val Thr Glu Val
            35                  40                  45

Ser Gly Thr Phe Thr Val Pro Arg Pro Ser Val Pro Ala Gly Gly Ser
        50                  55                  60

Ser Arg Glu Glu Tyr Cys Gly Ala Ala Trp Val Gly Ile Asp Gly Tyr
65                  70                  75                  80

Ser Asp Ala Asp Leu Ile Gln Thr Gly Val Leu Trp Cys Val Glu Asp
                85                  90                  95

Gly Glu Tyr Leu Tyr Glu Ala Trp Tyr Glu Tyr Leu Pro Ala Ala Leu
            100                 105                 110

Val Glu Tyr Ser Gly Ile Ser Val Thr Ala Gly Ser Val Val Thr Val
        115                 120                 125

Thr Ala Thr Lys Thr Gly Thr Asn Ser Gly Val Thr Thr Leu Thr Ser
130                 135                 140

Gly Gly Lys Thr Val Ser His Thr Phe Ser Arg Gln Asn Ser Pro Leu
145                 150                 155                 160

Pro Gly Thr Ser Ala Glu Trp Ile Val Glu Asp Phe Thr Ser Gly Ser
                165                 170                 175

Ser Leu Val Pro Phe Ala Asp Phe Gly Ser Val Thr Phe Thr Gly Ala
            180                 185                 190

Thr Ala Val Val Asn Gly Ala Thr Val Thr Ala Gly Gly Asp Ser Pro
        195                 200                 205

Val Ile Ile Asp Leu Glu Asp Ser Arg Gly Asp Ile Leu Thr Ser Thr
210                 215                 220

Thr Val Ser Gly Ser Thr Val Thr Val Glu Tyr Glu
225                 230                 235

<210> SEQ ID NO 34
<211> LENGTH: 612
<212> TYPE: PRT
<213> ORGANISM: Trichoderma reesei

<400> SEQUENCE: 34

Met Ala Lys Leu Ser Thr Leu Arg Leu Ala Ser Leu Leu Ser Leu Val
1               5                   10                  15

Ser Val Gln Val Ser Ala Ser Val His Leu Leu Glu Ser Leu Glu Lys
                20                  25                  30

Leu Pro His Gly Trp Lys Ala Ala Glu Thr Pro Ser Pro Ser Ser Gln
            35                  40                  45

Ile Val Leu Gln Val Ala Leu Thr Gln Gln Asn Ile Asp Gln Leu Glu
        50                  55                  60

Ser Arg Leu Ala Ala Val Ser Thr Pro Thr Ser Ser Thr Tyr Gly Lys
65                  70                  75                  80

Tyr Leu Asp Val Asp Glu Ile Asn Ser Ile Phe Ala Pro Ser Asp Ala
                85                  90                  95

Ser Ser Ser Ala Val Glu Ser Trp Leu Gln Ser His Gly Val Thr Ser
            100                 105                 110

Tyr Thr Lys Gln Gly Ser Ser Ile Trp Phe Gln Thr Asn Ile Ser Thr
        115                 120                 125
```

```
Ala Asn Ala Met Leu Ser Thr Asn Phe His Thr Tyr Ser Asp Leu Thr
130                 135                 140

Gly Ala Lys Lys Val Arg Thr Leu Lys Tyr Ser Ile Pro Glu Ser Leu
145                 150                 155                 160

Ile Gly His Val Asp Leu Ile Ser Pro Thr Thr Tyr Phe Gly Thr Thr
                165                 170                 175

Lys Ala Met Arg Lys Leu Lys Ser Ser Gly Val Ser Pro Ala Ala Asp
                180                 185                 190

Ala Leu Ala Ala Arg Gln Glu Pro Ser Ser Cys Lys Gly Thr Leu Val
                195                 200                 205

Phe Glu Gly Glu Thr Phe Asn Val Phe Gln Pro Asp Cys Leu Arg Thr
210                 215                 220

Glu Tyr Ser Val Asp Gly Tyr Thr Pro Ser Val Lys Ser Gly Ser Arg
225                 230                 235                 240

Ile Gly Phe Gly Ser Phe Leu Asn Glu Ser Ala Ser Phe Ala Asp Gln
                245                 250                 255

Ala Leu Phe Glu Lys His Phe Asn Ile Pro Ser Gln Asn Phe Ser Val
                260                 265                 270

Val Leu Ile Asn Gly Gly Thr Asp Leu Pro Gln Pro Ser Asp Ala
                275                 280                 285

Asn Asp Gly Glu Ala Asn Leu Asp Ala Gln Thr Ile Leu Thr Ile Ala
290                 295                 300

His Pro Leu Pro Ile Thr Glu Phe Ile Thr Ala Gly Ser Pro Pro Tyr
305                 310                 315                 320

Phe Pro Asp Pro Val Glu Pro Ala Gly Thr Pro Asn Glu Asn Glu Pro
                325                 330                 335

Tyr Leu Gln Tyr Tyr Glu Phe Leu Leu Ser Lys Ser Asn Ala Glu Ile
                340                 345                 350

Pro Gln Val Ile Thr Asn Ser Tyr Gly Asp Glu Glu Gln Thr Val Pro
                355                 360                 365

Arg Ser Tyr Ala Val Arg Val Cys Asn Leu Ile Gly Leu Leu Gly Leu
370                 375                 380

Arg Gly Ile Ser Val Leu His Ser Ser Gly Asp Glu Gly Val Gly Ala
385                 390                 395                 400

Ser Cys Val Ala Thr Asn Ser Thr Thr Pro Gln Phe Asn Pro Ile Phe
                405                 410                 415

Pro Ala Thr Cys Pro Tyr Val Thr Ser Val Gly Gly Thr Val Ser Phe
                420                 425                 430

Asn Pro Glu Val Ala Trp Ala Gly Ser Ser Gly Phe Ser Tyr Tyr
                435                 440                 445

Phe Ser Arg Pro Trp Tyr Gln Gln Glu Ala Val Gly Thr Tyr Leu Glu
450                 455                 460

Lys Tyr Val Ser Ala Glu Thr Lys Lys Tyr Tyr Gly Pro Tyr Val Asp
465                 470                 475                 480

Phe Ser Gly Arg Gly Phe Pro Asp Val Ala Ala His Ser Val Ser Pro
                485                 490                 495

Asp Tyr Pro Val Phe Gln Gly Gly Leu Thr Pro Ser Gly Gly Thr
                500                 505                 510

Ser Ala Ala Ser Pro Val Val Ala Ile Val Ala Leu Leu Asn Asp
                515                 520                 525

Ala Arg Leu Arg Glu Gly Lys Pro Thr Leu Gly Phe Leu Asn Pro Leu
530                 535                 540

Ile Tyr Leu His Ala Ser Lys Gly Phe Thr Asp Ile Thr Ser Gly Gln
```

```
                         545                 550                 555                 560
Ser Glu Gly Cys Asn Gly Asn Asn Thr Gln Thr Gly Ser Pro Leu Pro
                    565                 570                 575

Gly Ala Gly Phe Ile Ala Gly Ala His Trp Asn Ala Thr Lys Gly Trp
                580                 585                 590

Asp Pro Thr Thr Gly Phe Gly Val Pro Asn Leu Lys Lys Leu Leu Ala
            595                 600                 605

Leu Val Arg Phe
        610

<210> SEQ ID NO 35
<211> LENGTH: 477
<212> TYPE: PRT
<213> ORGANISM: Trichoderma reesei

<400> SEQUENCE: 35

Met Arg Phe Val Gln Tyr Val Ser Leu Ala Gly Leu Phe Ala Ala Ala
1               5                   10                  15

Thr Val Ser Ala Gly Val Val Thr Val Pro Phe Glu Lys Arg Asn Leu
                20                  25                  30

Asn Pro Asp Phe Ala Pro Ser Leu Leu Arg Arg Asp Gly Ser Val Ser
            35                  40                  45

Leu Asp Ala Ile Asn Asn Leu Thr Gly Gly Tyr Tyr Ala Gln Phe
50                  55                  60

Ser Val Gly Thr Pro Pro Gln Lys Leu Ser Phe Leu Leu Asp Thr Gly
65                  70                  75                  80

Ser Ser Asp Thr Trp Val Asn Ser Val Thr Ala Asp Leu Cys Thr Asp
                85                  90                  95

Glu Phe Thr Gln Gln Thr Val Gly Glu Tyr Cys Phe Arg Gln Phe Asn
            100                 105                 110

Pro Arg Arg Ser Ser Ser Tyr Lys Ala Ser Thr Glu Val Phe Asp Ile
        115                 120                 125

Thr Tyr Leu Asp Gly Arg Arg Ile Arg Gly Asn Tyr Phe Thr Asp Thr
    130                 135                 140

Val Thr Ile Asn Gln Ala Asn Ile Thr Gly Gln Lys Ile Gly Leu Ala
145                 150                 155                 160

Leu Gln Ser Val Arg Gly Thr Gly Ile Leu Gly Leu Gly Phe Arg Glu
                165                 170                 175

Asn Glu Ala Ala Asp Thr Lys Tyr Pro Thr Val Ile Asp Asn Leu Val
            180                 185                 190

Ser Gln Lys Val Ile Pro Val Pro Ala Phe Ser Leu Tyr Leu Asn Asp
        195                 200                 205

Leu Gln Thr Ser Gln Gly Ile Leu Leu Phe Gly Gly Val Asp Thr Asp
    210                 215                 220

Lys Phe His Gly Gly Leu Ala Thr Leu Pro Leu Gln Ser Leu Pro Pro
225                 230                 235                 240

Ser Ile Ala Glu Thr Gln Asp Ile Val Met Tyr Ser Val Asn Leu Asp
                245                 250                 255

Gly Phe Ser Ala Ser Asp Val Asp Thr Pro Asp Val Ser Ala Lys Ala
            260                 265                 270

Val Leu Asp Ser Gly Ser Thr Ile Thr Leu Leu Pro Asp Ala Val Val
        275                 280                 285

Gln Glu Leu Phe Asp Glu Tyr Asp Val Leu Asn Ile Gln Gly Leu Pro
    290                 295                 300
```

Val Pro Phe Ile Asp Cys Ala Lys Ala Asn Ile Lys Asp Ala Thr Phe
305                 310                 315                 320

Asn Phe Lys Phe Asp Gly Lys Thr Ile Lys Val Pro Ile Asp Glu Met
            325                 330                 335

Val Leu Asn Asn Leu Ala Ala Ala Ser Asp Glu Ile Met Ser Asp Pro
        340                 345                 350

Ser Leu Ser Lys Phe Phe Lys Gly Trp Ser Gly Val Cys Thr Phe Gly
    355                 360                 365

Met Gly Ser Thr Lys Thr Phe Gly Ile Gln Ser Asp Glu Phe Val Leu
370                 375                 380

Leu Gly Asp Thr Phe Leu Arg Ser Ala Tyr Val Val Tyr Asp Leu Gln
385                 390                 395                 400

Asn Lys Gln Ile Gly Ile Ala Gln Ala Thr Leu Asn Ser Thr Ser Ser
            405                 410                 415

Thr Ile Val Glu Phe Lys Ala Gly Ser Lys Thr Ile Pro Gly Pro Ala
        420                 425                 430

Ser Thr Gly Asp Asp Ser Asp Asp Ser Asp Asp Ser Asp Glu Asp
    435                 440                 445

Ser Ala Gly Ala Ala Leu His Pro Thr Phe Ser Ile Ala Leu Ala Gly
    450                 455                 460

Thr Leu Phe Thr Ala Val Ser Met Met Met Ser Val Leu
465                 470                 475

<210> SEQ ID NO 36
<211> LENGTH: 1263
<212> TYPE: DNA
<213> ORGANISM: Trichoderma reesei

<400> SEQUENCE: 36
atggcgtcac tcatcaaaac tgccgtggac attgccaacg ccgccatgc gctgtccaga      60 tatgtcatct ttgggctctg gcttgcggat gcggtgctgt gcgggctgat tatctggaaa    120
gtgccttata cggaaatcga ctgggtcgcc tacatggagc aagtcaccca gttcgtccac    180
ggagagcgag actacccaa gatggagggc ggcacagggc ccctggtgta tcccgcggcc    240
catgtgtaca tctacacagg gctctactac ctgacgaaca agggcaccga catcctgctg    300
gcgcagcagc tctttgccgt gctctacatg gctactctgg cggtcgtcat gacatgctac    360
tccaaggcca aggtcccgcc gtacatcttc ccgcttctca tcctctccaa aagacttcac    420
agcgtcttcg tcctgagatg cttcaacgac tgcttcgccg ccttcttcct ctggctctgc    480
atcttcttct tccagaggcg agagtggacc atcggagctc tcgcatacag catcggcctg    540
ggcgtcaaaa tgtcgctgct actggttctc cccgccgtgg tcatcgtcct ctacctcggc    600
cgcggcttca agggcgccct gcggctgctc tggctcatgg tgcaggtcca gctcctcctc    660 gccatacct tcatcacgac aaattggcgc ggctacctcg gccgtgcatt cgagctctcg    720
aggcagttca gtttgaatg gacagtcaat tgggcgcatg ctgggcgagga tctgttcctc    780 agccggggct tctctatcac gctactggca tttcacgcca tcttcctcct cgcctttatc    840
ctcggccggt ggctgaagat tagggaacgg accgtactcg ggatgatccc ctatgtcatc    900
cgattcagat cgcccttac cgagcaggaa gagcgcgcca tctccaaccg cgtcgtcacg    960
cccggctatg tcatgtccac catcttgtcg gccaacgtgg tgggactgct gtttgcccgg   1020
tctctgcact accagttcta tgcatatctg gcgtgggcga cccctatct cctgtggacg   1080 gcctgcccca tcttttggt ggtggccccc ctctgggcgg cgcaagaatg ggcctggaac   1140

```
gtcttcccca gcacgcctct tagctcgagc gtcgtggtga gcgtgctggc cgtgacggtg    1200
gccatggcgt ttgcaggttc aaatccgcag ccacgtgaaa catcgaagcc gaagcagcac    1260
taa                                                                 1263
```

<210> SEQ ID NO 37
<211> LENGTH: 420
<212> TYPE: PRT
<213> ORGANISM: Trichoderma reesei

<400> SEQUENCE: 37

| | | | | | | | | | | | | | | |
|---|---|---|---|---|---|---|---|---|---|---|---|---|---|---|
| Met | Ala | Ser | Leu | Ile | Lys | Thr | Ala | Val | Asp | Ile | Ala | Asn | Gly | Arg | His |
| 1 | | | | 5 | | | | | 10 | | | | | 15 | |
| Ala | Leu | Ser | Arg | Tyr | Val | Ile | Phe | Gly | Leu | Trp | Leu | Ala | Asp | Ala | Val |
| | | | 20 | | | | | 25 | | | | | 30 | | |
| Leu | Cys | Gly | Leu | Ile | Ile | Trp | Lys | Val | Pro | Tyr | Thr | Glu | Ile | Asp | Trp |
| | | 35 | | | | | 40 | | | | | 45 | | | |
| Val | Ala | Tyr | Met | Glu | Gln | Val | Thr | Gln | Phe | Val | His | Gly | Glu | Arg | Asp |
| | 50 | | | | | 55 | | | | | 60 | | | | |
| Tyr | Pro | Lys | Met | Glu | Gly | Gly | Thr | Gly | Pro | Leu | Val | Tyr | Pro | Ala | Ala |
| 65 | | | | | 70 | | | | | 75 | | | | | 80 |
| His | Val | Tyr | Ile | Tyr | Thr | Gly | Leu | Tyr | Tyr | Leu | Thr | Asn | Lys | Gly | Thr |
| | | | | 85 | | | | | 90 | | | | | 95 | |
| Asp | Ile | Leu | Leu | Ala | Gln | Gln | Leu | Phe | Ala | Val | Leu | Tyr | Met | Ala | Thr |
| | | | | 100 | | | | | 105 | | | | | 110 | |
| Leu | Ala | Val | Val | Met | Thr | Cys | Tyr | Ser | Lys | Ala | Lys | Val | Pro | Pro | Tyr |
| | | | 115 | | | | | 120 | | | | | 125 | | |
| Ile | Phe | Pro | Leu | Leu | Ile | Leu | Ser | Lys | Arg | Leu | His | Ser | Val | Phe | Val |
| | | 130 | | | | | 135 | | | | | 140 | | | |
| Leu | Arg | Cys | Phe | Asn | Asp | Cys | Phe | Ala | Ala | Phe | Phe | Leu | Trp | Leu | Cys |
| 145 | | | | | 150 | | | | | 155 | | | | | 160 |
| Ile | Phe | Phe | Phe | Gln | Arg | Arg | Glu | Trp | Thr | Ile | Gly | Ala | Leu | Ala | Tyr |
| | | | | 165 | | | | | 170 | | | | | 175 | |
| Ser | Ile | Gly | Leu | Gly | Val | Lys | Met | Ser | Leu | Leu | Val | Leu | Pro | Ala |
| | | | 180 | | | | | 185 | | | | | 190 | | |
| Val | Val | Ile | Val | Leu | Tyr | Leu | Gly | Arg | Gly | Phe | Lys | Gly | Ala | Leu | Arg |
| | | | 195 | | | | | 200 | | | | | 205 | | |
| Leu | Leu | Trp | Leu | Met | Val | Gln | Val | Gln | Leu | Leu | Leu | Ala | Ile | Pro | Phe |
| | | | 210 | | | | | 215 | | | | | 220 | | |
| Ile | Thr | Thr | Asn | Trp | Arg | Gly | Tyr | Leu | Gly | Arg | Ala | Phe | Glu | Leu | Ser |
| 225 | | | | | 230 | | | | | 235 | | | | | 240 |
| Arg | Gln | Phe | Lys | Phe | Glu | Trp | Thr | Val | Asn | Trp | Arg | Met | Leu | Gly | Glu |
| | | | | 245 | | | | | 250 | | | | | 255 | |
| Asp | Leu | Phe | Leu | Ser | Arg | Gly | Phe | Ser | Ile | Thr | Leu | Leu | Ala | Phe | His |
| | | | | 260 | | | | | 265 | | | | | 270 | |
| Ala | Ile | Phe | Leu | Leu | Ala | Phe | Ile | Leu | Gly | Arg | Trp | Leu | Lys | Ile | Arg |
| | | | 275 | | | | | 280 | | | | | 285 | | |
| Glu | Arg | Thr | Val | Leu | Gly | Met | Ile | Pro | Tyr | Val | Ile | Arg | Phe | Arg | Ser |
| | | 290 | | | | | 295 | | | | | 300 | | | |
| Pro | Phe | Thr | Glu | Gln | Glu | Glu | Arg | Ala | Ile | Ser | Asn | Arg | Val | Val | Thr |
| 305 | | | | | 310 | | | | | 315 | | | | | 320 |
| Pro | Gly | Tyr | Val | Met | Ser | Thr | Ile | Leu | Ser | Ala | Asn | Val | Val | Gly | Leu |
| | | | | 325 | | | | | 330 | | | | | 335 | |
| Leu | Phe | Ala | Arg | Ser | Leu | His | Tyr | Gln | Phe | Tyr | Ala | Tyr | Leu | Ala | Trp |
| | | | 340 | | | | | 345 | | | | | 350 | | |

```
Ala Thr Pro Tyr Leu Leu Trp Thr Ala Cys Pro Asn Leu Val Val
            355                 360                 365

Ala Pro Leu Trp Ala Ala Gln Glu Trp Ala Trp Asn Val Phe Pro Ser
370                 375                 380

Thr Pro Leu Ser Ser Val Val Ser Val Leu Ala Val Thr Val
385                 390                 395                 400

Ala Met Ala Phe Ala Gly Ser Asn Pro Gln Pro Arg Glu Thr Ser Lys
                405                 410                 415

Pro Lys Gln His
            420

<210> SEQ ID NO 38
<211> LENGTH: 445
<212> TYPE: PRT
<213> ORGANISM: Homo sapiens

<400> SEQUENCE: 38

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ala Pro Gly Arg Pro Pro Ser Val Ser Ala Leu Asp Gly Asp Pro Ala
            35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Ala Gln Pro Arg
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
            165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
            195                 200                 205

Glu Asp Asp Leu Glu Val Ala Pro Asp Phe Phe Glu Tyr Phe Arg Ala
210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
            245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
            275                 280                 285

Asp Asp Trp Met Arg Arg Pro Glu Gln Arg Gln Gly Arg Ala Cys Ile
```

-continued

```
                290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
                340                 345                 350

Ala Tyr Asp Arg Asp Phe Leu Ala Arg Val Tyr Gly Ala Pro Gln Leu
                355                 360                 365

Gln Val Glu Lys Val Arg Thr Asn Asp Arg Lys Glu Leu Gly Glu Val
                370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
                420                 425                 430

Pro Pro Leu Thr Trp Glu Gly Tyr Asp Pro Ser Trp Asn
            435                 440                 445

<210> SEQ ID NO 39
<211> LENGTH: 447
<212> TYPE: PRT
<213> ORGANISM: Homo sapiens

<400> SEQUENCE: 39

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
            35                  40                  45

Gly Ala Gly Gly Arg Gly Gly Asp His Pro Ser Val Ala Val Gly Ile
        50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220
```

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln
        435                 440                 445

<210> SEQ ID NO 40
<211> LENGTH: 85
<212> TYPE: PRT
<213> ORGANISM: Trichoderma reesei

<400> SEQUENCE: 40

Met Ala Ser Thr Asn Ala Arg Tyr Val Arg Tyr Leu Leu Ile Ala Phe
1               5                   10                  15

Phe Thr Ile Leu Val Phe Tyr Phe Val Ser Asn Ser Lys Tyr Glu Gly
            20                  25                  30

Val Asp Leu Asn Lys Gly Thr Phe Thr Ala Pro Asp Ser Thr Lys Thr
        35                  40                  45

Thr Pro Lys Pro Pro Ala Thr Gly Asp Ala Lys Asp Phe Pro Leu Ala
    50                  55                  60

Leu Thr Pro Asn Asp Pro Gly Phe Asn Asp Leu Val Gly Ile Ala Pro
65                  70                  75                  80

Gly Pro Arg Met Asn
            85

<210> SEQ ID NO 41
<211> LENGTH: 255
<212> TYPE: DNA
<213> ORGANISM: Trichoderma reesei

<400> SEQUENCE: 41
atggcgtcaa caaatgcgcg ctatgtgcgc tatctactaa tcgccttctt cacaatcctc    60
gtcttctact tgtctccaa ttcaaagtat gagggcgtcg atctcaacaa ggcaccttc    120

```
acagctccgg attcgaccaa gacgacacca aagccgccag ccactggcga tgccaaagac      180
tttcctctgg ccctgacgcc gaacgatcca ggcttcaacg acctcgtcgg catcgctccc      240
ggccctcgaa tgaac                                                       255
```

<210> SEQ ID NO 42
<211> LENGTH: 58
<212> TYPE: PRT
<213> ORGANISM: Homo sapiens

<400> SEQUENCE: 42

```
Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro
    50                  55
```

<210> SEQ ID NO 43
<211> LENGTH: 51
<212> TYPE: PRT
<213> ORGANISM: Trichoderma reesei

<400> SEQUENCE: 43

```
Met Ala Ser Thr Asn Ala Arg Tyr Val Arg Tyr Leu Leu Ile Ala Phe
1               5                   10                  15

Phe Thr Ile Leu Val Phe Tyr Phe Val Ser Asn Ser Lys Tyr Glu Gly
            20                  25                  30

Val Asp Leu Asn Lys Gly Thr Phe Thr Ala Pro Asp Ser Thr Lys Thr
        35                  40                  45

Thr Pro Lys
    50
```

<210> SEQ ID NO 44
<211> LENGTH: 52
<212> TYPE: PRT
<213> ORGANISM: Trichoderma reesei

<400> SEQUENCE: 44

```
Met Ala Ile Ala Arg Pro Val Arg Ala Leu Gly Gly Leu Ala Ala Ile
1               5                   10                  15

Leu Trp Cys Phe Phe Leu Tyr Gln Leu Leu Arg Pro Ser Ser Ser Tyr
            20                  25                  30

Asn Ser Pro Gly Asp Arg Tyr Ile Asn Phe Glu Arg Asp Pro Asn Leu
        35                  40                  45

Asp Pro Thr Gly
    50
```

<210> SEQ ID NO 45
<211> LENGTH: 33
<212> TYPE: PRT
<213> ORGANISM: Trichoderma reesei

<400> SEQUENCE: 45

```
Met Leu Asn Pro Arg Arg Ala Leu Ile Ala Ala Ala Phe Ile Leu Thr
1               5                   10                  15

Val Phe Phe Leu Ile Ser Arg Ser His Asn Ser Glu Ser Ala Ser Thr
```

```
                    20                  25                  30

Ser

<210> SEQ ID NO 46
<211> LENGTH: 84
<212> TYPE: PRT
<213> ORGANISM: Trichoderma reesei

<400> SEQUENCE: 46

Met Met Pro Arg His His Ser Ser Gly Phe Ser Asn Gly Tyr Pro Arg
1               5                   10                  15

Ala Asp Thr Phe Glu Ile Ser Pro His Arg Phe Gln Pro Arg Ala Thr
            20                  25                  30

Leu Pro Pro His Arg Lys Arg Lys Arg Thr Ala Ile Arg Val Gly Ile
        35                  40                  45

Ala Val Val Val Ile Leu Val Leu Val Leu Trp Phe Gly Gln Pro Arg
    50                  55                  60

Ser Val Ala Ser Leu Ile Ser Leu Gly Ile Leu Ser Gly Tyr Asp Asp
65                  70                  75                  80

Leu Lys Leu Glu

<210> SEQ ID NO 47
<211> LENGTH: 55
<212> TYPE: PRT
<213> ORGANISM: Trichoderma reesei

<400> SEQUENCE: 47

Met Leu Leu Pro Lys Gly Gly Leu Asp Trp Arg Ser Ala Arg Ala Gln
1               5                   10                  15

Ile Pro Pro Thr Arg Ala Leu Trp Asn Ala Val Thr Arg Thr Arg Phe
            20                  25                  30

Ile Leu Leu Val Gly Ile Thr Gly Leu Ile Leu Leu Trp Arg Gly
        35                  40                  45

Val Ser Thr Ser Ala Ser Glu
    50                  55

<210> SEQ ID NO 48
<211> LENGTH: 69
<212> TYPE: DNA
<213> ORGANISM: Artificial Sequence
<220> FEATURE:
<223> OTHER INFORMATION: Primer

<400> SEQUENCE: 48
cgattaagtt gggtaacgcc agggttttcc cagtcacgac ggtttaaacg ctgcagggcg    60
tacagaact                                                            69

<210> SEQ ID NO 49
<211> LENGTH: 69
<212> TYPE: DNA
<213> ORGANISM: Artificial Sequence
<220> FEATURE:
<223> OTHER INFORMATION: Primer

<400> SEQUENCE: 49
atctctcaaa ggaagaatcc cttcagggtt gcgtttccag tgcggccgcg gctctaaaat    60
gcttcacag                                                            69

<210> SEQ ID NO 50
```

```
<211> LENGTH: 68
<212> TYPE: DNA
<213> ORGANISM: Artificial Sequence
<220> FEATURE:
<223> OTHER INFORMATION: Primer

<400> SEQUENCE: 50
cggttctcat ctgggcttgc tcggtcctgg cgtagatcta gcggccgcac gatgatgatg      60
acagccag                                                               68

<210> SEQ ID NO 51
<211> LENGTH: 69
<212> TYPE: DNA
<213> ORGANISM: Artificial Sequence
<220> FEATURE:
<223> OTHER INFORMATION: Primer

<400> SEQUENCE: 51
gtggaattgt gagcggataa caatttcaca caggaaacag cgtttaaacc gtccagctcc      60
cgcagcgcc                                                              69

<210> SEQ ID NO 52
<211> LENGTH: 84
<212> TYPE: DNA
<213> ORGANISM: Artificial Sequence
<220> FEATURE:
<223> OTHER INFORMATION: Primer

<400> SEQUENCE: 52
atcgctaact gctttctctt ctgtgaagca ttttagagcc gcggccgcgg ccggccgcga      60
tcgcctagat ctacgccagg accg                                             84

<210> SEQ ID NO 53
<211> LENGTH: 48
<212> TYPE: DNA
<213> ORGANISM: Artificial Sequence
<220> FEATURE:
<223> OTHER INFORMATION: Primer

<400> SEQUENCE: 53
cggtcctggc gtagatctag ggcgcgccac tggaaacgca accctgaa                   48

<210> SEQ ID NO 54
<211> LENGTH: 48
<212> TYPE: DNA
<213> ORGANISM: Artificial Sequence
<220> FEATURE:
<223> OTHER INFORMATION: Primer

<400> SEQUENCE: 54
ttcagggttg cgtttccagt ggcgcgccct agatctacgc caggaccg                   48

<210> SEQ ID NO 55
<211> LENGTH: 68
<212> TYPE: DNA
<213> ORGANISM: Artificial Sequence
<220> FEATURE:
<223> OTHER INFORMATION: Primer

<400> SEQUENCE: 55
agcatcatga ccgccccctt ctggctgtca tcatcgt gcggccgcga ttattgcaca         60
agcagcga                                                               68
```

```
<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
tatggcttta gatggggaca                                               20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tgcgtcgccg tctcgctcct                                               20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ttaggcgacc tcttttcca                                                20

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
cctgtatcgt cctgttcc                                                 18

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gcgcctgtcg agtcggcatt                                               20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
caccggccat gctcttgcca                                               20

<210> SEQ ID NO 62
<211> LENGTH: 18
<212> TYPE: DNA
<213> ORGANISM: Artificial Sequence
<220> FEATURE:
<223> OTHER INFORMATION: Primer
```

<400> SEQUENCE: 62
caaggtgccc tatgtcgc                                              18

<210> SEQ ID NO 63
<211> LENGTH: 18
<212> TYPE: DNA
<213> ORGANISM: Artificial Sequence
<220> FEATURE:
<223> OTHER INFORMATION: Primer

<400> SEQUENCE: 63
gatcgggtca ggacggaa                                              18

<210> SEQ ID NO 64
<211> LENGTH: 18
<212> TYPE: DNA
<213> ORGANISM: Artificial Sequence
<220> FEATURE:
<223> OTHER INFORMATION: Primer

<400> SEQUENCE: 64
agcctgtctg agggacgg                                              18

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
caaggtcgag attcggca                                              18

<210> SEQ ID NO 66
<211> LENGTH: 17
<212> TYPE: DNA
<213> ORGANISM: Artificial Sequence
<220> FEATURE:
<223> OTHER INFORMATION: Primer

<400> SEQUENCE: 66
cagaaggggg cggtcat                                               17

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
gtcccagctc ccgctct                                               17

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
gcgcctgtcg agtcggcatt                                            20

<210> SEQ ID NO 69
<211> LENGTH: 20

```
<212> TYPE: DNA
<213> ORGANISM: Artificial Sequence
<220> FEATURE:
<223> OTHER INFORMATION: Primer

<400> SEQUENCE: 69
caccggccat gctcttgcca                                                    20

<210> SEQ ID NO 70
<211> LENGTH: 69
<212> TYPE: DNA
<213> ORGANISM: Artificial Sequence
<220> FEATURE:
<223> OTHER INFORMATION: Primer

<400> SEQUENCE: 70
cgattaagtt gggtaacgcc agggttttcc cagtcacgac ggtttaaacg tttcaggtac        60
caacacctg                                                                69

<210> SEQ ID NO 71
<211> LENGTH: 69
<212> TYPE: DNA
<213> ORGANISM: Artificial Sequence
<220> FEATURE:
<223> OTHER INFORMATION: Primer

<400> SEQUENCE: 71
atctctcaaa ggaagaatcc cttcagggtt gcgtttccag tgcggccgcg gcgaagagtc        60
tggcgggga                                                                69

<210> SEQ ID NO 72
<211> LENGTH: 68
<212> TYPE: DNA
<213> ORGANISM: Artificial Sequence
<220> FEATURE:
<223> OTHER INFORMATION: Primer

<400> SEQUENCE: 72
cggttctcat ctgggcttgc tcggtcctgg cgtagatcta gcggccgcaa gaggatgggg        60
gtaaagct                                                                 68

<210> SEQ ID NO 73
<211> LENGTH: 69
<212> TYPE: DNA
<213> ORGANISM: Artificial Sequence
<220> FEATURE:
<223> OTHER INFORMATION: Primer

<400> SEQUENCE: 73
gtggaattgt gagcggataa caatttcaca caggaaacag cgtttaaacg aggaggactc        60
gtgagttat                                                                69

<210> SEQ ID NO 74
<211> LENGTH: 84
<212> TYPE: DNA
<213> ORGANISM: Artificial Sequence
<220> FEATURE:
<223> OTHER INFORMATION: Primer

<400> SEQUENCE: 74
gcgcccttcc gcctcgacaa tcccgccag actcttcgcc gcggccgcgg ccggccgcga        60
tcgcctagat ctacgccagg accg                                               84
```

<210> SEQ ID NO 75
<211> LENGTH: 48
<212> TYPE: DNA
<213> ORGANISM: Artificial Sequence
<220> FEATURE:
<223> OTHER INFORMATION: Primer

<400> SEQUENCE: 75
cggtcctggc gtagatctag ggcgcgccac tggaaacgca accctgaa                48

<210> SEQ ID NO 76
<211> LENGTH: 48
<212> TYPE: DNA
<213> ORGANISM: Artificial Sequence
<220> FEATURE:
<223> OTHER INFORMATION: Primer

<400> SEQUENCE: 76
ttcagggttg cgtttccagt ggcgcgccct agatctacgc caggaccg                48

<210> SEQ ID NO 77
<211> LENGTH: 68
<212> TYPE: DNA
<213> ORGANISM: Artificial Sequence
<220> FEATURE:
<223> OTHER INFORMATION: Primer

<400> SEQUENCE: 77
gagctggcca gaaaagacca agctttaccc ccatcctctt gcggccgcga ttattgcaca     60
agcagcga                                                              68

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
acgagttgtt tcgtgtaccg                                                 20

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
ctttccattc atcagggatg g                                               21

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ggagactcag tgaagagagg                                                 20

<210> SEQ ID NO 81
<211> LENGTH: 18
<212> TYPE: DNA
<213> ORGANISM: Artificial Sequence
<220> FEATURE:
<223> OTHER INFORMATION: Primer

<400> SEQUENCE: 81
atgttgcagt tgcgaaag                                                18

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
ccctcgtcgc agaaaagatg                                              20

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
agcctccttg ggaacctcag                                              20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cttagtgcgg ctggagggcg                                              20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
ggccggttcg tgcaactgga                                              20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
ggccgcaaga ggatgggggt                                              20

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
tcgggccagc tgaagcacaa c                                            21

```
<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
ttgaggaacg gctgcctgcg                                                   20

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
cgatggctcc gtcatccgcc                                                   20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
acgagttgtt tcgtgtaccg                                                   20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
tgcgtcgccg tctcgctcct                                                   20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
ttaggcgacc tcttttttcca                                                  20

<210> SEQ ID NO 93
<211> LENGTH: 18
<212> TYPE: DNA
<213> ORGANISM: Artificial Sequence
<220> FEATURE:
<223> OTHER INFORMATION: Primer

<400> SEQUENCE: 93
atgttgcagt tgcgaaag                                                     18

<210> SEQ ID NO 94
<211> LENGTH: 20
<212> TYPE: DNA
<213> ORGANISM: Artificial Sequence
<220> FEATURE:
<223> OTHER INFORMATION: Primer
```

```
<400> SEQUENCE: 94
ccctcgtcgc agaaaagatg                                              20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
agcctccttg ggaacctcag                                              20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
cttagtgcgg ctggagggcg                                              20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
ggccggttcg tgcaactgga                                              20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ggccgcaaga ggatgggggt                                              20

<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99
tcgggccagc tgaagcacaa c                                            21

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
ccctcgtcgc agaaaagatg                                              20

<210> SEQ ID NO 101
```

```
<211> LENGTH: 20
<212> TYPE: DNA
<213> ORGANISM: Artificial Sequence
<220> FEATURE:
<223> OTHER INFORMATION: Primer

<400> SEQUENCE: 101
agcctccttg ggaacctcag                                               20

<210> SEQ ID NO 102
<211> LENGTH: 69
<212> TYPE: DNA
<213> ORGANISM: Artificial Sequence
<220> FEATURE:
<223> OTHER INFORMATION: Primer

<400> SEQUENCE: 102
cgattaagtt gggtaacgcc agggttttcc cagtcacgac ggtttaaacg tgtttaaatt   60
tgatgaggc                                                           69

<210> SEQ ID NO 103
<211> LENGTH: 69
<212> TYPE: DNA
<213> ORGANISM: Artificial Sequence
<220> FEATURE:
<223> OTHER INFORMATION: Primer

<400> SEQUENCE: 103
atctctcaaa ggaagaatcc cttcagggtt gcgtttccag tgcggccgcg gtctcagaga   60
cagccttct                                                           69

<210> SEQ ID NO 104
<211> LENGTH: 68
<212> TYPE: DNA
<213> ORGANISM: Artificial Sequence
<220> FEATURE:
<223> OTHER INFORMATION: Primer

<400> SEQUENCE: 104
cggttctcat ctgggcttgc tcggtcctgg cgtagatcta gcggccgcac tcggcttctt   60
tgtccgag                                                            68

<210> SEQ ID NO 105
<211> LENGTH: 69
<212> TYPE: DNA
<213> ORGANISM: Artificial Sequence
<220> FEATURE:
<223> OTHER INFORMATION: Primer

<400> SEQUENCE: 105
gtggaattgt gagcggataa caatttcaca caggaaacag cgtttaaact cctcgtcggc   60
aacaaggcc                                                           69

<210> SEQ ID NO 106
<211> LENGTH: 84
<212> TYPE: DNA
<213> ORGANISM: Artificial Sequence
<220> FEATURE:
<223> OTHER INFORMATION: Primer

<400> SEQUENCE: 106
gcagatctgg gggaggaatc agaaggctgt ctctgagacc gcggccgcgg ccggccgcga   60
tcgcctagat ctacgccagg accg                                          84
```

<210> SEQ ID NO 107
<211> LENGTH: 48
<212> TYPE: DNA
<213> ORGANISM: Artificial Sequence
<220> FEATURE:
<223> OTHER INFORMATION: Primer

<400> SEQUENCE: 107
cggtcctggc gtagatctag ggcgcgccac tggaaacgca accctgaa        48

<210> SEQ ID NO 108
<211> LENGTH: 48
<212> TYPE: DNA
<213> ORGANISM: Artificial Sequence
<220> FEATURE:
<223> OTHER INFORMATION: Primer

<400> SEQUENCE: 108
ttcagggttg cgtttccagt ggcgcgccct agatctacgc caggaccg        48

<210> SEQ ID NO 109
<211> LENGTH: 68
<212> TYPE: DNA
<213> ORGANISM: Artificial Sequence
<220> FEATURE:
<223> OTHER INFORMATION: Primer

<400> SEQUENCE: 109
aaagtgggcg agctgagata ctcggacaaa gaagccgagt gcggccgcga ttattgcaca        60
agcagcga        68

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
acgggagatc tcggaaaa        18

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
ctttccattc atcagggatg g        21

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
ggagactcag tgaagagagg        20

<210> SEQ ID NO 113
<211> LENGTH: 18
<212> TYPE: DNA

```
<213> ORGANISM: Artificial Sequence
<220> FEATURE:
<223> OTHER INFORMATION: Primer

<400> SEQUENCE: 113
atgaagctca gcctgtgg                                                 18

<210> SEQ ID NO 114
<211> LENGTH: 18
<212> TYPE: DNA
<213> ORGANISM: Artificial Sequence
<220> FEATURE:
<223> OTHER INFORMATION: Primer

<400> SEQUENCE: 114
ggggacggct tgaggaag                                                 18

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
ctgcttgctg cttccagtca                                               20

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
tggcagatgc cgaaaggcgg                                               20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
tggcaaccag ctgtggctcc                                               20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
cggccgcact cggcttcttt                                               20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
gagtgggcta ggcgcaacgg                                               20
```

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
ggatcggcca ctgccaccac                                          20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
gcccacttct ctgcgcgtgt                                          20

<210> SEQ ID NO 122
<211> LENGTH: 18
<212> TYPE: DNA
<213> ORGANISM: Artificial Sequence
<220> FEATURE:
<223> OTHER INFORMATION: Primer

<400> SEQUENCE: 122
acgggagatc tcggaaaa                                            18

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
ccatgagctt gaacaggtaa                                          20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
ttaggcgacc tcttttccca                                          20

<210> SEQ ID NO 125
<211> LENGTH: 18
<212> TYPE: DNA
<213> ORGANISM: Artificial Sequence
<220> FEATURE:
<223> OTHER INFORMATION: Primer

<400> SEQUENCE: 125
atgaagctca gcctgtgg                                            18

<210> SEQ ID NO 126
<211> LENGTH: 20
<212> TYPE: DNA
<213> ORGANISM: Artificial Sequence
<220> FEATURE:

<223> OTHER INFORMATION: Primer

<400> SEQUENCE: 126
ggatcggcca ctgccaccac                                               20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
gcccacttct ctgcgcgtgt                                               20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
tggcagatgc cgaaaggcgg                                               20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
tggcaaccag ctgtggctcc                                               20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
cggccgcact cggcttcttt                                               20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
gagtgggcta ggcgcaacgg                                               20

<210> SEQ ID NO 132
<211> LENGTH: 17
<212> TYPE: DNA
<213> ORGANISM: Artificial Sequence
<220> FEATURE:
<223> OTHER INFORMATION: Primer

<400> SEQUENCE: 132
ctctgcgcgt gttgtgg                                                  17

```
<210> SEQ ID NO 133
<211> LENGTH: 17
<212> TYPE: DNA
<213> ORGANISM: Artificial Sequence
<220> FEATURE:
<223> OTHER INFORMATION: Primer

<400> SEQUENCE: 133
taagggtgcg gattcgg                                                    17

<210> SEQ ID NO 134
<211> LENGTH: 488
<212> TYPE: PRT
<213> ORGANISM: Trichoderma reesei

<400> SEQUENCE: 134
```

Met Arg Ala Ser Pro Leu Ala Val Ala Gly Val Ala Leu Ala Ser Ala
1               5                   10                  15

Ala Gln Ala Gln Val Val Gln Phe Asp Ile Glu Lys Arg His Ala Pro
            20                  25                  30

Arg Leu Ser Arg Arg Asp Gly Thr Ile Asp Gly Thr Leu Ser Asn Gln
        35                  40                  45

Arg Val Gln Gly Gly Tyr Phe Ile Asn Val Gln Val Gly Ser Pro Gly
    50                  55                  60

Gln Asn Ile Thr Leu Gln Leu Asp Thr Gly Ser Ser Asp Val Trp Val
65                  70                  75                  80

Pro Ser Ser Thr Ala Ala Ile Cys Thr Gln Val Ser Glu Arg Asn Pro
                85                  90                  95

Gly Cys Gln Phe Gly Ser Phe Asn Pro Asp Asp Ser Asp Thr Phe Asp
            100                 105                 110

Glu Val Gly Gln Gly Leu Phe Asp Ile Thr Tyr Val Asp Gly Ser Ser
        115                 120                 125

Ser Lys Gly Asp Tyr Phe Gln Asp Asn Phe Gln Ile Asn Gly Val Thr
    130                 135                 140

Val Lys Asn Leu Thr Met Gly Leu Gly Leu Ser Ser Ser Ile Pro Asn
145                 150                 155                 160

Gly Leu Ile Gly Val Gly Tyr Met Asn Asp Glu Ala Ser Val Ser Thr
                165                 170                 175

Thr Arg Ser Thr Tyr Pro Asn Leu Pro Ile Val Leu Gln Gln Gln Lys
            180                 185                 190

Leu Ile Asn Ser Val Ala Phe Ser Leu Trp Leu Asn Asp Leu Asp Ala
        195                 200                 205

Ser Thr Gly Ser Ile Leu Phe Gly Gly Ile Asp Thr Glu Lys Tyr His
    210                 215                 220

Gly Asp Leu Thr Ser Ile Asp Ile Ile Ser Pro Asn Gly Gly Lys Thr
225                 230                 235                 240

Phe Thr Glu Phe Ala Val Asn Leu Tyr Ser Val Gln Ala Thr Ser Pro
                245                 250                 255

Ser Gly Thr Asp Thr Leu Ser Thr Ser Glu Asp Thr Leu Ile Ala Val
            260                 265                 270

Leu Asp Ser Gly Thr Thr Leu Thr Tyr Leu Pro Gln Asp Met Ala Glu
        275                 280                 285

Glu Ala Trp Asn Glu Val Gly Ala Glu Tyr Ser Asn Glu Leu Gly Leu
    290                 295                 300

Ala Val Val Pro Cys Ser Val Gly Asn Thr Asn Gly Phe Phe Ser Phe
305                 310                 315                 320

```
Thr Phe Ala Gly Thr Asp Gly Pro Thr Ile Asn Val Thr Leu Ser Glu
                325                 330                 335

Leu Val Leu Asp Leu Phe Ser Gly Gly Pro Ala Pro Arg Phe Ser Ser
            340                 345                 350

Gly Pro Asn Lys Gly Gln Ser Ile Cys Glu Phe Gly Ile Gln Asn Gly
        355                 360                 365

Thr Gly Ser Pro Phe Leu Leu Gly Asp Thr Phe Leu Arg Ser Ala Phe
    370                 375                 380

Val Val Tyr Asp Leu Val Asn Asn Gln Ile Ala Ile Ala Pro Thr Asn
385                 390                 395                 400

Phe Asn Ser Thr Arg Thr Asn Val Val Ala Phe Ala Ser Ser Gly Ala
                405                 410                 415

Pro Ile Pro Ser Ala Thr Ala Pro Asn Gln Ser Arg Thr Gly His
            420                 425                 430

Ser Ser Ser Thr His Ser Gly Leu Ser Ala Ala Ser Gly Phe His Asp
        435                 440                 445

Gly Asp Asp Glu Asn Ala Gly Ser Leu Thr Ser Val Phe Ser Gly Pro
    450                 455                 460

Gly Met Ala Val Val Gly Met Thr Ile Cys Tyr Thr Leu Leu Gly Ser
465                 470                 475                 480

Ala Ile Phe Gly Ile Gly Trp Leu
                485

<210> SEQ ID NO 135
<211> LENGTH: 761
<212> TYPE: PRT
<213> ORGANISM: Trichoderma reesei

<400> SEQUENCE: 135

Met Arg Ser Thr Leu Tyr Gly Leu Ala Ala Leu Pro Leu Ala Ala Gln
1               5                   10                  15

Ala Leu Glu Phe Ile Asp Asp Thr Val Ala Gln Gln Asn Gly Ile Met
            20                  25                  30

Arg Tyr Thr Leu Thr Thr Thr Lys Gly Ala Thr Ser Lys His Leu His
        35                  40                  45

Arg Arg Gln Asp Ser Ala Asp Leu Met Ser Gln Gln Thr Gly Tyr Phe
    50                  55                  60

Tyr Ser Ile Gln Leu Glu Ile Gly Thr Pro Pro Gln Ala Val Ser Val
65                  70                  75                  80

Asn Phe Asp Thr Gly Ser Ser Glu Leu Trp Val Asn Pro Val Cys Ser
                85                  90                  95

Lys Ala Thr Asp Pro Ala Phe Cys Lys Thr Phe Gly Gln Tyr Asn His
            100                 105                 110

Ser Thr Thr Phe Val Asp Ala Lys Ala Pro Gly Gly Ile Lys Tyr Gly
        115                 120                 125

Thr Gly Phe Val Asp Phe Asn Tyr Gly Tyr Asp Tyr Val Gln Leu Gly
    130                 135                 140

Ser Leu Arg Ile Asn Gln Gln Val Phe Gly Val Ala Thr Asp Ser Glu
145                 150                 155                 160

Phe Ala Ser Val Gly Ile Leu Gly Ala Gly Pro Asp Leu Ser Gly Trp
                165                 170                 175

Thr Ser Pro Tyr Pro Phe Val Ile Asp Asn Leu Val Lys Gln Gly Phe
            180                 185                 190

Ile Lys Ser Arg Ala Phe Ser Leu Asp Ile Arg Gly Leu Asp Ser Asp
        195                 200                 205
```

-continued

Arg Gly Ser Val Thr Tyr Gly Gly Ile Asp Ile Lys Lys Phe Ser Gly
    210             215             220

Pro Leu Ala Lys Lys Pro Ile Ile Pro Ala Ala Gln Ser Pro Asp Gly
225             230             235             240

Tyr Thr Arg Tyr Trp Val His Met Asp Gly Met Ser Ile Thr Lys Glu
                245             250             255

Asp Gly Ser Lys Phe Glu Ile Phe Asp Lys Pro Asn Gly Gln Pro Val
            260             265             270

Leu Leu Asp Ser Gly Tyr Thr Val Ser Thr Leu Pro Gly Pro Leu Met
        275             280             285

Asp Lys Ile Leu Glu Ala Phe Pro Ser Ala Arg Leu Glu Ser Thr Ser
    290             295             300

Gly Asp Tyr Ile Val Asp Cys Asp Ile Ile Asp Thr Pro Gly Arg Val
305             310             315             320

Asn Phe Lys Phe Gly Asn Val Val Asp Val Glu Tyr Lys Asp Phe
                325             330             335

Ile Trp Gln Gln Pro Asp Leu Gly Ile Cys Lys Leu Gly Val Ser Gln
                340             345             350

Asp Asp Asn Phe Pro Val Leu Gly Asp Thr Phe Leu Arg Ala Ala Tyr
            355             360             365

Val Val Phe Asp Trp Asp Asn Gln Glu Val His Ile Ala Ala Asn Glu
    370             375             380

Asp Cys Gly Asp Glu Leu Ile Pro Ile Gly Ser Gly Pro Asp Ala Ile
385             390             395             400

Pro Ala Ser Ala Ile Gly Lys Cys Ser Pro Ser Val Lys Thr Asp Thr
                405             410             415

Thr Thr Ser Val Ala Glu Thr Thr Ala Thr Ser Ala Ala Ala Ser Thr
            420             425             430

Ser Glu Leu Ala Ala Thr Thr Ser Glu Ala Ala Thr Thr Ser Ser Glu
        435             440             445

Ala Ala Thr Thr Ser Ala Ala Ala Glu Thr Thr Ser Val Pro Leu Asn
    450             455             460

Thr Ala Pro Ala Thr Thr Gly Leu Leu Pro Thr Thr Ser His Arg Phe
465             470             475             480

Ser Asn Gly Thr Ala Pro Tyr Pro Ile Pro Ser Leu Ser Ser Val Ala
                485             490             495

Ala Ala Ala Gly Ser Ser Thr Val Pro Ser Glu Ser Ser Thr Gly Ala
            500             505             510

Ala Ala Ala Gly Thr Thr Ser Ala Ala Thr Gly Ser Gly Ser Gly Ser
        515             520             525

Gly Ser Gly Asp Ala Thr Thr Ala Ser Ala Thr Tyr Thr Ser Thr Phe
    530             535             540

Thr Thr Thr Asn Val Tyr Thr Val Thr Ser Cys Pro Pro Ser Val Thr
545             550             555             560

Asn Cys Pro Val Gly His Val Thr Thr Glu Val Val Ala Tyr Thr
                565             570             575

Thr Trp Cys Pro Val Glu Asn Gly Pro His Pro Thr Ala Pro Pro Lys
            580             585             590

Pro Ala Ala Pro Glu Ile Thr Ala Thr Phe Thr Leu Pro Asn Thr Tyr
        595             600             605

Thr Cys Ser Gln Gly Lys Asn Thr Cys Ser Asn Pro Lys Thr Ala Pro
    610             615             620

```
Asn Val Ile Val Val Thr Pro Ile Val Thr Gln Thr Ala Pro Val Val
625                 630                 635                 640

Ile Pro Gly Ile Ala Ala Pro Thr Pro Thr Pro Ser Val Ala Ala Ser
            645                 650                 655

Ser Pro Ala Ser Pro Ser Val Val Pro Ser Pro Thr Ala Pro Val Ala
            660                 665                 670

Thr Ser Pro Ala Gln Ser Ala Tyr Tyr Pro Pro Pro Pro Pro Pro Glu
            675                 680                 685

His Ala Val Ser Thr Pro Val Ala Asn Pro Pro Ala Val Thr Pro Ala
            690                 695                 700

Pro Ala Pro Phe Pro Ser Gly Gly Leu Thr Thr Val Ile Ala Pro Gly
705                 710                 715                 720

Ser Thr Gly Val Pro Ser Gln Pro Ala Gln Ser Gly Leu Pro Pro Val
            725                 730                 735

Pro Ala Gly Ala Ala Gly Phe Arg Ala Pro Ala Ala Val Ala Leu Leu
            740                 745                 750

Ala Gly Ala Val Ala Ala Ala Leu Leu
            755                 760

<210> SEQ ID NO 136
<211> LENGTH: 439
<212> TYPE: PRT
<213> ORGANISM: Neurospora crassa

<400> SEQUENCE: 136

Met Val Ala Leu Thr Asn Leu Leu Thr Thr Leu Leu Ala Ser Ala
1               5                   10                  15

Gly Leu Gly Ala Ala Leu Pro Pro Arg Ile Gly Ser Thr Val Ile Glu
                20                  25                  30

Ala Arg Glu Pro Glu Leu Pro Val Ser Gly Arg Lys Ile Thr Leu Pro
            35                  40                  45

Gln Gln Lys Asn Pro Arg Phe His Lys Phe Asn Gly Ala Leu Ser Val
        50                  55                  60

Tyr Lys Thr Tyr Leu Lys Tyr Gly Ala Pro Val Pro Asp His Leu Val
65                  70                  75                  80

Gln Ala Val Ala Asn His Leu Gly Ile Ser Val Glu Glu Val His Asn
                85                  90                  95

Tyr Ala Asn Thr Thr Ala Asn Ala Arg Arg Asp Gln Gly Ser Ala Thr
            100                 105                 110

Ala Ala Pro Ile Asp Gln Ser Asp Ser Ala Tyr Ile Thr Pro Val Ser
        115                 120                 125

Ile Gly Thr Pro Ala Gln Thr Leu Asn Leu Asp Phe Asp Thr Gly Ser
130                 135                 140

Ser Asp Leu Trp Val Phe Ser Asn Ser Leu Pro Ser Ser Gln Arg Ala
145                 150                 155                 160

Gly His Thr Ile Tyr Asn Pro Ser Lys Ser Ser Thr Ala Lys Arg Val
                165                 170                 175

Asn Gly Ala Ser Trp Asp Ile Ser Tyr Gly Asp Gly Ser Ser Ser Lys
            180                 185                 190

Gly Gln Val Tyr Leu Asp Lys Val Thr Ile Gly Gly Leu Val Val Ser
        195                 200                 205

Asn Gln Ala Val Glu Thr Ala Gln Gln Val Ser Gln Ser Phe Thr Ala
    210                 215                 220

Glu Thr Ser Ile Asp Gly Leu Val Gly Leu Ala Phe Gly Ser Leu Asn
225                 230                 235                 240
```

```
Thr Val Arg Pro Arg Gln Gln Lys Thr Trp Phe Glu Asn Ala Ile Gly
                245                 250                 255

Gln Leu Asp Gln Pro Leu Phe Ala Ala Asp Leu Lys Tyr Glu Ala Ser
            260                 265                 270

Gly Thr Tyr Asp Phe Gly Phe Ile Asp Pro Ala Lys His Thr Gly Asp
        275                 280                 285

Ile Thr Tyr Val Pro Val Asn Thr Asn Pro Gly Tyr Trp Thr Trp Thr
    290                 295                 300

Ser Thr Gly Tyr Gln Val Gly Ser Ser Pro Phe Val Ser Gln Ser Ile
305                 310                 315                 320

Thr Asn Ile Ala Asp Thr Gly Thr Thr Leu Met Tyr Val Pro Asp Ser
                325                 330                 335

Ile Leu Arg Ala Tyr Tyr Gly Gln Ile Arg Gly Ala Thr Asn Ser Gln
            340                 345                 350

Ser Tyr Gly Gly Tyr Val Phe Pro Cys Ser Thr Glu Ala Pro Asp Phe
        355                 360                 365

Thr Phe Gly Val Thr Asp Glu Ala Thr Ile Thr Ile Pro Gly Arg Phe
    370                 375                 380

Ile Asn Tyr Gly Pro Val Thr Asp Asp Gly Glu Thr Cys Phe Gly Gly
385                 390                 395                 400

Leu Gln Thr Ser Ser Asp Val Gly Ile Asn Ile Phe Gly Asp Val Ala
                405                 410                 415

Leu Lys Ala Ala Tyr Val Val Phe Lys Gly Gly Asp Ser Pro Ser Leu
            420                 425                 430

Gly Trp Ala Ser Lys Gln Leu
        435

<210> SEQ ID NO 137
<211> LENGTH: 417
<212> TYPE: PRT
<213> ORGANISM: Myceliophthora thermophila

<400> SEQUENCE: 137

Met His Leu Thr Pro Ala Leu Ala Ala Thr Cys Ala Val Glu Val
1               5                   10                  15

Cys Ala Gly Val Leu Pro Arg Ser Ser Thr Pro Thr Thr Phe Gly
            20                  25                  30

Ser Gly Thr Leu Ser Leu Lys Gln Val Arg Asn Pro Asn Phe Val Arg
        35                  40                  45

Asn Gly Pro Val Gln Leu Ala Arg Ile Tyr His Lys Tyr Gly Val Pro
    50                  55                  60

Leu Pro His Asp Leu Arg Glu Ala Val Ala Arg Phe Arg Ala Glu Ile
65                  70                  75                  80

Arg Lys Arg Ser Asn Gly Ser Thr Glu Thr Asn Pro Glu Thr Asn Asp
                85                  90                  95

Val Glu Tyr Leu Thr Pro Val Ser Ile Gly Thr Pro Pro Gln Val Leu
            100                 105                 110

Asn Leu Asp Phe Asp Thr Gly Ser Ser Asp Leu Trp Val Phe Ser Ser
        115                 120                 125

Glu Thr Arg Ser Ser Asp Val Gln Gly Gln Thr Ile Tyr Asp Pro Asn
    130                 135                 140

Glu Ser Ser Thr Ala Gln Lys Leu Gln Gly Tyr Ser Trp Gln Ile Ser
145                 150                 155                 160

Tyr Gly Asp Gly Ser Ser Ser Ser Gly Asp Val Tyr Thr Asp Ala Val
```

```
                165                 170                 175
Thr Val Gly Gly Leu Thr Val Pro Ser Gln Ala Val Glu Val Ala Arg
            180                 185                 190

Arg Val Ser Asp Glu Phe Thr Ser Asp Pro Asn Asn Asp Gly Leu Leu
        195                 200                 205

Gly Leu Gly Phe Ser Ser Ile Asn Thr Val Gln Pro Val Pro Gln Lys
    210                 215                 220

Thr Phe Asp Asn Ala Lys Ala Asp Leu Asp Ala Pro Ile Phe Thr
225                 230                 235                 240

Ala Asp Leu Lys Ala Ser Ala Pro Gly Phe Asn Phe Gly Tyr Ile
                245                 250                 255

Asp His Gly Ala Tyr Thr Gly Glu Ile Thr Tyr Met Pro Val Asp Ser
            260                 265                 270

Ser Asp Gly Phe Trp Ala Trp Thr Ser Pro Gly Tyr Ala Val Gly Ser
        275                 280                 285

Gly Ser Phe Lys Arg Thr Thr Ile Gln Gly Ile Ala Asp Thr Gly Thr
    290                 295                 300

Ser Leu Phe Leu Leu Pro Ser Ser Val Val Ser Ala Tyr Tyr Gly Gln
305                 310                 315                 320

Ile Ser Gly Ala Lys Tyr Asp Ser Ile Gln Gly Gly Tyr Thr Leu Pro
                325                 330                 335

Cys Ser Gly Ser Val Pro Asp Phe Ala Phe Gly Ile Gly Asp Ser Asn
            340                 345                 350

Thr Thr Ile Ser Val Pro Gly Asp Tyr Val Arg Tyr Ala Ala Thr Asp
        355                 360                 365

Ser Ser Gly Ile Ile Cys Phe Gly Gly Ile Gln Ala Asn Thr Gly Ile
    370                 375                 380

Gly Phe Ser Ile Phe Gly Asp Val Ala Leu Lys Ala Ala Phe Val Val
385                 390                 395                 400

Phe Asp Gly Ala Lys Gln Gln Leu Gly Trp Ala Ser Lys Pro Leu Pro
                405                 410                 415

Ser

<210> SEQ ID NO 138
<211> LENGTH: 434
<212> TYPE: PRT
<213> ORGANISM: Neurospora crassa

<400> SEQUENCE: 138

Met Leu Leu Phe Pro Thr Ile Leu Thr Ala Ala Leu Ala Ala Thr Gly
1               5                   10                  15

Met Ala Ala Ala Ile Pro Ser Arg Asp Asp Thr Thr Ala Asn Lys Gly
            20                  25                  30

Thr Ala Ser Leu Leu Gln Val Arg Asn Pro Ser Phe Glu Phe Arg His
        35                  40                  45

Gly Pro Leu Ala Leu Ala Lys Ala Tyr Gln Lys Phe Gly Ala Pro Met
    50                  55                  60

Pro Glu Asp Leu Arg Ala Ala Ile Ala Arg Phe Arg Gln Asn Gln Lys
65                  70                  75                  80

Arg Thr Thr Gly Thr Ile Ala Thr Asp Pro Glu Lys His Asp Val Glu
                85                  90                  95

Tyr Leu Thr Pro Ile Ser Val Gly Thr Pro Ser Gln Asp Leu Val Val
            100                 105                 110

Asp Phe Asp Thr Gly Ser Ser Asp Leu Trp Val Phe Ser Thr Glu Met
```

```
                115                 120                 125
Ser Thr Ser Asp Ile Lys Gly Gln Thr Val Tyr Asp Pro Asn Asn Ser
    130                 135                 140

Ser Thr Ser Glu Lys Val Gln Gly Ser Thr Trp Lys Ile Thr Tyr Gly
145                 150                 155                 160

Asp Gly Ser Ser Ser Gly Asp Val Tyr Leu Asp Thr Val Thr Ile
                165                 170                 175

Gly Asn Leu Thr Val Pro Ser Gln Ala Val Glu Ala Lys Lys Val
            180                 185                 190

Ser Ser Glu Phe Thr Asp Asp Ser His Asn Asp Gly Leu Leu Gly Leu
                195                 200                 205

Gly Phe Ser Ala Ile Asn Ala Val Glu Pro Thr Pro Gln Asn Thr Phe
    210                 215                 220

Phe Asp Asn Ile Lys Gly Ser Leu Asp Ala Pro Leu Phe Thr Val Asp
225                 230                 235                 240

Leu Lys His Gly Thr Pro Gly Ser Phe Asn Phe Gly Tyr Ile Asp Pro
                245                 250                 255

Ala Ala Tyr Ile Gly Asn Ile Ser Trp Thr Pro Val Asp Ser Ser Gln
            260                 265                 270

Gly Tyr Trp Gly Phe Thr Ser Pro Gly Tyr Ala Val Gly Thr Gly Ala
        275                 280                 285

Phe Arg Asn His Ser Ile Ser Gly Ile Ala Asp Thr Gly Thr Thr Leu
    290                 295                 300

Leu Leu Leu Pro Lys Ser Val Val Ser Ala Tyr Tyr Lys Glu Ile Gln
305                 310                 315                 320

Gly Ala Gln Tyr Asp Ser Asp Gln Gly Tyr Ile Phe Pro Cys Ser
                325                 330                 335

Pro Thr Pro Pro Asp Phe Val Phe Gly Val Asn Lys Gly Ile Val Thr
                340                 345                 350

Val Pro Gly Asp Met Val Ser Tyr Ala Pro Ala Asp Ser Ala Asn Gln
                355                 360                 365

Asn Cys Phe Gly Gly Ile Gln Thr Asp Thr Gly Ile Gly Phe Ser Ile
    370                 375                 380

Phe Gly Asp Val Ala Leu Lys Thr Ser Phe Val His Leu His Gly Ser
385                 390                 395                 400

Ile Val Pro Gly Tyr Tyr Ala Asp Cys Ala Met Arg Phe Asn Arg Met
                405                 410                 415

Leu Arg Ser Tyr Ser Asn Asp Gln Leu Val Asp Phe Ser Ser Ser Gly
            420                 425                 430

Pro Leu

<210> SEQ ID NO 139
<211> LENGTH: 466
<212> TYPE: PRT
<213> ORGANISM: Myceliophthora thermophila

<400> SEQUENCE: 139

Met Asp Ala Leu Phe Glu Thr His Ala Lys Leu Arg Lys Arg Met Ala
1               5                   10                  15

Leu Tyr Arg Val Arg Ala Val Pro Asn Gln Asn Tyr Gln Arg Asp Gly
            20                  25                  30

Thr Lys Ser Tyr Val Ser Val Leu Asn Arg Phe Gly Phe Gln Pro Thr
        35                  40                  45

Lys Pro Gly Pro Tyr Phe Gln Ile Phe Glu Glu Ser Glu Glu Ala Pro
```

```
            50                  55                  60
Ser Met Ser Ala Ala Pro Gly Val Lys Pro Gly His Val Trp Gln Gly
 65                  70                  75                  80

Leu Phe Lys Lys Leu Lys Asp Gln Glu Glu Pro Gly Glu Val Thr Ala
                 85                  90                  95

Glu Asp Gln Gln Asn Asp Ser Glu Tyr Leu Cys Glu Val Met Ile Gly
                100                 105                 110

Thr Ala Trp Thr Ala Glu Arg Gln Ile Val Lys Met Asp Phe Asp Thr
                115                 120                 125

Gly Leu Ala Asp Phe Trp Val Ser Gln Lys Ser Phe Asp Pro Lys Lys
            130                 135                 140

Ser Val Thr Trp Gln Leu Ala Lys Asp Lys Ser Trp Lys Val Gln Tyr
145                 150                 155                 160

Gly Asp Gly Ser Ser Ala Ser Gly Ile Val Gly His Asp Ile Leu Ile
                165                 170                 175

Ile Gly Gly Ile Gln Ile Lys Arg Gln Ala Ile Glu Ile Ala Thr Glu
            180                 185                 190

Met Ser Ala Gln Phe Ser Glu Gly Thr Met Asp Gly Ile Leu Gly Leu
            195                 200                 205

Ala Phe Ser Lys Leu Asn Thr Val Gln Thr Asp Gly Lys Pro Asp Pro
            210                 215                 220

Gln Arg Thr Val Val Asp Asn Met Met Ala Gln Asp Ile Pro Pro
225                 230                 235                 240

Glu Ala Glu Leu Phe Ser Thr Ala Leu Tyr Ser Asn Arg Glu Asp Asp
                245                 250                 255

Gln Arg Ser Phe Tyr Thr Phe Gly Trp Ile Asp Glu Asp Leu Val Lys
            260                 265                 270

Ala Ser Gly Glu Glu Ile Val Trp Thr Asp Val Asp Asn Ser Glu Gly
            275                 280                 285

Phe Trp Met Phe Ser Ser Glu His Val Thr Ile Asp Gly Gln Gln Val
            290                 295                 300

Arg Ile Glu Gly Asn Lys Ala Ile Ala Asp Thr Gly Thr Ser Leu Val
305                 310                 315                 320

Leu Val Ser Asp Gln Val Cys Asp Ala Leu Tyr Ala His Ile Pro Ser
                325                 330                 335

Ala Glu Tyr Ser Glu Glu Tyr Gln Gly Trp Thr Phe Pro Gln Glu Thr
                340                 345                 350

Glu Val Asp Lys Leu Pro Glu Phe Ser Ile Ala Ile Gly Asp Lys Glu
            355                 360                 365

Phe Val Leu Gln Lys Glu Asp Leu Ile Phe Ala Pro Ala Asp Glu Arg
370                 375                 380

Val Phe Tyr Gly Ser Val Gln Ser Arg Gly Glu Asn Pro Phe Asp Ile
385                 390                 395                 400

Leu Gly Ile Ala Phe Leu Lys Ser Ile Tyr Ala Ile Trp Asp Gln Gly
            405                 410                 415

His Lys Arg Phe Gly Ala Val Pro Lys Met Glu Ala Phe Val Pro Pro
            420                 425                 430

Thr Lys Tyr Asp Arg Pro Arg Leu Thr Asp Gln Asp Arg Lys Asp Leu
            435                 440                 445

Gly Val Thr Ile Gly Tyr Gly Asp Ile Ser Ser Thr Phe Phe Glu Lys
            450                 455                 460

Arg Ala
465
```

<210> SEQ ID NO 140
<211> LENGTH: 481
<212> TYPE: PRT
<213> ORGANISM: Neurospora crassa

<400> SEQUENCE: 140

| | | | | | | | | | | | | | | |
|---|---|---|---|---|---|---|---|---|---|---|---|---|---|---|
| Met | Gly | Ser | Met | Tyr | Gln | Val | Gln | Ser | Lys | Leu | Arg | Gln | Asp | Leu | Gly |
| 1 | | | | 5 | | | | | 10 | | | | | 15 | |
| Leu | His | Lys | Val | Gln | Ala | Val | Arg | Lys | Pro | Gly | Arg | Glu | Leu | Asn | Gly |
| | | | 20 | | | | | 25 | | | | | 30 | | |
| Thr | Lys | Ala | Tyr | Val | Ser | Ala | Met | Ala | Arg | Tyr | Gly | Phe | Asn | Pro | Thr |
| | | 35 | | | | | 40 | | | | | 45 | | | |
| Glu | Glu | Ser | Arg | Phe | Phe | His | Leu | Lys | Lys | Thr | Asp | Leu | Thr | Lys | Glu |
| | 50 | | | | | 55 | | | | | 60 | | | | |
| Phe | Gln | Arg | Arg | Gly | Tyr | Ile | Arg | His | Trp | Glu | Gln | Leu | Val | Arg | Thr |
| 65 | | | | | 70 | | | | | 75 | | | | | 80 |
| Pro | Gln | Glu | Arg | Pro | Asp | Asp | Pro | His | Thr | Asp | Asn | Glu | Pro | Val | Pro |
| | | | | 85 | | | | | 90 | | | | | 95 | |
| Ala | Glu | Asp | Gln | Gln | Tyr | Asp | Thr | Gln | Tyr | Leu | Cys | Glu | Ile | Gly | Ile |
| | | | 100 | | | | | 105 | | | | | 110 | | |
| Gly | Thr | Pro | Gln | Gln | Lys | Val | Lys | Leu | Asp | Phe | Asp | Thr | Gly | Ser | Ala |
| | | 115 | | | | | 120 | | | | | 125 | | | |
| Asp | Leu | Trp | Val | Arg | Cys | Thr | Asp | Ser | Ser | Leu | Leu | His | His | Ala | Asp |
| | 130 | | | | | 135 | | | | | 140 | | | | |
| Lys | Lys | Phe | Asp | Pro | Lys | Lys | Ser | Asp | Thr | Phe | Gln | Glu | Ser | Lys | Thr |
| 145 | | | | | 150 | | | | | 155 | | | | | 160 |
| Asp | Gln | Thr | Trp | Lys | Ile | Gln | Tyr | Gly | Asp | Gly | Ser | Thr | Ala | Ser | Gly |
| | | | | 165 | | | | | 170 | | | | | 175 | |
| Thr | Val | Gly | Thr | Asp | Val | Ile | Thr | Val | Gly | Gly | Leu | Gln | Ile | Lys | Asn |
| | | | 180 | | | | | 185 | | | | | 190 | | |
| Gln | Ala | Ile | Glu | Leu | Ala | Lys | Lys | Val | Ser | Ser | Ala | Phe | Ser | Ser | Gly |
| | | 195 | | | | | 200 | | | | | 205 | | | |
| Glu | Ala | Asp | Gly | Leu | Leu | Gly | Leu | Ala | Phe | Ser | Thr | Ile | Asn | Thr | Ile |
| | 210 | | | | | 215 | | | | | 220 | | | | |
| Glu | Ser | Asp | Gly | Lys | Pro | Asp | Pro | Gln | Pro | Thr | Pro | Val | Glu | Asn | Met |
| 225 | | | | | 230 | | | | | 235 | | | | | 240 |
| Ile | Ser | Gln | Glu | Asp | Ile | Pro | Lys | Glu | Ala | Glu | Leu | Phe | Thr | Ser | Ala |
| | | | | 245 | | | | | 250 | | | | | 255 | |
| Phe | Tyr | Ser | Ala | Arg | Asp | Asp | Lys | Ser | Glu | Glu | Lys | Ser | Phe | Tyr | Thr |
| | | | 260 | | | | | 265 | | | | | 270 | | |
| Phe | Gly | Trp | Val | Asp | Glu | Asp | Leu | Val | Lys | Ala | Ser | Gly | Lys | Asp | Ile |
| | | 275 | | | | | 280 | | | | | 285 | | | |
| Thr | Trp | Thr | Pro | Ile | Asp | Asn | Ser | Glu | Gly | Phe | Trp | Lys | Phe | Pro | Ser |
| | 290 | | | | | 295 | | | | | 300 | | | | |
| Glu | Ser | Ala | Thr | Val | Asp | Gly | Asp | Asn | Val | Ser | Val | Ser | Gly | Asn | Thr |
| 305 | | | | | 310 | | | | | 315 | | | | | 320 |
| Ala | Ile | Ala | Asp | Thr | Gly | Thr | Thr | Leu | Ala | Leu | Val | Ser | Asp | Thr | Val |
| | | | | 325 | | | | | 330 | | | | | 335 | |
| Cys | Lys | Ala | Leu | Tyr | Ala | Lys | Ile | Pro | Gly | Ser | Lys | Tyr | Ser | Tyr | Arg |
| | | | 340 | | | | | 345 | | | | | 350 | | |
| Tyr | Gln | Gly | Tyr | Leu | Ile | Pro | Ser | Thr | Ile | Thr | Ala | Asp | Gln | Leu | Pro |
| | | 355 | | | | | 360 | | | | | 365 | | | |
| Gln | Leu | Ser | Val | Ala | Val | Gly | Gly | Glu | Gln | Phe | Val | Ile | Gln | Asn | Glu |

```
               370                 375                 380
Asp Leu Leu Leu Ala Pro Ala Asp Asp His Trp Tyr Gly Gly Val
385                 390                 395                 400

Gln Ser Arg Gly Thr Met Pro Phe Asp Ile Leu Gly Asp Thr Phe Leu
                405                 410                 415

Lys Ser Ile Tyr Ala Ile Trp Asp Gln Gly Asn Asn Arg Phe Gly Ala
                420                 425                 430

Val Pro Lys Ile Glu Val Asn Gln His Thr Val Phe Pro Asp Thr Glu
            435                 440                 445

Pro Ser Pro Glu Ala Ser Ser Pro Glu Pro Ala Asp Lys Val Gly Asp
    450                 455                 460

Val Ser Pro Val Glu Gln Val Lys Gly Ala Val Lys Ser Leu Lys Val
465                 470                 475                 480

Leu
```

<210> SEQ ID NO 141
<211> LENGTH: 397
<212> TYPE: PRT
<213> ORGANISM: Myceliophthora thermophila

<400> SEQUENCE: 141

```
Met Lys Asp Ala Phe Leu Leu Thr Ala Ala Val Leu Leu Gly Ser Ala
1               5                   10                  15

Gln Gly Ala Val His Lys Met Lys Leu Gln Lys Ile Pro Leu Ser Glu
                20                  25                  30

Gln Leu Glu Ala Val Pro Ile Asn Thr Gln Leu Glu His Leu Gly Gln
            35                  40                  45

Lys Tyr Met Gly Leu Arg Pro Arg Glu Ser Gln Ala Asp Ala Ile Phe
    50                  55                  60

Lys Gly Met Val Ala Asp Val Lys Gly Asn His Pro Ile Pro Ile Ser
65                  70                  75                  80

Asn Phe Met Asn Ala Gln Tyr Phe Ser Glu Ile Thr Ile Gly Thr Pro
                85                  90                  95

Pro Gln Ser Phe Lys Val Val Leu Asp Thr Gly Ser Ser Asn Leu Trp
                100                 105                 110

Val Pro Ser Val Glu Cys Gly Ser Ile Ala Cys Tyr Leu His Ser Lys
            115                 120                 125

Tyr Asp Ser Ser Ala Ser Ser Thr Tyr Lys Lys Asn Gly Thr Ser Phe
    130                 135                 140

Glu Ile Arg Tyr Gly Ser Gly Ser Leu Ser Gly Phe Val Ser Gln Asp
145                 150                 155                 160

Thr Val Ser Ile Gly Asp Ile Thr Ile Gln Gly Gln Asp Phe Ala Glu
                165                 170                 175

Ala Thr Ser Glu Pro Gly Leu Ala Phe Ala Phe Gly Arg Phe Asp Gly
                180                 185                 190

Ile Leu Gly Leu Gly Tyr Asp Arg Ile Ser Val Asn Gly Ile Val Pro
            195                 200                 205

Pro Phe Tyr Lys Met Val Glu Gln Lys Leu Ile Asp Glu Pro Val Phe
    210                 215                 220

Ala Phe Tyr Leu Ala Asp Thr Asn Gly Gln Ser Glu Val Val Phe Gly
225                 230                 235                 240

Gly Val Asp His Asp Lys Tyr Lys Gly Lys Ile Thr Thr Ile Pro Leu
                245                 250                 255

Arg Arg Lys Ala Tyr Trp Glu Val Asp Phe Asp Ala Ile Ser Tyr Gly
```

```
            260                 265                 270
Asp Asp Thr Ala Glu Leu Glu Asn Thr Gly Ile Ile Leu Asp Thr Gly
            275                 280                 285

Thr Ser Leu Ile Ala Leu Pro Ser Gln Leu Ala Glu Met Leu Asn Ala
            290                 295                 300

Gln Ile Gly Ala Lys Lys Ser Tyr Thr Gly Gln Tyr Thr Ile Asp Cys
305                 310                 315                 320

Asn Lys Arg Asp Ser Leu Lys Asp Val Thr Phe Asn Leu Ala Gly Tyr
                325                 330                 335

Asn Phe Thr Leu Gly Pro Tyr Asp Tyr Val Leu Glu Val Gln Gly Ser
            340                 345                 350

Cys Ile Ser Thr Phe Met Gly Met Asp Phe Pro Ala Pro Thr Gly Pro
            355                 360                 365

Leu Ala Ile Leu Gly Asp Ala Phe Leu Arg Arg Tyr Tyr Ser Ile Tyr
            370                 375                 380

Asp Leu Gly Ala Asp Thr Val Gly Leu Ala Glu Ala Lys
385                 390                 395

<210> SEQ ID NO 142
<211> LENGTH: 396
<212> TYPE: PRT
<213> ORGANISM: Neurospora crassa

<400> SEQUENCE: 142

Met Lys Gly Ala Leu Leu Thr Ala Ala Met Leu Leu Gly Ser Ala Gln
1               5                   10                  15

Ala Gly Val His Thr Met Lys Leu Lys Lys Val Pro Leu Ala Glu Gln
            20                  25                  30

Leu Glu Ser Val Pro Ile Asp Val Gln Val Gln His Leu Gly Gln Lys
        35                  40                  45

Tyr Thr Gly Leu Arg Thr Glu Ser His Thr Gln Ala Met Phe Lys Ala
50                  55                  60

Thr Asp Ala Gln Val Ser Gly Asn His Pro Val Pro Ile Thr Asn Phe
65                  70                  75                  80

Met Asn Ala Gln Tyr Phe Ser Glu Ile Thr Ile Gly Thr Pro Pro Gln
                85                  90                  95

Thr Phe Lys Val Val Leu Asp Thr Gly Ser Ser Asn Leu Trp Val Pro
            100                 105                 110

Ser Ser Gln Cys Gly Ser Ile Ala Cys Tyr Leu His Asn Lys Tyr Glu
        115                 120                 125

Ser Ser Glu Ser Ser Thr Tyr Lys Lys Asn Gly Thr Ser Phe Lys Ile
    130                 135                 140

Glu Tyr Gly Ser Gly Ser Leu Ser Gly Phe Val Ser Gln Asp Arg Met
145                 150                 155                 160

Thr Ile Gly Asp Ile Thr Ile Asn Asp Gln Leu Phe Ala Glu Ala Thr
                165                 170                 175

Ser Glu Pro Gly Leu Ala Phe Ala Phe Gly Arg Phe Asp Gly Ile Leu
            180                 185                 190

Gly Leu Gly Tyr Asp Arg Ile Ala Val Asn Gly Ile Thr Pro Pro Phe
        195                 200                 205

Tyr Lys Met Val Glu Gln Lys Leu Val Asp Glu Pro Val Phe Ser Phe
    210                 215                 220

Tyr Leu Ala Asp Gln Asp Gly Glu Ser Glu Val Val Phe Gly Gly Val
225                 230                 235                 240
```

```
Asn Lys Asp Arg Tyr Thr Gly Lys Ile Thr Thr Ile Pro Leu Arg Arg
                245                 250                 255

Lys Ala Tyr Trp Glu Val Asp Phe Asp Ala Ile Gly Tyr Gly Lys Asp
            260                 265                 270

Phe Ala Glu Leu Glu Gly His Gly Val Ile Leu Asp Thr Gly Thr Ser
            275                 280                 285

Leu Ile Ala Leu Pro Ser Gln Leu Ala Glu Met Leu Asn Ala Gln Ile
        290                 295                 300

Gly Ala Lys Lys Ser Trp Asn Gly Gln Phe Thr Ile Asp Cys Gly Lys
305                 310                 315                 320

Lys Ser Ser Leu Glu Asp Val Thr Phe Thr Leu Ala Gly Tyr Asn Phe
                325                 330                 335

Thr Leu Gly Pro Glu Asp Tyr Ile Leu Glu Ala Ser Gly Ser Cys Leu
            340                 345                 350

Ser Thr Phe Met Gly Met Asp Met Pro Ala Pro Val Gly Pro Leu Ala
            355                 360                 365

Ile Leu Gly Asp Ala Phe Leu Arg Lys Tyr Tyr Ser Ile Tyr Asp Leu
        370                 375                 380

Gly Ala Asp Thr Val Gly Ile Ala Thr Ala Lys Arg
385                 390                 395

<210> SEQ ID NO 143
<211> LENGTH: 454
<212> TYPE: PRT
<213> ORGANISM: Myceliophthora thermophila

<400> SEQUENCE: 143

Met Lys Phe Ala Ala Leu Ala Leu Ala Ala Ser Leu Val Ala Ala
1               5                   10                  15

Pro Arg Val Val Lys Val Asp Pro Ser Asp Ile Lys Pro Arg Arg Leu
            20                  25                  30

Gly Gly Thr Lys Phe Lys Leu Gly Gln Ile His Asn Asp Leu Phe Arg
        35                  40                  45

Gln His Gly Arg Gly Pro Arg Ala Leu Ala Lys Ala Tyr Glu Lys Tyr
    50                  55                  60

Asn Ile Glu Leu Pro Pro Asn Leu Leu Glu Val Val Gln Arg Ile Leu
65                  70                  75                  80

Lys Asp Leu Gly Ile Glu Pro His Ser Lys Lys Ile Pro Gly Ser Lys
                85                  90                  95

Ser Ser Tyr Gly Asn Gly Ala Pro Tyr Thr Asn Glu Thr Asp Asp Ser
            100                 105                 110

Gly Glu Val Ser Ala Ile Pro Gln Leu Phe Asp Val Glu Tyr Leu Ala
        115                 120                 125

Pro Val Gln Ile Gly Thr Pro Pro Gln Thr Leu Met Leu Asn Phe Asp
    130                 135                 140

Thr Gly Ser Ser Asp Leu Trp Val Phe Ser Ser Glu Thr Pro Ser Arg
145                 150                 155                 160

Gln Gln Asn Gly Gln Lys Ile Tyr Lys Ile Glu Ser Ser Thr Ala
                165                 170                 175

Arg Arg Leu Ser Asn His Thr Trp Ser Ile Gln Tyr Gly Asp Gly Ser
            180                 185                 190

Arg Ser Ala Gly Asn Val Tyr Leu Asp Thr Val Ser Val Gly Gly Val
        195                 200                 205

Asn Val Phe Asn Gln Ala Val Glu Ser Ala Thr Phe Val Ser Ser Ser
    210                 215                 220
```

```
Phe Val Thr Asp Ala Ala Ser Ser Gly Leu Leu Gly Leu Gly Phe Asp
225                 230                 235                 240

Ser Ile Asn Thr Val Lys Pro Thr Lys Gln Lys Thr Phe Ile Ser Asn
                245                 250                 255

Ala Leu Glu Ser Leu Glu Met Gly Leu Phe Thr Ala Asn Leu Lys Lys
            260                 265                 270

Ala Glu Pro Gly Asn Tyr Asn Phe Gly Phe Ile Asp Glu Thr Glu Phe
        275                 280                 285

Val Gly Pro Leu Ser Phe Ile Asp Val Asp Ser Thr Asp Gly Phe Trp
    290                 295                 300

Gln Phe Asp Ala Thr Gly Tyr Ser Ile Gln Leu Pro Glu Pro Ser Gly
305                 310                 315                 320

Asn Ile Thr Gly Thr Pro Phe Arg Ala Val Ala His Thr Ala Ile Ala
                325                 330                 335

Asp Thr Gly Thr Thr Leu Leu Leu Leu Pro Pro Gly Ile Ala Gln Ala
            340                 345                 350

Tyr Tyr Trp Gln Val Gln Gly Ala Arg Gln Ala Pro Glu Val Gly Gly
        355                 360                 365

Trp Val Met Pro Cys Asn Ala Ser Met Pro Asp Leu Thr Leu His Ile
    370                 375                 380

Gly Thr Tyr Lys Ala Val Ile Pro Gly Glu Leu Ile Pro Tyr Ala Pro
385                 390                 395                 400

Val Asp Thr Asp Asp Met Asp Thr Ala Thr Val Cys Tyr Gly Gly Ile
                405                 410                 415

Gln Ser Ala Ser Gly Met Pro Phe Ala Ile Tyr Gly Asp Ile Phe Phe
            420                 425                 430

Lys Ala Gln Phe Thr Val Phe Asp Val Glu Asn Leu Lys Leu Gly Phe
        435                 440                 445

Ala Pro Lys Pro Glu Leu
    450

<210> SEQ ID NO 144
<211> LENGTH: 489
<212> TYPE: PRT
<213> ORGANISM: Myceliophthora thermophila

<400> SEQUENCE: 144

Met Ala Ile Pro Val Leu Phe Ser Ala Leu Val Leu Val Ala Leu
1               5                   10                  15

Leu Cys Cys His Ala Thr Ala Leu Gln Gln Leu Ala His Asp Val
            20                  25                  30

Gly Cys Val His Leu Pro Val Val His Ser Thr Lys Val Asp Arg Phe
        35                  40                  45

Ser Asp Lys Arg Gly Ile Gln Leu Gln Leu Ala Asn Arg Ser Asp Val
    50                  55                  60

Ala Tyr Tyr Ala Gln Leu Ser Ile Gly Thr Pro Pro Gln Pro Val Phe
65                  70                  75                  80

Val Gln Leu Asp Thr Gly Ser Phe Glu Leu Trp Val Asn Pro Asp Cys
                85                  90                  95

Thr Thr Val Ser Gly Ser Asp Ala Val Phe Cys Glu Arg Ala Gly Arg
            100                 105                 110

Tyr Asp Val Thr Lys Ser Ser Thr Ala Thr Ser Leu Gly Thr Asn Arg
        115                 120                 125

Thr Leu Arg Tyr Gly Ile Gly Ala Ala Asn Ile Ser Tyr Phe Thr Asp
```

```
                    130                 135                 140
Thr Ile Ser Leu Ala Gly Ser Pro Met Met Leu Gln Asp Val Gln Phe
145                 150                 155                 160

Gly Val Ala Thr Ala Ser Glu Asp Ala Phe Ser Gly Ile Leu Gly Ile
                165                 170                 175

Gly Tyr Gly Lys Gly Ile Gly Thr Gly Tyr Pro Asn Phe Val Asp Gln
            180                 185                 190

Leu Trp Glu Gln Asn Val Thr Arg Val Lys Ala Tyr Thr Leu Ala Leu
        195                 200                 205

Gly Ser Lys Asp Ser Gln Glu Gly Val Ile Val Phe Gly Gly Val Asp
    210                 215                 220

Thr Ser Lys Phe Ala Gly Lys Leu Ala Arg Leu Pro Val Ile Pro Pro
225                 230                 235                 240

Ala Gln Ser Pro Asp Gly Val Pro Arg Phe Trp Val Glu Met Lys Ser
                245                 250                 255

Leu Ser Ile Thr Arg Pro Ser Gly Leu Asn Thr Val Tyr Asp Gly Gly
            260                 265                 270

Ala Met Pro Val Phe Leu Asp Ser Gly Ser Thr Met Thr Leu Leu Pro
        275                 280                 285

Ala Asn Leu Thr Met Ala Val Ala Arg Asp Phe Gly Ala Gln Ala Pro
    290                 295                 300

Asp Ala Asn Gly Phe Tyr Lys Ile Asp Cys Ala Leu Thr Ala Leu Asn
305                 310                 315                 320

Gly Thr Leu Asp Phe Ala Phe Asp Gly Val Thr Val Arg Val Pro Tyr
                325                 330                 335

Lys Glu Leu Thr Arg Glu Val Ala Ser Asn Pro Ser Cys Phe Leu
            340                 345                 350

Gly Ile Val Ala Ser Asp Arg Phe Thr Leu Leu Gly Asp Thr Phe Leu
        355                 360                 365

Arg Ser Ala Tyr Thr Val Phe Asp Leu Glu Thr Asp Ser Ile Trp Met
    370                 375                 380

Ala Pro Ala Val Asn Cys Gly Ser Ser Pro Ala Ala Leu Ser Asn Val
385                 390                 395                 400

Gln Asp Leu Ser Ala Val Thr Gly Glu Cys Gly Val Arg Glu Ile Ala
                405                 410                 415

Glu Ser Thr Ser Ser Thr Gln Val Pro Ser Thr Gly Val Asp Asp Thr
            420                 425                 430

Glu Ala Gly Ala Val Pro Thr Ser Thr Thr Val Val Ser Gln Pro
        435                 440                 445

Ser Gly Thr Thr Thr Gln Met Gly Ala Arg Pro Thr Leu Asp Asn Ala
    450                 455                 460

Ser Asn Pro Leu Gly Ala His Arg Leu Thr Trp Val Leu Val Ile Thr
465                 470                 475                 480

Ala Ala Leu His Leu Phe Thr Gly Ile
                485

<210> SEQ ID NO 145
<211> LENGTH: 518
<212> TYPE: PRT
<213> ORGANISM: Neurospora crassa

<400> SEQUENCE: 145

Met Ala Ala Phe Pro Phe Leu Ser Ala Ser Phe Val Leu Leu Gln Leu
1               5                   10                  15
```

```
Ala Leu Thr Cys Leu Ala Gln His Leu Asn Leu Thr Thr Gly Pro Leu
                20                  25                  30

His Leu Thr Gly His Thr Pro Gly Asp Gly Cys Val His Leu Pro Ile
        35                  40                  45

Ile His Ser Thr Asn Thr Asp His Phe Ala Arg Arg Gly Ile Gln Leu
50                  55                  60

Ala Leu Asn Asn Arg Ser Asp Val Ala Tyr Tyr Ala Gln Leu Glu Ile
65                  70                  75                  80

Gly Thr Pro Pro Gln Thr Val Tyr Thr Gln Leu Asp Thr Gly Ser Phe
                85                  90                  95

Glu Leu Trp Val Asn Pro Asp Cys Thr Val Ser Pro Ser Asp Ser
            100                 105                 110

Ser Phe Cys Asp His Ile Gly Phe Tyr Asn Ala Ser Leu Ser Ser Thr
        115                 120                 125

Ser Lys Ser Leu Gly Thr Ser Lys Thr Leu Arg Tyr Gly Ile Gly Ala
        130                 135                 140

Ala Asn Ile Ser Tyr Val Thr Asp Thr Ile Ser Leu Ser Gly Ser Ser
145                 150                 155                 160

Thr Ser Leu Lys Asp Ile Gln Phe Gly Val Ala Thr Ser Ser Lys Asp
                165                 170                 175

Ala Phe Ser Gly Ile Leu Gly Ile Gly Tyr Gly Gln Gly Leu Ala Thr
            180                 185                 190

Lys Tyr Pro Asn Phe Ile Asp Gln Leu Tyr Ala Gln Lys Ile Thr Lys
        195                 200                 205

Val Lys Ala Tyr Thr Leu Ala Leu Gly Ser Lys Thr Ala Gln Gln Gly
    210                 215                 220

Ser Ile Val Phe Gly Gly Val Asp Thr Ser Lys Phe Ala Gly Pro Leu
225                 230                 235                 240

Gly Arg Leu Pro Ile Ile Pro Ala Glu Asp Ser Pro Asp Gly Val Pro
                245                 250                 255

Arg Phe Trp Val Gln Met Asn Gly Ile Ser Leu Thr Pro Pro Ser Gly
            260                 265                 270

Gln Ser Met Gly Val Tyr Glu Gly Ser Lys Ile Pro Ala Phe Leu Asp
        275                 280                 285

Ser Gly Ser Thr Met Thr Ile Leu Pro Pro Ala Leu Ala Asn Lys Ile
    290                 295                 300

Ala Glu Asp Phe Gly Ser Pro Glu Met Asp Ala Asn Gly Phe Tyr Arg
305                 310                 315                 320

Val Gly Cys Gly Tyr Val Glu Met Asn Gly Thr Met Asp Phe Glu Phe
                325                 330                 335

Val Gly Ala Gly Gln Lys Val Thr Val Arg Val Pro Tyr Lys Glu Met
            340                 345                 350

Ile Arg Glu Val Gly Gln Gly Glu Ser Lys Met Cys Phe Leu Gly Ile
        355                 360                 365

Met Gly Ser Glu Ser Phe Thr Leu Leu Gly Asp Thr Phe Leu Arg Ser
    370                 375                 380

Ala Tyr Ala Thr Ser Cys Gly Asn Thr Pro Ala Ala Leu Arg Asp Val
385                 390                 395                 400

Thr Asp Leu Ser Arg Val Gly Asn Cys Gln Ile Gln Leu Gly Glu
                405                 410                 415

Lys Glu Ala Val Val Asp Val Val Ser Glu Thr Ser Ile Ala Pro Pro
            420                 425                 430

Thr Gly Ser Thr Gly Asp Thr Asp Gly Val Thr Gly Thr Gly Gly Asn
```

```
                435                 440                 445
Gly Ser Gly Asn Gly Gly Thr Arg Thr Ala Trp Gly Phe Val Thr Thr
450                 455                 460

Thr Leu Ala Val Pro Met Ala Thr Gly Leu Ala Gly Val Gly Gly Ser
465                 470                 475                 480

Gly Ser Gly Ser Met Ser Ala Thr Ala Leu Asp Ser Gly Arg Ser
                485                 490                 495

Met Ala Gly Asp Val Val Leu Ser Ala Ala Val Ala Gly Ala Ala
                500                 505                 510

Val Leu Gly Ser Leu Leu
            515

<210> SEQ ID NO 146
<211> LENGTH: 501
<212> TYPE: PRT
<213> ORGANISM: Myceliophthora thermophila

<400> SEQUENCE: 146

Met Arg Gly Tyr Ala Ala Val Ala Phe Gly Ala Ile Leu Ala Gly Ala
1               5                   10                  15

Val His Ala Ser Ala Gly Asn Gly Val Val Gln Trp Asp Ile Arg Arg
                20                  25                  30

Thr Gln Arg Gln Glu Leu Gln Arg Leu Asn Arg Arg Leu Arg Lys
                35                  40                  45

Arg Ala Asn Pro Val Leu Glu Val Ile Thr Asn Glu Lys Ile Arg Gly
            50                  55                  60

Gly Tyr Phe Ala Thr Cys Lys Ile Gly Thr Pro Gly Gln Asp Leu Thr
65                  70                  75                  80

Leu Gln Leu Asp Thr Gly Ser Ser Asp Ile Trp Val Pro Asp Ser Ala
                85                  90                  95

Ala Gln Val Cys Arg Glu Ile Gly Thr Glu Gly Cys Ala Leu Gly Thr
                100                 105                 110

Phe Asn Pro Asn Arg Ser Ser Ser Phe Glu Val Ile Gly Glu Gly Gln
            115                 120                 125

Phe Asp Ile Glu Tyr Val Asp Gly Ser Ser Ser Lys Gly Asp Tyr Phe
            130                 135                 140

Thr Asp Val Phe Gln Ile Gly Asp Ile Ser Val Gln Asn Met Thr Met
145                 150                 155                 160

Gly Leu Gly Leu His Thr Asp Ile Ala Tyr Gly Leu Val Gly Val Gly
                165                 170                 175

Tyr Ala Ile Asn Glu Ala Ile Val Ala Thr Thr Gln Ser Arg Asp Ser
                180                 185                 190

Val Tyr Pro Asn Leu Pro Val Gln Met Val Asp Gln Gly Leu Ile Asn
            195                 200                 205

Thr Val Ala Tyr Ser Leu Trp Leu Asn Asp Leu Asp Ala Ser Ser Gly
210                 215                 220

Ser Ile Leu Phe Gly Gly Ile Asp Thr Glu Lys Tyr Gln Gly Glu Leu
225                 230                 235                 240

Thr Arg Ile Asp Ile Tyr Pro Thr Ser Gln Gly Asp Phe Ser Ser Phe
                245                 250                 255

Val Val Ala Leu Thr Ser Leu Glu Ala Arg Ser Pro Ser Gly Gln Asp
            260                 265                 270

Thr Leu Thr Ser Gln Glu Phe Pro Ile Pro Val Val Leu Asp Ser Gly
            275                 280                 285
```

```
Thr Thr Leu Ser Tyr Leu Pro Thr Asp Leu Ala Thr Gln Ala Trp Lys
    290                 295                 300

Glu Val Gly Ala Phe Tyr Leu Pro Glu Val Gly Ala Val Leu Pro
305                 310                 315                 320

Cys Asp Met Glu Asn Ser Lys Gly Ser Phe Ser Phe Gly Phe Ala Gly
                    325                 330                 335

Pro Asp Gly Pro Arg Ile Thr Val Gly Met Asp Glu Leu Val Leu Asp
                340                 345                 350

Met Thr Asp Gly Gln Ala Pro Gln Phe Leu Ser Gly Pro Tyr Lys Gly
                355                 360                 365

Arg Asp Val Cys Gln Phe Gly Ile Gln Asn Phe Thr Ser Ala Pro Phe
            370                 375                 380

Leu Leu Gly Asp Thr Phe Leu Arg Ser Ala Tyr Val Val Tyr Asp Leu
385                 390                 395                 400

Val Asn Asn Gln Ile Gly Ile Ala Ala Thr Asp Phe Asn Ser Thr Asp
                    405                 410                 415

Ser Asn Ile Val Pro Phe Pro Ser Met Gly Ala Pro Ile Pro Ser Ala
                420                 425                 430

Thr Val Ala Ala Asn Gln Arg Glu Val Thr Arg Val Pro Thr Val Thr
                435                 440                 445

Glu Pro Ala Tyr Ser Ala Ser Gln Gly Phe Met Glu Ser Ala Ser Gly
450                 455                 460

Glu Glu Ser Leu Ala Pro Gly Met Pro Ala Ala Trp Gly Met Gly Gln
465                 470                 475                 480

Leu Leu Val Val Gly Val Thr Met Ala Leu Thr Ala Leu Gly Ser Gly
                485                 490                 495

Leu Phe Phe Val Leu
                500

<210> SEQ ID NO 147
<211> LENGTH: 492
<212> TYPE: PRT
<213> ORGANISM: Neurospora crassa

<400> SEQUENCE: 147

Met Lys Gly Tyr Thr Ser Ser Ala Leu Leu Gly Pro Ala Leu Leu
1               5                   10                  15

Ser Gln Leu Ala Leu Ala Gln Gln Ala Pro Asn Gly Val His Trp
                20                  25                  30

Gly Ile Gln Lys Arg His Ala Pro Asn Ala Pro Asn Arg Leu Leu Arg
            35                  40                  45

Arg Ala Gly Pro Thr His Gln Ala Ile Leu Gln Asn Glu Gln Ala Arg
50                  55                  60

Gly Gly Tyr Phe Ala Thr Cys Ala Met Gly Thr Pro Gly Gln Lys Val
65                  70                  75                  80

Thr Leu Gln Leu Asp Thr Gly Ser Ser Asp Val Trp Val Pro Asp Ser
                85                  90                  95

Thr Ala Ser Ile Cys Asn Lys Gly Ala Cys Asp Leu Gly Ser Trp Gln
                100                 105                 110

Gly Glu Phe Asp Ile Ser Tyr Val Asp Gly Ser Ser Ser Lys Gly Asp
            115                 120                 125

Tyr Phe Thr Asp Val Phe Asn Ile Gly Gly Thr Thr Val Thr Asn Leu
            130                 135                 140

Thr Met Gly Leu Gly Ala Gln Thr Asp Ile Ala Tyr Gly Leu Val Gly
145                 150                 155                 160
```

Ile Gly Tyr Ala Ile Asn Glu Ala Ile Val Gly Asn Ser His Ser Leu
            165                 170                 175

Ser Ser Gln Tyr Pro Asn Leu Pro Val Ala Met Val Asp Asp Gly Leu
            180                 185                 190

Ile Asn Thr Ile Ala Tyr Ser Leu Trp Leu Asn Asp Leu Asp Ala Gly
            195                 200                 205

Glu Gly Ser Ile Leu Phe Gly Gly Ile Asp Thr Lys Lys Tyr Lys Gly
            210                 215                 220

Asp Leu Thr Arg Ile Arg Ile Tyr Pro Ser Ser Asn Gly Tyr Tyr Phe
225                 230                 235                 240

Ser Phe Ile Val Ala Leu Thr Ser Leu Gln Ala Ile Ser Pro Ser Gly
            245                 250                 255

Asn Asp Thr Leu Thr Ser Gln Glu Phe Pro Ile Pro Val Val Leu Asp
            260                 265                 270

Ser Gly Thr Thr Leu Ser Tyr Leu Pro Gln Asp Ile Val Asp Gln Ile
            275                 280                 285

Trp Gln Glu Val Gly Ala Glu Tyr Ser Asp Arg Leu Glu Leu Ala Val
            290                 295                 300

Ile Pro Cys Ser Lys Lys Ser Ser Asn Gly Tyr Phe Ser Phe Gly Phe
305                 310                 315                 320

Ala Gly Pro Asp Gly Pro Arg Ile Thr Val Arg Met Asp Glu Leu Val
            325                 330                 335

Leu Asp Leu Thr Ser Gly Asp Pro Pro Lys Tyr Thr Ser Gly Pro Asn
            340                 345                 350

Lys Gly Gln Asp Val Cys Glu Phe Gly Ile Gln Asn Ser Thr Ser Ala
            355                 360                 365

Pro Tyr Leu Leu Gly Asp Thr Phe Leu Arg Ser Ala Tyr Val Val Tyr
            370                 375                 380

Asp Leu Val Asn Asn Glu Ile Gly Leu Ala Glu Thr Asp Phe Asn Ser
385                 390                 395                 400

Thr Glu Ser Asn Ile Val Ala Phe Ala Ser Met Ser Ala Thr Ile Pro
            405                 410                 415

Ser Ala Thr Gln Ala Pro Asn Gln Ala Ala Val Thr Asn Arg Pro Val
            420                 425                 430

Ala Thr Met Pro Ser Phe Ala Ala Ser Ser Gly Phe Ser Asp Thr Gly
            435                 440                 445

Gly Ser Gly Asn Asp Gly Lys Asp Glu Asn Ala Ser Ala Gly Met Pro
450                 455                 460

Ser Ala Phe Gly Val Ala Gln Met Ser Val Met Gly Ile Ala Met Val
465                 470                 475                 480

Phe Ala Met Val Gly Ser Gly Val Phe Val Leu Leu
            485                 490

<210> SEQ ID NO 148
<211> LENGTH: 668
<212> TYPE: PRT
<213> ORGANISM: Myceliophthora thermophila

<400> SEQUENCE: 148

Met Ser Phe Ala Leu Tyr Ala Ala Leu Leu Pro Val Ala Val Leu
1               5                   10                  15

Gly Ala Gly Leu Ser Val Pro Glu Asp Asn Arg Met Val Gln Gln Asp
            20                  25                  30

Gly Leu Leu Arg Tyr Pro Leu Met Pro Arg Leu Gly Asn Leu Leu Phe

```
                35                  40                  45
Gly Lys His Ala Asn Ile Thr Arg Arg Gln Ile Asp Thr Gly Ile Phe
 50                  55                  60

Asp Pro Leu Ser Gly Thr Leu Tyr Thr Ile Glu Leu Thr Leu Gly Thr
 65                  70                  75                  80

Pro Gly Gln Thr Val Pro Val Gln Phe Asp Thr Gly Ser Asp Met Leu
                 85                  90                  95

Trp Val Asn Pro Val Cys Ser Lys Ala Ala Glu Pro Glu Phe Cys Ala
                100                 105                 110

Ala Gln Pro Arg Phe Thr Asp Ser Ser Thr Leu Val Asp Phe Gly Glu
                115                 120                 125

Gln Gly Asn Ile Thr Tyr Gly Thr Gly Tyr Ala Tyr Tyr Glu Tyr Val
                130                 135                 140

Ala Asp Tyr Val Ala Ile Gly Ser Ala Arg Ile Thr Gln Gln Val Phe
145                 150                 155                 160

Gly Val Ala Leu Asp Ser Ala His Ala Asp Val Gly Ile Phe Gly Ala
                165                 170                 175

Gly Pro Asn Leu Asp Gly Trp Asp Ser Ala Tyr Pro Leu Val Val Asp
                180                 185                 190

Ser Leu Ala Gln Gln Gly Tyr Thr Ser Ser Arg Ala Phe Ser Met Asp
                195                 200                 205

Leu Lys Gly Phe Glu Ser Ala Arg Gly Ser Val Ile Phe Gly Gly Ile
                210                 215                 220

Asp Thr Lys Lys Tyr Arg Gly Ser Leu Ile Lys Arg Leu Ile Ile Pro
225                 230                 235                 240

Ala Ala Glu Ser Pro Asp Gly Tyr Thr Arg Phe Trp Ile Tyr Leu Asp
                245                 250                 255

Gly Ile Ser Val Asn Gln Pro Asp Gly Asp Val Val Thr Val Phe Ser
                260                 265                 270

Thr Pro Asp Gly Gly Lys Gly Gln Pro Val Leu Leu Asp Ser Gly Tyr
                275                 280                 285

Thr Leu Ser Ala Leu Pro Arg Pro Ile Phe Gln Lys Leu Val Ala Ala
290                 295                 300

Phe Pro Ser Ala Gln Tyr Val Ser Ser Ala Asp Val Tyr Val Val Asp
305                 310                 315                 320

Cys Val Asp His Gly Glu Gly Gly Ser Leu Asp Phe Ile Phe Gly Gly
                325                 330                 335

Lys Thr Ile Asn Val Pro Tyr His Glu Phe Val Trp Ala Gln Pro Glu
                340                 345                 350

Ser Asn Thr Cys Val Leu Gly Ala Phe Glu Asp Asp Phe Pro Val Leu
                355                 360                 365

Gly Asp Thr Phe Leu Arg Ser Ala Tyr Val Val Tyr Asp Trp Asp Asn
                370                 375                 380

Arg Asn Ile Tyr Leu Ala Gln Ser Asp Asp Cys Gly Ser Asn Leu Val
385                 390                 395                 400

Ala Ile Gly Ser Gly Pro Asp Ala Val Pro Ser Ile Val Gly Glu Cys
                405                 410                 415

Gly Lys Pro Lys Pro Thr Ser Ser Thr Phe Ser Lys Thr Ser Ser
                420                 425                 430

Lys Thr Ser Thr Ala Ser Lys Thr Ser Ser Ser Asp Ser Thr Ser
                435                 440                 445

Ser Ser Ser Ser His Val Thr Ser Ser Ser Ser Thr Thr Ala Thr
                450                 455                 460
```

-continued

Thr Leu Ser Thr His Lys Pro Pro Phe Pro Thr Ala Ser Gly Asn Phe
465                 470                 475                 480

Thr Thr Thr Arg Ser Pro Thr Thr Thr Ala Ser Ser Thr Ile Ser
            485                 490                 495

Lys Ser Thr Leu Thr Ile Thr Ser Ala Thr Thr Tyr Thr Ile Thr Ser
            500                 505                 510

Cys Pro Pro Thr Val Thr Arg Cys Pro Ala His Glu Val Thr Thr Glu
            515                 520                 525

Ile Ile Thr Lys Thr Thr Ala Val Cys Pro Glu Thr Thr Ala Thr Tyr
530                 535                 540

Thr Ile Pro Arg Thr Ile Thr Cys Pro Gly Ser Gly Gly Gly Asp Asp
545                 550                 555                 560

Cys Pro Pro Gly Ala Thr Arg Thr Thr Thr Leu Thr Val Thr Leu Ser
            565                 570                 575

Pro Val Gly Pro Thr Asp Arg Thr Thr His Val Val Pro Gly Val Thr
            580                 585                 590

Thr Thr Thr Pro Thr Thr Ile Thr Ala Pro Pro Thr Gly Gln Thr Thr
            595                 600                 605

Thr Thr Leu Val Pro Ala Leu Pro Pro Thr Thr Thr Met Ser Gly
            610                 615                 620

His Arg Gly Ile Asn Gly Thr Val Thr Ala Thr Ser Lys Pro Pro Ala
625                 630                 635                 640

Val Thr Ala Gly Ser Ala Lys Val Gly Leu Val Ser Gly Ala Thr Ala
            645                 650                 655

Ile Val Ala Gly Val Met Ala Val Leu Met Ala Leu
            660                 665

<210> SEQ ID NO 149
<211> LENGTH: 551
<212> TYPE: PRT
<213> ORGANISM: Neurospora crassa

<400> SEQUENCE: 149

Met Leu Pro Val Pro Leu Thr Thr Leu Ser Leu Tyr Val Val Ala Leu
1               5                   10                  15

Leu Ser Pro Pro Ala Ala Gly Val Leu Ala Ser Ala Thr Thr Lys
            20                  25                  30

Leu Pro Ile Lys Leu Pro Ile Ser Pro Ala Gln Gly His Arg Ser Ser
            35                  40                  45

Thr Ala Ala Ser Pro Ser Leu Thr Ser Arg Ser Ser Ser Gly Asn
    50                  55                  60

Gly Phe Ile Arg Ala Ser Val His Ala Ala His Gly Ala Pro Pro Lys
65                  70                  75                  80

Leu Arg Arg Arg Gln Glu Asp Glu Gly Leu Lys Asn Gln Asn Leu Gly
                85                  90                  95

Thr Thr Tyr Thr Ile Asp Ile Asp Ile Gly Thr Pro Pro Gln Thr Val
            100                 105                 110

Thr Leu Ile Leu Asp Thr Gly Ser Pro Asp Leu Trp Val Asn Pro Gln
            115                 120                 125

Cys Glu Thr Ser Gly Gln Glu Lys Tyr Cys Asn Ser Phe Arg Gln Phe
            130                 135                 140

Asp Tyr Thr Lys Ser Lys Thr Ile Gln Asp Thr Gly Ala Ala Asp Ile
145                 150                 155                 160

Leu Lys Tyr Gly Lys Gly Asn Val Thr Ile Glu Tyr Val Thr Asp Asp

```
                165                 170                 175
Val Ile Ile Gly Ser Ala Lys Ile Lys Ser Gln Ile Leu Gly Ile Gly
            180                 185                 190

Phe Glu Ser Ile Asp Ile Pro Leu Gly Ile Gly Leu Ser Pro Ser
            195                 200             205

Val Ser Pro Asp Gly Thr Ser Pro Tyr Pro Tyr Leu Leu Asp Ser Met
210                 215                 220

Ala Ser Gln Gly Ile Ile Ser Ser Arg Ala Phe Ser Leu Asp Leu Arg
225                 230                 235                 240

Ser Ile Asp Asn Pro Ser Gly Ala Ile Ile Phe Gly Gly Val Asp Leu
                245                 250                 255

Gly Lys Phe Ser Gly Ser Leu Ala Lys Leu Pro Met Leu Asp Pro Ser
            260                 265                 270

Gln Thr Pro Ala Gly Val Asp Arg Tyr Trp Ile Val Leu Ser Gly Val
            275                 280                 285

Gly Met Thr Tyr Pro Asp Gly Glu Glu Val Glu Ser Glu Glu Ile Gly
            290                 295                 300

Val Pro Val Phe Leu Asp Ser Gly Gly Thr Leu Ser Arg Leu Pro Glu
305                 310                 315                 320

Thr Ile Phe Gln Ala Ile Gly Asp Ser Phe Pro Gly Ser Gln Tyr Asp
                325                 330                 335

Pro Glu Ser Gly Phe Tyr Ile Val Asp Cys Ala Val Ala Glu Gln Ala
            340                 345                 350

Gly Ser Val Asp Phe Ile Phe Gly Ser Gly Ser Arg Ser Ser Lys
            355                 360                 365

Lys Ile Arg Val Pro Tyr Gly Asp Phe Val Trp Glu Val Gln Thr Gly
370                 375                 380

Val Cys Val Val Gly Val Leu Pro Thr Asp Asp Glu Pro Val Phe Gly
385                 390                 395                 400

Asp Ser Phe Leu Arg Ala Ala Tyr Val Val Phe Asp Gln Asp Asn Arg
                405                 410                 415

Asn Leu His Leu Ala Gln Ala Ala Asn Cys Gly Glu Gln Ile Val Glu
            420                 425                 430

Ile Gly Ser Gly Gln Asp Ala Val Pro Ser Ser Thr Gly Lys Cys Lys
            435                 440                 445

Asp Gly Ser Ala Gly Ser Thr Lys Thr Ala Gly Gly Gly Leu Asp
            450                 455                 460

Val Thr Ala Thr Arg Ala Pro Thr Arg Thr Ala Gly Ser Gly Pro
465                 470                 475                 480

Ala Val Thr Asn Ser Asp Phe Gly Pro Gly Pro Ala Gly Thr Arg Val
                485                 490                 495

Ser Thr Gly Gly Ile Gly Leu Pro Thr Gly Thr Gly Gly Gly Gly
            500                 505                 510

Ser Gly Asp Gly Asn Gly Asn Asn Asp Asp Asp Ser Ala Ala Ser
            515                 520                 525

Gly Leu Asp Val Gly Val Thr Ala Ala Val Leu Ala Gly Leu Asn
            530                 535                 540

Met Leu Ile Val Trp Leu Leu
545                 550

<210> SEQ ID NO 150
<211> LENGTH: 529
<212> TYPE: PRT
<213> ORGANISM: Neurospora crassa
```

<400> SEQUENCE: 150

Met Lys Ser Thr Leu Ala Thr Leu Leu Ala Leu Ala Ser Val Ala Val
1               5                   10                  15

Ala Glu Asn Gly Val Val Asn Phe Pro Leu Asn Arg Gly Val Pro His
            20                  25                  30

Phe Arg Val Gly Asn Val Arg Gln Asn Val Lys Arg Asp Thr Tyr Ser
        35                  40                  45

Gln Ala Leu Ile Asn Asn Ile Thr Gly Gly Ala Tyr Tyr Ala Glu Val
    50                  55                  60

Thr Val Gly Thr Pro Gly Gln Lys Val Ser Val Val Leu Asp Thr Gly
65                  70                  75                  80

Ser Ser Asp Leu Trp Val Val Ser Tyr Lys Ala Asp Leu Cys Thr Asp
                85                  90                  95

Pro Ser Ile Gln Arg Gln Trp Gly Asp Ser Cys Asp Lys Thr Tyr Asn
            100                 105                 110

Pro Thr Lys Ser Ser Tyr Lys Val Leu Glu Glu Asp Ser Phe Glu
        115                 120                 125

Ile Arg Tyr Leu Asp Asn Ser Thr Ala Ala Gly Asp Tyr Ile Thr Asp
130                 135                 140

Asp Leu Asn Ile Gly Gly Ala Thr Ile Lys Ser Leu Gln Met Gly Tyr
145                 150                 155                 160

Ala Thr Lys Thr Val Arg Gly Ala Gly Ile Leu Gly Val Gly Tyr Ser
                165                 170                 175

Ser Asn Val Ala Ser Gln Gln Arg Tyr Pro Asn Leu Ile Asp Gln Phe
            180                 185                 190

Val Ala Gln Lys Leu Ile Thr Thr Lys Ala Tyr Ser Leu Tyr Leu Asn
        195                 200                 205

Asp Arg Arg Ser Asp Thr Gly Ser Ile Leu Phe Gly Gly Ile Asp Lys
    210                 215                 220

Asp Lys Phe Ile Gly Asp Leu Ser Ile Leu Pro Ile Tyr Leu Ala Lys
225                 230                 235                 240

Gly Gln Ala Glu Pro Ile His Phe Glu Val Glu Met Gln Ser Val Ser
                245                 250                 255

Leu Ala Leu Thr Lys Asn Gly Lys Thr Thr Lys Ile Ile Ser Thr Asp
            260                 265                 270

Pro Ser Leu Ser Gln Thr Ser Thr Ile Ala Ile Leu Asp Ser Gly Thr
        275                 280                 285

Thr Leu Ser Tyr Leu Pro Ser Lys Ile Thr Asp Gln Ile His Thr Lys
    290                 295                 300

Leu Ser Val Tyr Val Asp Glu Ile Trp Thr Gly Leu Thr Phe Ile Asp
305                 310                 315                 320

Cys Gln Tyr Leu Thr Ser Asn Pro Asp Leu Arg Leu Ser Phe Thr Phe
                325                 330                 335

Gly Ala Asn Ala Thr Ile Ser Val Pro Val Trp Glu Leu Val Leu Asp
            340                 345                 350

Leu Leu Gly Glu Ser Gln Ser Glu Leu Pro Phe Lys Met Pro Phe Lys
        355                 360                 365

Asn Ala Cys Ile Phe Gly Ile Gln Ser Thr Ala Gly Phe Gln Glu Asp
    370                 375                 380

Asn Phe Asp Glu Asp Trp Ala Leu Leu Gly Glu Thr Phe Leu Arg Ser
385                 390                 395                 400

Ala Tyr Val Val Tyr Asp Leu Thr His His Gln Ile Gly Ile Ala Gln

```
                405                 410                 415
Ala Asn Leu Asn Ser Thr Thr Thr Asp Ile Val Glu Leu Ser Gly Ala
            420                 425                 430

Asp Gly Gly Leu Pro Thr Gly Leu Thr Gly Val Lys Glu Gln Gln Thr
            435                 440                 445

Ser Asn Asp Pro Ser Gly Asn Ala Gly Ser Gly Ser Gly Ser Ser Thr
            450                 455                 460

Asp Lys Asp Gly Ala Lys Glu Thr Glu Thr Val Thr Ala Gly Ser Thr
465                 470                 475                 480

Ala Ala Thr Gly Thr Ala Ala Ser Gly Ala Lys Glu Thr Asp Ser Ala
            485                 490                 495

Ala Ala Gly Leu Ser Ala Arg Gly Gly Ala Val Gly Ala Leu Ala Val
            500                 505                 510

Ala Ser Leu Thr Gly Phe Leu Ala Leu Val Gly Gly Ala Val Val Ala
            515                 520                 525

Leu

<210> SEQ ID NO 151
<211> LENGTH: 566
<212> TYPE: PRT
<213> ORGANISM: Myceliophthora thermophila

<400> SEQUENCE: 151

Met Lys Pro Ser Ser Ala Ile Leu Leu Ala Leu Ala Pro Gly Ser Ser
1               5                   10                  15

Ser Lys Asn Val Val Glu Phe Ser Val Ser Arg Gly Leu Pro Gly Asn
            20                  25                  30

Arg Thr Pro Leu Ser Phe Pro Pro Leu Thr Arg Arg Glu Thr Tyr Ser
            35                  40                  45

Glu Arg Leu Ile Asn Asn Ile Ala Gly Gly Tyr Tyr Val Gln Val
    50                  55                  60

Gln Val Gly Thr Pro Pro Gln Asn Leu Thr Met Leu Leu Asp Thr Gly
65                  70                  75                  80

Ser Ser Asp Ala Trp Val Leu Ser His Glu Ala Asp Leu Cys Ile Ser
            85                  90                  95

Pro Ala Leu Gln Asp Phe Tyr Gly Met Pro Cys Thr Asp Thr Tyr Asp
            100                 105                 110

Pro Ser Lys Ser Ser Lys Lys Met Val Glu Glu Gly Gly Phe Lys
            115                 120                 125

Ile Thr Tyr Leu Asp Gly Gly Thr Ala Ser Gly Asp Tyr Ile Thr Asp
            130                 135                 140

His Phe Thr Ile Gly Gly Val Thr Val Gln Ser Leu Gln Met Ala Cys
145                 150                 155                 160

Val Thr Lys Ala Val Arg Gly Thr Gly Ile Leu Gly Leu Gly Phe Ser
            165                 170                 175

Ile Ser Glu Arg Ala Ser Thr Lys Tyr Pro Asn Ile Ile Asp Glu Met
            180                 185                 190

Tyr Ser Gln Gly Leu Ile Lys Ser Lys Ala Phe Ser Leu Tyr Leu Asn
            195                 200                 205

Asp Arg Arg Ala Asp Ser Gly Thr Leu Leu Phe Gly Gly Ile Asp Thr
            210                 215                 220

Asp Lys Phe Ile Gly Pro Leu Gly Val Leu Pro Leu His Lys Pro Pro
225                 230                 235                 240

Gly Asp Arg Asp Tyr Ser Ser Phe Glu Val Asn Phe Thr Ser Val Ser
```

```
                245                 250                 255
Leu Thr Tyr Thr Asn Gly Ser Arg His Thr Ile Pro Thr Ala Ile Leu
            260                 265                 270

Asn His Pro Ala Pro Ala Val Leu Asp Ser Gly Thr Thr Leu Ser Tyr
        275                 280                 285

Leu Pro Asp Glu Leu Ala Asp Pro Ile Asn Thr Ala Leu Asp Thr Phe
    290                 295                 300

Tyr Asp Asp Arg Leu Gln Met Thr Leu Ile Asp Cys Ser His Pro Leu
305                 310                 315                 320

Leu Arg Thr Asp Pro Asp Phe His Leu Ala Phe Thr Phe Thr Pro Thr
            325                 330                 335

Thr Ser Ile Thr Val Pro Leu Gly Asp Leu Val Leu Asp Ile Leu Pro
        340                 345                 350

Pro Thr Tyr Pro Gln Ser Asn Ser Asn Asn Asn Glu Val Glu Asp
    355                 360                 365

Asp Asp Asp Asp Asp Asp Asp Asp Asp Asp Lys Val Pro Pro
370                 375                 380

Ala Thr Glu Arg Arg Trp Cys Val Phe Gly Ile Gln Ser Thr Thr Arg
385                 390                 395                 400

Phe Ala Ala Ser Ser Gly Gln Ser Glu Ala Asn Phe Thr Leu Leu Gly
            405                 410                 415

Asp Thr Phe Leu Arg Ser Ala Tyr Val Val Tyr Asp Leu Ser His Tyr
        420                 425                 430

Gln Ile Gly Leu Ala Gln Ala Asn Leu Asn Ser Ser Ser Ser Ser Thr
    435                 440                 445

Asn Thr Asn Thr Ile Val Glu Leu Thr Ala Asp Asn His Asp Asp Gly
450                 455                 460

Ala Ser Glu Arg Gly Glu Gly Ala Gly Ala Gly Ala Asp Ala Gly Thr
465                 470                 475                 480

Arg Thr Val Ile Ala Gly Gly Leu Pro Ser Gly Leu Met Gly Val Glu
            485                 490                 495

Ala Gln Gln Thr Thr Phe Thr Pro Thr Ala Thr Ala Asn Gly His Pro
        500                 505                 510

Gly Tyr Gly Gly Gly Pro Gly Gly Ser Thr Arg Pro Gly Ser Glu Arg
    515                 520                 525

Asn Ala Ala Gly Gly Phe Thr Ala Val Arg Thr Gly Leu Leu Gly
530                 535                 540

Glu Leu Val Gly Val Ala Ala Val Thr Ala Leu Phe Ile Leu Leu Gly
545                 550                 555                 560

Gly Ala Leu Ile Ala Val
            565

<210> SEQ ID NO 152
<211> LENGTH: 897
<212> TYPE: PRT
<213> ORGANISM: Myceliophthora thermophila

<400> SEQUENCE: 152

Met Val Arg Leu Asp Trp Ala Ala Val Leu Leu Ala Ala Thr Ala Val
1               5                   10                  15

Ala Lys Ala Val Thr Pro His Thr Pro Ser Phe Val Pro Gly Ala Tyr
            20                  25                  30

Ile Val Glu Tyr Glu Glu Asp Gln Asp Ser His Ala Phe Val Asn Lys
        35                  40                  45
```

```
Leu Gly Gly Lys Ala Ser Leu Arg Lys Asp Leu Arg Phe Lys Leu Phe
     50                  55                  60

Lys Gly Ala Ser Ile Gln Phe Lys Asp Thr Glu Thr Ala Asp Gln Met
 65                  70                  75                  80

Val Ala Lys Val Ala Glu Met Pro Lys Val Lys Ala Val Tyr Pro Val
                 85                  90                  95

Arg Arg Tyr Pro Val Pro Asn His Val Val His Ser Thr Gly Asn Val
                100                 105                 110

Ala Asp Glu Val Leu Val Lys Arg Gln Ala Ala Gly Asn Asp Thr Phe
            115                 120                 125

Ser Thr His Leu Met Thr Gln Val Asn Lys Phe Arg Asp Ala Gly Ile
130                 135                 140

Thr Gly Lys Gly Ile Lys Ile Ala Val Ile Asp Thr Gly Ile Asp Tyr
145                 150                 155                 160

Leu His Glu Ala Leu Gly Gly Cys Phe Gly Pro Asp Cys Leu Val Ser
                165                 170                 175

Tyr Gly Thr Asp Leu Val Gly Asp Asp Phe Asn Gly Ser Asn Thr Pro
                180                 185                 190

Lys Pro Asp Pro Asp Pro Ile Asp Asn Cys Gln Gly His Gly Thr His
                195                 200                 205

Val Ala Gly Ile Ile Ala Ala Gln Thr Asn Asn Pro Phe Gly Ile Ile
210                 215                 220

Gly Ala Ala Thr Asp Val Thr Leu Gly Ala Tyr Arg Val Phe Gly Cys
225                 230                 235                 240

Asn Gly Asp Thr Pro Asn Asp Val Leu Ile Ala Ala Tyr Asn Met Ala
                245                 250                 255

Tyr Glu Ala Gly Ser Asp Ile Ile Thr Ala Ser Ile Gly Gly Pro Ser
                260                 265                 270

Gly Ser Trp Ser Glu Asp Pro Trp Ala Ala Val Val Thr Arg Ile Val Glu
                275                 280                 285

Asn Gly Val Pro Cys Val Val Ser Ala Gly Asn Asp Gly Asp Ala Gly
                290                 295                 300

Ile Phe Tyr Ala Ser Thr Ala Ala Asn Gly Lys Lys Val Thr Ala Ile
305                 310                 315                 320

Ala Ser Val Asp Asn Ile Val Thr Pro Ala Leu Leu Ser Asn Ala Ser
                325                 330                 335

Tyr Thr Leu Asn Gly Thr Asp Asp Phe Phe Gly Phe Thr Ala Gly Asp
                340                 345                 350

Pro Gly Ser Trp Asp Asp Val Asn Leu Pro Leu Trp Ala Val Ser Phe
                355                 360                 365

Asp Thr Thr Asp Pro Ala Asn Gly Cys Asn Pro Tyr Pro Asp Ser Thr
370                 375                 380

Pro Asp Leu Ser Gly Tyr Ile Val Leu Ile Arg Arg Gly Thr Cys Thr
385                 390                 395                 400

Phe Val Glu Lys Ala Ser Tyr Ala Ala Lys Gly Ala Lys Tyr Val
                405                 410                 415

Met Phe Tyr Asn Asn Val Gln Gln Gly Thr Val Thr Val Ser Ala Ala
                420                 425                 430

Glu Ala Lys Gly Ile Glu Gly Val Ala Met Val Thr Ala Gln Gln Gly
                435                 440                 445

Glu Ala Trp Val Arg Ala Leu Glu Ala Gly Ser Glu Val Val Leu His
450                 455                 460

Met Lys Asp Pro Leu Lys Ala Gly Lys Phe Leu Thr Thr Thr Pro Asn
```

```
              465                 470                 475                 480
         Thr Ala Thr Gly Gly Phe Met Ser Asp Tyr Thr Ser Trp Gly Pro Thr
                         485                 490                 495

Trp Glu Val Glu Val Lys Pro Gln Phe Gly Thr Pro Gly Gly Ser Ile
                         500                 505                 510

Leu Ser Thr Tyr Pro Arg Ala Leu Gly Ser Tyr Ala Val Leu Ser Gly
                         515                 520                 525

Thr Ser Met Ala Cys Pro Leu Ala Ala Ala Ile Tyr Ala Leu Leu Ile
                         530                 535                 540

Asn Thr Arg Gly Thr Lys Asp Pro Lys Thr Leu Glu Asn Leu Ile Ser
         545                 550                 555                 560

Ser Thr Ala Arg Pro Asn Leu Phe Arg Leu Asn Gly Glu Ser Leu Pro
                             565                 570                 575

Leu Leu Ala Pro Val Pro Gln Gln Gly Gly Ile Val Gln Ala Trp
                         580                 585                 590

Asp Ala Ala Gln Ala Thr Thr Leu Leu Ser Val Ser Ser Leu Ser Phe
                         595                 600                 605

Asn Asp Thr Asp His Phe Lys Pro Val Gln Thr Phe Thr Ile Thr Asn
         610                 615                 620

Thr Gly Lys Lys Ala Val Thr Tyr Ser Leu Ser Asn Val Gly Ala Ala
         625                 630                 635                 640

Thr Ala Tyr Thr Phe Ala Asp Ala Lys Ser Ile Glu Pro Ala Pro Phe
                             645                 650                 655

Pro Asn Glu Leu Thr Ala Asp Phe Ala Ser Leu Thr Phe Val Pro Lys
                         660                 665                 670

Arg Leu Thr Ile Pro Ala Gly Lys Arg Gln Thr Val Thr Val Ile Ala
                         675                 680                 685

Lys Pro Ser Glu Gly Val Asp Ala Lys Arg Leu Pro Val Tyr Ser Gly
                         690                 695                 700

Tyr Ile Ala Ile Asn Gly Ser Asp Ser Ser Ala Leu Ser Leu Pro Tyr
         705                 710                 715                 720

Leu Gly Val Val Gly Ser Leu His Ser Ala Val Val Leu Asp Ser Asn
                             725                 730                 735

Gly Ala Arg Ile Ser Leu Ala Ser Asp Asp Thr Asn Lys Pro Leu Pro
                         740                 745                 750

Ala Asn Thr Ser Phe Val Leu Pro Pro Ala Gly Phe Pro Asn Asp Thr
                         755                 760                 765

Ser Tyr Ala Asn Ser Thr Asp Leu Pro Lys Leu Val Val Asp Leu Ala
                         770                 775                 780

Met Gly Ser Ala Leu Leu Arg Ala Asp Val Val Pro Leu Ser Gly Gly
         785                 790                 795                 800

Ala Ala Thr Ala Thr Ala Arg Leu Thr Arg Thr Val Phe Gly Thr Arg
                         805                 810                 815

Thr Ile Gly Gln Pro Tyr Gly Leu Pro Ala Arg Tyr Asn Pro Arg Gly
                         820                 825                 830

Thr Phe Glu Tyr Ala Trp Asp Gly Arg Leu Asp Asp Gly Ser Tyr Ala
                         835                 840                 845

Pro Ala Gly Arg Tyr Arg Phe Ala Val Lys Ala Leu Arg Ile Phe Gly
                         850                 855                 860

Asp Ala Lys Arg Ala Arg Glu Tyr Asp Ala Ala Glu Thr Val Glu Phe
         865                 870                 875                 880

Asn Ile Glu Tyr Leu Pro Gly Pro Ser Ala Lys Phe Arg Arg Arg Leu
                         885                 890                 895
```

Phe

<210> SEQ ID NO 153
<211> LENGTH: 876
<212> TYPE: PRT
<213> ORGANISM: Neurospora crassa

<400> SEQUENCE: 153

Met Val Arg Leu Gly Leu Ala Thr Thr Leu Leu Ala Ala Ser Phe
1               5                   10                  15

Ala Gln Ala Ala His Gln Lys Ala Pro Ala Val Val Pro Gly Ala Tyr
            20                  25                  30

Ile Val Glu Tyr Glu Asp Ser His Asp Pro Thr Ser Ile Leu Ala Ser
            35                  40                  45

Ile Lys Gly Asp Ala Thr Ile Arg Lys Asp Ile Arg His Glu Leu Phe
50                  55                  60

Lys Gly Ala Ser Phe Gln Phe Lys Asp Leu Asn Lys Ala Asp Asp Leu
65                  70                  75                  80

Ala Ser Lys Val Ala Ala Met Ser Gly Val Lys Ala Leu Tyr Pro Val
                85                  90                  95

Arg Arg Tyr Ser Ile Pro Glu His Thr Val His Ser Thr Gly Ser Ala
            100                 105                 110

Val Gln Glu Val Ala Lys Arg Asp Thr Gly Asn Asp Thr Phe Ser
            115                 120                 125

Pro His Leu Met Thr Gln Val Asn Lys Phe Arg Asp Ser Gly Ile Thr
            130                 135                 140

Gly Lys Gly Ile Lys Ile Ala Val Ile Asp Thr Gly Val Asp Tyr Leu
145                 150                 155                 160

His Pro Ala Leu Gly Gly Cys Phe Gly Pro Gly Cys Leu Val Ser Tyr
                165                 170                 175

Gly Thr Asp Leu Val Gly Asp Asp Phe Asn Gly Ser Asn Thr Pro Val
            180                 185                 190

Pro Asp Ser Asp Pro Met Asp Thr Cys Asn Gly His Gly Ser His Val
            195                 200                 205

Leu Gly Leu Leu Ser Ala Asn Thr Asn Asn Pro Tyr Gly Ile Ile Gly
            210                 215                 220

Ala Ala Pro Asp Val Thr Leu Gly Ala Tyr Arg Val Phe Gly Cys Ser
225                 230                 235                 240

Gly Asp Val Gly Asn Asp Ile Leu Ile Glu Ala Tyr Leu Lys Ala Tyr
                245                 250                 255

Asp Asp Gly Ser Asp Ile Ile Thr Ala Ser Ile Gly Gly Ala Ser Gly
            260                 265                 270

Trp Pro Glu Asp Ser Trp Ala Val Val Ser Arg Ile Val Glu Lys
            275                 280                 285

Gly Val Pro Cys Leu Val Ser Ala Gly Asn Asp Gly Ala Thr Gly Ile
            290                 295                 300

Phe Tyr Ala Ser Thr Ala Ala Asn Gly Lys Arg Val Thr Ala Val Ala
305                 310                 315                 320

Ser Val Asp Asn Ile Leu Ala Pro Ala Leu Leu Ser Glu Ala Ser Tyr
                325                 330                 335

Ser Val Ala Asn Gly Ser Leu Ser Thr Phe Gly Phe Thr Ala Gly Ser
            340                 345                 350

Pro Ser Ala Trp Ala Asn Val Ser Leu Pro Val Trp Ser Val Asn Phe
            355                 360                 365

```
Asn Thr Ala Asp Ala Ala Asn Gly Cys Glu Ala Phe Pro Asp Thr
    370             375                 380

Pro Asp Leu Ser Lys Tyr Ile Val Leu Ile Arg Arg Gly Thr Cys Thr
385             390                 395                 400

Phe Val Gln Lys Ala Gln Asn Ala Ala Ala Lys Gly Ala Lys Tyr Ile
                405                 410                 415

Ile Tyr Tyr Asn Asn Ala Ser Gly Ser Thr Lys Val Asp Val Ser Ala
            420                 425                 430

Val Ala Asp Val Lys Ala Ala Met Val Thr Ser Glu Thr Gly Ala
        435                 440                 445

Ala Trp Ile Lys Ala Leu Gln Ala Gly Thr Gln Val Thr Val Asn Met
    450                 455                 460

Ala Asp Pro Glu Thr Ala Pro Lys Asn Leu Asn Asn Phe Pro Asn Thr
465             470                 475                 480

Ala Thr Pro Gly Phe Leu Ser Thr Tyr Thr Ser Trp Gly Pro Thr Tyr
                485                 490                 495

Glu Val Asp Val Lys Pro Gln Ile Ser Ser Pro Gly Gly Met Ile Leu
            500                 505                 510

Ser Thr Tyr Pro Arg Ala Leu Gly Ser Tyr Ala Val Leu Ser Gly Thr
    515                 520                 525

Ser Met Ala Cys Pro Leu Ala Ala Ala Thr Trp Ala Leu Val Met Gln
    530                 535                 540

Lys Arg Gly Thr Lys Asp Pro Lys Val Leu Glu Asn Leu Phe Ser Ala
545             550                 555                 560

Thr Ala His Pro Asn Leu Phe Asn Asp Gly Thr Lys Thr Tyr Pro Met
                565                 570                 575

Leu Ala Pro Val Ala Gln Gln Gly Ala Gly Leu Ile Gln Ala Trp Asp
            580                 585                 590

Ala Ala Asn Ala Asn Ala Leu Leu Ser Val Ser Ser Ile Ser Phe Asn
    595                 600                 605

Asp Thr Glu His Phe Lys Pro Leu Gln Ser Phe Glu Val Thr Asn Thr
    610                 615                 620

Gly Lys Lys Ala Val Thr Tyr Gln Leu Gly His Thr Ser Ala Ala Thr
625             630                 635                 640

Ala Tyr Thr Phe Ala Asn Asp Thr Ser Ile Gly Pro Ala Ala Phe Pro
            645                 650                 655

Asn Glu Leu Val Asp Ala Lys Ala Thr Leu Val Leu Thr Pro Ala Lys
            660                 665                 670

Leu Thr Leu Asn Pro Gly Gln Lys Lys Thr Val Thr Val Leu Ala Ile
    675                 680                 685

Pro Pro Leu Gly Leu Asp Ala Lys Arg Leu Pro Val Tyr Ser Gly Tyr
    690                 695                 700

Ile Thr Leu Asn Gly Thr Asp Ser Thr Gly Tyr Ser Leu Pro Tyr Gln
705             710                 715                 720

Gly Val Val Gly Ser Met Arg Ser Val Thr Val Leu Asp Lys Gln Asn
                725                 730                 735

Ser Tyr Leu Ser Gln Ser Ser Asp Ala Thr Tyr Ala Pro Val Ala Ala
            740                 745                 750

Gly Thr Thr Phe Thr Leu Pro Pro Ala Gly Lys Ala Asn Asp Thr Leu
        755                 760                 765

Tyr Ala Thr Thr Val Tyr Pro Thr Ile Val Leu Thr Leu Ser Met Gly
    770                 775                 780
```

```
Ser Ala Glu Val His Ala Asp Val Val Asn Ser Lys Gly Lys Thr Ile
785                 790                 795                 800

Gly Gln Val Leu Thr Phe Pro Ala Arg Trp Asn Pro Arg Gly Thr Phe
            805                 810                 815

Glu Trp Asn Trp Asp Gly Ala Leu Ser Asp Gly Thr Tyr Ala Pro Ala
        820                 825                 830

Asp Thr Tyr Lys Ile Thr Leu Lys Ala Leu Lys Ile Tyr Gly Asn Ser
            835                 840                 845

Lys Trp Pro Leu Asp Trp Glu Thr Gln Thr Thr Glu Pro Phe Thr Ile
850                 855                 860

Lys Tyr Ala Ala Lys Ser Lys Arg Ala Phe Thr Ala
865                 870                 875

<210> SEQ ID NO 154
<211> LENGTH: 534
<212> TYPE: PRT
<213> ORGANISM: Myceliophthora thermophila

<400> SEQUENCE: 154

Met Arg Gly Leu Val Ala Phe Ser Leu Ala Ala Cys Val Ser Ala Ala
1               5                   10                  15

Pro Ser Phe Lys Thr Glu Thr Ile Asn Gly Glu His Ala Pro Ile Leu
            20                  25                  30

Ser Ser Ser Asn Ala Glu Val Val Pro Asn Ser Tyr Ile Ile Lys Phe
        35                  40                  45

Lys Lys His Val Asp Glu Ser Ser Ala Ser Ala His His Ala Trp Ile
    50                  55                  60

Gln Asp Ile His Thr Ser Arg Glu Lys Val Arg Gln Asp Leu Lys Lys
65                  70                  75                  80

Arg Gly Gln Val Pro Leu Leu Asp Asp Val Phe His Gly Leu Lys His
                85                  90                  95

Thr Tyr Lys Ile Gly Gln Glu Phe Leu Gly Tyr Ser Gly His Phe Asp
            100                 105                 110

Asp Glu Thr Ile Glu Gln Val Arg Arg His Pro Asp Val Glu Tyr Ile
        115                 120                 125

Glu Arg Asp Ser Ile Val His Thr Met Arg Val Thr Glu Glu Thr Cys
    130                 135                 140

Asp Gly Glu Leu Glu Lys Ala Ala Pro Trp Gly Leu Ala Arg Ile Ser
145                 150                 155                 160

His Arg Asp Thr Leu Gly Phe Ser Thr Phe Asn Lys Tyr Leu Tyr Ala
                165                 170                 175

Ala Glu Gly Gly Glu Gly Val Asp Ala Tyr Val Ile Asp Thr Gly Thr
            180                 185                 190

Asn Ile Glu His Val Asp Phe Glu Gly Arg Ala Lys Trp Gly Lys Thr
        195                 200                 205

Ile Pro Ala Gly Asp Ala Asp Val Asp Gly Asn Gly His Gly Thr His
    210                 215                 220

Cys Ser Gly Thr Ile Ala Gly Lys Lys Tyr Gly Val Ala Lys Lys Ala
225                 230                 235                 240

Asn Val Tyr Ala Val Lys Val Leu Arg Ser Asn Gly Ser Gly Thr Met
                245                 250                 255

Ala Asp Val Val Ala Gly Val Glu Trp Ala Ala Lys Ser His Leu Glu
            260                 265                 270

Gln Val Gln Ala Ala Lys Asp Gly Lys Arg Lys Gly Phe Lys Gly Ser
        275                 280                 285
```

```
Val Ala Asn Met Ser Leu Gly Gly Lys Thr Arg Ala Leu Asp Asp
    290                 295                 300

Thr Val Asn Ala Ala Val Ser Val Gly Ile His Phe Ala Val Ala Ala
305                 310                 315                 320

Gly Asn Asp Asn Ala Asp Ala Cys Asn Tyr Ser Pro Ala Ala Ala Glu
                325                 330                 335

Lys Ala Val Thr Val Gly Ala Ser Ala Ile Asp Asp Ser Arg Ala Tyr
                340                 345                 350

Phe Ser Asn Tyr Gly Lys Cys Thr Asp Ile Phe Ala Pro Gly Leu Ser
                355                 360                 365

Ile Leu Ser Thr Trp Ile Gly Ser Lys Tyr Ala Thr Asn Thr Ile Ser
    370                 375                 380

Gly Thr Ser Met Ala Ser Pro His Ile Ala Gly Leu Leu Ala Tyr Tyr
385                 390                 395                 400

Leu Ser Leu Gln Pro Ala Thr Asp Ser Glu Tyr Ser Val Ala Pro Ile
                405                 410                 415

Thr Pro Glu Lys Met Lys Ser Asn Leu Leu Lys Ile Ala Thr Gln Asp
                420                 425                 430

Ala Leu Thr Asp Ile Pro Asp Glu Thr Pro Asn Leu Leu Ala Trp Asn
                435                 440                 445

Gly Gly Gly Cys Asn Asn Tyr Thr Ala Ile Val Glu Ala Gly Gly Tyr
450                 455                 460

Lys Ala Lys Lys Lys Thr Thr Thr Asp Lys Val Asp Ile Gly Ala Ser
465                 470                 475                 480

Val Ser Glu Leu Glu Lys Leu Ile Glu His Asp Phe Glu Val Ile Ser
                485                 490                 495

Gly Lys Val Val Lys Gly Val Ser Ser Phe Ala Asp Lys Ala Glu Lys
                500                 505                 510

Phe Ser Glu Lys Ile His Glu Leu Val Asp Glu Leu Lys Glu Phe
                515                 520                 525

Leu Glu Asp Ile Ala Ala
    530

<210> SEQ ID NO 155
<211> LENGTH: 396
<212> TYPE: PRT
<213> ORGANISM: Neurospora crassa

<400> SEQUENCE: 155

Met Lys Leu Ser Ala Val Leu Ala Leu Leu Pro Leu Ala Met Ala Ala
1               5                   10                  15

Pro Ser Ala Pro Ile Asp Lys Arg Ala Pro Ile Leu Glu Ala Arg Ala
                20                  25                  30

Gly Thr Gln Ala Val Pro Gly Lys Tyr Ile Val Lys Leu Arg Glu Thr
                35                  40                  45

Ala Ser Asp Asp Asp Leu Asp Lys Ala Val Lys Lys Leu Gly Asn Ser
                50                  55                  60

Lys Ala Asp His Val Tyr Lys His Ala Phe Arg Gly Phe Ala Gly Arg
65                  70                  75                  80

Ile Asp Asp Lys Thr Leu Asp Asp Ile Arg Ser Leu Pro Glu Val Glu
                85                  90                  95

Tyr Val Glu Gln Glu Ala Val Phe Thr Ile Asn Thr Tyr Thr Ser Gln
                100                 105                 110

Ser Ser Val Pro Ser Trp Gly Leu Ala Arg Leu Ser Ser Lys Thr Thr
```

```
                115                 120                 125
Gly Lys Thr Thr Tyr Val Tyr Asp Ser Ser Ala Gly Ala Gly Thr Cys
    130                 135                 140

Ala Tyr Ile Ile Asp Thr Gly Ile Asn Thr Ala His Ser Asp Phe Gly
145                 150                 155                 160

Gly Arg Ala Thr Trp Leu Ala Asn Tyr Ala Gly Asp Gly Ile Asn Ser
                165                 170                 175

Asp Gly Asn Gly His Gly Thr His Val Ala Gly Thr Val Gly Gly Thr
            180                 185                 190

Thr Tyr Gly Val Ala Lys Lys Thr Gln Leu Tyr Ala Val Lys Val Leu
        195                 200                 205

Asp Ser Asn Gly Ser Gly Ser Asn Ser Gly Val Ile Ala Gly Met Asn
    210                 215                 220

Phe Val Ala Gln Asp Ala Gln Ser Arg Asn Cys Pro Asn Gly Thr Val
225                 230                 235                 240

Ala Asn Met Ser Leu Gly Gly Gly Tyr Ser Ala Ser Thr Asn Ser Ala
                245                 250                 255

Ala Ala Ala Met Val Arg Ala Gly Val Phe Leu Ala Val Ala Ala Gly
            260                 265                 270

Asn Asp Gly Ala Asn Ala Ala Asn Tyr Ser Pro Ala Ser Glu Pro Thr
        275                 280                 285

Val Cys Thr Val Gly Ala Thr Thr Ser Ala Asp Ala Ile Ala Tyr Tyr
    290                 295                 300

Ser Asn Tyr Gly Thr Ile Val Asp Ile Phe Ala Pro Gly Thr Ser Ile
305                 310                 315                 320

Thr Ser Ala Trp Ile Gly Ser Thr Thr Ala Lys Asn Thr Ile Ser Gly
                325                 330                 335

Thr Ser Met Ala Thr Pro His Ile Thr Gly Leu Gly Ala Tyr Leu Leu
            340                 345                 350

Thr Leu Leu Gly Lys Lys Ser Pro Ala Ala Leu Cys Ser Tyr Ile Ala
        355                 360                 365

Ser Thr Ala Asn Ser Gly Val Ile Ser Gly Ile Pro Arg Gly Thr Val
    370                 375                 380

Asn Lys Leu Ala Phe Asn Gly Asn Pro Ser Ala Tyr
385                 390                 395

<210> SEQ ID NO 156
<211> LENGTH: 392
<212> TYPE: PRT
<213> ORGANISM: Myceliophthora thermophila

<400> SEQUENCE: 156

Met His Phe Ser Thr Ala Leu Leu Ala Phe Leu Pro Ala Ala Leu Ala
1               5                   10                  15

Ala Pro Thr Ala Glu Thr Leu Asp Lys Arg Ala Pro Ile Leu Thr Ala
                20                  25                  30

Arg Ala Gly Gln Val Val Pro Gly Lys Tyr Ile Ile Lys Leu Arg Asp
            35                  40                  45

Gly Ala Ser Asp Asp Val Leu Glu Ala Ala Ile Gly Lys Leu Arg Ser
        50                  55                  60

Lys Ala Asp His Val Tyr Arg Gly Lys Phe Arg Gly Phe Ala Gly Lys
65                  70                  75                  80

Leu Glu Asp Asp Val Leu Asp Ala Ile Arg Leu Leu Pro Glu Val Glu
                85                  90                  95
```

```
Tyr Val Glu Glu Ala Ile Phe Thr Ile Asn Ala Tyr Thr Ser Gln
             100                 105                 110

Ser Asn Ala Pro Trp Gly Leu Ala Arg Leu Ser Ser Lys Thr Ala Gly
        115                 120                 125

Ser Thr Thr Tyr Thr Tyr Asp Thr Ser Ala Gly Glu Gly Thr Cys Ala
    130                 135                 140

Tyr Val Ile Asp Thr Gly Ile Tyr Thr Ser His Ser Asp Phe Gly Gly
145                 150                 155                 160

Arg Ala Thr Phe Ala Ala Asn Phe Val Asp Ser Ser Asn Thr Asp Gly
                165                 170                 175

Asn Gly His Gly Thr His Val Ala Gly Thr Ile Gly Gly Thr Thr Tyr
            180                 185                 190

Gly Val Ala Lys Lys Thr Lys Leu Tyr Ala Val Lys Val Leu Gly Ser
        195                 200                 205

Asp Gly Ser Gly Thr Thr Ser Gly Val Ile Ala Gly Ile Asn Phe Val
    210                 215                 220

Ala Asp Asp Ala Pro Lys Arg Ser Cys Pro Lys Gly Val Val Ala Asn
225                 230                 235                 240

Met Ser Leu Gly Gly Ser Tyr Ser Ala Ser Ile Asn Asn Ala Ala Ala
                245                 250                 255

Ala Leu Val Arg Ser Gly Val Phe Leu Ala Val Ala Ala Gly Asn Glu
            260                 265                 270

Asn Gln Asn Ala Ala Asn Ser Ser Pro Ala Ser Glu Ala Ser Ala Cys
        275                 280                 285

Thr Val Gly Ala Thr Asp Arg Asn Asp Ala Lys Ala Ser Tyr Ser Asn
    290                 295                 300

Tyr Gly Ser Val Val Asp Ile Gln Ala Pro Gly Ser Asn Ile Leu Ser
305                 310                 315                 320

Thr Trp Ile Gly Ser Thr Ser Ala Thr Asn Thr Ile Ser Gly Thr Ser
                325                 330                 335

Met Ala Ser Pro His Ile Ala Gly Leu Gly Ala Tyr Leu Leu Ala Leu
            340                 345                 350

Glu Gly Ser Lys Thr Pro Ala Glu Leu Cys Asn Tyr Ile Lys Ser Thr
        355                 360                 365

Gly Asn Ala Ala Ile Thr Gly Val Pro Ser Gly Thr Thr Asn Arg Ile
    370                 375                 380

Ala Phe Asn Gly Asn Pro Ser Ala
385                 390

<210> SEQ ID NO 157
<211> LENGTH: 433
<212> TYPE: PRT
<213> ORGANISM: Neurospora crassa

<400> SEQUENCE: 157

Met Val Arg Phe Ser Val Ala Ala Ala Phe Leu Leu Ser Ala Leu Gly
1               5                   10                  15

Val Thr Ala Ala Pro Ser Gly Gly Arg His Asn His Gln Asn Thr Gln
            20                  25                  30

Asn Thr Gly Ala Thr Ala Gly Asn Ala Ala Gly Val Pro Val Ala Asn
        35                  40                  45

Ser Asp Ile Ser Asn Ile Ile Pro Gly Arg Tyr Ile Val Val Tyr Asn
    50                  55                  60

Asn Thr Phe Gly Glu Glu Ala Ile Asn Ala His Gln Ile Lys Val Thr
65                  70                  75                  80
```

Ser Leu Val Ala Lys Arg Asn Leu Gly Lys Arg Asp Ala Lys Thr Gly
            85                  90                  95

Arg Ile Met Ser Pro Ser Val Lys Ala Phe Lys Met Gly Thr Trp Arg
            100                 105                 110

Ala Met Ala Leu Asp Ala Asp Asp Met Ile Asn Asp Ile Asn Ser
            115                 120                 125

Ala Gln Glu Val Glu Tyr Ile Glu Ala Asp Gln Tyr Val Lys Leu Asn
130                 135                 140

Ala Leu Thr Ser Gln Asn Ser Thr Thr Thr Gly Leu Ala Arg Leu Ser
145                 150                 155                 160

His Ala Gly Pro Ser Lys Lys Ala Ala Pro Tyr Ile Phe Asp Ser Ser
            165                 170                 175

Ala Gly Glu Gly Ile Thr Ala Phe Val Val Asp Thr Gly Ile Arg Val
            180                 185                 190

Thr His Ser Glu Tyr Glu Gly Arg Ala Thr Phe Ala Ala Asn Phe Val
            195                 200                 205

Asn Asn Val Asp Thr Asp Glu Asn Gly His Gly Ser His Val Ala Gly
            210                 215                 220

Thr Ile Ala Gly Ala Thr Phe Gly Val Ala Lys Lys Ala Lys Leu Val
225                 230                 235                 240

Ala Val Lys Val Leu Asp Gly Ser Gly Ser Gly Ser Asn Ser Gly Val
            245                 250                 255

Leu Gln Gly Met Gln Phe Val Ala Asp Thr Ala Thr Ser Gln Lys Leu
            260                 265                 270

Gly Gly Lys Ala Val Leu Asn Met Ser Leu Gly Gly Gly Lys Ser Arg
            275                 280                 285

Ala Ile Asn Ser Ala Ile Asn Gln Ile Ala Ala Gly Val Val Pro
            290                 295                 300

Val Val Ala Ala Gly Asn Glu Asn Gln Asp Thr Ala Asn Thr Ser Pro
305                 310                 315                 320

Gly Ser Ala Pro Ala Ala Ile Thr Val Gly Ala Ile Asp Gln Arg Thr
            325                 330                 335

Asp Ala Arg Ala Ser Phe Ser Asn Phe Gly Ala Gly Val Asp Ile Phe
            340                 345                 350

Ala Pro Gly Val Asn Val Leu Ser Val Gly Ile Lys Ser Asp Thr Asp
            355                 360                 365

Thr Asp Thr Leu Ser Gly Thr Ser Met Ala Ser Pro His Val Ala Gly
370                 375                 380

Leu Ala Ala Tyr Leu Met Ala Leu Glu Gly Leu Thr Asp Val Thr Ala
385                 390                 395                 400

Val Gly Asn Arg Ile Lys Glu Leu Ala Gln Lys Thr Gly Ala Lys Val
            405                 410                 415

Thr Asn Asn Val Arg Gly Thr Thr Ser Leu Ile Ala Asn Asn Gly Asn
            420                 425                 430

Leu

<210> SEQ ID NO 158
<211> LENGTH: 420
<212> TYPE: PRT
<213> ORGANISM: Myceliophthora thermophila

<400> SEQUENCE: 158

Met Ala Gly Arg Leu Leu Leu Cys Leu Thr Ala Ala Leu Ser Ala Leu
1               5                   10                  15

```
Gly Val Ser Ala Ala Pro Ala Pro Asp Ala Ser Gly Arg Pro Phe Ile
            20                  25                  30

Gly Val Pro Val Ser Asn Pro Gly Ile Ala Asn Ala Ile Pro Asn Arg
        35                  40                  45

Tyr Ile Val Val Tyr Asn Asn Thr Phe Asn Asp Glu Asp Ile Asp Leu
50                      55                  60

His Gln Ser Asn Val Ile Lys Thr Ile Ala Lys Arg Asn Ile Ala Lys
65                      70                  75                  80

Arg Ser Leu Thr Gly Lys Leu Leu Ser Thr Thr Val Asn Thr Tyr Lys
                85                  90                  95

Ile Asn Asn Trp Arg Ala Met Ala Leu Glu Ala Asp Ala Thr Ile
            100                 105                 110

Asn Glu Ile Phe Ala Ala Lys Glu Val Ser Tyr Ile Glu Gln Asp Ala
        115                 120                 125

Val Ile Ser Leu Asn Val Arg Gln Met Gln Ser Gln Ala Thr Thr Gly
130                     135                 140

Leu Ala Arg Ile Ser His Ala Gln Pro Gly Ala Arg Thr Tyr Ile Phe
145                     150                 155                 160

Asp Ser Ser Ala Gly Glu Gly Ile Thr Ala Tyr Val Val Asp Thr Gly
                165                 170                 175

Ile Arg Val Thr His Glu Glu Phe Glu Gly Arg Ala Thr Phe Ala Ala
            180                 185                 190

Asn Phe Ile Asp Asp Val Asp Thr Asp Glu Gln Gly His Gly Ser His
        195                 200                 205

Val Ala Gly Thr Ile Gly Gly Lys Thr Phe Gly Val Ala Lys Lys Val
210                     215                 220

Asn Leu Val Ala Val Lys Val Leu Gly Ala Asp Gly Ser Gly Ser Asn
225                     230                 235                 240

Ser Gly Val Ile Ala Gly Met Gln Phe Val Ala Ser Asn Ala Thr Ala
                245                 250                 255

Met Gly Leu Lys Gly Arg Ala Val Met Asn Met Ser Leu Gly Gly Pro
            260                 265                 270

Ala Ser Arg Ala Val Asn Ser Ala Ile Asn Gln Val Glu Ala Ala Gly
        275                 280                 285

Val Val Pro Val Val Ala Ala Gly Asn Glu Ser Gln Asp Thr Ala Asn
290                     295                 300

Thr Ser Pro Gly Ser Ala Glu Ala Ile Thr Val Gly Ala Ile Asp
305                     310                 315                 320

Gln Thr Asn Asp Arg Met Ala Ser Phe Ser Asn Phe Gly Glu Leu Val
                325                 330                 335

Asp Ile Phe Ala Pro Gly Val Asn Val Gln Ser Val Gly Ile Arg Ser
            340                 345                 350

Asp Thr Ser Thr Asn Thr Leu Ser Gly Thr Ser Met Ala Ser Pro His
        355                 360                 365

Val Ala Gly Leu Ala Ala Tyr Ile Met Ser Leu Glu Asn Ile Thr Gly
370                     375                 380

Val Gln Ala Val Ser Asp Arg Leu Lys Glu Leu Ala Gln Ala Thr Gly
385                     390                 395                 400

Ala Arg Ala Arg Gly Val Pro Arg Gly Thr Thr Leu Ile Ala Asn
                405                 410                 415

Asn Gly Phe Ala
            420
```

<210> SEQ ID NO 159
<211> LENGTH: 421
<212> TYPE: PRT
<213> ORGANISM: Neurospora crassa

<400> SEQUENCE: 159

```
Met Val Gly Leu Lys Asn Val Ala Leu Phe Ala Ala Ser Ile Ile Leu
1               5                   10                  15

Pro Ala Ser Ile Thr Trp Ala Ala Pro Ile Ile Glu Val Glu Thr Lys
            20                  25                  30

Pro Ile Pro Glu Lys Tyr Ile Val Leu Leu Lys Pro His Ala Asp Leu
        35                  40                  45

Glu Gly His Leu Ser Trp Ala Lys Asp Val His Ala Arg Ser Leu Ser
    50                  55                  60

Arg Arg Asp Thr Ala Gly Val His Lys Ala Trp Ser Val Gly Ser Lys
65                  70                  75                  80

Phe Lys Ala Tyr Ala Gly Glu Phe Asp Glu Thr Leu Lys Ile Ile
                85                  90                  95

Gln Arg Asp Glu Arg Asn Val His Ser Ile Glu Pro Asp Lys Ser Trp
            100                 105                 110

Arg Leu Tyr Lys Ser Asn Lys Lys Asp Asn Asp Ser Asn Ser Asp
        115                 120                 125

Asn Thr Thr Ile Ile Thr Gln Lys Gln Ala Pro Trp Gly Leu Gly Tyr
    130                 135                 140

Leu Ser His Lys Gly Lys Thr Ser Ser Asp Tyr Val Tyr Asn Ser Thr
145                 150                 155                 160

Ala Gly Thr Gly Thr Tyr Ala Tyr Val Val Asp Thr Gly Cys Trp Lys
                165                 170                 175

Asp His Val Glu Phe Glu Gly Arg Val Gln Leu Gly Tyr Asn Ala Tyr
            180                 185                 190

Pro Asp Ser Pro Phe Ile Asp Met Asp Gly His Gly Thr His Val Thr
        195                 200                 205

Gly Thr Leu Ile Ser Lys Thr Tyr Gly Val Ala Lys Asn Ala Thr Val
    210                 215                 220

Ile Cys Val Lys Val Phe His Gly Gly Ser Ala Asn Thr Ile Val
225                 230                 235                 240

Met Asp Gly Phe Glu Trp Ala Val Lys Asp Ile Ile Ala Lys Lys Arg
                245                 250                 255

Gln Arg Asn Ser Val Ile Asn Met Ser Leu Gly Cys Asp Arg Ser Glu
            260                 265                 270

Ala Phe Asn Ala Ile Val Asp Ala Tyr Asp Gln Gly Ile Leu Thr
        275                 280                 285

Val Val Ala Ala Gly Asn Glu Asn Gln Pro Ala Leu Val Ser Pro
    290                 295                 300

Ala Ser Ser Ala Arg Ala Phe Ser Val Gly Ala Ile Asp Asn Lys Asn
305                 310                 315                 320

Thr Arg Ala Tyr Phe Ser Asn Tyr Gly Ala Ile Val Asp Ile Phe Ala
                325                 330                 335

Pro Gly Val Asn Ile Val Ser Thr Tyr Ile Gly Lys Lys Asp Gly Asp
            340                 345                 350

Asn Asn Arg Thr Met Thr Met Ser Gly Thr Ser Met Ala Ser Pro His
        355                 360                 365

Val Ala Gly Leu Ala Leu Tyr Leu Lys Ser Leu Asp Pro Glu Lys Tyr
    370                 375                 380
```

```
Gly Asn Ser Ser Asp Ala His Ser Gly Leu Arg Ala Leu Gly Val Pro
385                 390                 395                 400

Asp Lys Val Trp Asp Ala Gly Glu Met Ser Pro Asn Leu Val Ala Tyr
                405                 410                 415

Asn Gly Val Gln Gly
            420

<210> SEQ ID NO 160
<211> LENGTH: 243
<212> TYPE: PRT
<213> ORGANISM: Myceliophthora thermophila

<400> SEQUENCE: 160

Met Lys Leu Ala Val Leu Ile Ala Thr Thr Ala Gly Leu Ala Ala Ala
1               5                   10                  15

Leu Pro Gln Gly Val Ala Arg Arg Gly Val Gly Arg Pro Leu His His
            20                  25                  30

Ser Gly Pro Asn Ile Arg Asn Thr Thr Tyr Pro Gln Tyr Ser Ser Asn
        35                  40                  45

Trp Ala Gly Ala Val Gln Ile Gly Thr Gly Phe Thr Ser Val Tyr Gly
    50                  55                  60

Thr Ile Thr Val Pro Ser Val His Asp Arg Asn Pro Asn Ala Ala Ala
65                  70                  75                  80

Ser Ala Trp Val Gly Ile Asp Gly Asp Thr Cys Gln Gln Ala Ile Leu
                85                  90                  95

Gln Thr Gly Val Ser Phe Tyr Gly Asp Gly Ser Phe Asp Ala Trp Tyr
            100                 105                 110

Glu Trp Ile Pro Asp Tyr Ala Tyr Ser Phe Ser Asn Phe Arg Leu Ser
        115                 120                 125

Ala Gly Asp Gln Ile Arg Met Ser Val Glu Ala Ser Ser Lys Arg Ala
130                 135                 140

Gly Val Ala Thr Leu Glu Asn Leu Ser Thr Gly Gln Lys Val Ser His
145                 150                 155                 160

Thr Phe Thr Ser Thr Pro Ser Thr Leu Cys Glu Thr Asn Ala Glu Trp
                165                 170                 175

Ile Val Glu Asp Phe Gln Glu Gly Ser Ser Leu Val Pro Phe Ala Asp
            180                 185                 190

Phe Gly Thr Val Thr Phe Thr Asp Ala Tyr Ala Thr Gly Ser Ser Gly
        195                 200                 205

Thr Val Thr Pro Ser Gly Ala Thr Ile Ile Asp Ile Lys Gln Gly Asn
    210                 215                 220

Glu Val Leu Thr Asn Cys Ala Thr Ser Gly Ser Asp Leu Thr Cys Ser
225                 230                 235                 240

Tyr Thr Gly

<210> SEQ ID NO 161
<211> LENGTH: 288
<212> TYPE: PRT
<213> ORGANISM: Neurospora crassa

<400> SEQUENCE: 161

Met Lys Leu Leu Ser Pro Ala Ile Ser Leu Leu Gly Val Ile Ser Gln
1               5                   10                  15

Pro Ile Leu Ala Gln Phe Thr Phe Thr Ser Thr Val Glu His Asn Gly
            20                  25                  30
```

Val Pro Val Pro Gln Ala Glu Thr Asp Leu Lys Pro Phe Lys Pro Gly
         35                  40                  45

Thr Leu Gly Arg Ile Arg Ser Arg Thr Asp Asp Ser Gly Pro Glu
 50                  55                  60

Ile Gly Thr Thr Thr Leu Arg Arg Val Lys Arg Thr Asn Pro Thr Ala
 65                  70                  75                  80

Asn Ser Asn Asn Trp Cys Gly Ser Val Gln Ser Thr Thr Ser Ser Asn
             85                  90                  95

Gln Ile Lys Leu Val His Gly Thr Phe Gln His Pro Thr Cys Thr Gln
             100                 105                 110

Arg Pro Gly Val Thr Gln Tyr Pro Gln Ala Ala Ala Trp Ile Gly
         115                 120                 125

Ile Asp Gly Asp Ser Trp Thr Ser Ala Leu Leu Gln Ala Gly Thr Val
 130                 135                 140

Cys Lys Ile Asn Asn Ser Thr Gly Ile Val Glu Asn Glu Val Trp Trp
 145                 150                 155                 160

Gln Trp Val Pro Asn Gly Ala Tyr Thr Ile Thr Asn Ile Pro Val Phe
             165                 170                 175

Ala Gly Asp Trp Phe Asp Ile Thr Ile Asn Thr Thr Ser Ser Thr Ala
         180                 185                 190

Ala Thr Ile Lys Ile Met Ser Asn Arg Gly Tyr Thr Tyr Ser Val Asn
         195                 200                 205

Ala Trp Gln Gly Ala Thr Leu Ala Arg Val Asp Ala Asp Trp Val Val
 210                 215                 220

Glu Arg Pro Tyr Tyr Gly Ser Thr Leu Ala Gly Phe Ala Gln Phe Thr
 225                 230                 235                 240

Gln Val Trp Phe Gln Asn Ala Tyr Ala Thr Leu Thr Ser Gly Thr Ser
             245                 250                 255

Ser Leu Gly Ile Thr Gly Ala Lys Gln Tyr Gln Ile Pro Gly Gly Cys
         260                 265                 270

Ala Ser Ala Glu Tyr Asp Asn Ser Lys Leu Tyr Ala Ala Val Ala Ala
         275                 280                 285

<210> SEQ ID NO 162
<211> LENGTH: 285
<212> TYPE: PRT
<213> ORGANISM: Myceliophthora thermophila

<400> SEQUENCE: 162

Met Trp Ser Ile Val Arg Ser Leu Ser Leu Ala Ser Leu Ile Ser Ser
 1                   5                  10                  15

Ala Cys Thr Val Thr Ala Gln Leu Ser Phe Val Ala Ser Val Lys Gln
             20                  25                  30

His Gly Lys Asp Val Asp Ala Ser Gly Leu Ser Phe Val Arg Ile Pro
         35                  40                  45

Pro Leu Glu His Arg Trp His Ala Ser Pro Arg Arg Gly Gln Asn
     50                  55                  60

Asn Arg Thr Val Glu Arg Asp Ala Val Ser Tyr Ser Ala Asn Trp Cys
 65                  70                  75                  80

Gly Ala Ser Gln His Ala Ser Asp Ser Asp Gly Ile Lys Ser Val Leu
             85                  90                  95

Gly Tyr Phe Thr Ala Pro Asp Leu Thr Leu Arg Pro Gly Thr Pro Ala
         100                 105                 110

Pro Gln Phe Ala Ala Ala Trp Val Gly Ile Asp Gly Ala Ala Cys Asn
         115                 120                 125

```
Thr Thr Leu Leu Gln Ala Gly Val Thr Thr Ile Val Asn Ser Asp Gly
    130                 135                 140

Gly Gln Ser Ala Ser Ala Trp Trp Glu Trp Tyr Pro Glu Ala Ser Tyr
145                 150                 155                 160

Thr Ile Ser Gly Leu Lys Val Lys Ala Gly Glu Trp Met Ser Val Asn
                165                 170                 175

Ile Thr Thr Lys Asp Ala Ser Ser Ala Ile Leu Val Ile Glu Asn Ala
                180                 185                 190

Asp Thr Gly Thr Ser Val Thr Leu Glu Leu Asn Asn Gly Pro Gln Leu
                195                 200                 205

Cys Arg Arg Asp Ala Glu Trp Ile Leu Glu Asp Phe Tyr Glu Ser Gly
                210                 215                 220

Lys Gln Val Ala Leu Ala Asn Phe Ala Asp Leu Trp Phe Val Asp Ser
225                 230                 235                 240

Gly Ala Thr Thr Val Gly Gly Lys Asn Val Gly Phe Asp Gly Ala Thr
                245                 250                 255

Met Val His Leu Arg Asp Glu Asn Gly Asn Val Leu Cys Ser Pro Glu
                260                 265                 270

Pro Tyr Asp Asn Ser Asn Phe Val Val Ser Lys Pro
                275                 280                 285

<210> SEQ ID NO 163
<211> LENGTH: 307
<212> TYPE: PRT
<213> ORGANISM: Myceliophthora thermophila

<400> SEQUENCE: 163

Met Lys Pro Thr Val Leu Phe Thr Leu Leu Ala Ser Gly Ala Tyr Ala
1               5                   10                  15

Ala Ala Thr Pro Ala Ile Pro Gly Tyr Ser Pro Arg Thr Arg Gly Met
                20                  25                  30

Asn Pro His His His Ala Pro Leu Arg Leu Leu His Thr Phe Thr Pro
                35                  40                  45

Ile Ser Thr Ser Gly Lys Ser Phe Arg Leu Leu Ala Ser Ser Thr Glu
                50                  55                  60

Ser Thr Lys Gly Gly Ala Ile Leu Gly Leu Pro Asp Asn Asp Leu Ser
65                  70                  75                  80

Thr Val Arg Thr Thr Ile Arg Ile Pro Ala Ala Lys Met Pro Thr Ala
                    85                  90                  95

Gly Pro Thr Ala Asn Asn Thr Val Gly Glu Tyr Ala Ala Ser Phe Trp
                100                 105                 110

Val Gly Ile Asp Ser Ala Thr Asp Ala Cys Gly Ala Gly Gly Ser Leu
                115                 120                 125

Arg Ala Gly Val Asp Ile Phe Trp Asp Gly Thr Leu Gly Gly Gln Gln
                130                 135                 140

Thr Pro Phe Ala Trp Tyr Gln Gly Pro Gly Gln Ala Asp Val Val Gly
145                 150                 155                 160

Phe Gly Gly Gly Phe Pro Val Gly Glu Gly Asp Leu Val Arg Leu Thr
                165                 170                 175

Leu Glu Ala Gly Pro Ala Gly Gly Glu Ile Ala Val Val Ala Glu
                180                 185                 190

Asn Phe Gly Arg Asn Val Thr Arg Ala Asp Glu Gly Ala Val Pro Val
                195                 200                 205

Arg Lys Val Arg Lys Val Leu Pro Ala Glu Ala Gly Gly Gln Lys Leu
```

```
Cys Arg Gly Glu Ala Ala Trp Met Val Glu Asp Phe Pro Leu Gln Gly
225                 230                 235                 240

Arg Pro Glu Phe Pro Thr Ala Leu Ala Asn Phe Thr Ser Val Thr Phe
                245                 250                 255

Asn Thr Gly Ile Thr Leu Asp Asp Gly Thr Glu Lys Asp Leu Thr Gly
            260                 265                 270

Ala Glu Val Leu Asp Ile Gln Leu Glu Ala Gln Gly Gly Arg Leu Thr
        275                 280                 285

Ser Cys Glu Val Val Asp Asp Arg Asn Val Lys Cys Ala Arg Val Val
    290                 295                 300

Gly Asp Asn
305

<210> SEQ ID NO 164
<211> LENGTH: 197
<212> TYPE: PRT
<213> ORGANISM: Myceliophthora thermophila

<400> SEQUENCE: 164

Met Arg Trp Pro Leu Ala Ala Leu Leu Gly Ser Ala Leu Val Ala Arg
1               5                   10                  15

Gln Ala Leu Ala Glu Leu Thr Phe Thr Val Glu Ala Thr Arg Asn Gly
            20                  25                  30

Val Pro Ile Pro Ala Ser Glu Ile Arg Leu Glu Pro Phe Glu Pro Gly
        35                  40                  45

Arg Thr Arg Met Gly Ala Val Ala Glu Ala Pro Arg Ala Gln Arg Lys
    50                  55                  60

Thr Arg Arg Ser Asn Ala Gln Ala Asp Ser Ala Asn Trp Cys Gly Ser
65                  70                  75                  80

Val Asn Met Ala Pro Thr Gly Thr Asn Ile Gln Leu Ala His Gly Ser
                85                  90                  95

Phe Gln His Pro Ser Cys Ser Ile Arg Pro Gly Tyr Thr Phe Pro Gln
            100                 105                 110

Ala Ala Ala Ser Trp Val Gly Ile Asp Gly Asp Ser Tyr Arg Asp Ala
        115                 120                 125

Leu Leu Gln Ala Gly Thr Val Cys Lys Ile Asp Asn Ser Thr Gly Val
    130                 135                 140

Val Arg His Glu Ala Trp Trp Gln Trp Val Pro Ser Ala Ala Phe Thr
145                 150                 155                 160

Ile Thr Ser Met Pro Gly Gln Ser Asn Thr Thr Gly Phe Cys Ile Pro
                165                 170                 175

Tyr Ser Ala Pro Phe Val Ser Leu Cys Phe Phe Gly Arg Thr Arg Thr
            180                 185                 190

Cys Leu Phe Leu His
        195

<210> SEQ ID NO 165
<211> LENGTH: 621
<212> TYPE: PRT
<213> ORGANISM: Myceliophthora thermophila

<400> SEQUENCE: 165

Met Leu Arg Asn Ile Phe Leu Thr Ala Ala Leu Ala Ala Phe Gly Gln
1               5                   10                  15

Cys Gly Ser Thr Val Phe Glu Ser Val Pro Ala Lys Pro Arg Gly Trp
```

```
            20                  25                  30
Thr Arg Leu Gly Asp Ala Ser Ala Asp Gln Pro Leu Arg Leu Arg Ile
            35                  40                  45
Ala Leu Gln Gln Pro Asn Glu Asp Leu Phe Glu Arg Thr Leu Tyr Glu
 50                  55                  60
Val Ser Asp Pro Ser His Ala Arg Tyr Gly Gln His Leu Ser Arg Asp
 65                  70                  75                  80
Glu Leu Ser Ala Leu Leu Ala Pro Arg Ala Glu Ser Thr Ala Ala Val
                85                  90                  95
Leu Asn Trp Leu Arg Asp Ala Gly Ile Pro Ser Asp Lys Ile Glu Glu
            100                 105                 110
Asp Gly Glu Trp Ile Asn Leu Arg Val Thr Val Arg Glu Ala Ser Glu
            115                 120                 125
Leu Leu Asp Ala Asp Phe Gly Val Trp Ala Tyr Glu Gly Thr Asn Val
            130                 135                 140
Lys Arg Val Arg Ala Leu Gln Tyr Ser Val Pro Glu Glu Ile Ala Pro
145                 150                 155                 160
His Ile Arg Met Val Ala Pro Val Arg Phe Gly Gln Ile Arg Pro
                165                 170                 175
Glu Arg Ser Gln Val Phe Glu Val Val Glu Thr Ala Pro Ser Gln Val
                180                 185                 190
Lys Val Ala Ala Ile Pro Pro Gln Asp Leu Asp Val Lys Ala Cys
            195                 200                 205
Asn Thr Ser Ile Thr Pro Glu Cys Leu Arg Ala Leu Tyr Lys Val Gly
            210                 215                 220
Ser Tyr Gln Ala Glu Pro Ser Lys Lys Ser Leu Phe Gly Val Ala Gly
225                 230                 235                 240
Tyr Leu Glu Gln Trp Ala Lys Tyr Asp Gln Leu Glu Leu Phe Ala Ser
                245                 250                 255
Thr Tyr Ala Pro Tyr Ala Ala Asp Ala Asn Phe Thr Ser Val Gly Val
            260                 265                 270
Asn Gly Gly Glu Asn Asn Gln Gly Pro Ser Asp Gln Gly Asp Ile Glu
            275                 280                 285
Ala Asn Leu Asp Ile Gln Tyr Ala Val Ala Leu Ser Tyr Lys Thr Pro
            290                 295                 300
Ile Thr Tyr Tyr Ile Thr Gly Gly Arg Gly Pro Leu Val Pro Asp Leu
305                 310                 315                 320
Asp Gln Pro Asp Pro Asn Asp Val Ser Asn Glu Pro Tyr Leu Glu Phe
                325                 330                 335
Phe Ser Tyr Leu Leu Lys Leu Pro Asp Ser Glu Leu Pro Gln Thr Leu
                340                 345                 350
Thr Thr Ser Tyr Gly Glu Asp Glu Gln Ser Val Pro Arg Pro Tyr Ala
                355                 360                 365
Glu Lys Val Cys Gln Met Ile Gly Gln Leu Gly Ala Arg Gly Val Ser
            370                 375                 380
Val Ile Phe Ser Ser Gly Asp Thr Gly Val Gly Ser Ala Cys Gln Thr
385                 390                 395                 400
Asn Asp Gly Lys Asn Thr Thr Arg Phe Leu Pro Ile Phe Pro Gly Ala
                405                 410                 415
Cys Pro Tyr Val Thr Ser Ile Gly Ala Thr Arg Tyr Val Glu Pro Glu
            420                 425                 430
Gln Ala Ala Phe Ser Ser Gly Gly Phe Ser Asp Ile Phe Lys Arg
            435                 440                 445
```

```
Pro Ala Tyr Gln Glu Ala Ala Val Ser Thr Tyr Leu His Lys His Leu
    450                 455                 460

Gly Ser Arg Trp Lys Gly Leu Tyr Asn Pro Gln Gly Arg Gly Phe Pro
465                 470                 475                 480

Asp Val Ser Ala Gln Gly Val Ala Tyr His Val Phe Ser Gln Asp Lys
                485                 490                 495

Asp Ile Lys Val Ser Gly Thr Ser Ala Ser Pro Leu Phe Ala Ala
                500                 505                 510

Leu Val Ser Leu Leu Asn Asn Ala Arg Leu Ala Gln Gly Arg Pro Pro
            515                 520                 525

Leu Gly Phe Leu Asn Pro Trp Leu Tyr Ser Glu Lys Val Gln Lys Ala
    530                 535                 540

Gly Ala Leu Thr Asp Ile Val His Gly Ser Ser Gly Cys Thr Gly
545                 550                 555                 560

Lys Asp Met Tyr Ser Gly Leu Pro Thr Pro Tyr Val Pro Tyr Ala Ser
                565                 570                 575

Trp Asn Ala Thr Pro Gly Trp Asp Pro Val Thr Gly Leu Gly Thr Pro
                580                 585                 590

Val Phe Asp Lys Leu Leu Glu Leu Ser Ser Pro Gly Lys Lys Leu Pro
                595                 600                 605

His Ile Gly Gly Gly His Gly His Gly Ala Gly Gly His
    610                 615                 620

<210> SEQ ID NO 166
<211> LENGTH: 587
<212> TYPE: PRT
<213> ORGANISM: Neurospora crassa

<400> SEQUENCE: 166

Met Leu Trp Ser Val Leu Leu Ala Ala Gly Ala Ser Ala His Val
1               5                   10                  15

Lys Ser Ser Leu Pro Ser Val Pro Ser Gly Trp Lys Lys Val Arg Ala
                20                  25                  30

Ala Ser Ala Asp Glu Ser Val Ser Leu Lys Ile Ala Leu Pro Ala His
            35                  40                  45

Gln Pro Asp Ala Leu Glu Thr Ala Ile Leu Arg Val Ser Asp Pro Asn
    50                  55                  60

His His Glu Tyr Gly Met His Leu Ser Ser Glu Glu Val Arg Ser Leu
65                  70                  75                  80

Val Ala Pro Ala Asp Glu Thr Thr Asp Ala Val Thr Ser Trp Leu Asn
                85                  90                  95

Arg Asn Gly Ile Lys Gly Lys Val Asp Asn Asp Trp Val Ser Phe Thr
                100                 105                 110

Thr Ser Val Ala Lys Ala Asn Asn Leu Leu Asn Thr Thr Phe Asp Trp
            115                 120                 125

Tyr Gln Gln Asp Gly Asp Lys Thr Gly Pro Lys Leu Arg Thr Leu Gln
    130                 135                 140

Tyr Ser Val Pro Asp Glu Leu Asp Ala His Val Asp Met Ile Gln Pro
145                 150                 155                 160

Thr Thr Arg Phe Gly Lys Leu Ala Ala Lys Ala Ser Thr Ile Phe Glu
                165                 170                 175

Ile Phe Asp Glu Pro Glu Pro Lys Asn Ile Ala Asn Val Lys Val Gly
                180                 185                 190

Gly Asp His Pro Thr Cys Thr Gly Cys Ile Tyr Pro Asp Glu Ile Arg
```

```
                195                 200                 205
Ser Leu Tyr Asn Ile Lys Tyr Lys Pro Ser Ala Ser Asp Lys Asn Thr
210                 215                 220

Ile Ala Phe Ala Ser Tyr Leu Glu Gln Tyr Ser Asn Tyr Asp Asp Phe
225                 230                 235                 240

Thr Ser Phe Ala Lys Ala Phe Ile Pro Asp Ala Asp Arg Asn Tyr
        245                 250                 255

Thr Val Lys Leu Val Lys Gly Leu His Asp Gln Ser Pro Asp Lys
        260                 265                 270

Ile Gly Val Glu Ala Asn Leu Asp Leu Gln Tyr Ile Leu Ala Ile Ser
        275                 280                 285

Asn Pro Ile Pro Ile Arg Glu Tyr Ser Ile Gly Gly Arg Gly Pro Leu
290                 295                 300

Val Pro Thr Ala Asn Gln Pro Gly Pro Glu Ile Ser Asn Glu Pro Tyr
305                 310                 315                 320

Leu Asp Phe Phe Gln Tyr Leu Leu Ser Leu Lys Asn Ser Glu Leu Pro
                325                 330                 335

Ala Thr Leu Ser Thr Ser Tyr Gly Glu Glu Gln Ser Val Pro Arg
        340                 345                 350

Glu Tyr Ala Leu Lys Val Cys Ser Met Ile Gly Gln Leu Gly Ala Arg
        355                 360                 365

Gly Val Ser Val Ile Phe Ser Ser Gly Asp Ser Gly Pro Gly Asp Ala
370                 375                 380

Cys Ile Arg Asn Asp Gly Thr Asn Ser Thr Tyr Phe Glu Pro Thr Phe
385                 390                 395                 400

Pro Gly Ala Cys Pro Trp Val Thr Ser Val Gly Gly Thr Tyr Gln Thr
                405                 410                 415

Gly Pro Glu Lys Ala Val Asp Phe Ser Ser Gly Gly Phe Ser Met Tyr
        420                 425                 430

His Lys Arg Pro Val Tyr Gln Glu Arg Val Val Lys Lys Tyr Leu Asp
        435                 440                 445

Lys Ile Gly Asp Thr Tyr Ser Asp Phe Phe Asp Glu Gln Gly Arg Gly
450                 455                 460

Phe Pro Asp Val Ser Ala Gln Ala Ser Arg Tyr Ala Val Tyr Val Asp
465                 470                 475                 480

Gly Arg Leu Val Gly Val Ser Gly Thr Ser Ala Ser Ala Pro Met Phe
                485                 490                 495

Ala Gly Leu Val Ala Leu Leu Asn Ala Ala Arg Lys Ser His Gly Leu
        500                 505                 510

Pro Ser Leu Gly Phe Ile Asn Pro Leu Leu Tyr Ala Ser Lys Asp Ala
        515                 520                 525

Phe Thr Asp Ile Val Asn Gly Ala Gly Thr Gly Cys Arg Gly Arg Pro
530                 535                 540

Glu Phe Ala Gly Asp Val Gly Gly Thr Ala Lys Trp Asn Ala Thr Glu
545                 550                 555                 560

Gly Trp Asp Pro Val Thr Gly Leu Gly Thr Pro Lys Phe Asp Lys Leu
                565                 570                 575

Leu Ala Leu Ala Ala Pro Gly Val Lys Asn Ala
        580                 585
```

<210> SEQ ID NO 167
<211> LENGTH: 720
<212> TYPE: PRT
<213> ORGANISM: Myceliophthora thermophila

<400> SEQUENCE: 167

Met Arg Ile Arg His Ala Leu Val Gly Ile Ala Ser Leu Cys Cys Leu
1               5                   10                  15

Leu Gly Thr Ala Ser Gly Ala Arg Ile Ser Ser Arg Asp Met Leu Ser
            20                  25                  30

Arg Arg Val Val Pro Pro Ser His Thr Leu His Glu Arg His Glu Ala
        35                  40                  45

Gly Asn Val Glu Gly Trp Val Lys Arg Gly Leu Ala Asp Ala Glu Ser
    50                  55                  60

Thr Val Pro Val Arg Ile Gly Leu Lys Gln Ser Asn Val Asp Ala Ala
65                  70                  75                  80

His Asp Leu Leu Met Asp Ile Ser Asp Pro Arg Ser Pro Asn Tyr Gly
                85                  90                  95

Lys His Leu Ser Arg Ser Glu Val Glu Asp Leu Phe Ala Pro Arg Glu
            100                 105                 110

His Ser Val Ala Lys Val Lys Arg Trp Leu Ala Ser Ala Gly Val Asp
        115                 120                 125

Glu Gly Arg Ile Ser Gln Ser Ala Asn Lys Gln Trp Ile Gln Phe Asp
130                 135                 140

Ala Pro Val Tyr Glu Leu Glu Lys Leu Leu Leu Thr Arg Tyr His Ile
145                 150                 155                 160

Phe Glu Asn Leu Glu Thr Gly Val Gln Asn Ile Ala Cys Ser Glu Tyr
                165                 170                 175

His Val Pro Arg Asp Val Ser His His Ile Asp Tyr Ile Thr Pro Gly
            180                 185                 190

Ile Lys Leu Met Ala Gly Gly Arg Glu Glu Arg Met Val Arg Trp Arg
        195                 200                 205

Lys Ala Asp Arg Arg Ser Leu Val Ala Gly Leu Ala Ser Gln Gly Arg
210                 215                 220

Lys Gly Ala His Gly Met Gly His Gly Gly Gly Ser Arg Ser
225                 230                 235                 240

Pro Asp Asp Pro Val Val Asp Asp Ser Pro Phe Arg Val Thr Gly Pro
                245                 250                 255

Cys Ser Ala Glu Ile Thr Pro Asn Cys Ile Arg Ala Gln Tyr Gln Leu
            260                 265                 270

Pro Asn Gly Thr Arg Ala Ala Ser Gly Asn Glu Leu Gly Ile Phe Gln
        275                 280                 285

Gly Leu Gly Gln His Tyr Ser Gln Glu Asp Leu Asp Asn Tyr Trp Lys
290                 295                 300

Tyr Val Ala Pro Trp Val Pro Arg Gly Thr His Pro Glu Leu Arg Ser
305                 310                 315                 320

Ile Asn Gly Ala Leu Gly Pro Ala Asn Asp Thr Leu Arg Ala Gly Glu
                325                 330                 335

Glu Ala Asp Leu Asp Phe Gln Ile Ala Ile Pro Leu Ile Trp Pro Gln
            340                 345                 350

Arg Thr Val Leu Phe Gln Thr Asp Asp Glu Trp Tyr Gln Gln Asp Gln
        355                 360                 365

Gln Arg Ala Asp Thr Lys Tyr Pro Gly Phe Phe Asn Thr Phe Asp
370                 375                 380

Ala Ile Asp Gly Ser Tyr Cys His Met Thr Ala Phe Asn Met Thr Gly
385                 390                 395                 400

Asn Cys Val Thr Pro Glu Cys Arg Asp Pro Glu Tyr Pro Asn Pro Asn

```
                    405                 410                 415
Ala Thr Pro Glu Gln Gly Gly Tyr Ala Gly Ala Leu Met Cys Gly Arg
                420                 425                 430

His Arg Pro Thr Ser Val Val Ser Val Ser Tyr Ser Gly Thr Glu Asp
            435                 440                 445

Ser Trp Pro Ala Ser Tyr Met Arg Arg Gln Cys Leu Glu Val Leu Lys
        450                 455                 460

Leu Ala Leu Gln Gly Val Thr Val Val Glu Ser Ser Gly Asp Phe Gly
465                 470                 475                 480

Val Gly Gly Arg Pro Phe Asp Pro Arg Ala Gly Cys Leu Gly Pro Asp
                485                 490                 495

Arg Ala Val Phe Ser Pro Arg Val Met Ala Asn Cys Pro Tyr Val Leu
            500                 505                 510

Ser Val Gly Ala Thr Ala Leu Val Asp Pro Glu Gln Glu Gln Gln Gln
        515                 520                 525

Gln His Ala Asp Arg Gly Gly Ser Gly Lys Glu Pro Arg Leu Val Glu
530                 535                 540

Val Ala Ala Arg Thr Phe Ala Ser Gly Gly Phe Ser Asn Ile Phe
545                 550                 555                 560

Gly Arg Pro Lys Trp Gln Asp Arg His Val Arg Glu Tyr Leu Arg Lys
                565                 570                 575

Thr Asn Leu Ser Glu Leu Gly Tyr Asp Asn Ala Ala Gly Met Ser Phe
            580                 585                 590

Asp Ser Leu Arg Pro Pro Ala Gly Gly Lys Leu Phe Asn Arg Leu
        595                 600                 605

Gly Arg Gly Tyr Pro Asp Val Ala Ala Val Gly Gln Asn Phe Arg Val
        610                 615                 620

Val Leu Arg Gly Tyr Pro Asn Arg Met His Gly Thr Ser Ala Ala Ala
625                 630                 635                 640

Pro Val Trp Ala Ser Ile Leu Thr Leu Ile Asn Glu Glu Arg Arg Ala
                645                 650                 655

Val Gly Lys Gly Pro Val Gly Phe Val His Gln Val Leu Tyr Gln His
            660                 665                 670

Pro Glu Val Phe Thr Asp Ile Thr Val Gly Ser Asn Pro Gly Cys Gly
        675                 680                 685

Thr Asp Gly Phe Pro Val Glu Glu Gly Trp Asp Pro Val Thr Gly Leu
        690                 695                 700

Gly Ser Pro Ile Tyr Pro Lys Leu Leu Lys Leu Phe Met Ser Leu Pro
705                 710                 715                 720

<210> SEQ ID NO 168
<211> LENGTH: 719
<212> TYPE: PRT
<213> ORGANISM: Neurospora crassa

<400> SEQUENCE: 168

Met Phe Arg Phe His Leu Trp Thr Leu Leu Arg Leu Phe Ala Leu Leu
1               5                   10                  15

Ser Ser Leu Val Thr Ala Ser Arg Ile Val Leu Glu Glu Ala Gly His
            20                  25                  30

Leu Pro Ala Gly Trp Lys Val Glu Arg His Ala Thr Ala Ser Asp Arg
        35                  40                  45

Ile Gln Leu Ser Ile Ala Leu Lys Glu Pro Gly Ile Glu Glu Leu Lys
    50                  55                  60
```

```
Arg Arg Leu Leu Gln Gln Ser Thr Ser Asp Asp His Pro Asn Ser Arg
 65                  70                  75                  80

Gln Phe Thr Lys Glu Glu Val Glu Lys His Arg Gln Pro Asp Gln Arg
                 85                  90                  95

Ser Val Thr Ala Val Gly Arg Trp Leu Gln Ser His Gly Ile Lys Ser
            100                 105                 110

Tyr Asn Ala Asp Asn Ser Trp Ile Thr Phe Lys Ala Thr Ala Ala Thr
        115                 120                 125

Val Gln Met Leu Phe Glu Ala Asp Leu Ala Tyr Tyr Ser Tyr Asn Gly
    130                 135                 140

Asp Pro Ser Thr Gln Ile Leu Arg Ser Arg Ser Tyr Thr Ile Pro Arg
145                 150                 155                 160

Trp Leu Ser Asp Asp Ile Asp Phe Val His Pro Leu Thr Asn Phe Met
                165                 170                 175

Pro Pro Arg Asn Arg Asn Asp Gly Thr Leu Gly Ile Gly Arg Arg Gln
            180                 185                 190

Pro Ile Gln Pro Lys Leu Ser Ala Arg Glu Asp Phe Phe Ala Pro Pro
        195                 200                 205

Cys Trp Thr Gly Thr Phe Pro Gly Cys Ile Arg Lys Leu Tyr Asn Leu
    210                 215                 220

Thr Tyr Thr Pro Ser Pro Asp Phe Arg Ser Pro Ser Pro Val Arg Phe
225                 230                 235                 240

Gly Ile Ala Ser Phe Leu Glu Gln Tyr Ile Thr His Arg Asp Val Thr
                245                 250                 255

Ser Phe Leu Ala Thr Tyr Ala Arg Glu Leu Leu Pro Leu Arg Pro Thr
            260                 265                 270

Pro Ser Arg Gly Gly Ser Gly Gly Ser Leu Thr Leu Pro Pro Val Thr
        275                 280                 285

Asn Thr Thr Ser Glu Pro Pro Tyr Asn Ile Thr Ile Thr Leu Leu Asn
290                 295                 300

Asn Ala Thr Arg Trp Asp Pro His Ser Thr Asp Pro Ala Leu Ser Gly
305                 310                 315                 320

Leu Glu Ala Asn Leu Asp Val Gln Tyr Ala Leu Ser Leu Gly His Pro
                325                 330                 335

Thr Arg Val Ile Tyr Tyr Ala Thr Gly Gly Arg Gly Thr Lys Leu Asp
            340                 345                 350

Ser Ser Gly Arg Pro Leu Pro Thr Asn Asp Pro Arg Ala Asn Asn Glu
        355                 360                 365

Pro Phe Leu Glu Phe Leu Gln Ala Leu Leu Ala Leu Pro Asp Asn Gln
    370                 375                 380

Ile Pro His Val Leu Ser Ile Ser Tyr Ala Asp Asp Glu Gln Ser Val
385                 390                 395                 400

Pro Arg Lys Tyr Ala His Arg Val Cys Asp Leu Phe Ala Ala Val Ala
                405                 410                 415

Ala Arg Gly Thr Ser Val Leu Val Ala Thr Gly Asp Gly Gly Ala Ala
            420                 425                 430

Gly Ile Gly Phe Ser Ala Gly Gly Asp Thr Cys Ile Lys Asn Asp
        435                 440                 445

Gly Ser Gly Arg Arg Ala Phe Val Pro Thr Phe Pro Ala Ser Cys Pro
    450                 455                 460

Trp Val Thr Ser Val Gly Ala Thr Asp Asn Thr Ala Leu Asn Leu Thr
465                 470                 475                 480

Gly Ala Ala Phe Ser Ser Gly Gly Phe Ser Glu Tyr Phe Asp Arg Pro
```

```
                            485                 490                 495
Leu Trp Gln Arg Ala Ala Val Asp Pro Tyr Val Ser Ser Leu Leu Arg
                500                 505                 510

Ser Arg Ser Ser Lys Pro Gly Gln Pro Ser Gln Pro Arg Asp Leu Lys
            515                 520                 525

Gly Val Tyr Phe Ser His Asn Gly Arg Gly Met Pro Asp Met Ala Ala
        530                 535                 540

Ile Gly Ser Gly Phe Gln Ile Ile His Arg Gly Glu Met Val Glu Val
545                 550                 555                 560

Arg Gly Thr Ser Ala Ser Thr Pro Val Val Ala Met Val Ala Leu
                565                 570                 575

Val Asn Asp Gln Arg Leu Arg Gln Gly Lys Arg Ser Leu Gly Trp Leu
            580                 585                 590

Asn Gly His Leu Tyr Leu Asp Pro Arg Val Arg Val Leu Thr Asp
                595                 600                 605

Val Lys Trp Gly Arg Ser Glu Gly Cys Val Phe Pro Gly Glu Ala Leu
        610                 615                 620

Glu Glu Gly Arg Gly Lys Gly Lys Glu Lys Tyr Trp Arg His Ser Val
625                 630                 635                 640

Val Glu Lys Arg Gln Gly Asn Ser Glu Glu Asp Gly Thr His Gly
                645                 650                 655

Gly Asp Gly Glu Gly Lys Ala Asp Glu Glu Asp Trp Gly Gly Glu Gly
            660                 665                 670

Glu Val Gly Glu Gly Glu Gly Asp Gln Ser Glu Asn Val Ile Leu Gly
        675                 680                 685

Gly Trp Asp Ala Arg Lys Gly Trp Asp Pro Val Thr Gly Leu Gly Val
        690                 695                 700

Pro Gly Asp Phe Gln Glu Met Leu Lys Val Leu Gly Ser Val Trp
705                 710                 715

<210> SEQ ID NO 169
<211> LENGTH: 454
<212> TYPE: PRT
<213> ORGANISM: Neurospora crassa

<400> SEQUENCE: 169

Met Arg Ala Thr Leu Val Val Leu Cys His Leu Ser Leu Ala Phe
1               5                   10                  15

Ala Leu Ala Ile Ser Pro Ala Ala Ser His Trp Lys Arg Ser Ala Arg
            20                  25                  30

Leu Ala Ser Asp Gln Thr Ala Ser Glu Arg Tyr Ser Leu Pro Ser Arg
        35                  40                  45

Val Ala Arg Tyr Ile Asp Tyr Val Leu Pro Ala Pro Asp Pro Asp
    50                  55                  60

Val Ser Ser Ala Pro Lys Ser Val Ala Val Gln Asp Pro Thr Leu
65                  70                  75                  80

Lys Gly Val Ile Gly Ala Arg Gln Thr Arg Asp Val Asp Cys Leu Gln
            85                  90                  95

Tyr Ile Ala Pro Gln Cys Leu Arg Gln Leu Ala Trp Leu Ala Glu Asp
        100                 105                 110

Leu Asp Met Phe Phe Gly Asp Phe Ala Pro Asp Leu Leu Thr Asn Phe
    115                 120                 125

Asn Leu Glu Pro Asn Leu Asp Tyr Lys Tyr Thr Met Ala Met Ala Lys
    130                 135                 140
```

```
Pro Ile Pro Val Thr Asn Ile Gln Val Gly Asp Phe Val Val Gln Gly
145                 150                 155                 160

Asn Met Asn Ile Met Leu Ala Ala Phe Asn Ala His Tyr Cys Arg Thr
            165                 170                 175

Gly Leu Asp Pro Gln Phe Asp Pro Val Tyr Pro Asn Pro Ala Pro Gly
        180                 185                 190

Gly Tyr Asn Ala Ser Asp Cys Gly Thr His Val Pro Pro Arg Val Ile
    195                 200                 205

Ala Ile Met Tyr Ala Trp Asn Lys Ala Trp Tyr Ser Asp Ala Asp Phe
210                 215                 220

Ala Ser Ile Phe Pro Ala Ser Asp Pro Trp Val Thr Ser Val Gly Gly
225                 230                 235                 240

Thr Gln Phe Leu Pro Val Val Ser Asn Gly Ser Ser Thr Thr Ala
                245                 250                 255

Ser Ser Gly Met Pro Ser Ser Ser Ser Ser Ser Ser Ser Ser Ser Ser
            260                 265                 270

Ser Ser Ser Ser Ser Ser Ser Ser Leu Phe Pro Gly Glu Thr Ala
        275                 280                 285

Leu Asp Asp Asn Asn Thr Gly Ser Ser Gly Ser Phe Ser Arg Leu
290                 295                 300

Phe Pro Gly Pro Trp Tyr Gln Gly Asn Leu Thr Arg Glu Tyr Leu Ala
305                 310                 315                 320

Ser Ala Pro Gly Ala Ala Glu Leu Ala Arg Gln Gly Tyr Phe Asn Gly
                325                 330                 335

Ser Gly Arg Gly Tyr Pro Asp Ile Ser Ala Met Ala Arg Ser Phe Leu
            340                 345                 350

Val Ala Leu His Gly Gly Tyr His Ala Val Ser Gly Thr Ser Ala Ser
                355                 360                 365

Thr Pro Val Ala Ala Met Val Ala Lys Ile Asn Asp Ala Arg Leu
370                 375                 380

His Ala Gly Lys Ser Thr Val Gly Phe Leu Asn Pro Val Leu Tyr Ser
385                 390                 395                 400

Ala Ala Ala Gly Lys Ala Gly Val Leu Arg Asp Val Pro Leu Gly Lys
                405                 410                 415

Asn His Asp Cys Gly Val Gly Glu Ala Phe Pro Ala Arg Arg Ala Trp
            420                 425                 430

Asp Ala Val Thr Gly Leu Gly Thr Pro Asp Phe Glu Lys Leu Lys Glu
                435                 440                 445

Leu Tyr Leu Gly Leu Pro
450

<210> SEQ ID NO 170
<211> LENGTH: 50
<212> TYPE: PRT
<213> ORGANISM: Aspergillus niger

<400> SEQUENCE: 170

Ile Val Thr Trp Asp Glu Ala His Phe Gly Lys Phe Gly Ser His Tyr
1               5                   10                  15

Leu Lys Arg Glu Phe Tyr Phe Asp Val His Pro Pro Leu Gly Lys Met
            20                  25                  30

Leu Val Gly Leu Ser Gly Phe Leu Ala Gly Tyr Asn Gly Ser Phe Glu
        35                  40                  45

Phe Lys
50
```

-continued

```
<210> SEQ ID NO 171
<211> LENGTH: 50
<212> TYPE: PRT
<213> ORGANISM: Aspergillus oryzae

<400> SEQUENCE: 171

Ile Val Thr Trp Asp Glu Ala His Phe Gly Lys Phe Gly Ser His Tyr
1               5                   10                  15

Leu Lys Arg Glu Phe Tyr Phe Asp Val His Pro Pro Leu Gly Lys Met
            20                  25                  30

Leu Val Gly Leu Ser Gly Tyr Leu Ala Gly Tyr Asn Gly Ser Phe Glu
        35                  40                  45

Phe Lys
    50

<210> SEQ ID NO 172
<211> LENGTH: 50
<212> TYPE: PRT
<213> ORGANISM: Aspergillus nidulans

<400> SEQUENCE: 172

Ile Val Thr Trp Asp Glu Ala His Phe Gly Lys Phe Gly Ser His Tyr
1               5                   10                  15

Leu Lys Arg Glu Phe Tyr Phe Asp Val His Pro Pro Leu Gly Lys Met
            20                  25                  30

Leu Val Gly Leu Ser Gly Leu Leu Ala Gly Tyr Asn Gly Ser Phe Glu
        35                  40                  45

Phe Lys
    50

<210> SEQ ID NO 173
<211> LENGTH: 50
<212> TYPE: PRT
<213> ORGANISM: Myceliophthora thermophila

<400> SEQUENCE: 173

Ile Val Thr Trp Asp Glu Ala His Phe Gly Lys Phe Gly Ser His Tyr
1               5                   10                  15

Leu Lys Arg Glu Phe Tyr Phe Asp Val His Pro Pro Ala Gly Lys Leu
            20                  25                  30

Leu Val Gly Leu Ser Gly Tyr Leu Ala Gly Tyr Asn Gly Ser Phe Glu
        35                  40                  45

Phe Lys
    50

<210> SEQ ID NO 174
<211> LENGTH: 50
<212> TYPE: PRT
<213> ORGANISM: Neurospora crassa

<400> SEQUENCE: 174

Ile Val Thr Trp Asp Glu Ala His Phe Gly Lys Phe Gly Ser His Tyr
1               5                   10                  15

Leu Lys Arg Glu Phe Tyr Phe Asp Val His Pro Pro Ala Gly Lys Leu
            20                  25                  30

Leu Val Gly Leu Ser Gly Leu Leu Ala Gly Tyr Asn Gly Ser Phe Glu
        35                  40                  45

Phe Lys
```

50

<210> SEQ ID NO 175
<211> LENGTH: 50
<212> TYPE: PRT
<213> ORGANISM: Trichoderma virens

<400> SEQUENCE: 175

Ile Val Thr Trp Asp Glu Ala His Phe Gly Lys Phe Gly Ser Tyr Tyr
1               5                   10                  15

Ile Lys His Glu Tyr Tyr Phe Asp Val His Pro Pro Leu Gly Lys Met
            20                  25                  30

Leu Val Gly Leu Ser Gly Val Leu Ala Gly Tyr Asn Gly Ser Phe Glu
        35                  40                  45

Phe Lys
    50

<210> SEQ ID NO 176
<211> LENGTH: 50
<212> TYPE: PRT
<213> ORGANISM: Trichoderma reesei

<400> SEQUENCE: 176

Ile Val Thr Trp Asp Glu Ala His Phe Gly Lys Phe Gly Ser Tyr Tyr
1               5                   10                  15

Ile Lys His Glu Tyr Tyr Phe Asp Val His Pro Pro Leu Gly Lys Met
            20                  25                  30

Leu Val Gly Leu Ser Gly Val Leu Ala Gly Tyr Asn Gly Ser Phe Glu
        35                  40                  45

Phe Lys
    50

<210> SEQ ID NO 177
<211> LENGTH: 50
<212> TYPE: PRT
<213> ORGANISM: Fusarium oxysporum

<400> SEQUENCE: 177

Ile Val Thr Trp Asp Glu Ala His Phe Gly Lys Phe Gly Ser Tyr Tyr
1               5                   10                  15

Ile Lys His Glu Tyr Tyr Phe Asp Val His Pro Pro Leu Gly Lys Met
            20                  25                  30

Leu Val Gly Leu Ser Gly Val Leu Ala Gly Tyr Asn Gly Thr Phe Glu
        35                  40                  45

Phe Lys
    50

<210> SEQ ID NO 178
<211> LENGTH: 50
<212> TYPE: PRT
<213> ORGANISM: Neurospora crassa

<400> SEQUENCE: 178

Ser Val Val Phe Asp Glu Val His Phe Gly Gly Phe Ala Ser Lys Tyr
1               5                   10                  15

Ile Lys Gly Lys Phe Phe Met Asp Val His Pro Pro Leu Ala Lys Leu
            20                  25                  30

Met Ile Thr Leu Phe Gly Trp Leu Ala Gly Phe Asp Gly Ser Phe Asp
        35                  40                  45

Phe Lys
    50

<210> SEQ ID NO 179
<211> LENGTH: 50
<212> TYPE: PRT
<213> ORGANISM: Myceliophthora thermophila

<400> SEQUENCE: 179

Ser Val Val Phe Asp Glu Val His Phe Gly Gly Phe Ala Thr Lys Tyr
1               5                   10                  15

Ile Lys Gly Lys Phe Phe Met Asp Val His Pro Pro Leu Ala Lys Leu
            20                  25                  30

Met Ile Thr Leu Phe Gly Trp Leu Ala Gly Phe Lys Gly Asn Phe Asp
        35                  40                  45

Phe Lys
    50

<210> SEQ ID NO 180
<211> LENGTH: 50
<212> TYPE: PRT
<213> ORGANISM: Trichoderma virens

<400> SEQUENCE: 180

Ser Val Val Phe Asp Glu Val His Phe Gly Gly Phe Ala Ser Lys Tyr
1               5                   10                  15

Ile Lys Gly Lys Phe Phe Met Asp Val His Pro Pro Leu Ala Lys Met
            20                  25                  30

Leu Ile Ala Leu Thr Gly Trp Leu Ala Gly Phe Asp Gly Asn Phe Asp
        35                  40                  45

Phe Lys
    50

<210> SEQ ID NO 181
<211> LENGTH: 50
<212> TYPE: PRT
<213> ORGANISM: Trichoderma atroviride

<400> SEQUENCE: 181

Ser Val Val Phe Asp Glu Val His Phe Gly Gly Phe Ala Ser Lys Tyr
1               5                   10                  15

Ile Lys Gly Arg Phe Phe Met Asp Val His Pro Pro Leu Ala Lys Met
            20                  25                  30

Leu Ile Ala Leu Thr Gly Trp Leu Ala Gly Phe Asp Gly Asp Phe Asp
        35                  40                  45

Phe Lys
    50

<210> SEQ ID NO 182
<211> LENGTH: 50
<212> TYPE: PRT
<213> ORGANISM: Trichoderma reesei

<400> SEQUENCE: 182

Ser Val Val Phe Asp Glu Val His Phe Gly Gly Phe Ala Ser Lys Tyr
1               5                   10                  15

Ile Lys Gly Arg Phe Phe Met Asp Val His Pro Pro Leu Ala Lys Met
            20                  25                  30

Leu Ile Ala Leu Thr Gly Trp Leu Ala Gly Phe Asp Gly Asn Phe Asp
        35                  40                  45

```
Phe Lys
    50

<210> SEQ ID NO 183
<211> LENGTH: 50
<212> TYPE: PRT
<213> ORGANISM: Fusarium oxysporum

<400> SEQUENCE: 183

Ser Val Val Phe Asp Glu Val His Phe Gly Gly Phe Ala Thr Lys Tyr
1               5                   10                  15

Ile Lys Gly Lys Phe Phe Met Asp Val His Pro Pro Leu Ala Lys Met
            20                  25                  30

Leu Ile Ala Leu Thr Gly Trp Leu Ala Gly Phe Asp Gly Ser Phe Asp
        35                  40                  45

Phe Lys
    50

<210> SEQ ID NO 184
<211> LENGTH: 50
<212> TYPE: PRT
<213> ORGANISM: Aspergillus nidulans

<400> SEQUENCE: 184

Ser Val Val Phe Asp Glu Val His Phe Gly Gly Phe Ala Thr Lys Tyr
1               5                   10                  15

Ile Lys Gly Arg Phe Phe Met Asp Val His Pro Pro Leu Ala Lys Leu
            20                  25                  30

Leu Ile Thr Leu Ala Gly Trp Leu Ala Gly Phe Lys Gly Asp Phe Asp
        35                  40                  45

Phe Lys
    50

<210> SEQ ID NO 185
<211> LENGTH: 50
<212> TYPE: PRT
<213> ORGANISM: Aspergillus oryzae

<400> SEQUENCE: 185

Ser Val Val Phe Asp Glu Val His Phe Gly Gly Phe Ala Ser Lys Tyr
1               5                   10                  15

Ile Lys Gly Arg Phe Phe Met Asp Val His Pro Pro Leu Ala Lys Leu
            20                  25                  30

Leu Ile Thr Leu Ala Gly Trp Leu Ala Gly Phe Asn Gly Asp Phe Asp
        35                  40                  45

Phe Lys
    50

<210> SEQ ID NO 186
<211> LENGTH: 50
<212> TYPE: PRT
<213> ORGANISM: Aspergillus niger

<400> SEQUENCE: 186

Ser Val Val Phe Asp Glu Val His Phe Gly Gly Phe Ala Thr Lys Tyr
1               5                   10                  15

Ile Lys Gly Arg Phe Phe Met Asp Val His Pro Pro Leu Ala Lys Leu
            20                  25                  30

Leu Ile Thr Leu Ala Gly Trp Leu Ala Gly Phe Asp Gly Glu Phe Asp
```

```
                35                  40                  45
Phe Lys
    50

<210> SEQ ID NO 187
<211> LENGTH: 50
<212> TYPE: PRT
<213> ORGANISM: Penicillium chrysogenum

<400> SEQUENCE: 187

Ser Val Val Phe Asp Glu Val His Phe Gly Gly Phe Ala Ser Lys Tyr
1               5                   10                  15

Ile Lys Gly Lys Phe Phe Met Asp Val His Pro Pro Leu Ala Lys Leu
            20                  25                  30

Leu Leu Thr Leu Ala Gly Trp Leu Ala Gly Phe Asp Gly Asn Phe Asp
        35                  40                  45

Phe Lys
    50

<210> SEQ ID NO 188
<211> LENGTH: 50
<212> TYPE: PRT
<213> ORGANISM: Trichoderma reesei

<400> SEQUENCE: 188

Glu Val Val Phe Asp Glu Val His Phe Gly Lys Phe Ala Ser Tyr Tyr
1               5                   10                  15

Leu Gln Arg Thr Tyr Phe Phe Asp Val His Pro Pro Phe Ala Lys Leu
            20                  25                  30

Leu Phe Ala Phe Val Gly Trp Leu Val Gly Tyr Asp Gly His Phe His
        35                  40                  45

Phe Asp
    50

<210> SEQ ID NO 189
<211> LENGTH: 50
<212> TYPE: PRT
<213> ORGANISM: Trichoderma virens

<400> SEQUENCE: 189

Glu Val Val Phe Asp Glu Val His Phe Gly Lys Phe Ala Ser Tyr Tyr
1               5                   10                  15

Leu Gln Arg Thr Tyr Phe Phe Asp Val His Pro Pro Phe Ala Lys Leu
            20                  25                  30

Leu Phe Ala Phe Val Gly Trp Leu Val Gly Tyr Asp Gly His Phe His
        35                  40                  45

Phe Glu
    50

<210> SEQ ID NO 190
<211> LENGTH: 50
<212> TYPE: PRT
<213> ORGANISM: Fusarium oxysporum

<400> SEQUENCE: 190

Glu Val Val Phe Asp Glu Val His Phe Gly Lys Phe Ala Ser Tyr Tyr
1               5                   10                  15

Leu Glu Arg Thr Tyr Phe Phe Asp Val His Pro Pro Phe Gly Lys Leu
            20                  25                  30
```

```
Leu Phe Ala Phe Val Gly Trp Leu Val Gly Tyr Asp Gly Asn Phe His
        35                  40                  45

Phe Glu
    50
```

<210> SEQ ID NO 191
<211> LENGTH: 50
<212> TYPE: PRT
<213> ORGANISM: Gibberella zeae

<400> SEQUENCE: 191

```
Glu Val Val Phe Asp Glu Val His Phe Gly Lys Phe Ala Ser Tyr Tyr
1               5                   10                  15

Leu Glu Arg Thr Tyr Phe Phe Asp Val His Pro Pro Phe Gly Lys Leu
            20                  25                  30

Leu Phe Ala Phe Val Gly Trp Leu Val Gly Tyr Asp Gly His Phe His
        35                  40                  45

Phe Asp
    50
```

<210> SEQ ID NO 192
<211> LENGTH: 50
<212> TYPE: PRT
<213> ORGANISM: Myceliophthora thermophila

<400> SEQUENCE: 192

```
Glu Val Val Phe Asp Glu Val His Phe Gly Lys Phe Ala Ser Tyr Tyr
1               5                   10                  15

Leu Glu Arg Thr Tyr Phe Phe Asp Val His Pro Pro Leu Gly Lys Leu
            20                  25                  30

Leu Phe Ala Phe Met Gly Trp Leu Val Gly Tyr Asp Gly His Phe His
        35                  40                  45

Phe Glu
    50
```

<210> SEQ ID NO 193
<211> LENGTH: 50
<212> TYPE: PRT
<213> ORGANISM: Neurospora crassa

<400> SEQUENCE: 193

```
Glu Val Val Phe Asp Glu Val His Phe Gly Lys Phe Ala Ser Tyr Tyr
1               5                   10                  15

Leu Glu Arg Thr Tyr Phe Phe Asp Val His Pro Pro Phe Gly Lys Leu
            20                  25                  30

Leu Phe Ala Phe Met Gly Trp Leu Val Gly Tyr Asp Gly His Phe His
        35                  40                  45

Phe Glu
    50
```

<210> SEQ ID NO 194
<211> LENGTH: 50
<212> TYPE: PRT
<213> ORGANISM: Aspergillus nidulans

<400> SEQUENCE: 194

```
Gln Val Val Phe Asp Glu Val His Phe Gly Lys Phe Ala Ser Tyr Tyr
1               5                   10                  15

Leu Arg Arg Thr Tyr Phe Phe Asp Val His Pro Pro Phe Ala Lys Leu
            20                  25                  30
```

```
Leu Leu Ala Phe Thr Gly Trp Leu Val Gly Tyr Asp Gly His Phe Leu
        35                  40                  45

Phe Glu
    50

<210> SEQ ID NO 195
<211> LENGTH: 50
<212> TYPE: PRT
<213> ORGANISM: Aspergillus niger

<400> SEQUENCE: 195

Glu Val Val Phe Asp Glu Val His Phe Gly Lys Phe Ala Ser Tyr Tyr
1               5                   10                  15

Leu Gln Arg Thr Tyr Phe Phe Asp Val His Pro Pro Phe Gly Lys Leu
            20                  25                  30

Leu Phe Ala Phe Met Gly Trp Leu Val Gly Tyr Asp Gly His Phe Leu
        35                  40                  45

Phe Asp
    50

<210> SEQ ID NO 196
<211> LENGTH: 50
<212> TYPE: PRT
<213> ORGANISM: Aspergillus oryzae

<400> SEQUENCE: 196

Glu Val Val Phe Asp Glu Val His Phe Gly Lys Phe Ala Ser Tyr Tyr
1               5                   10                  15

Leu Gln Arg Thr Tyr Phe Phe Asp Val His Pro Pro Phe Gly Lys Leu
            20                  25                  30

Leu Phe Ala Ala Val Gly Trp Leu Ile Gly Tyr Asp Gly His Phe Leu
        35                  40                  45

Phe Glu
    50

<210> SEQ ID NO 197
<211> LENGTH: 50
<212> TYPE: PRT
<213> ORGANISM: Penicillium chrysogenum

<400> SEQUENCE: 197

Glu Val Val Phe Asp Glu Val His Phe Gly Lys Phe Ala Ser Tyr Tyr
1               5                   10                  15

Leu Gln Arg Thr Tyr Phe Phe Asp Val His Pro Pro Phe Gly Lys Leu
            20                  25                  30

Leu Phe Ala Leu Met Gly Trp Leu Val Gly Phe Asp Gly Ser Phe Leu
        35                  40                  45

Phe Glu
    50
```